(12) United States Patent
Cowan et al.

(10) Patent No.: US 7,666,169 B2
(45) Date of Patent: Feb. 23, 2010

(54) SYRINGE AND SYRINGE PLUNGERS FOR USE WITH MEDICAL INJECTORS

(75) Inventors: Kevin P. Cowan, Allison Park, PA (US); John A. Haury, Sewickley, PA (US); Jared E. Neff, New Kensington, PA (US)

(73) Assignee: Medrad, Inc., Indianola, PA (US)

( * ) Notice: Subject to any disclaimer, the term of this patent is extended or adjusted under 35 U.S.C. 154(b) by 323 days.

(21) Appl. No.: 10/722,370

(22) Filed: Nov. 25, 2003

(65) Prior Publication Data

US 2005/0113754 A1    May 26, 2005

(51) Int. Cl.
*A61M 5/315* (2006.01)
*A61M 1/00* (2006.01)

(52) U.S. Cl. ....................... 604/228; 604/151
(58) Field of Classification Search ............. 604/187, 604/218–229, 151–155; 128/DIG. 12
See application file for complete search history.

(56) References Cited

U.S. PATENT DOCUMENTS

| | | | |
|---|---|---|---|
| 1,687,323 A | 10/1928 | Cook | |
| 2,842,126 A | 7/1958 | Brown | |
| 4,452,251 A | 6/1984 | Heilman et al. | |
| 4,677,980 A | 7/1987 | Reilly et al. | |
| 5,300,031 A | 4/1994 | Neer et al. | |
| 5,383,858 A | 1/1995 | Reilly et al. | |
| 5,520,653 A | 5/1996 | Reilly et al. | |
| 5,535,746 A | 7/1996 | Hoover et al. | |
| 5,808,203 A | 9/1998 | Nolan et al. | |
| 5,944,694 A | 8/1999 | Hitchins et al. | |
| 5,947,929 A * | 9/1999 | Trull | 604/152 |
| 6,017,330 A * | 1/2000 | Hitchins et al. | 604/218 |
| 6,336,913 B1 | 1/2002 | Spohn et al. | |
| 6,339,718 B1 | 1/2002 | Zatezalo et al. | |
| 6,652,489 B2 | 11/2003 | Trocki et al. | |
| 6,958,053 B1 | 10/2005 | Reilly | |

(Continued)

FOREIGN PATENT DOCUMENTS

WO    9820920    5/1998

(Continued)

OTHER PUBLICATIONS

International Search Report for Corresponding International Patent Application Publication PCT/US2004/039225.

*Primary Examiner*—Kevin C Sirmons
*Assistant Examiner*—Catherine N Witczak
(74) *Attorney, Agent, or Firm*—Jill Denesvich; Gregory L. Bradley

(57) ABSTRACT

A syringe plunger includes a wall having an inner surface and one or more inwardly projecting flanges disposed on the inner surface of the wall. Preferably, the inner surface of the wall defines a retaining shoulder formed along an axial plane thereof. An injector drive member preferably includes at least one retaining member adapted to engage the retaining shoulder of the syringe plunger to allow the drive member to retract the plunger with the body of the syringe. Further, the drive member preferably includes one or more outwardly extending flange members adapted to be engaged by the inwardly projecting flanges of the syringe plunger. When the syringe body is rotated, the at least one retaining member on the drive member is retracted and disengaged from the retaining shoulder of the syringe plunger.

12 Claims, 156 Drawing Sheets

U.S. PATENT DOCUMENTS

| | | |
|---|---|---|
| 7,018,363 B2 | 3/2006 | Cowan et al. |
| 7,029,459 B2 | 4/2006 | Reilly |
| 2001/0047153 A1* | 11/2001 | Trocki et al. ............ 604/155 |
| 2002/0128606 A1 | 9/2002 | Cowan et al. |
| 2004/0064041 A1 | 4/2004 | Lazzaro et al. |
| 2004/0068223 A1 | 4/2004 | Reilly |
| 2004/0116861 A1 | 6/2004 | Trocki et al. |
| 2004/0133153 A1 | 7/2004 | Trocki et al. |
| 2004/0133161 A1 | 7/2004 | Trocki et al. |
| 2004/0133162 A1 | 7/2004 | Trocki et al. |
| 2004/0133183 A1 | 7/2004 | Trocki et al. |
| 2004/0158205 A1 | 8/2004 | Savage |

FOREIGN PATENT DOCUMENTS

| | | |
|---|---|---|
| WO | 2007130061 | 11/2007 |

* cited by examiner

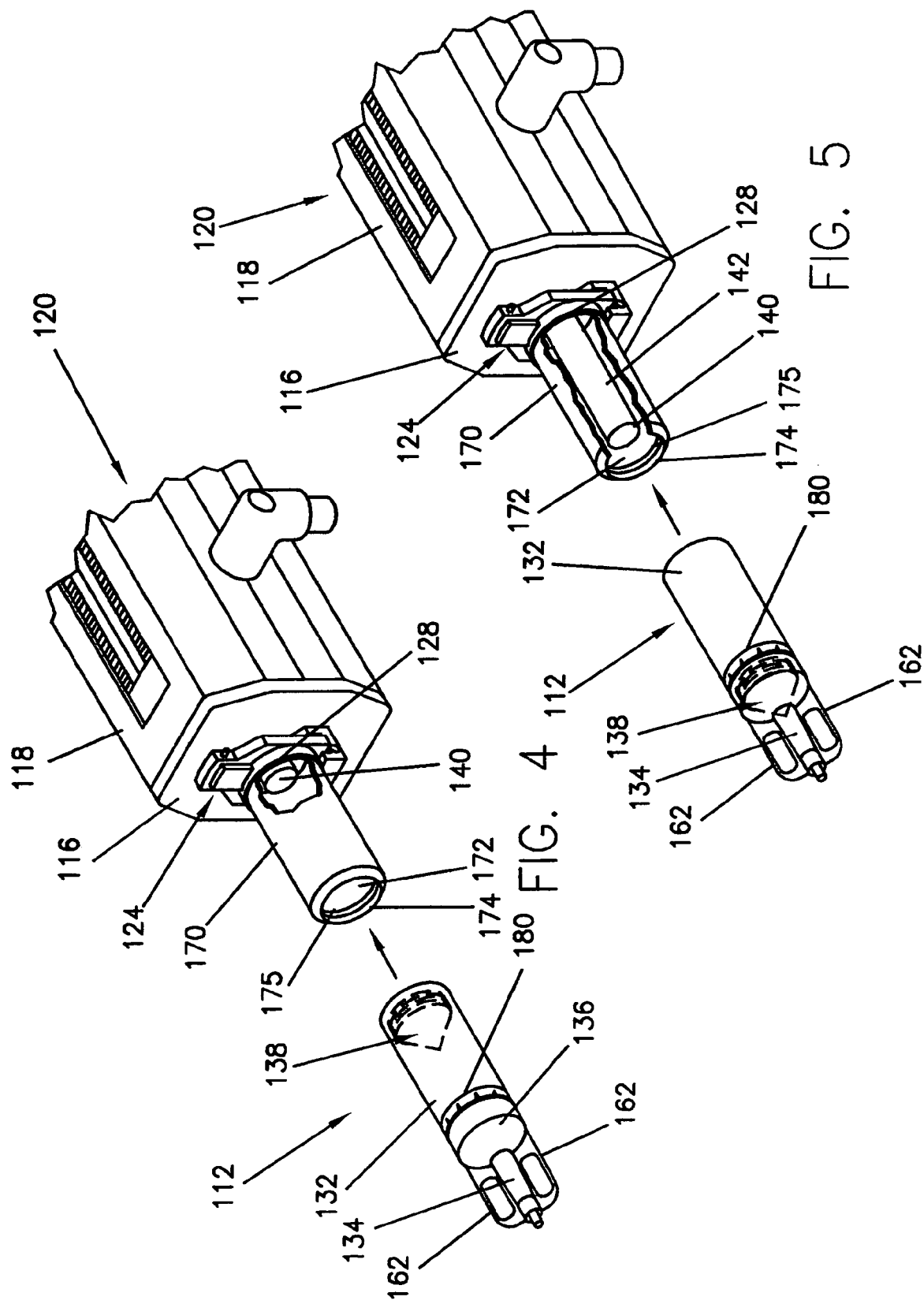

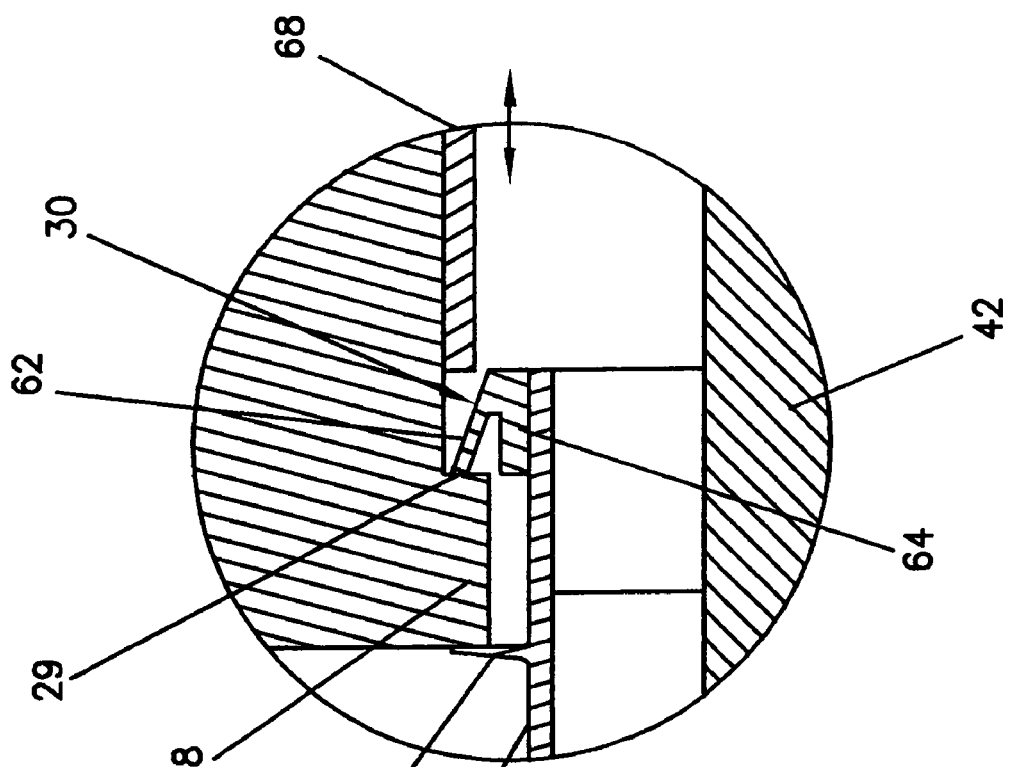
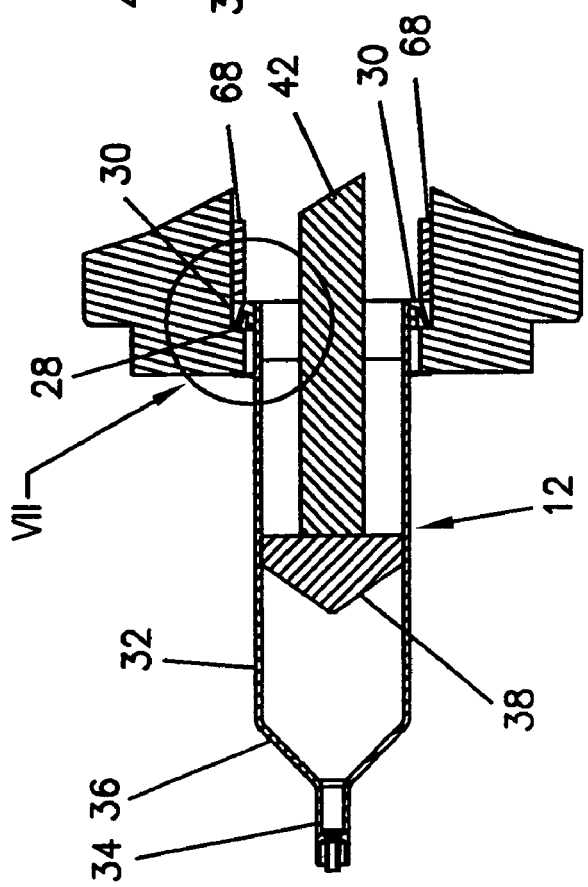

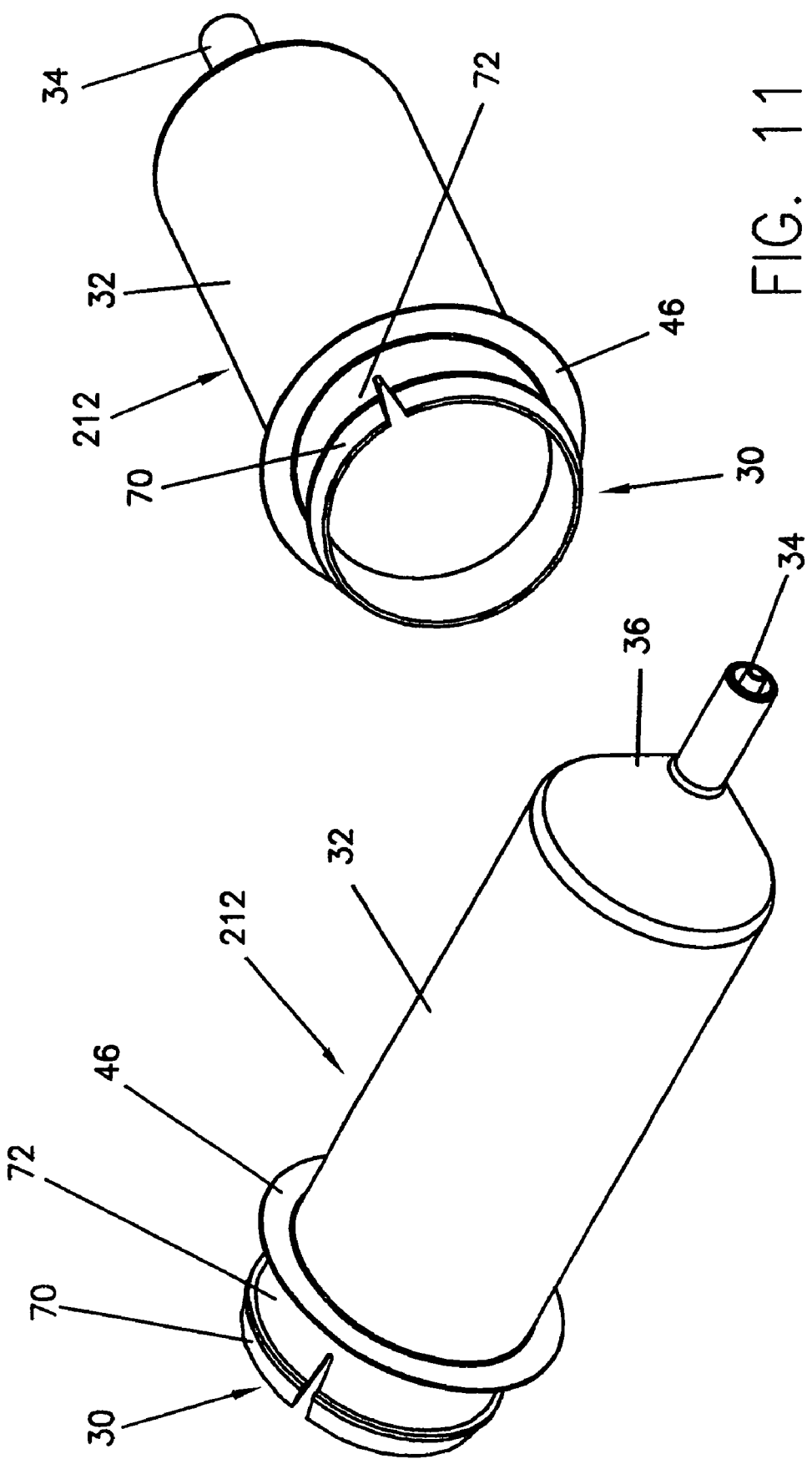

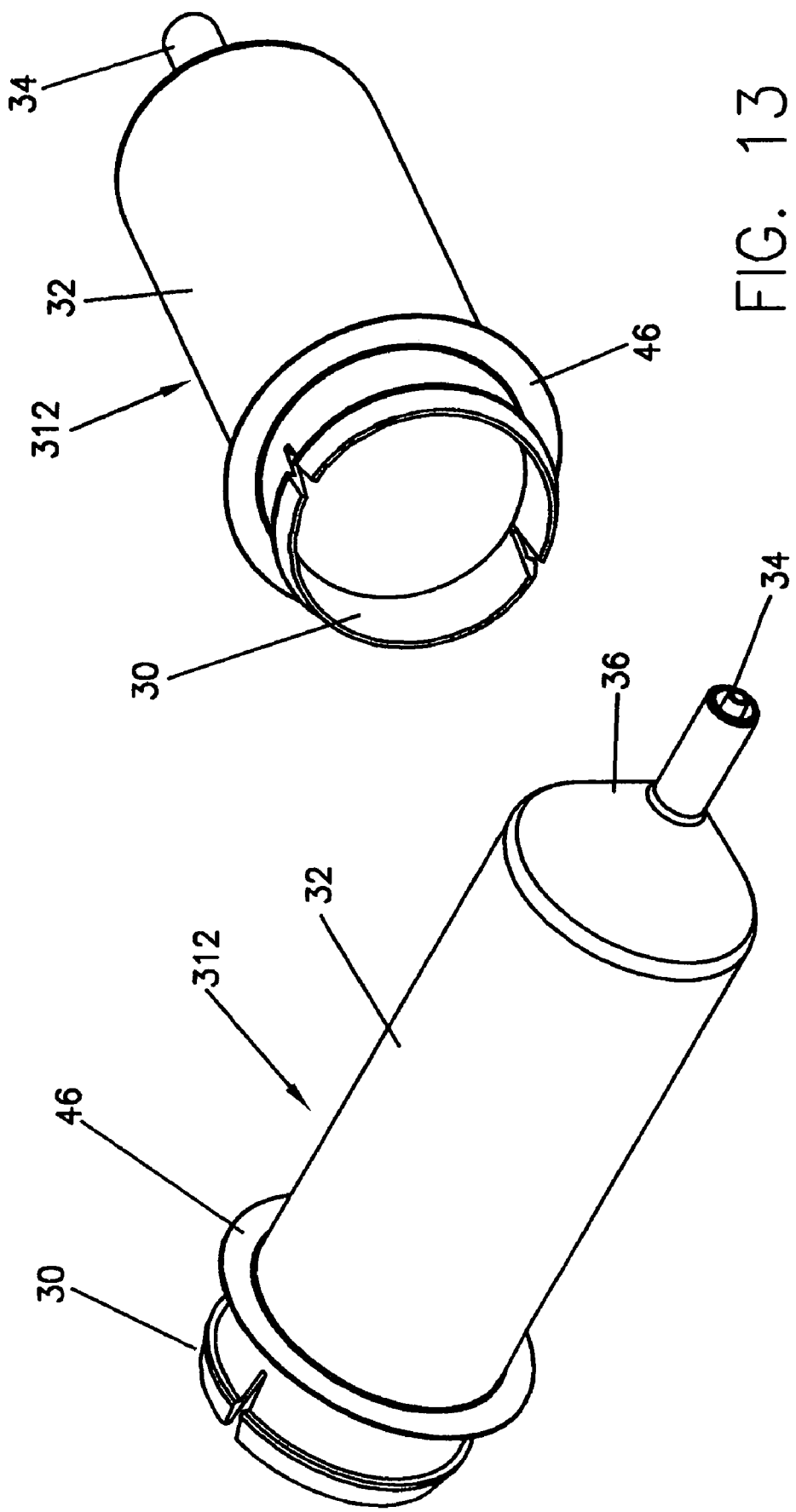

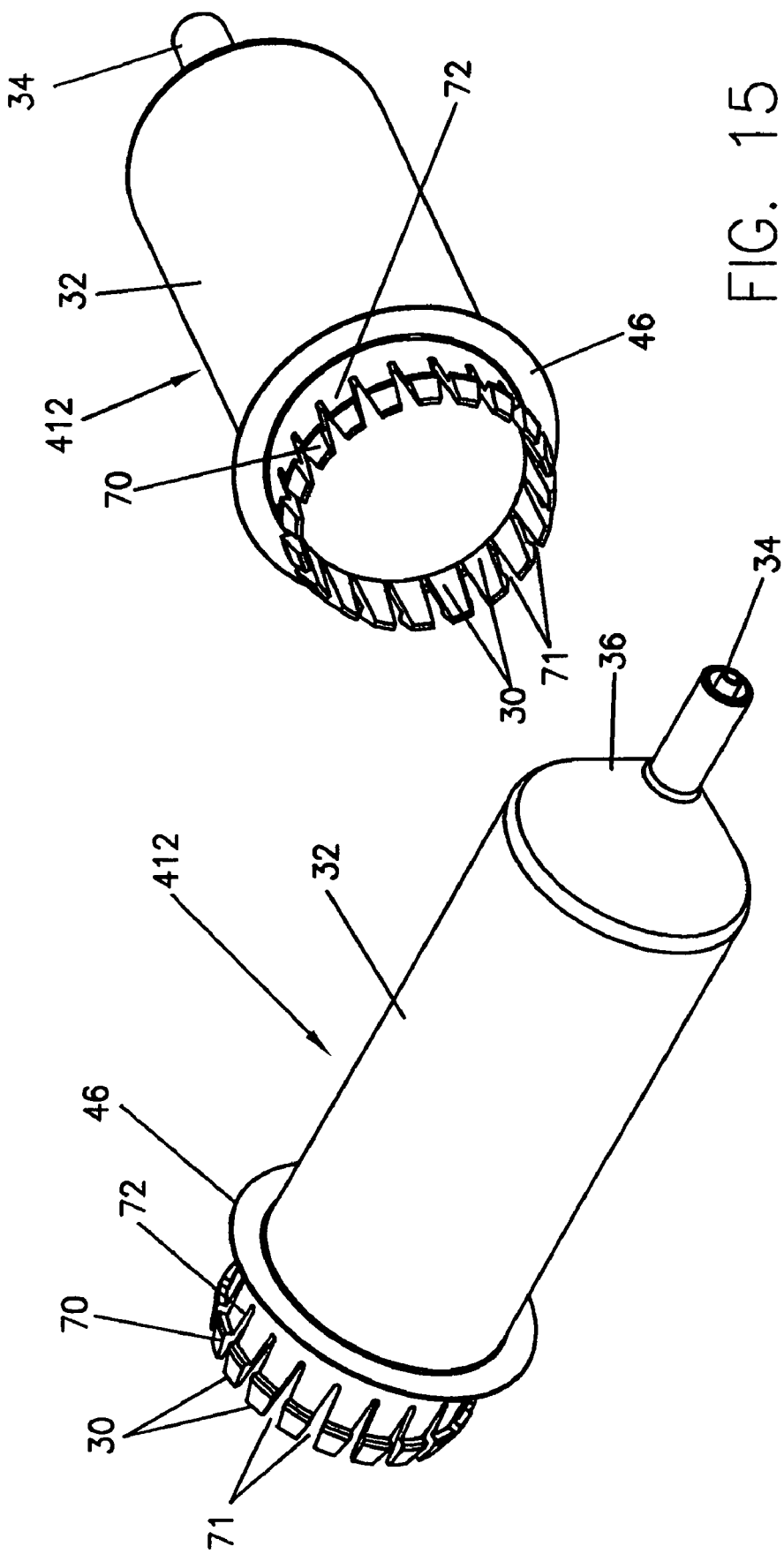

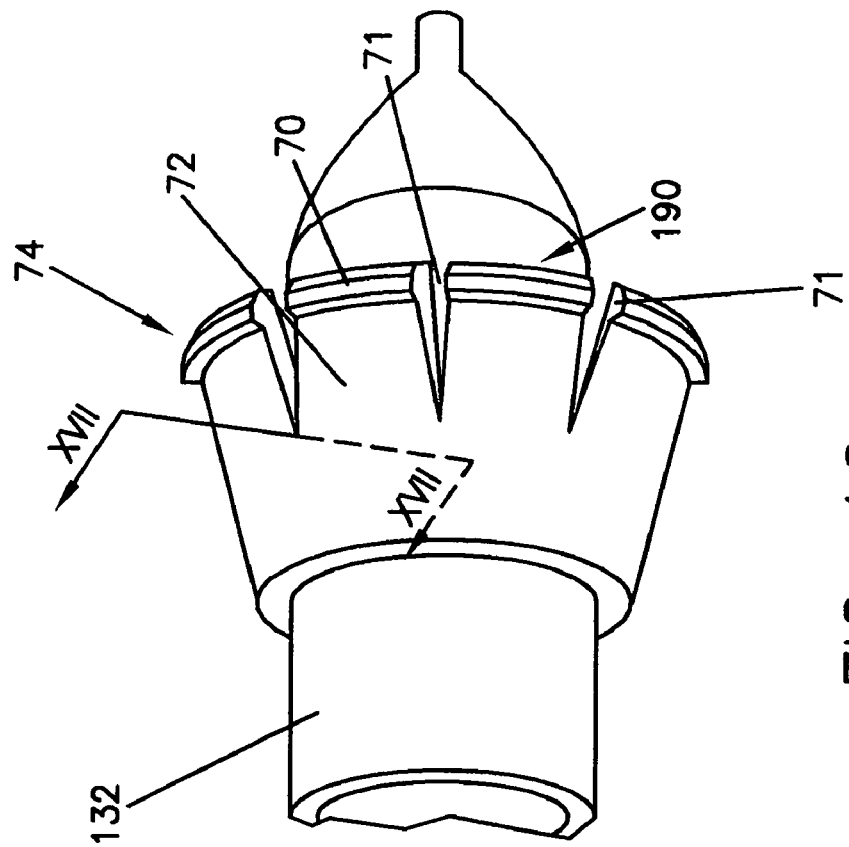
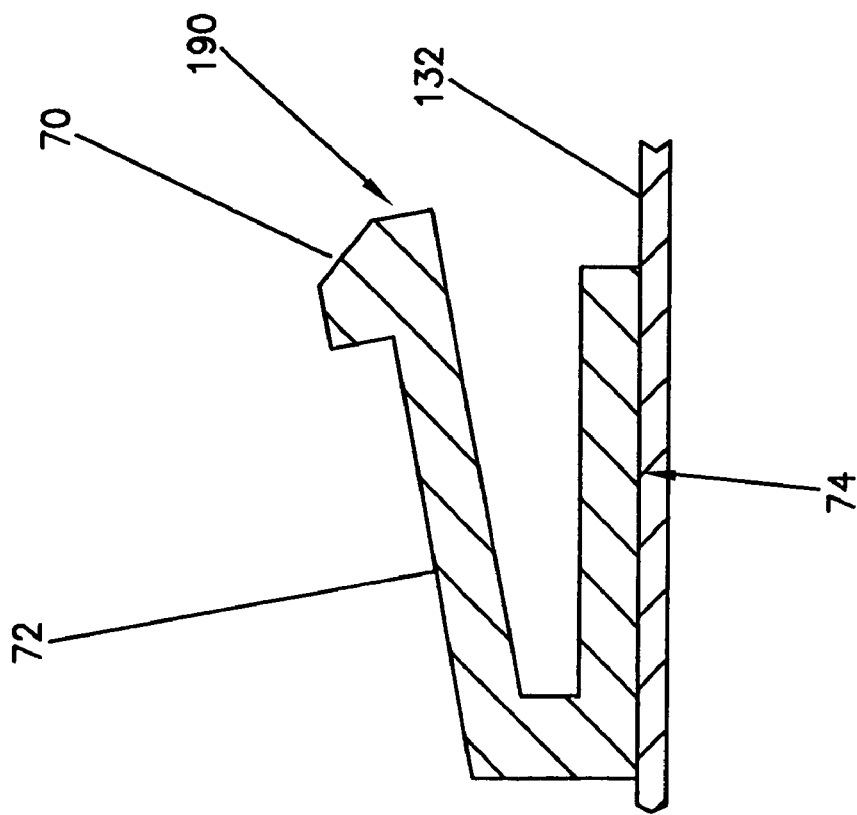
FIG. 16
FIG. 17

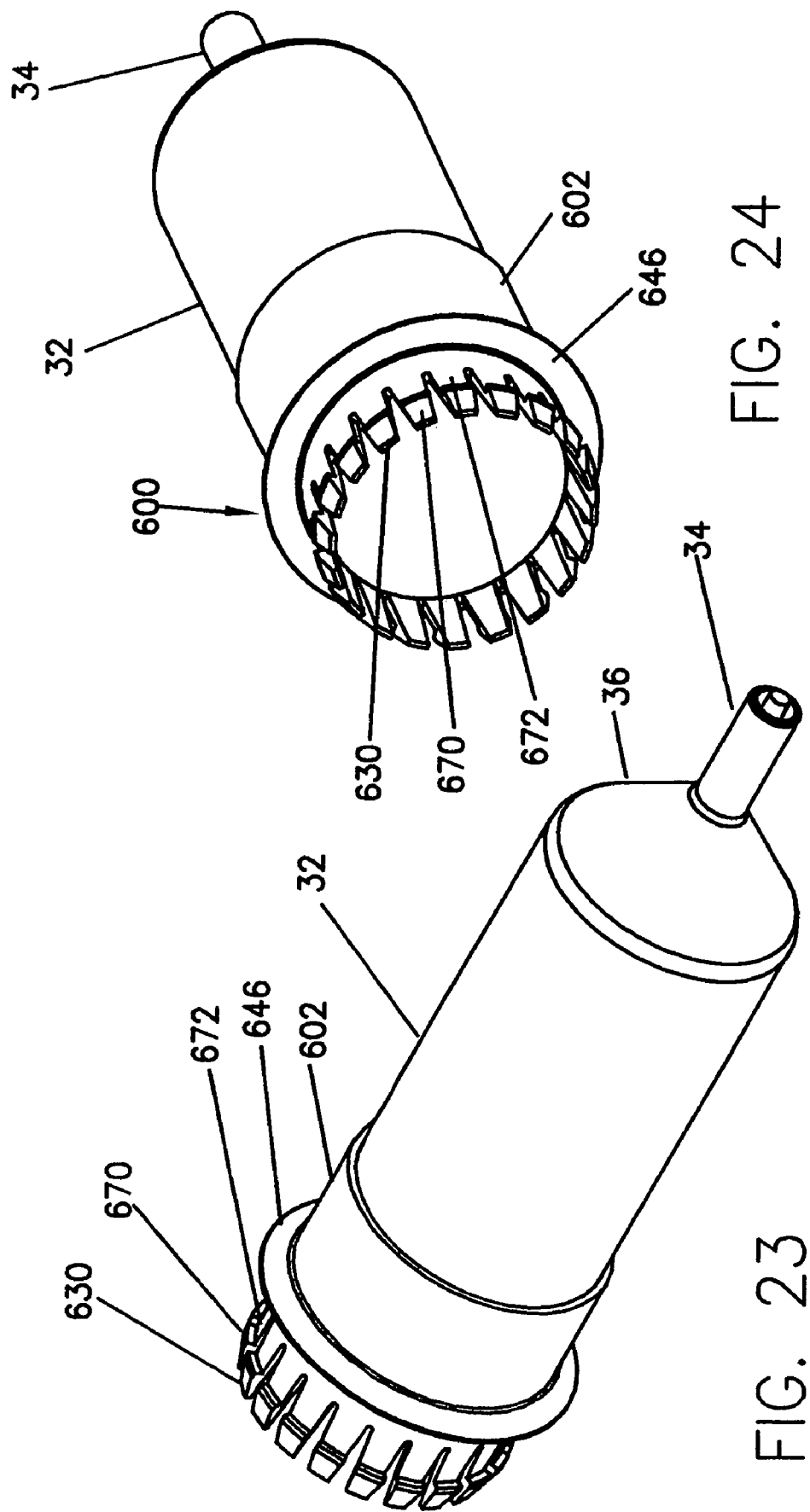

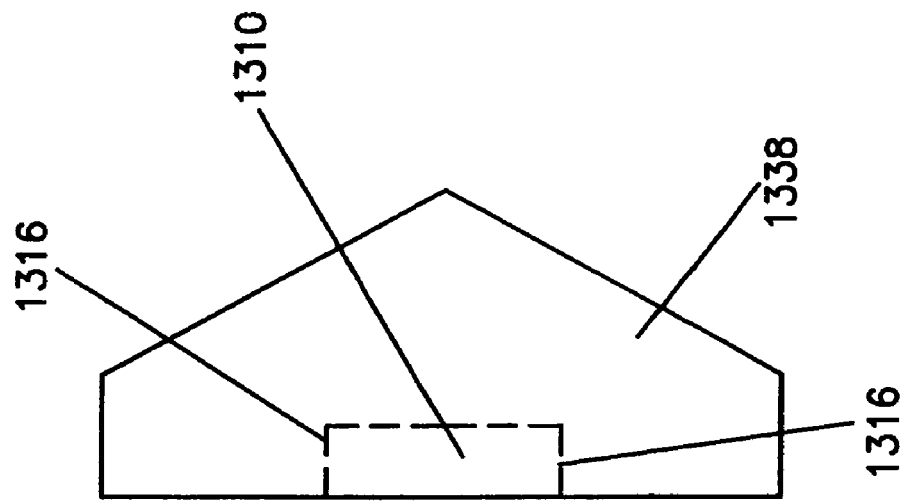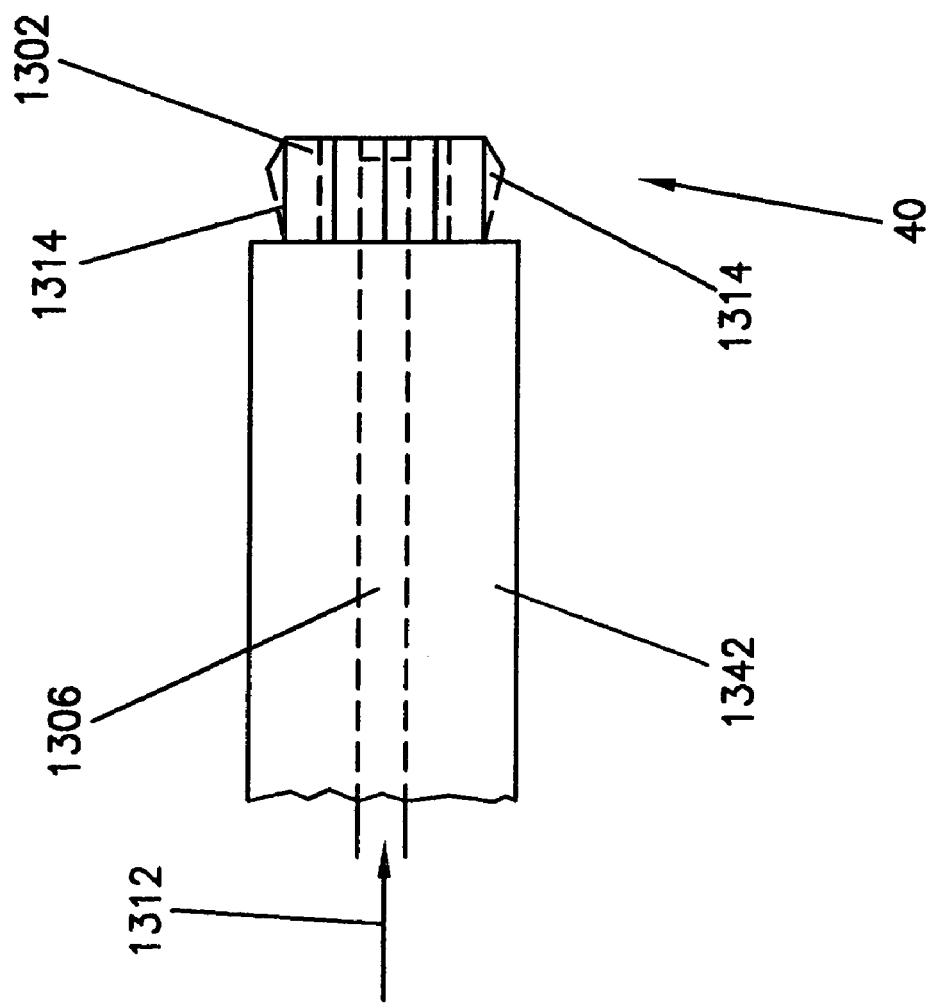
FIG. 36

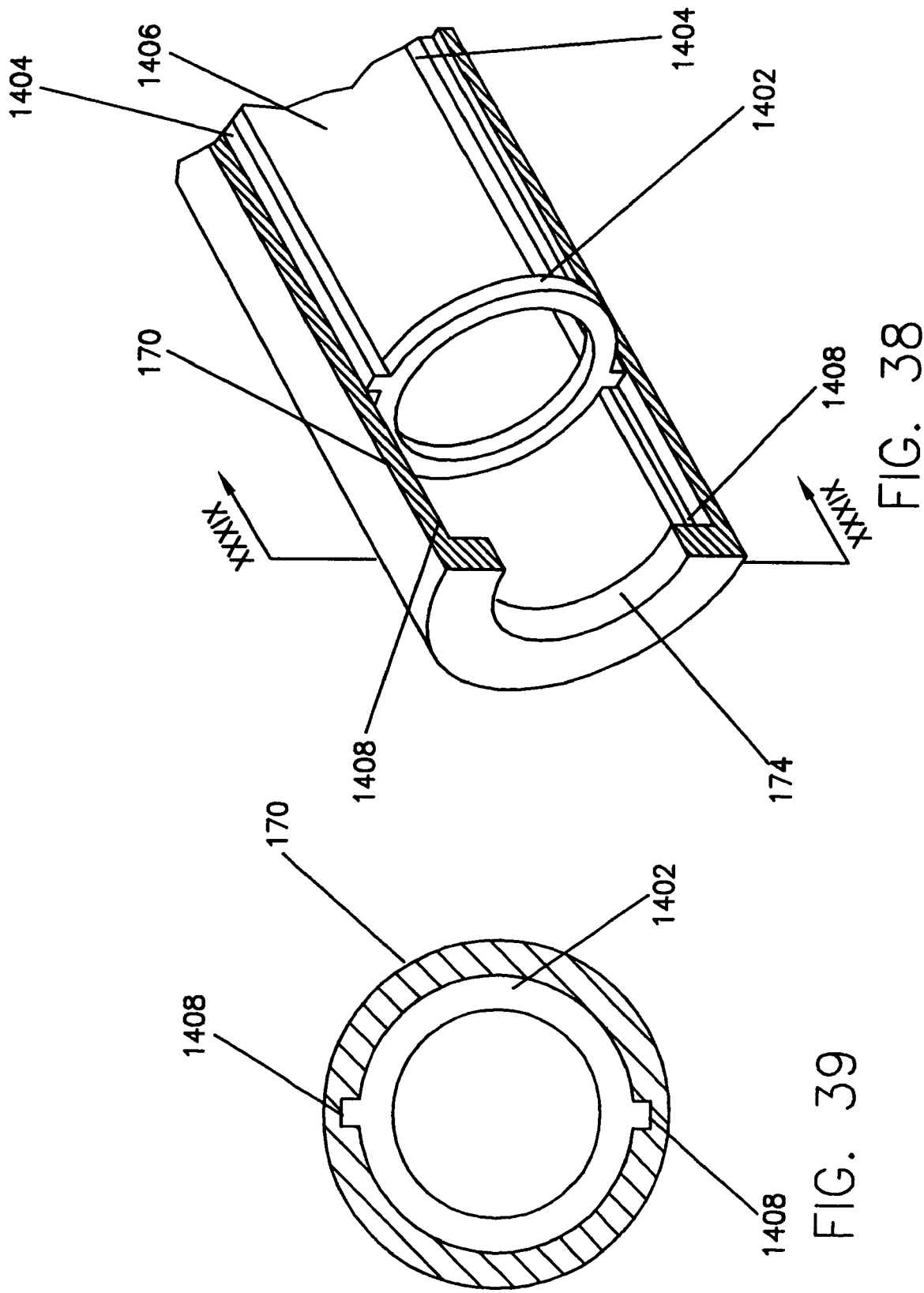

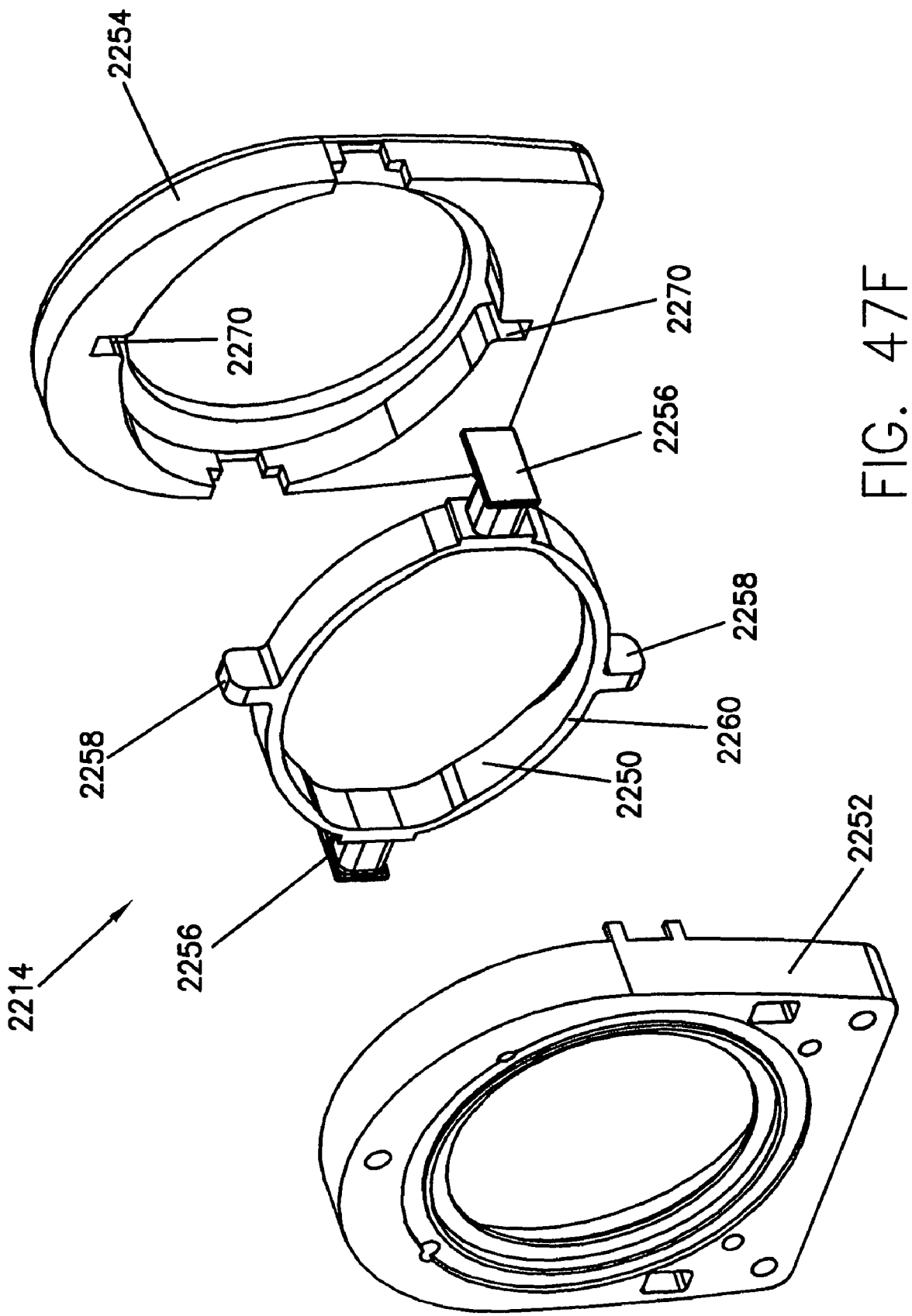

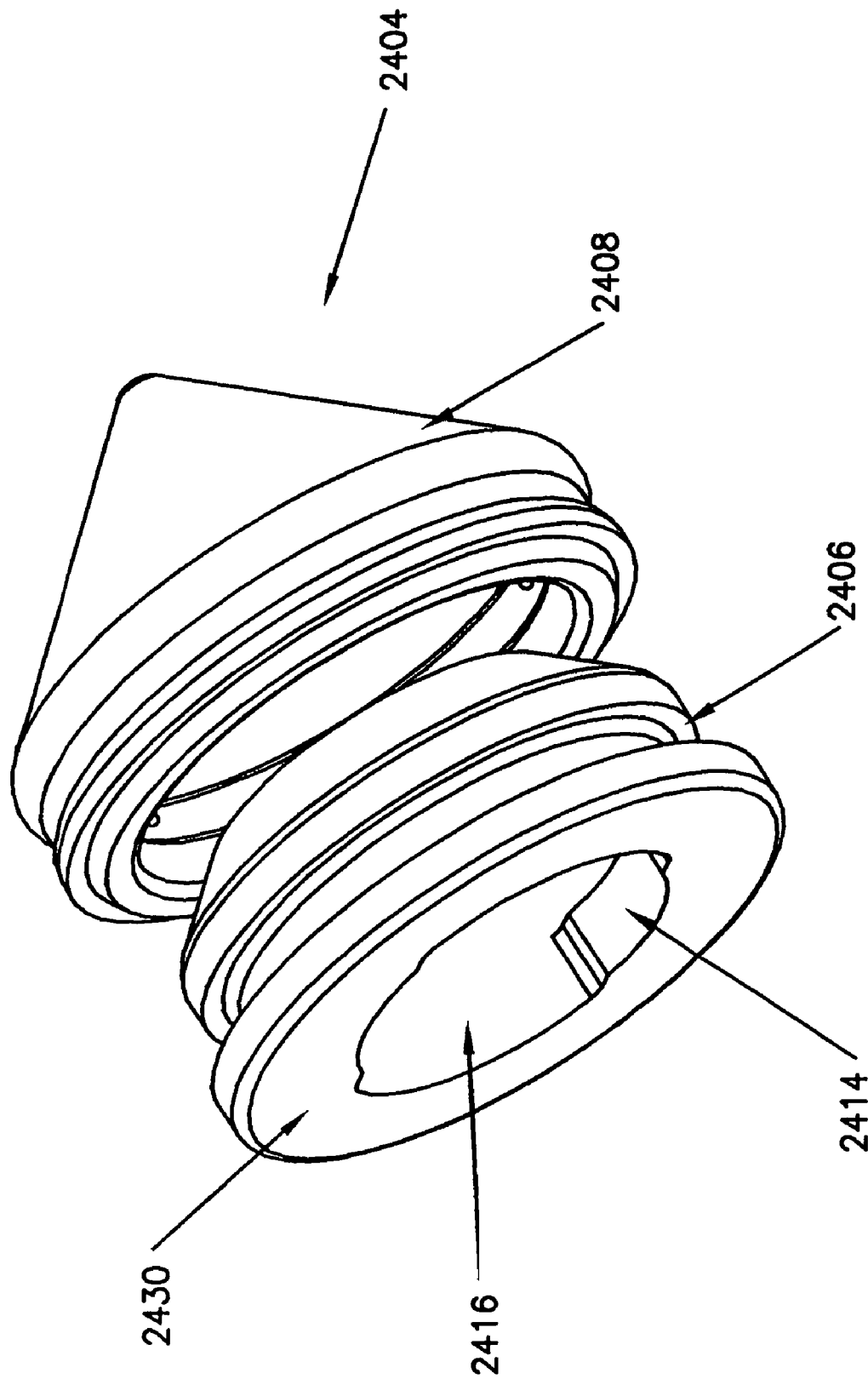

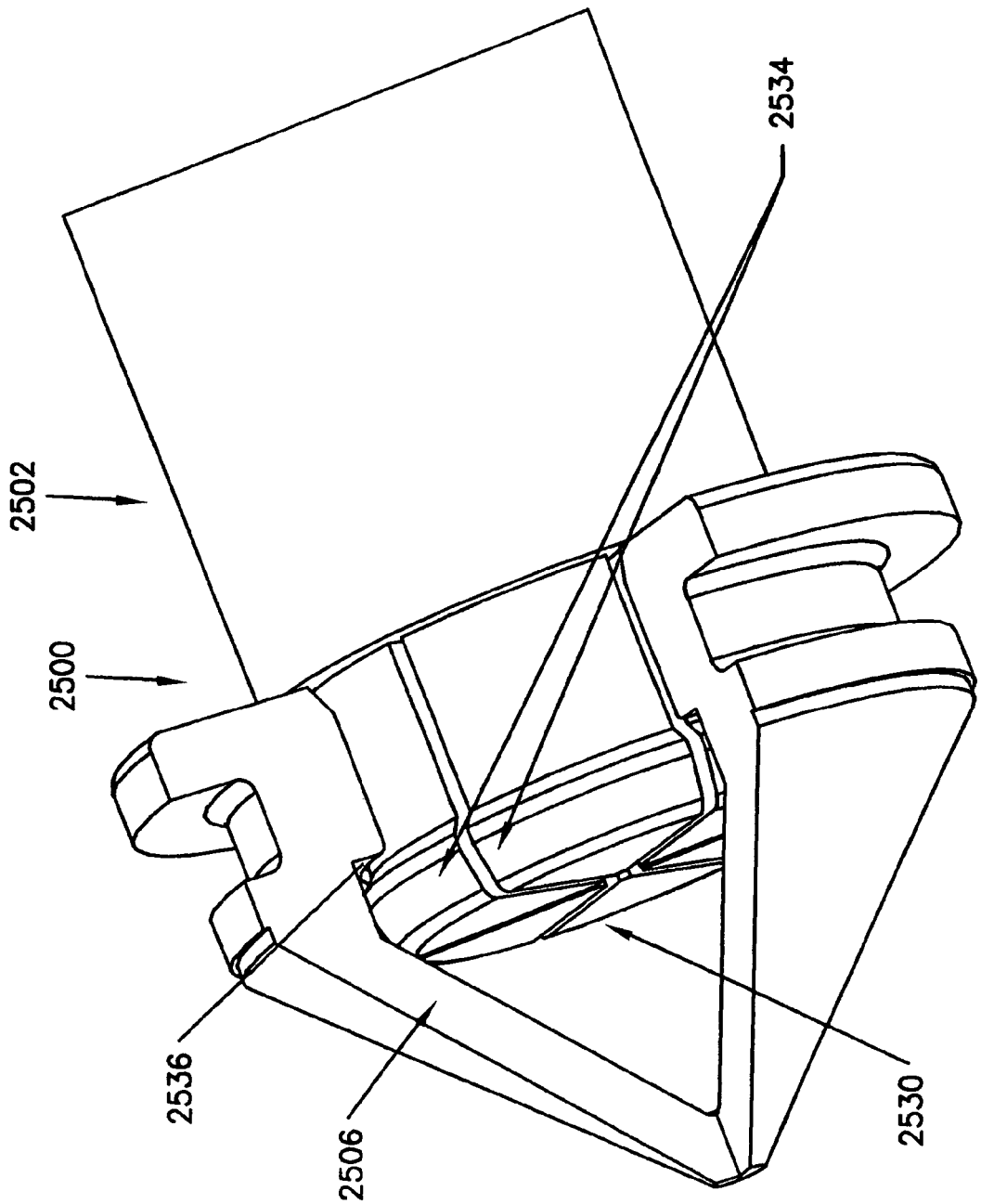

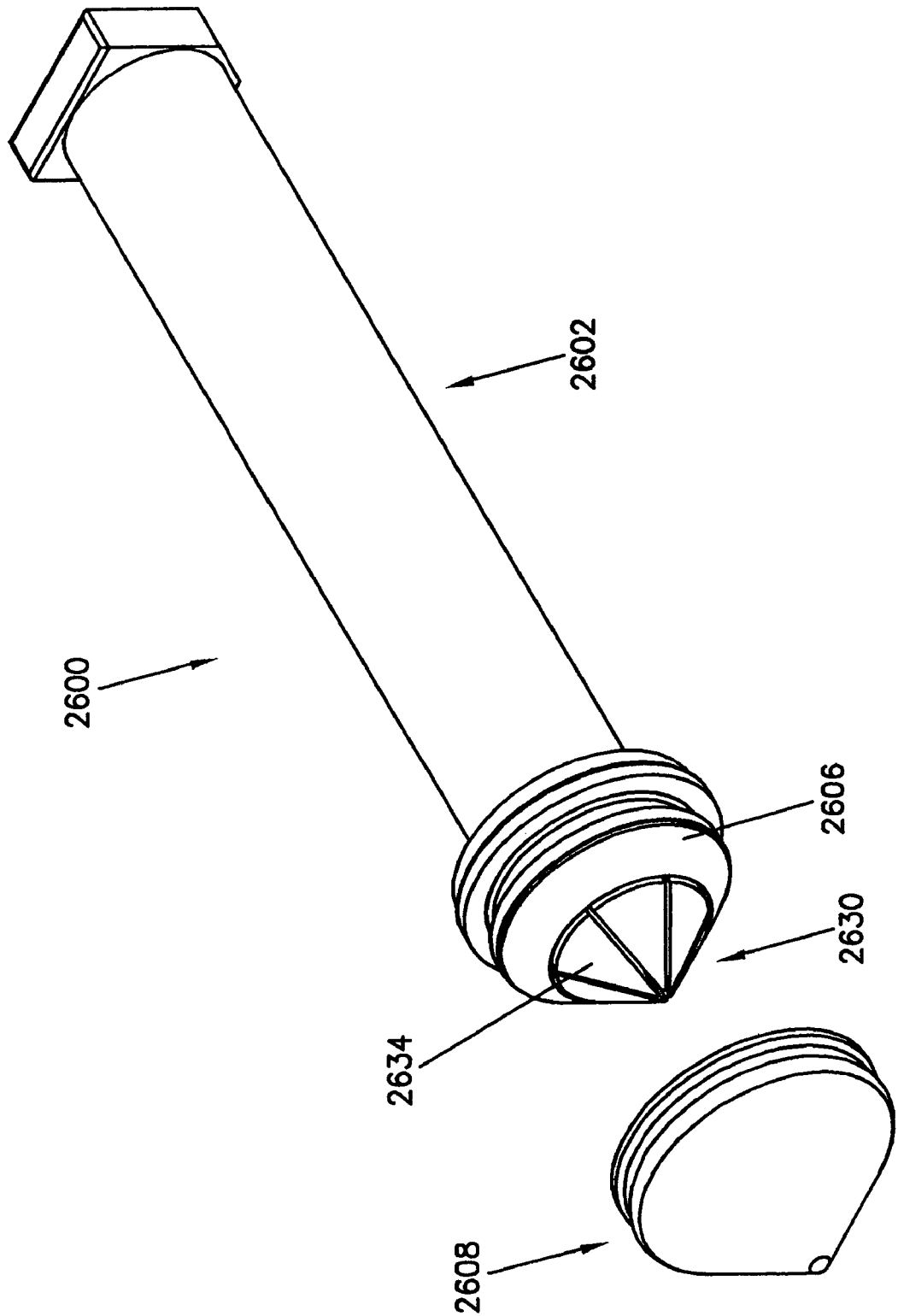

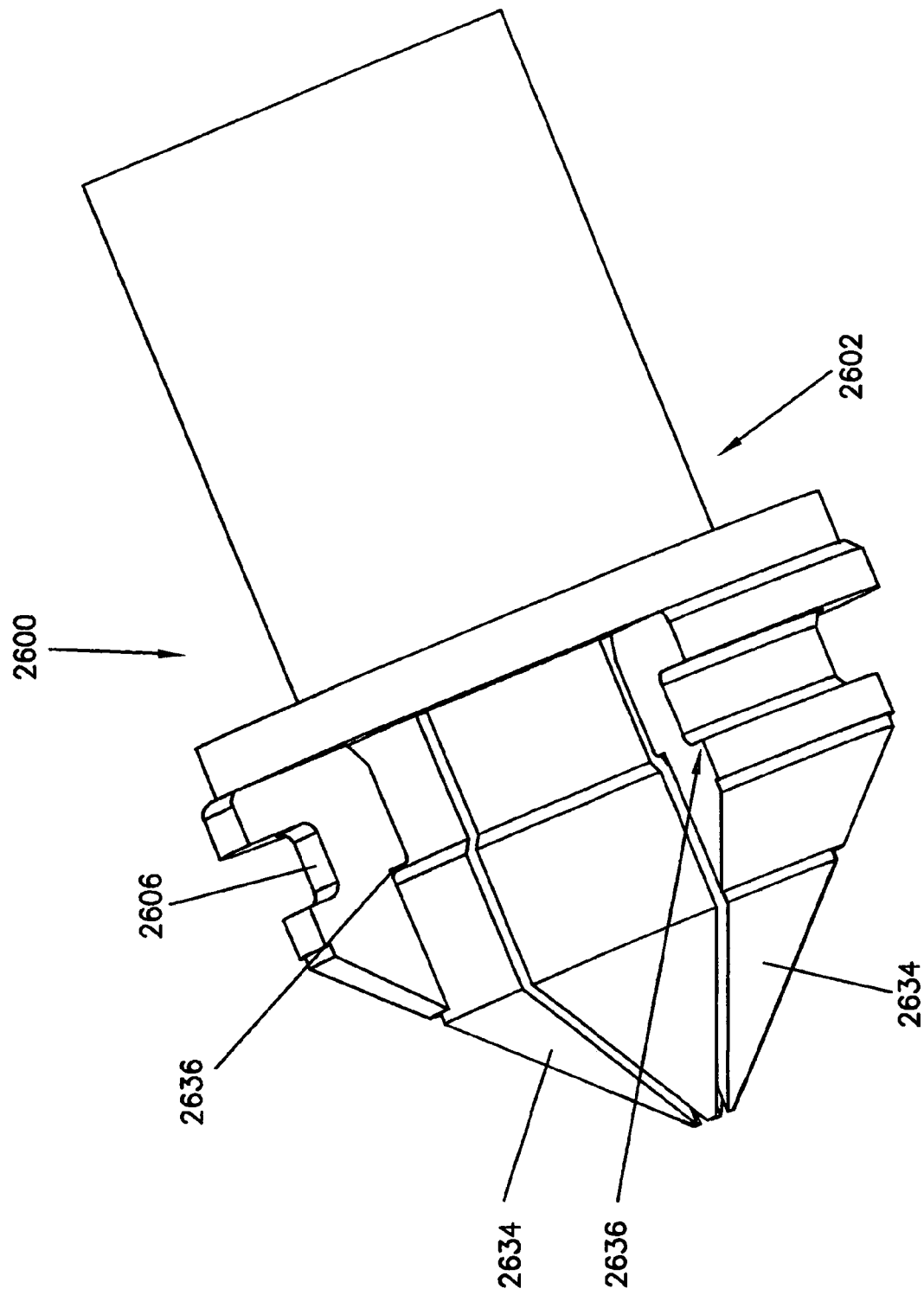

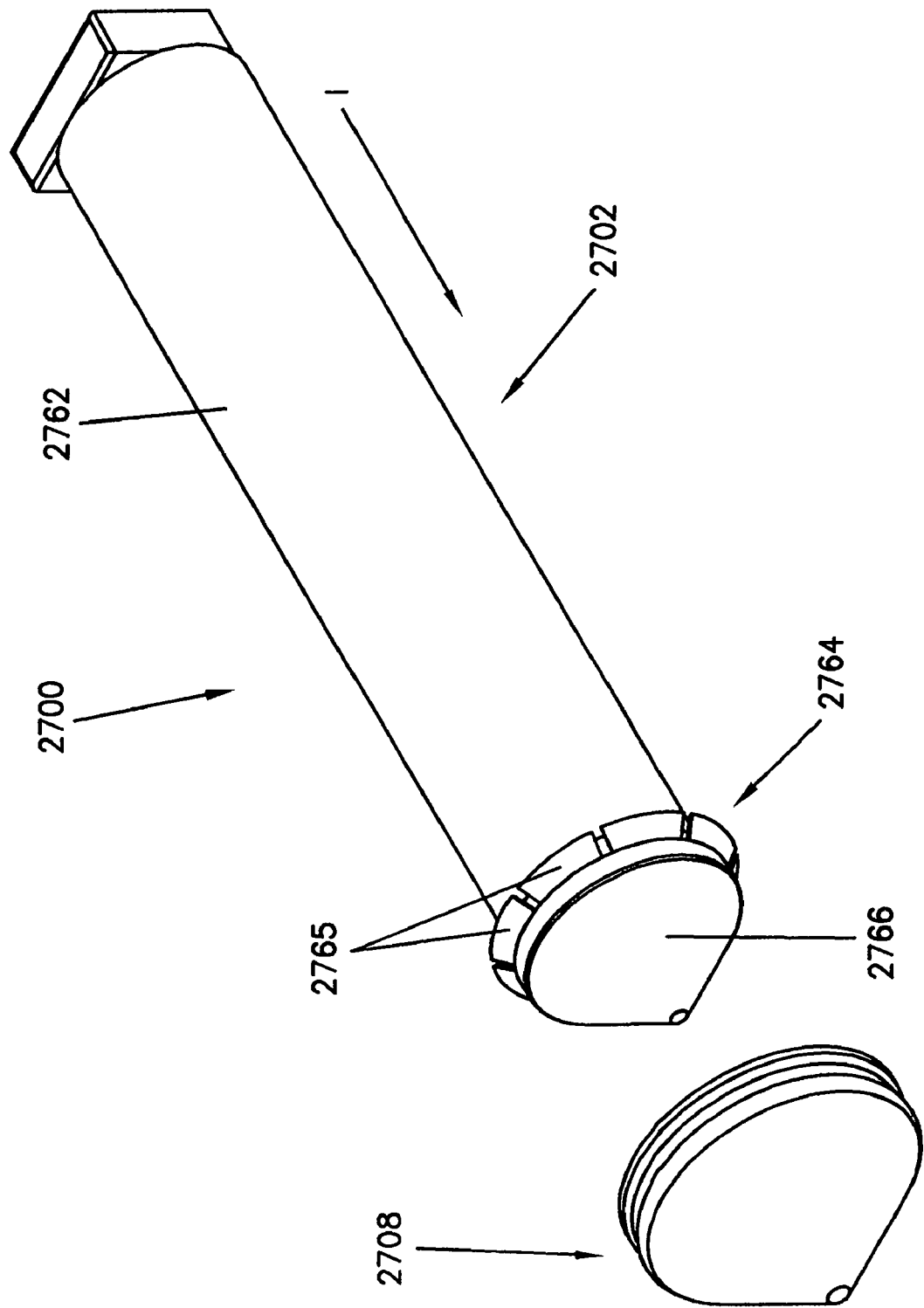

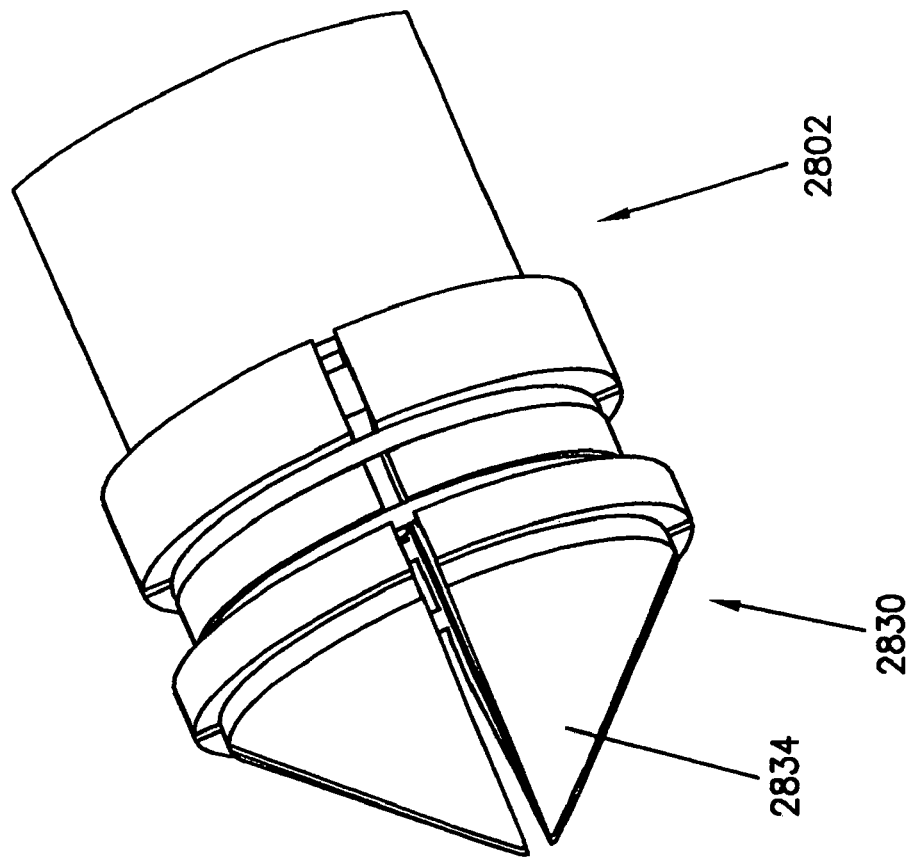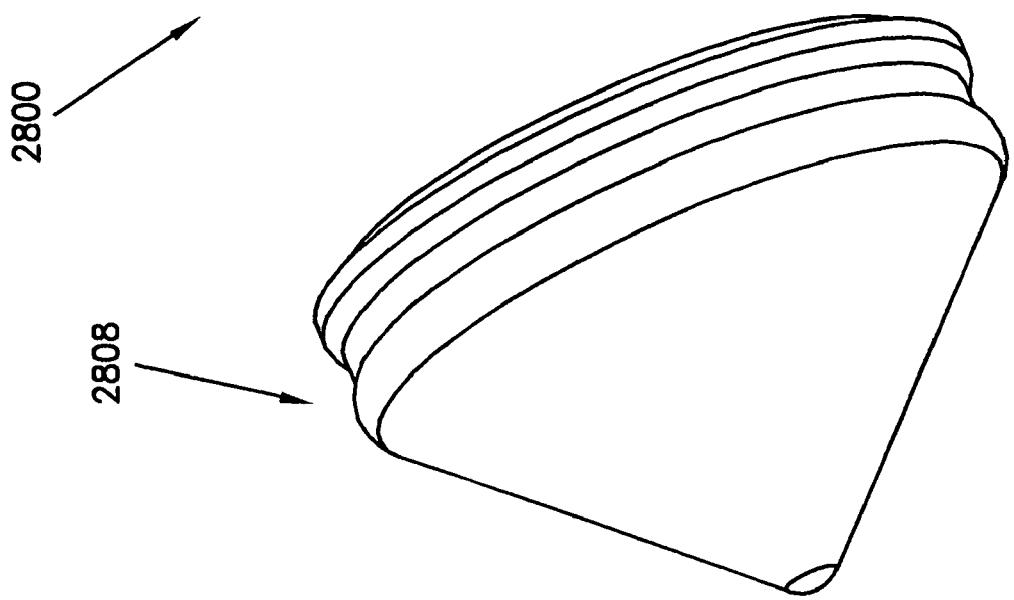
FIG. 53B

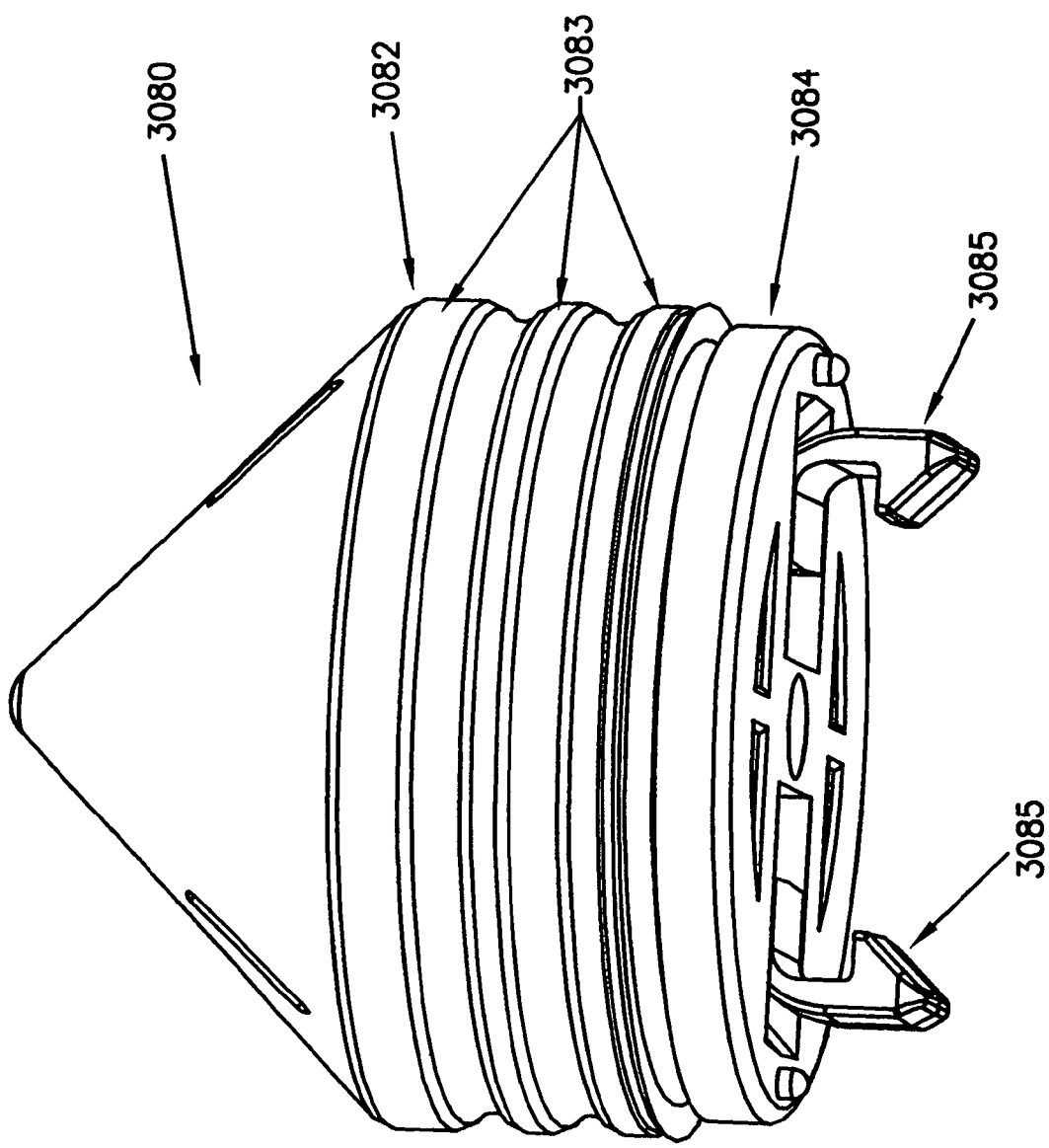

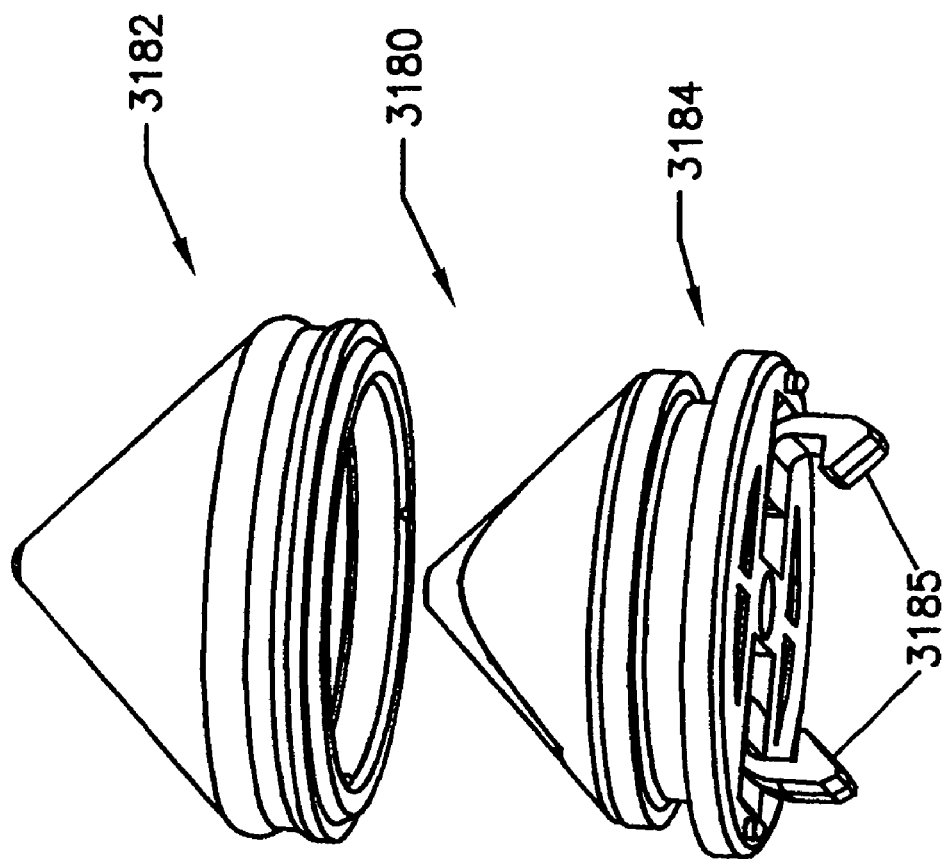

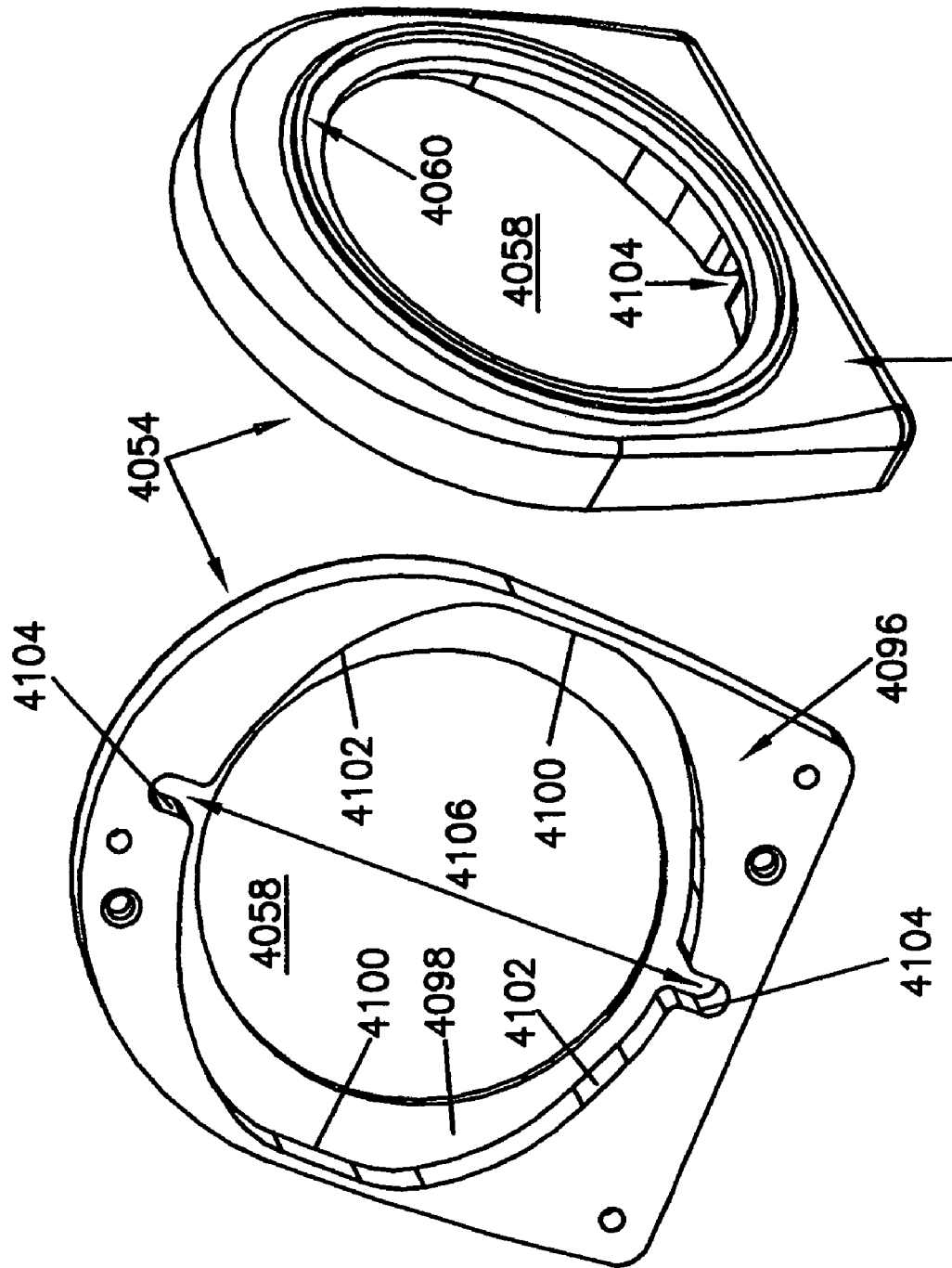

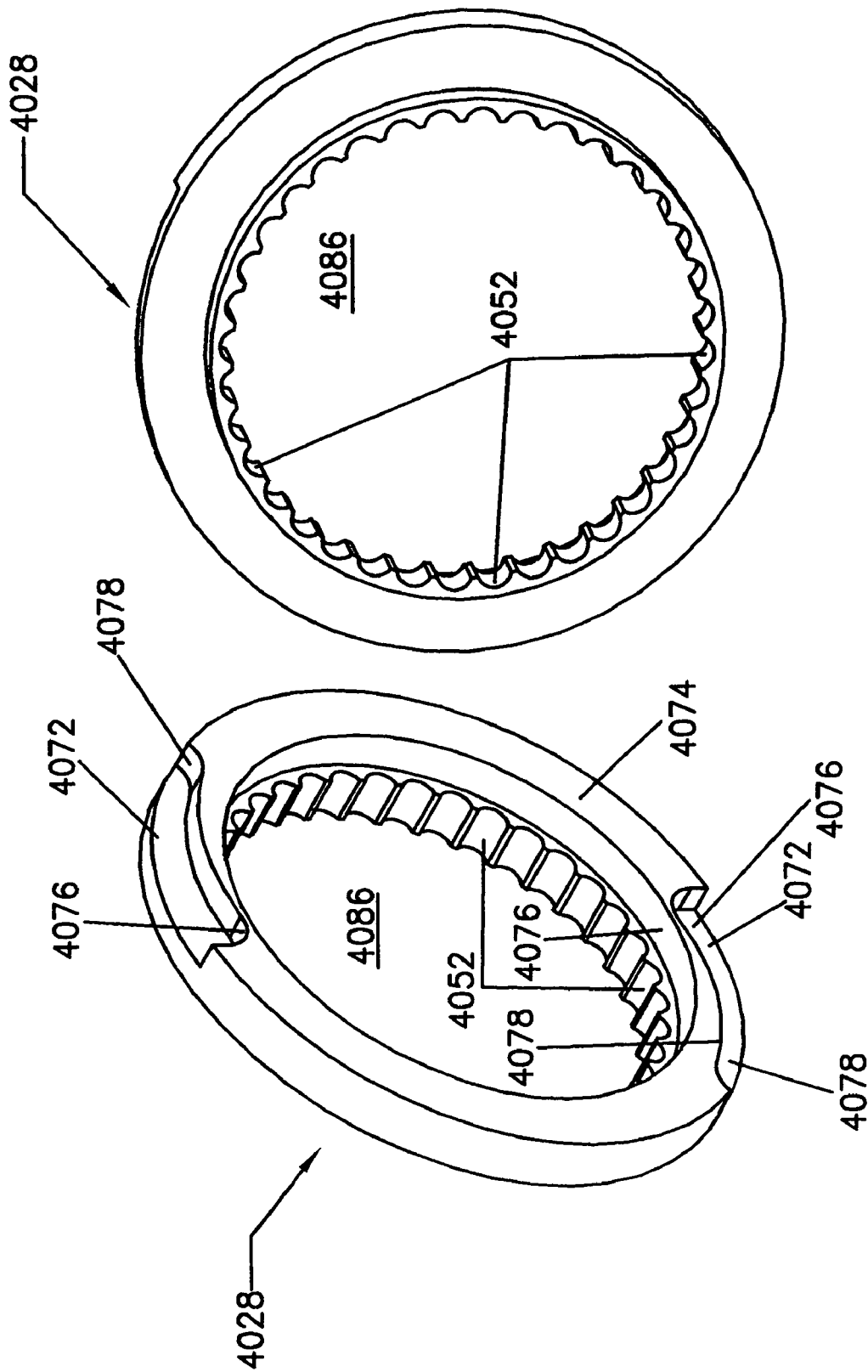

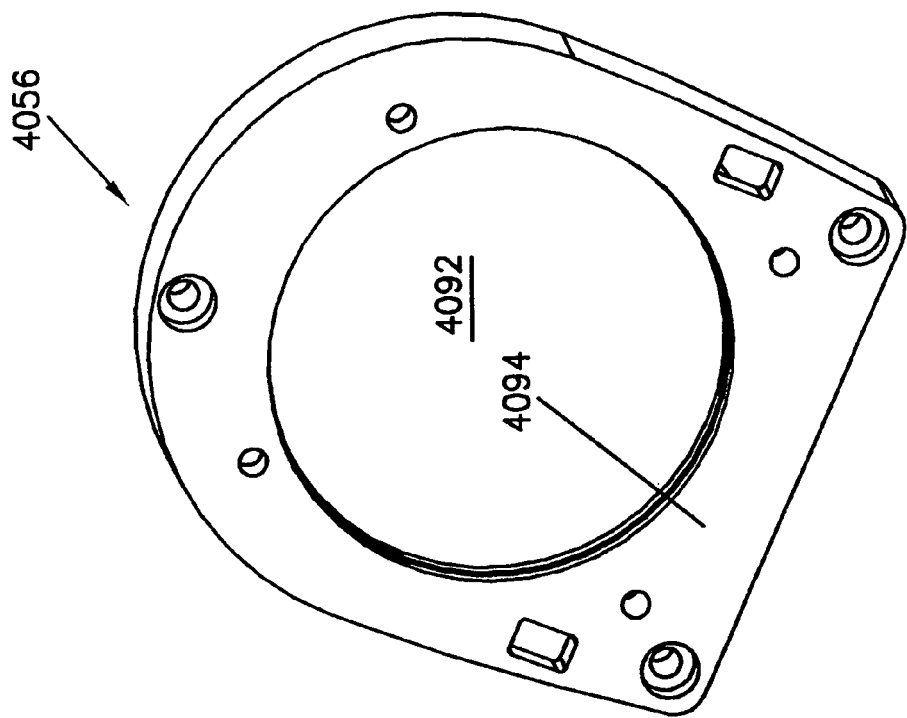
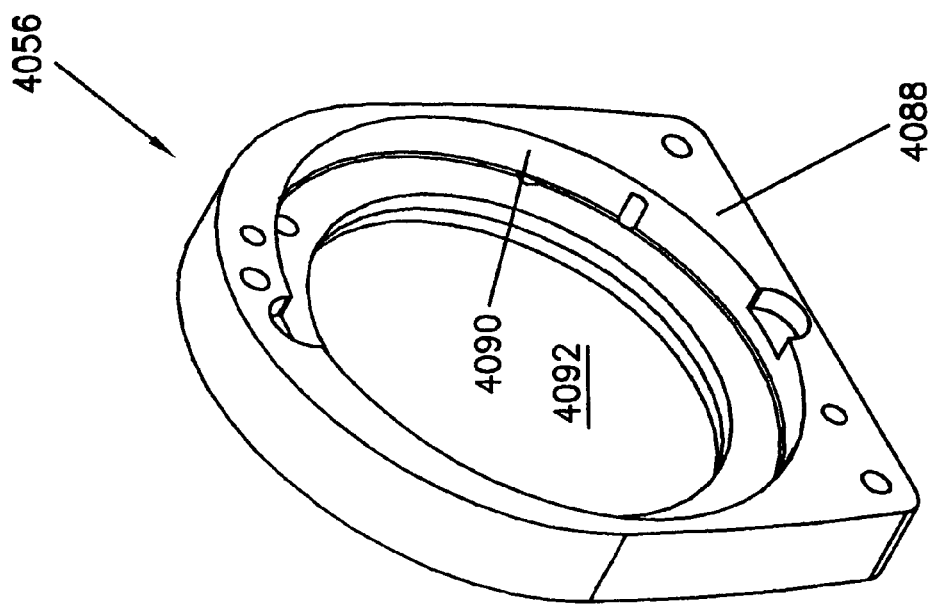

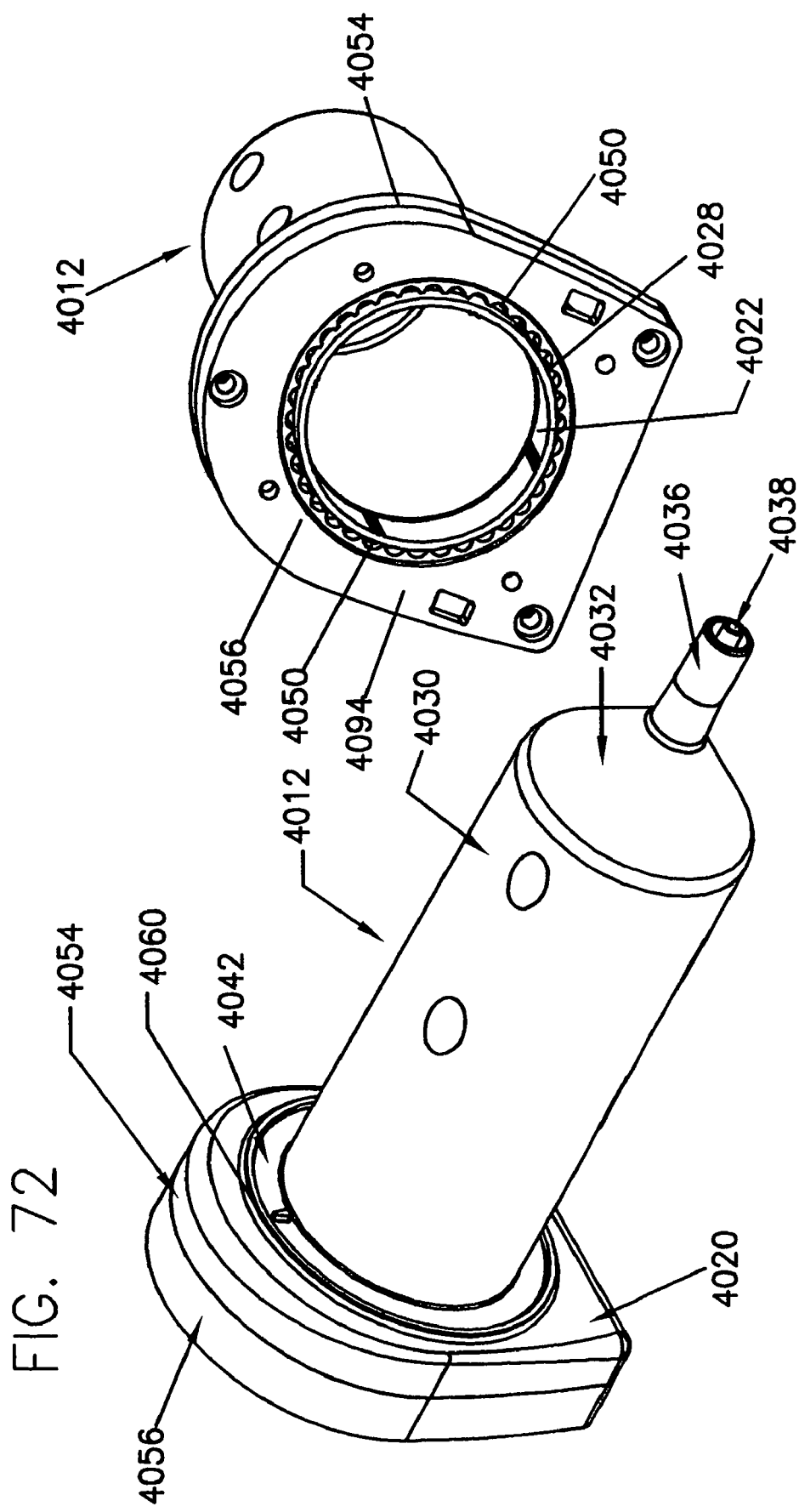

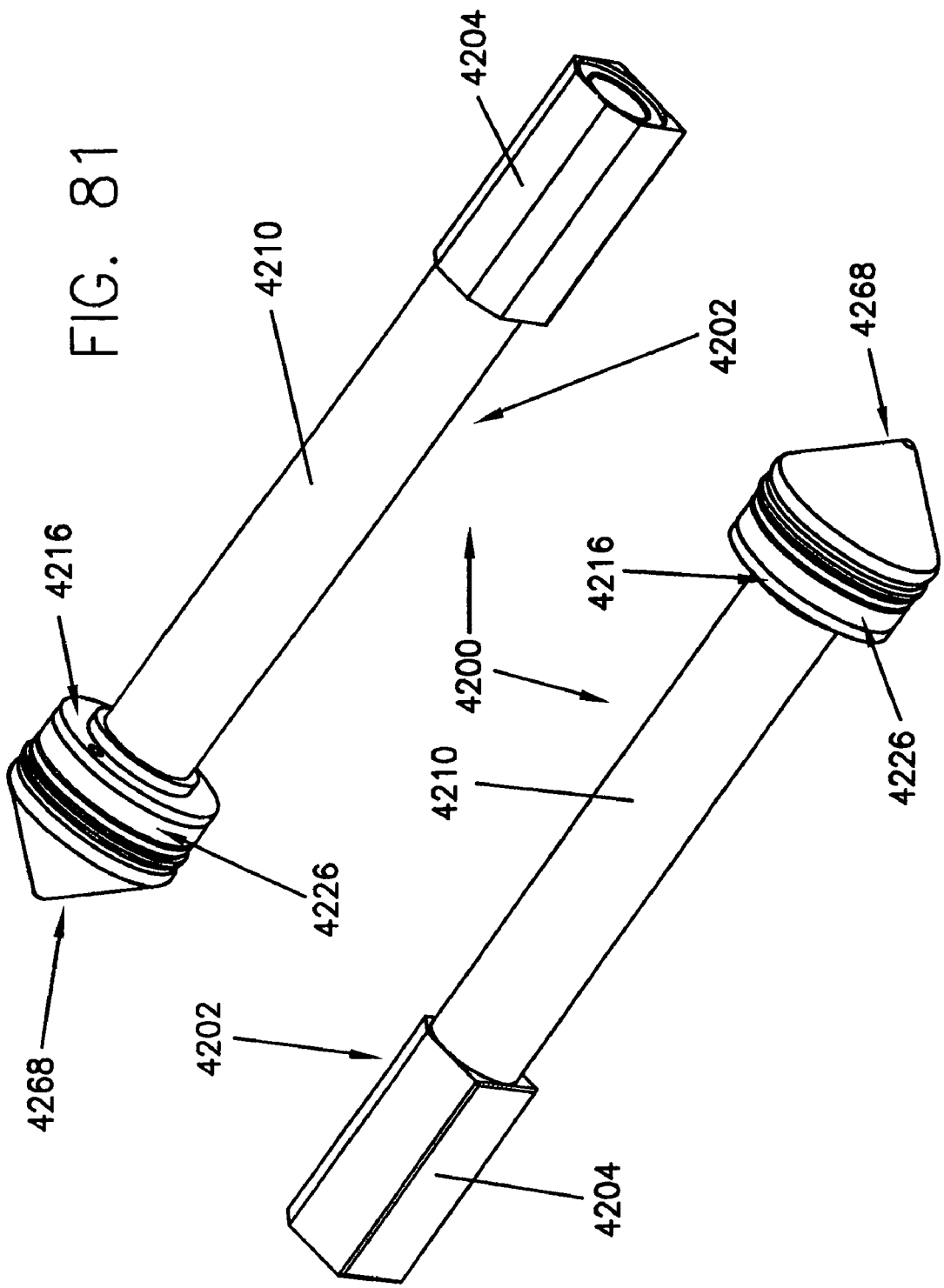

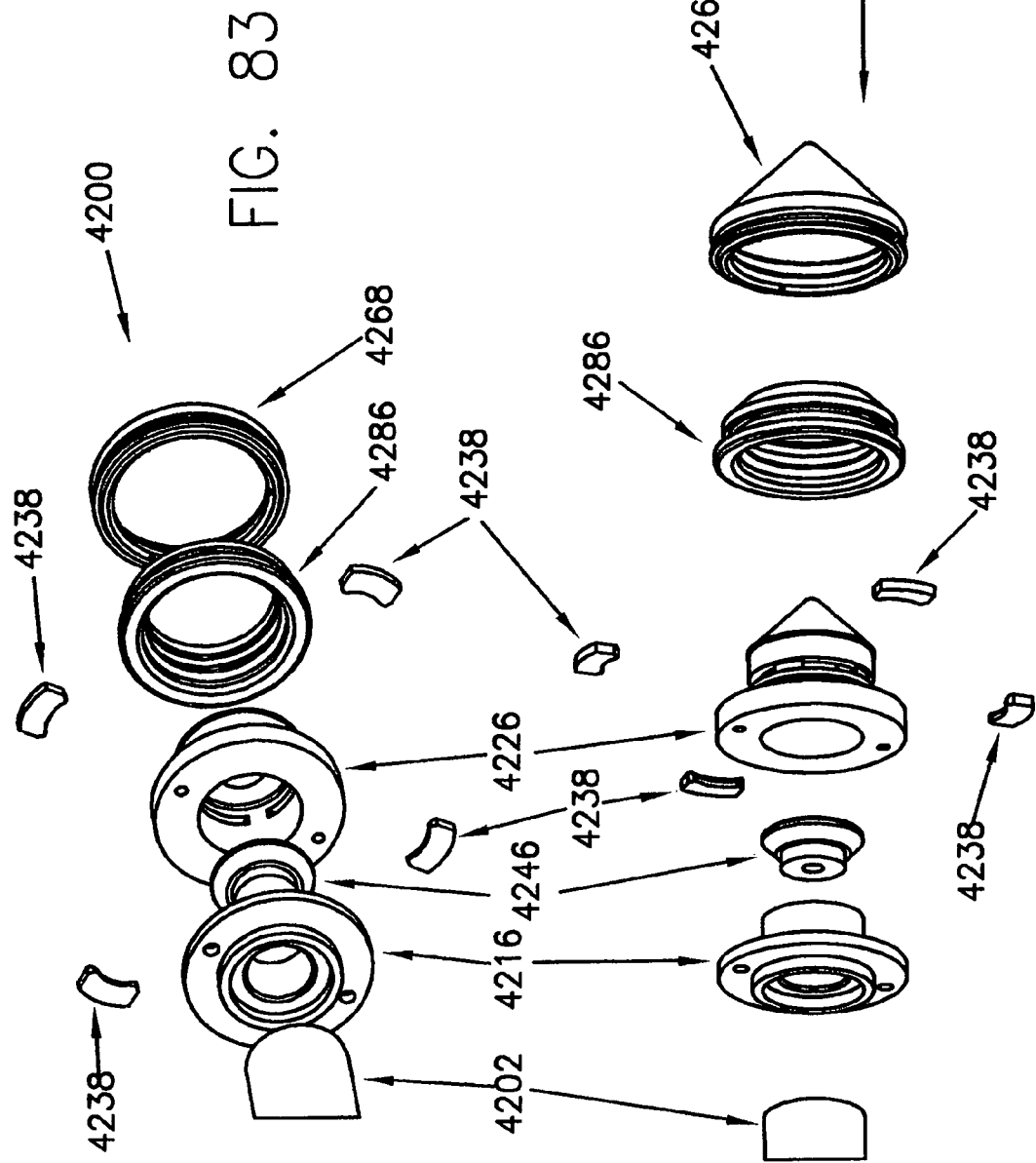

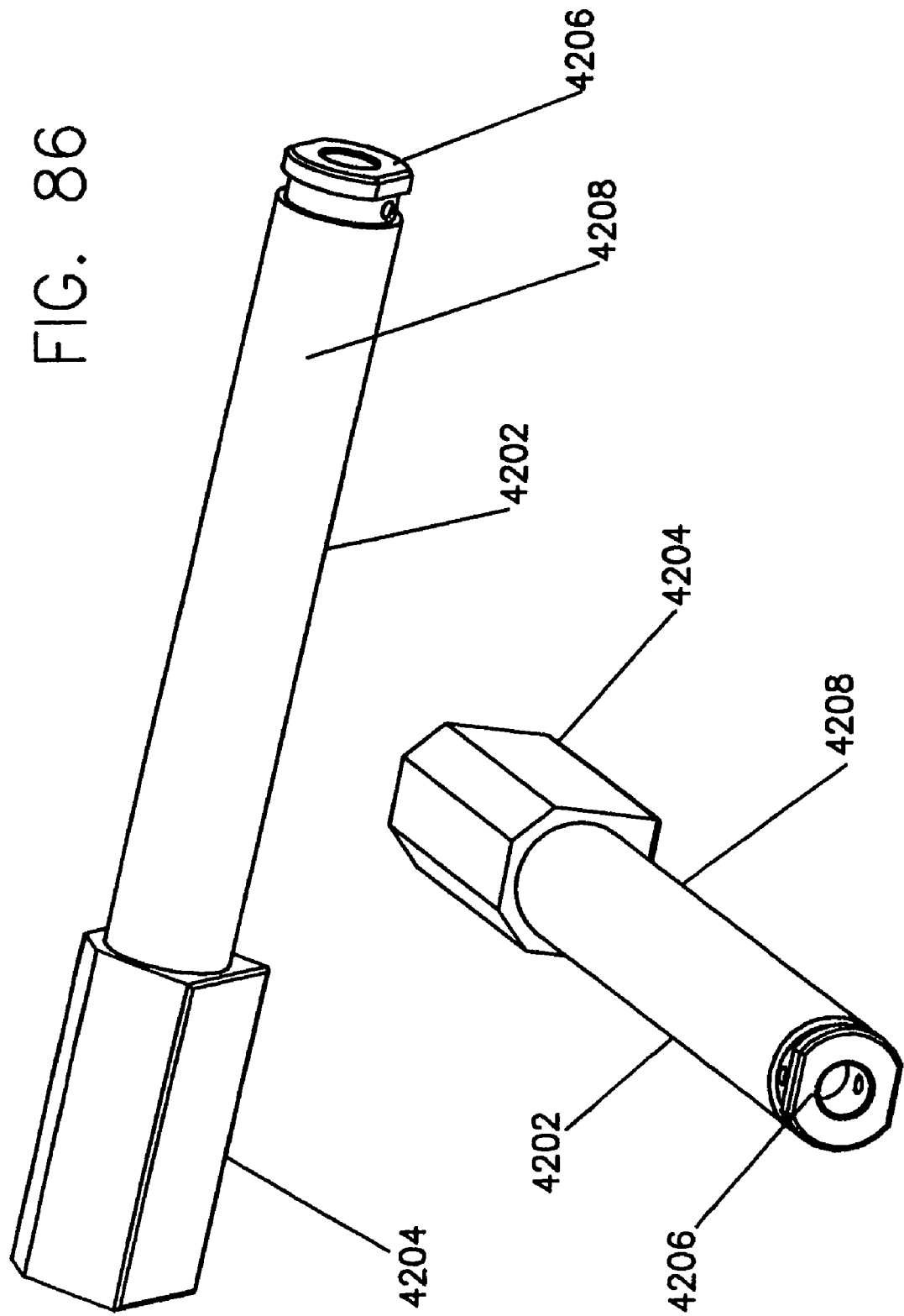

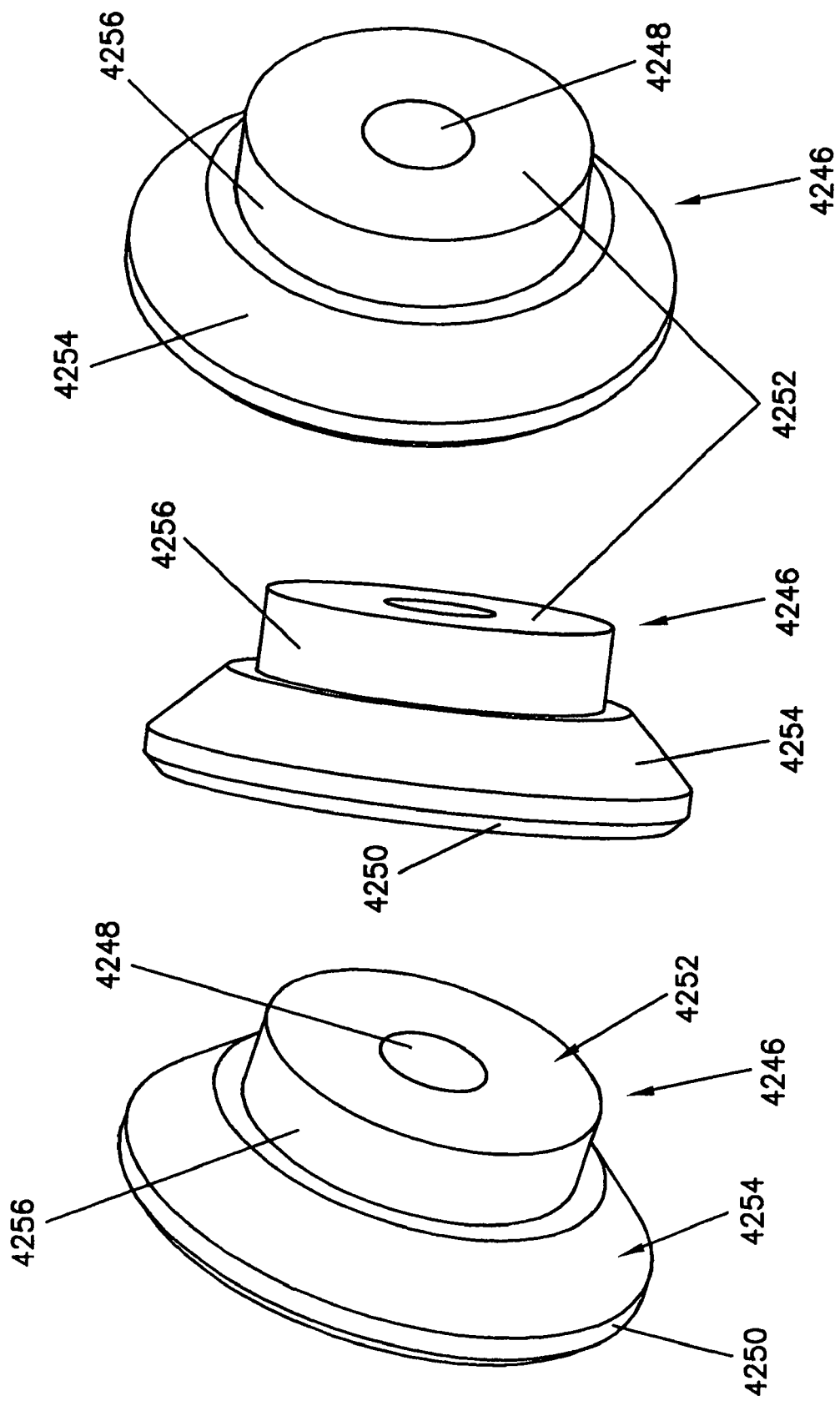

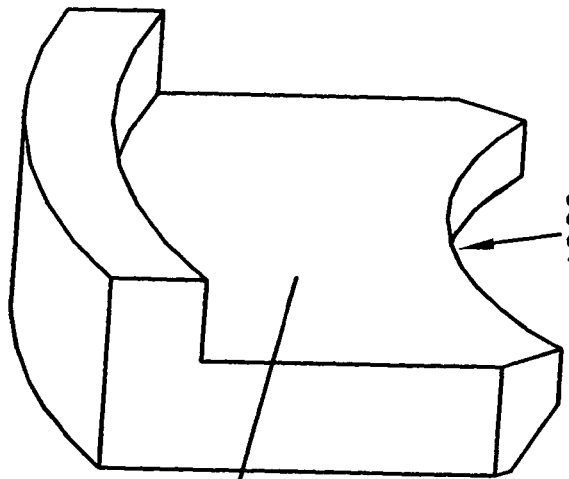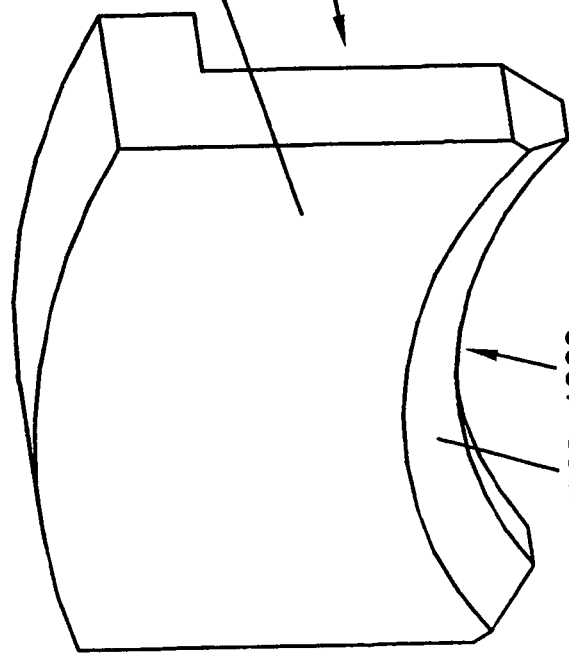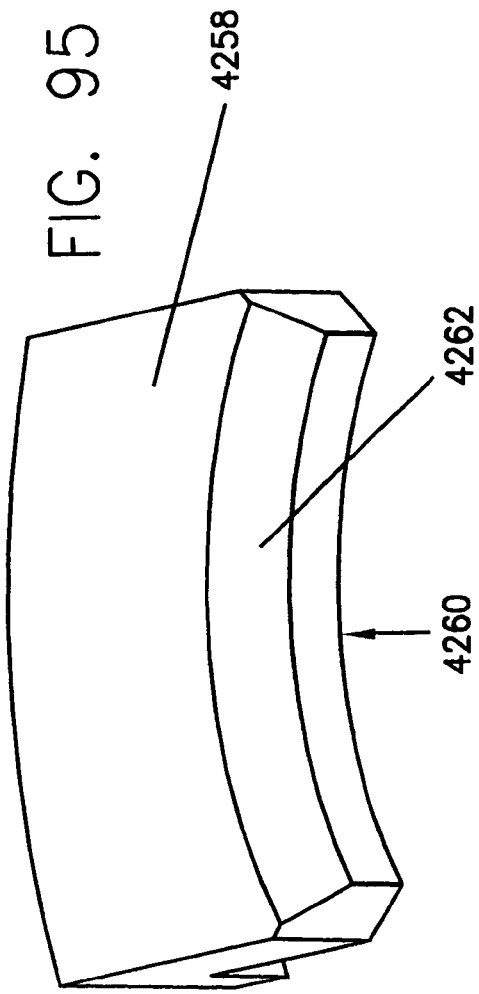

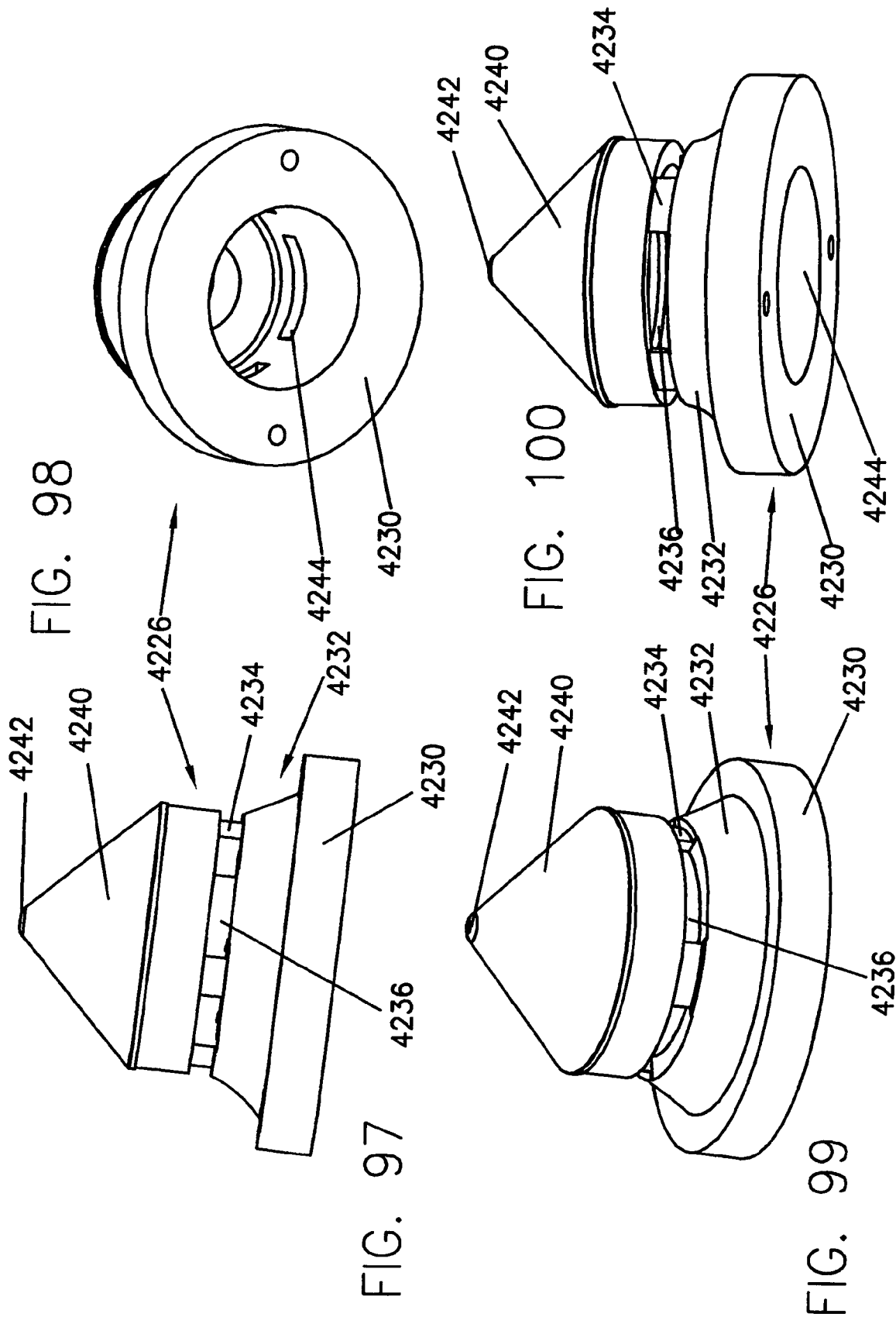

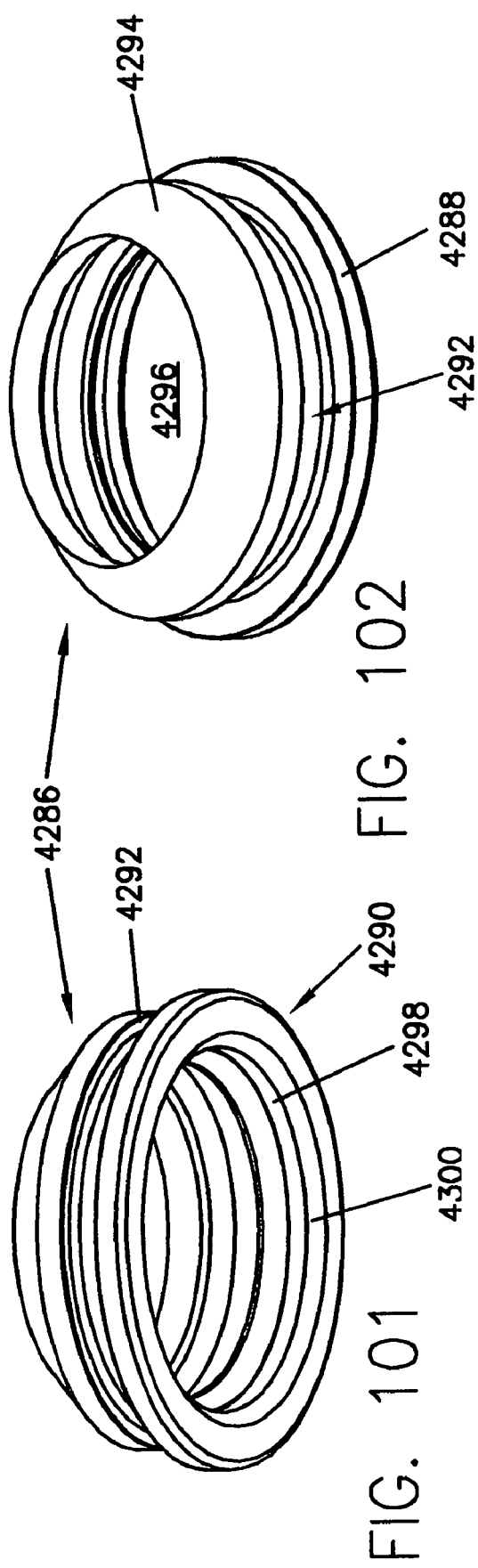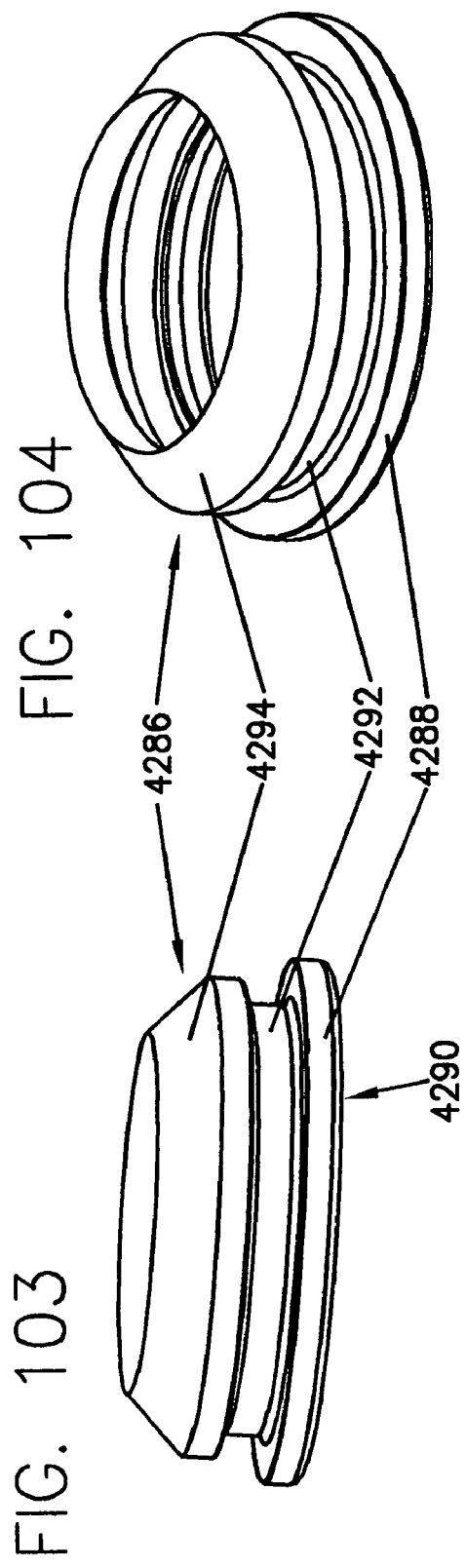

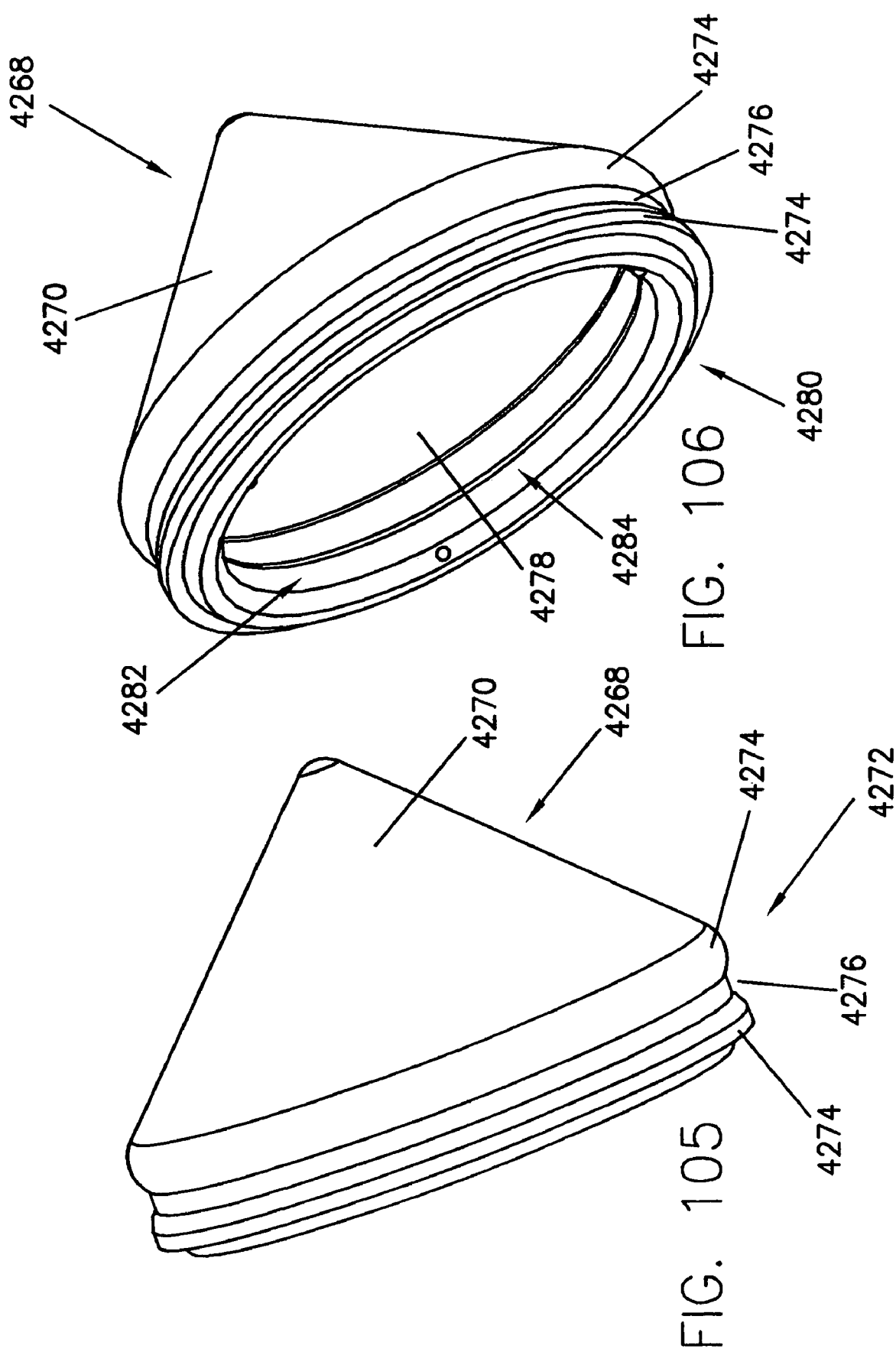

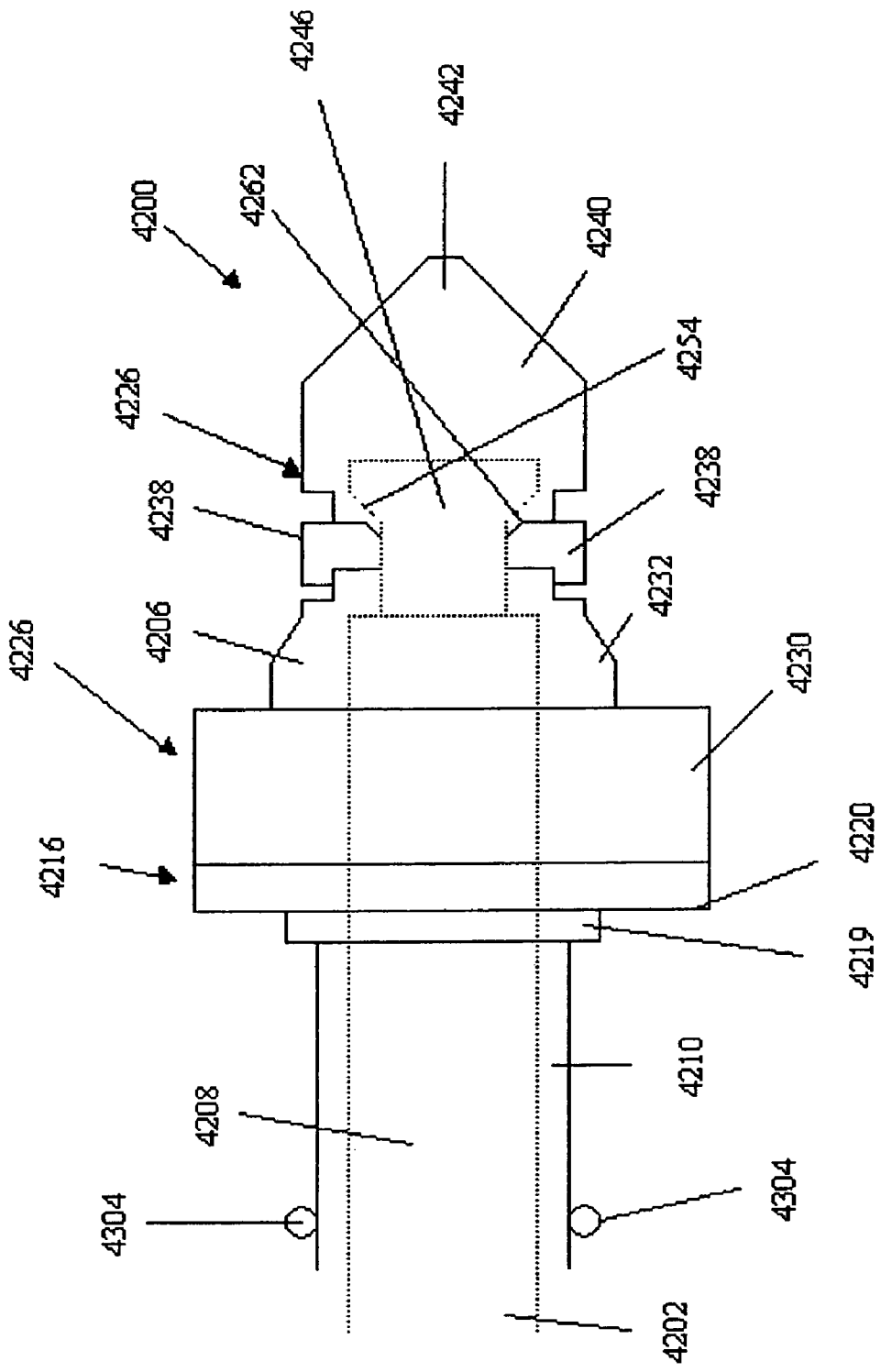

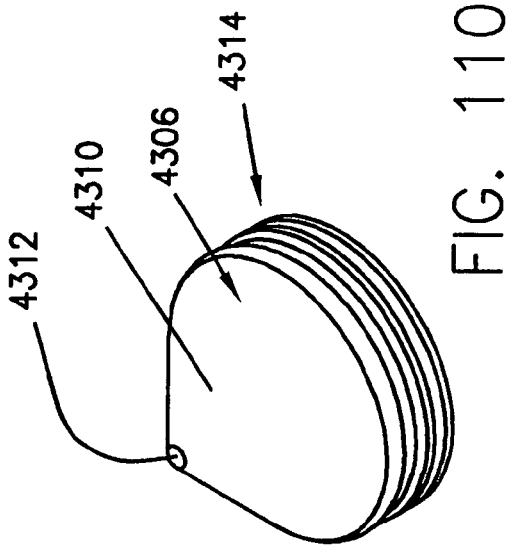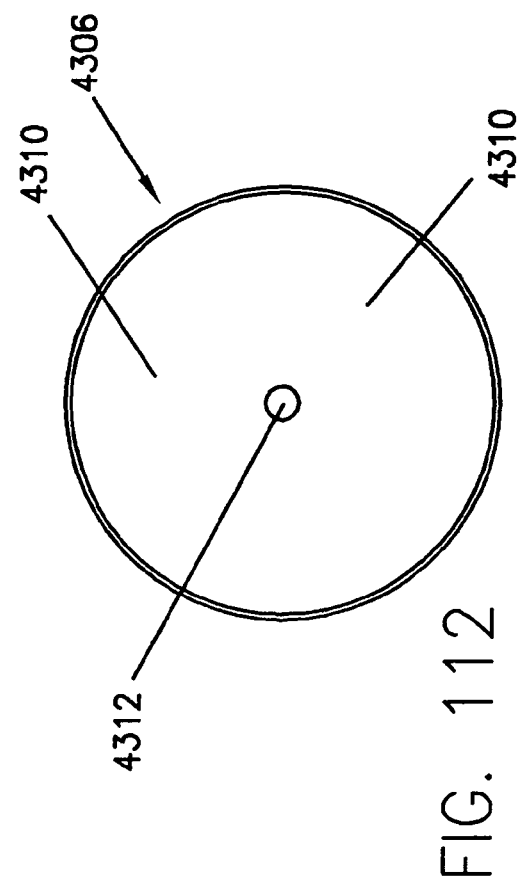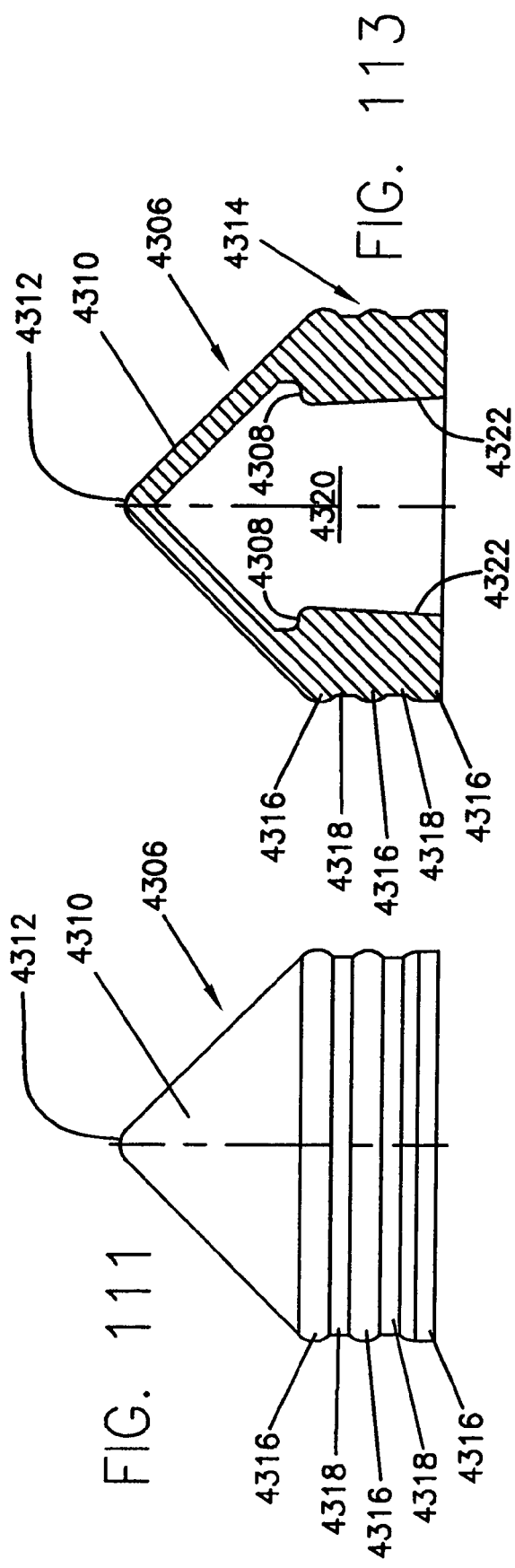

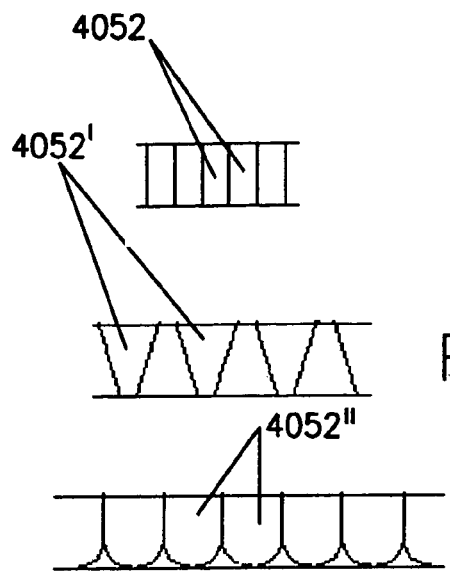
FIG. 118
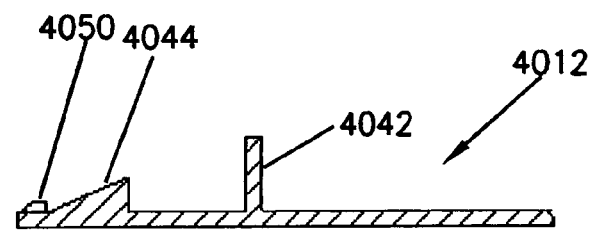
FIG. 116
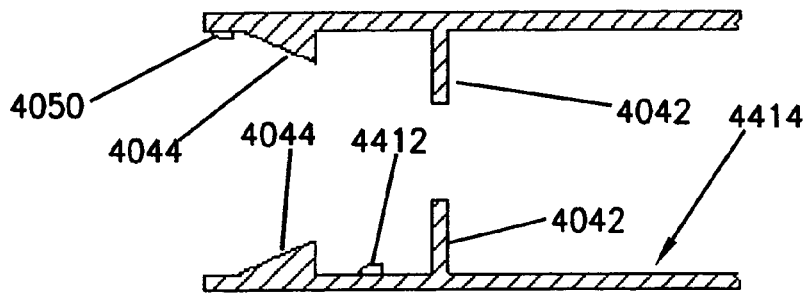
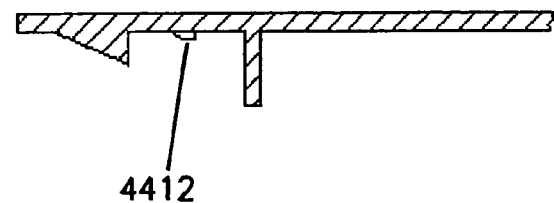
FIG. 117

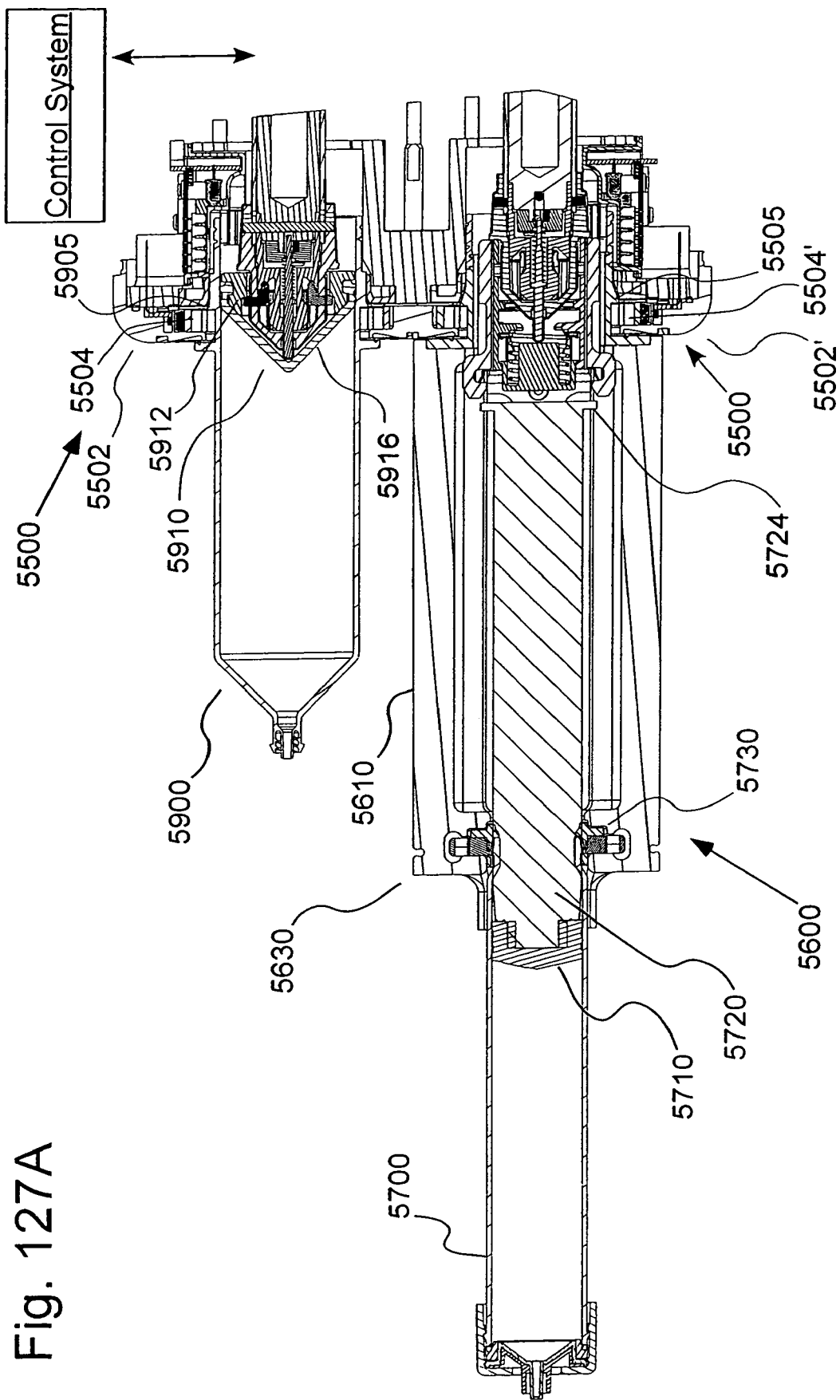

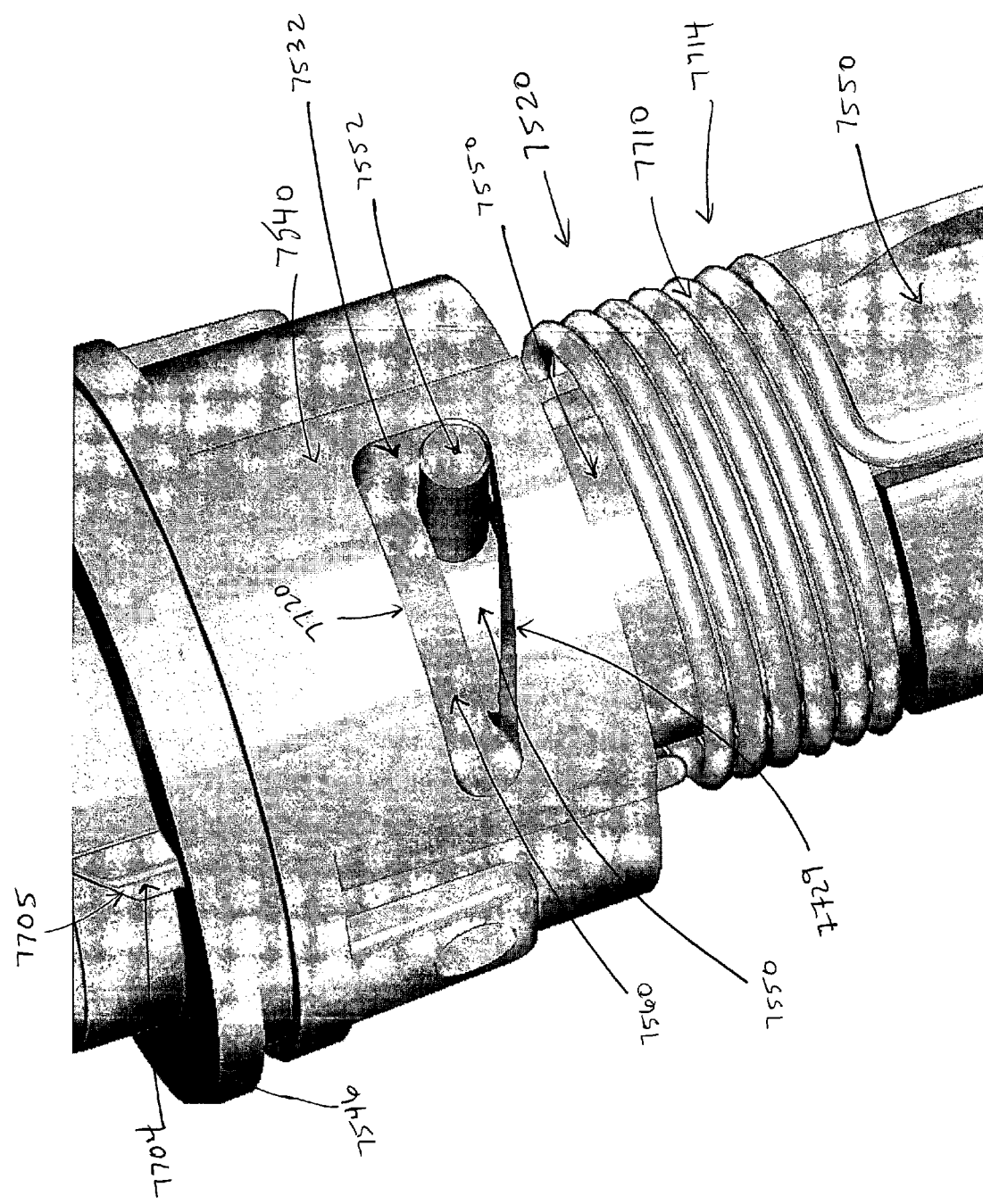

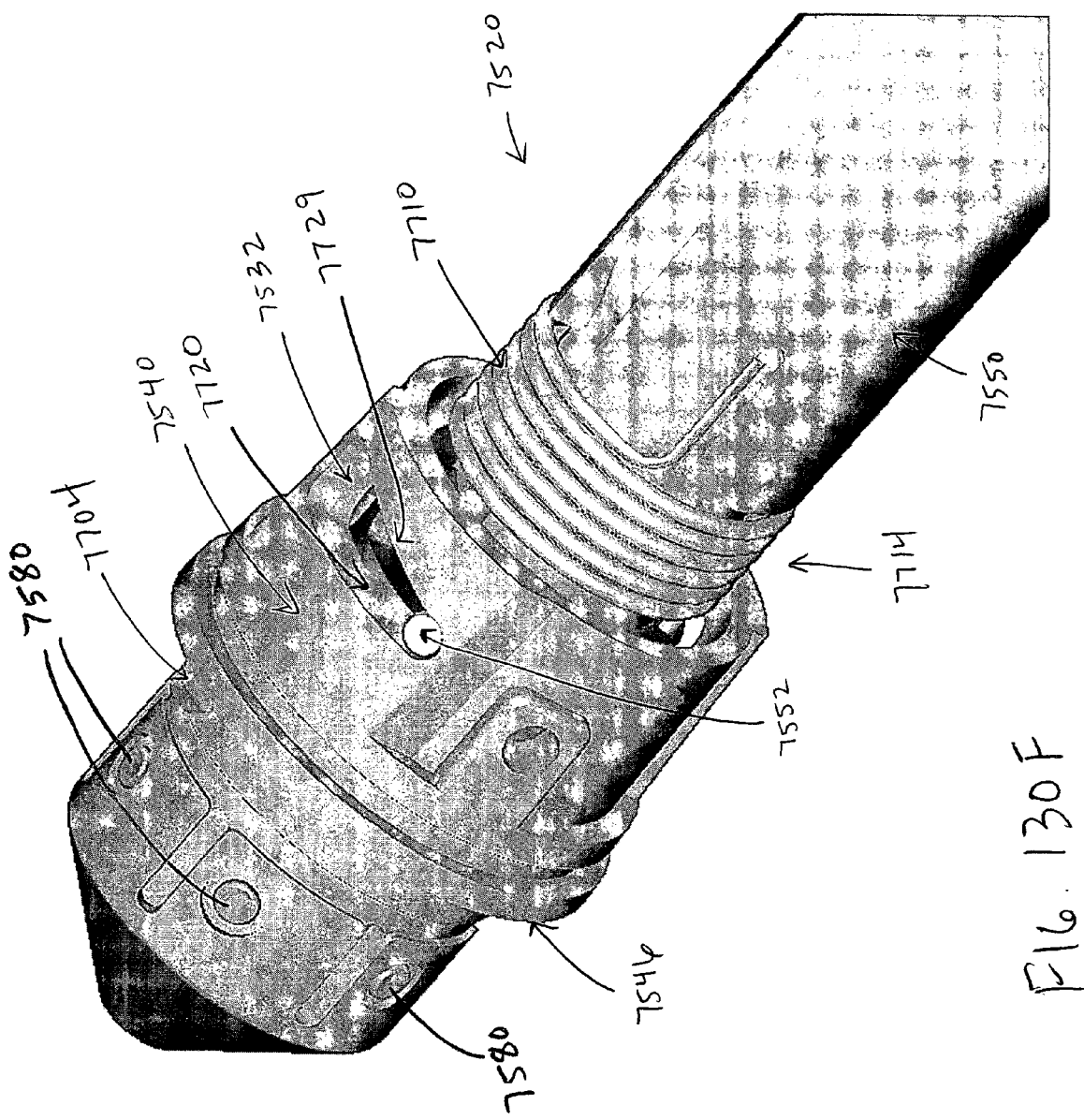

SYRINGE AND SYRINGE PLUNGERS FOR USE WITH MEDICAL INJECTORS

RELATED APPLICATIONS

This application may contain subject matter that is related to that disclosed or claimed in one or more of the following U.S. patents or pending applications: U.S. Pat. No. 6,652,489, filed on Feb. 5, 2001; application Ser. No. 10/159,592, filed on May 30, 2002; application Ser. No. 09/448,835, filed on Nov. 24, 1999; application Ser. No. 10/174,631, filed on Jun. 19, 2002; application Ser. No. 10/619,137, filed on Jul. 14, 2003; application Ser. No. 10/668,643, filed on Sep. 23, 2003; application Ser. No. 10/668,673, filed on Sep. 23, 2003; application Ser. No. 10/669,144, filed on Sep. 23, 2003; application Ser. No. 10/669,148, filed on Sep. 23, 2003; application Ser. No. 10/670,154, filed on Sep. 23, 2003;application Ser. No. 10/380,188, filed on Mar. 10, 2003; application Ser. No. 09/765,498, filed on Jan. 18, 2001; and application Ser. No. 10/606,157, filed on Jun. 25, 2003.

BACKGROUND OF THE INVENTION

This invention relates to medical injectors, and syringes, syringe interfaces, syringe adapters and syringe plungers for use therewith. More particularly, the present invention relates to front-loading medical injectors, and syringes, syringe interfaces, syringe plungers and adapters for use with new or existing medical injectors wherein a syringe of special construction is mountable upon and removable from the injectors by a releasable mechanism.

Medical injectors and syringes for injecting contrast media into a patient for imaging biological structures are known in the art. For example, U.S. Pat. No. 4,677,980, issued to D. M. Reilly et al. on Jul. 7, 1987, and entitled "Angiographic Injector and Angiographic Syringe for Use Therewith," which is assigned to the same Assignee as the subject application, discloses an angiographic injector apparatus. The apparatus is designed for injecting contrast media into the vascular system of an animal, in which syringes are rear-loaded into a pressure jacket of the injector. More specifically, the apparatus comprises a rotatable turret which carries a pair of the pressure jackets and which is rotatable so that when one of the pressure jackets, into which a syringe has been rear-loaded, is in an injection position, the other pressure jacket is in a position in which an associated syringe can be rear-loaded. Subsequently, when injection of contrast media from the first syringe is completed, the turret is rotated to move the first syringe to an unloading-loading position, with the second pressure jacket and the syringe concurrently being moved into the injection position.

In the apparatus disclosed in the '980 patent, a drive member of the angiographic injector can be drivingly connected to, or disconnected from, a plunger of a syringe at any point along the path of travel of the syringe plunger by a releasable mechanism. However, for the releasable mechanism to correctly operate, the syringe plunger must be properly oriented to mate with the injector piston. Further, during loading of the syringe on the injector, the syringe must be correctly aligned within a respective pressure jacket to allow the syringe plunger and the injector piston to connect to and disconnect from each other.

An improved apparatus over the '980 patent apparatus is disclosed in U.S. Pat. No. 5,383,858, issued to D. M. Reilly et al. on Jan. 24, 1995, and entitled "Front-Loading Medical Injector and Syringe for Use Therewith," which is also assigned to the same Assignee as the present application. In the apparatus described in the '858 patent, the syringe is front-loaded onto, in at least one embodiment, a pressure jacket-less injector, overcoming one of the drawbacks of the '980 patent injector apparatus.

The injector described in the '858 patent has a first release mechanism for attaching and releasing the syringe from the injector. In addition, the apparatus includes a second release mechanism that engages and disengages the injector piston from the syringe plunger. Upon rotation of the syringe, the syringe is attached to or released from the injector and, simultaneously, the plunger is attached to or released from the piston. The structure disclosed requires that the syringe be installed on the injector in a specific orientation so that the syringe can releasably engage the injector and, simultaneously, the plunger can releasably engage the piston. In addition, as with the syringe disclosed in the '980 patent, during assembly the syringe plunger must be correctly oriented within the syringe.

Another injector apparatus is disclosed in U.S. Pat. No. 5,300,031, issued to C. Neer et al. on Apr. 5, 1994, and entitled "Apparatus for Injecting Fluid into Animals and Disposable Front Loadable Syringe Therefor." The '031 patent discloses various embodiments of a pressure-jacketed injector wherein a syringe is loaded into and removed from an injector pressure jacket through an opening provided in the front end of the pressure jacket. To retain the syringe within the pressure jacket, for example, during an injection operation, the front end of the syringe is locked to the front end of the pressure jacket. To correctly connect the syringe to the pressure jacket, the syringe may only be inserted into the pressure jacket in one orientation.

In each example discussed above, the syringe must be connected to the injector in a specific orientation to assure proper syringe mounting. Proper alignment is required to assure that the syringe may be operated properly during a medical imaging procedure. The required orientation, however, hinders rapid attachment and replacement of the syringe. The required orientation may also increase the manufacturing assembly cost and complexity of the syringe.

Accordingly, while the above injector and syringe apparatuses have proven effective, a need has arisen for a simpler front-loading medical injector. More specifically, to facilitate further the loading operation, a need has arisen for a syringe that can be easily connected to the injector without regard for the specific orientation of the syringe and/or syringe plunger. In addition, to simplify assembly of the syringe components, a need has arisen for a syringe with a plunger that does not need to be oriented in a specific relation to the barrel or base of the syringe. Furthermore, to minimize the time required to prepare an injector for an injection procedure, a need has arisen for injectors providing automated features and/or improved control features.

SUMMARY OF THE INVENTION

The present invention provides medical injectors, syringe interfaces, syringe adapters, syringe plungers and syringes for use therewith which address the needs that have arisen for a simpler injector and syringe system. Specifically, the present invention provides, in one aspect, a syringe interface and a mating syringe that cooperate to allow the syringe to be easily, readily and securely fastened to a medical injector. The syringe need not be oriented in any particular manner before being connected to the injector. In addition, the plunger need not be oriented in any particular manner with respect to the barrel of the syringe. The syringe and plunger both are provided with release mechanisms so that the syringe can be quickly installed on and unloaded from the injector and replaced with a new syringe.

To accomplish these objectives, the present invention provides a syringe for engaging an injector. In a preferred embodiment, the syringe includes a body and a plunger movably disposed within the body. The plunger includes a wall having an inner surface and an outer surface, and one or more inwardly projecting flanges disposed on the inner surface of the wall. Further, a fluid injection system includes an injector and a syringe. The injector includes a housing, and a drive member at least partially disposed within the housing. The drive member includes at least one retaining member and one or more outwardly extending flange members. The syringe includes a body, and a plunger movably disposed within the body. The plunger includes a wall having an inner surface defining a retaining shoulder and one or more inwardly projecting flanges disposed on the inner surface of the wall. Preferably, the at least one retaining member on the drive member of the injector is adapted to engage the retaining shoulder on the plunger wall to enable the drive member to retract the plunger with the body of the syringe. Further, the one or more inwardly projecting flanges on the plunger wall are adapted to engage the one or more outwardly extending flange members on the drive member when the syringe body is rotated about its longitudinal axis. The one or more outwardly extending flange members are operable to cause the at least one retaining member on the drive member to disengage the retaining shoulder on the plunger wall upon rotation of the syringe body.

In another preferred embodiment, the syringe includes a syringe body having a syringe forward end adapted to dispense fluid and a syringe rearward end adapted to engage with the injector. A plunger or plunger cover is axially reciprocable within the syringe body. A flange member is disposed at the syringe rearward end. The flange is adapted to engage a flexible ring within a connector mechanism on the injector housing, or on a syringe interface or an adapter connected to the injector housing. The flange and flex ring combination provide for engagement of the syringe to and release of the syringe from the injector. Further, the syringe includes one or more members for engaging the flexible ring to permit disengagement of the syringe therefrom.

In an alternate embodiment, the flange member may be disposed at the syringe forward end and the flexible ring may be disposed on a forward end of a pressure jacket connected to an injector.

In another embodiment, the syringe includes a syringe body having a syringe forward end adapted to dispense fluid and a syringe rearward end adapted to engage with the injector. A plunger or plunger cover is axially reciprocable within the syringe body. At least one tab or flange member (which may be resilient) is disposed at the syringe rearward end. The at least one tab or flange is adapted to engage a wall portion on an injector, or a syringe interface or an adapter connected to the injector, when the syringe engages with the injector. The at least one tab or flange provides for engagement of the syringe to and release of the syringe from the injector.

In still another embodiment, the syringe includes a syringe body having a syringe forward end adapted to dispense fluid and a syringe rearward end adapted to engage with the injector. A plunger is axially reciprocable within the syringe body. At least one resilient tab is disposed at the syringe rearward end. The at least one resilient tab is adapted to engage a wall portion on the injector, or a syringe interface or an adapter connected to the injector, when the syringe engages with the injector. The at least one tab provides for engagement of the syringe to and release of the syringe from the injector.

In an alternate embodiment, the syringe includes at least two resilient tabs adapted to engage the wall portion of the injector when the syringe engages the injector. In still another embodiment, the syringe includes more than two tabs that are arranged around its base so that the syringe securely engages the injector.

The present invention further provides an injector system combining a syringe and an injector. The syringes have the same general constructions as described above. The injector includes an interface adapted to receive the rearward end of the syringe. In a preferred embodiment, the interface of the injector includes a flexible ring for engaging a flange member disposed on the syringe. In an alternate embodiment, the flexible ring may be disposed on a forward end of a pressure jacket connected to the injector, and the flange member may be disposed on the forward end of the syringe to engage the flexible ring.

In another embodiment, the injector includes a forward portion having a first diameter adapted to receive the syringe rearward end. The injector interface also includes a rearward portion having a second diameter, larger than the first diameter, and a ledge disposed between the forward portion and the rearward portion, joining the forward portion and the rearward portion together. The at least one tab on the syringe is adapted to resiliently engage the ledge when the syringe is engaged with the injector. The interface of the injector further includes a collar, reciprocable within the rearward portion adjacent a wall therein, adapted to urge the at least one tab inwardly to disengage the at least one tab from the ledge, thereby enabling removal of the syringe from the injector.

The present invention further provides an injector piston, a syringe plunger assembly and a combined piston/plunger assembly. In a preferred embodiment, the syringe plunger assembly includes a plunger cover and an associated plunger cover support ring disposed within the syringe. In an alternate embodiment, the syringe plunger assembly includes only a plunger cover disposed within the syringe. The injector piston is preferably shaped to complement the shape of the plunger cover. In addition, the injector piston is preferably adapted to push the syringe plunger cover during forward axial movement, without an actual connection being made therebetween. During retraction of the plunger, however, the injector piston is adapter to connectively engage the plunger or plunger cover.

In one embodiment, the piston/plunger assembly includes a piston associated with an injector, a piston sleeve surrounding the piston, a collar connected to one end of the piston sleeve, the collar defining an opening through which the piston extends, a plunger cap connected to the collar, the plunger cap defining an interior space, a gripper extender disposed on an end of the piston within the interior space of the plunger cap, a plurality of slots through a side of the plunger cap, a plurality of grippers disposed through the slots and being engageable with the gripper extender, and a biasing member in contact with the piston sleeve. Upon movement of the piston in a direction, the biasing member biases movement of the piston sleeve to restrict movement in the same direction to cause the gripper extender to push the plurality of grippers through the slots in the plunger cap for engagement with a plunger or rubber cover within a syringe.

In other embodiments, the plunger and piston may be adapted to connect together electromechanically or electromagnetically.

Further in accordance with the embodiments set forth above, the present invention also provides an adapter for receiving a syringe. The adapter engages with an injector and is disposed between the injector and the syringe. The adapter includes an adapter forward end adapted to engage the syringe. In one embodiment, the adapter rearward end has at least one resilient tab that is adapted to engage with the injector.

The present invention further provides for an adapter assembly. The adapter assembly includes an adapter and a syringe for use therewith. In a preferred embodiment, the adapter includes an adapter rearward end comprising a flange member adapted to engage with a flexible ring of an injector. In this embodiment, the adapter would allow an injector designed according to the present invention to accept conventional syringes.

In an alternate embodiment, the adapter may have a rearward end including a mechanism allowing it to mate with existing injectors (such as the injectors disclosed in U.S. Pat. Nos. 4,677,980, 5,383,858 and 5,300,031, the disclosures of which are hereby incorporated by reference) and a forward end including a flexible ring or a ledge or shoulder member allowing it to mate with syringes designed according to the present invention. In this embodiment, the adapter would allow conventional or existing injectors to accept syringes designed according to the present invention.

In addition, the present invention provides methods for engaging or installing the front-loading syringes and adapters of the present invention and/or existing syringes with the front-loading injectors of the present invention and /or existing injectors Furthermore, the present invention provides injectors and injector systems having certain automated features that facilitate the preparation thereof for injection procedures.

The present invention offers many advantages over the prior art. For example, the present invention provides a syringe that does not have to be aligned and/or oriented with respect to an injector for installation thereon. Further, the present invention provides a syringe in which alignment, either radially or axially, between the plunger and syringe is not required.

Moreover, the piston of the present invention may be designed so that it does not permanently engage the plunger. So designed, the plunger acts primarily as a pusher during the injection operation. Only when the plunger must be retracted, for example, to aspirate fluid into the syringe, may an engagement mechanism be activated so that the piston connects to the plunger. By virtue of this arrangement, the plunger may be left in any position when the syringe is removed from the injector system.

In another aspect the present invention provides an injector including a housing and at least one drive member at least partially disposed within the housing and operable to engage the plunger of a syringe mounted on the injector. The injector further includes at least one syringe retaining mechanism associated with the housing that is adapted to releasably engage the syringe and a first sensing pin positioned at a forward end of the drive member to sense contact with the syringe plunger. The first sensing pin can, for example, be biased in a forward extended position and forced rearward to impinge upon a sensor when contact with the syringe plunger is made during advancement of the drive member.

The injector can further include a sensing system to sense when a syringe or a syringe adapter is attached to the retaining mechanism. The sensing system can further sense the syringe configuration.

In one embodiment, the drive member automatically moves forward upon connection of a syringe to the retaining mechanism to engage the syringe plunger (for example, upon connection of the syringe to the retaining mechanism). Preferably, the forward movement of the drive member is stopped upon engagement with the syringe plunger but before the plunger is moved forward.

The injector can further include a second drive member at least partially disposed within the housing and operable to engage a plunger of a second syringe. In this embodiment, the injector also includes a second syringe retaining mechanism associated with the housing and adapted to releasably engage the second syringe. Preferably, a second sensing pin is positioned at a forward end of the second drive member to sense contact with the second syringe plunger.

The injector can also include a source of a first injection fluid in fluid connection with the first syringe, and a source of a second injection fluid in fluid connection with the second syringe.

The injector can also include a first control unit positioned outside of a scan room in which an injection procedure takes place and a second control unit positioned inside the scan room. For example, an injection protocol for control of the injection procedure can be entered at the first control unit. The first control unit can include a protocol edit lock function, which may be activated by the operator once an injection protocol has been set. Preferably, a change in injection protocol after activation of the protocol edit lock function is associated with deactivating the lock function. The second control unit preferably includes an indicator of the state (for example, activated or deactivated) of the lock function. In general, the second control unit preferably includes an indicator of whether an injection protocol set with the first control unit has been changed.

In one embodiment, the injector has a mode of operation in which the first fluid is injected from the first syringe and the second fluid is simultaneously injected from the second syringe into a single injection site. Preferably, the injector has three modes of operation including (1) sequential injection of the first fluid from the first syringe and of the second fluid from the second syringe into a single injection site; (2) simultaneous injection of the first fluid from the first syringe and the second fluid from the second syringe into a single injection site; and (3) simultaneous injection of the first fluid from the first syringe and the second fluid from the second syringe into two different injection sites.

In another aspect, the present invention provides a method of injecting fluids into a patient to a region of interest within the patient. The method preferably including the steps of (1) injecting a first fluid into a first injection site on the patient suitable to transport the first fluid to the region of interest; and (2) injecting a second fluid into a second injection site on the patient suitable to transport the second fluid to the region of interest. The first fluid and the second fluid can be the same. For example, the first fluid and the second fluid can be a contrast medium suitable to enhance an image in a medical scanning procedure.

In a further aspect, the present invention provides an injector including a housing and at least one drive member at least partially disposed within the housing and being operable to engage the plunger of the syringe. The injector also includes at least one syringe retaining mechanism associated with the housing. The syringe retaining mechanism is adapted to releasably engage the syringe. The injector further comprises a first control unit positioned in a control room. The first control unit includes a protocol edit lock function, which may be activated by the operator once an injection protocol has been set. A change in injection protocol after activation of the protocol edit lock function is preferably associated with deactivating of the lock function (for example, automatically upon editing the protocol or manually prior to editing the protocol). The injector further includes a second control unit positioned in a scan room. The second control unit includes an indicator of the state of the lock function.

In still another aspect, the present invention provides an injector including a housing and at least one drive member at least partially disposed within the housing. The drive member is operable to engage a plunger of the syringe. The injector also includes at least one syringe retaining mechanism associated with the housing. The syringe retaining mechanism is preferably adapted to releasably engage the syringe. The injector also includes a first control unit positioned in a control room. The first control unit enables setting of an injection protocol. The injector further includes a second control unit positioned in a scan room. The second control unit includes an indicator of whether the injection protocol set with the first control unit has been changed.

The present invention, along with the attributes and attendant advantages thereof, will best be appreciated and understood in view of the following detailed description taken in conjunction with the accompanying drawings.

BRIEF DESCRIPTION OF THE DRAWINGS

The various embodiments of the present invention are described in connection with the figures appended hereto, in which:

FIG. 4 is a perspective view of another embodiment of the present invention, illustrating a syringe and a pressure-jacketed injector in a disassembled relationship;

FIG. 5 is another perspective view of the embodiment illustrated in FIG. 4, showing a piston displaced at a more forward position than that illustrated in FIG. 4;

FIG. 6 is a cross-sectional view of the syringe and housing illustrated in FIGS. 1 and 2, showing the secure connection of the syringe to the front wall of the injector housing through tabs attached at the rearward end of the syringe;

FIG. 7 is an enlarged cross-sectional view of the structures enclosed by circle VII in FIG. 6, showing in greater detail the connection of the syringe to the front wall of the injector housing;

FIG. 10 is an enlarged perspective view of yet another embodiment of a syringe in accordance with the present invention, illustrating at least one tab at a base of the syringe for engagement with a ledge defined in an interface of an injector housing;

FIG. 11 is an enlarged perspective view of the syringe illustrated in FIG. 10, showing the at least one tab from the rearward end (or base side) of the syringe;

FIG. 12 is an enlarged perspective view of another embodiment of a syringe in accordance with the teachings of the present invention, illustrating two tabs at the base of the syringe for engagement with the injector housing;

FIG. 13 is an enlarged perspective view of the syringe shown in FIG. 12, illustrating the two tabs at the rearward end of the syringe;

FIG. 14 is an enlarged perspective view of still another embodiment of a syringe in accordance with the present invention, illustrating more than two tabs at a base of the syringe for engagement with an injector housing;

FIG. 15 is an enlarged perspective view of the syringe illustrated in FIG. 14, showing the base end of the syringe with the plurality of tabs;

FIG. 16 is a partial, enlarged perspective view of an alternate embodiment of the tab arrangement illustrated in FIGS. 1 and 8;

FIG. 17 is a cross-sectional view of the tab arrangement illustrated in FIG. 16, taken along line XVII-XVII;

FIG. 23 is a perspective view of the adapter and syringe illustrated in FIG. 22;

FIG. 24 is another perspective view of the adapter and syringe illustrated in FIG. 22;

FIG. 36 is a side view illustration of still another embodiment of the apparatus that releasably connects the plunger and piston to one another;

FIG. 38 is a perspective cut-away illustration of a pressure jacket embodiment of the present invention showing the reciprocating collar disposed within the pressure jacket;

FIG. 39 is a cross-sectional view of the pressure jacket embodiment illustrated in FIG. 38, taken along line XXXIX-XXXIX;

FIG. 47F is a rear, exploded, perspective view of the syringe interface shown in FIG. 47A;

FIG. 49F is an exploded, perspective view of the plunger base and the plunger cover shown in FIGS. 49C and 49D;

FIG. 50B is an enlarged view, partially in cross-section, of the plunger base and the piston shown in FIG. 50A in an engaged position;

FIG. 51B is a perspective view of the piston/plunger system shown in FIG. 51A with the plunger base separated from the plunger cover and associated with the piston;

FIG. 51C is an enlarged view, partially in cross-section, of the plunger base and the piston shown in FIG. 51A in an engaged position;

FIG. 52B is an exploded perspective view of the piston/plunger system shown in FIG. 52A;

FIG. 53B is an enlarged, perspective view of the piston/plunger system shown in FIG. 53A in a disengaged position;

FIG. 54C is a perspective view of an embodiment of a syringe plunger of the present invention;

FIG. 54F is an exploded, perspective view of the syringe plunger shown in FIG. 54E;

FIG. 64 is an isometric, rear view perspective illustration of the front plate of the release mechanism of the second preferred embodiment of the present invention;

FIG. 65 is an isometric, front view perspective illustration of the front plate shown in FIG. 64;

FIG. 68 is an isometric, front view perspective illustration of the rotating ring element of the release mechanism of the second preferred embodiment of the present invention, detailing several aspects thereof;

FIG. 69 is an isometric, rear view perspective illustration of the rotating ring shown in FIG. 68;

FIG. 70 is an isometric, front view perspective illustration of the rear plate of the second preferred embodiment of the release mechanism of the present invention, detailing several aspects thereof;

FIG. 71 is an isometric, rear view perspective illustration of the rear plate shown in FIG. 70;

FIG. 72 is an isometric, front view perspective illustration of the syringe interface and syringe system of the second preferred embodiment of the present invention;

FIG. 73 is an isometric, rear view perspective illustration of the syringe interface and syringe system shown in FIG. 72;

FIG. 74 is a cross-sectional schematic illustration of a portion of the syringe interface/release mechanism of the second preferred embodiment of the present invention before insertion of the syringe into the interface/release mechanism;

FIG. 75 is a side view, cross-sectional schematic illustration of the same elements shown in FIG. 74, with the syringe partially inserted into the interface/release mechanism;

FIG. 76 is a side view, cross-sectional schematic illustration of the same features of the second preferred embodiment of the present invention as shown in FIGS. 74 and 75, in this case illustrating the syringe after it has been fully inserted into the interface/release mechanism;

FIG. 77 is an end view, cross-sectional schematic illustration of the syringe and flex ring elements of the present invention as shown in FIG. 76, depicting the engagement of the syringe by the flex ring;

FIG. 78 is an end view, cross-sectional schematic illustration of the syringe and flex ring of the second preferred embodiment of the present invention, depicting the disengagement of the syringe from the flex ring after rotation of the syringe through a one quarter turn;

FIG. 79 is a perspective illustration of a related art syringe, showing the efficacy of the flange on the syringe for preventing contrast media from entering the injector housing;

FIG. 80 is an isometric, front view, perspective illustration of a first preferred embodiment of the injector piston and syringe plunger interface system of the present invention;

FIG. 81 is an isometric, rear view perspective illustration of the piston/plunger assembly depicted in FIG. 80;

FIG. 82 is an exploded, isometric view of the piston/plunger assembly depicted in FIGS. 80 and 81;

Figure 55:
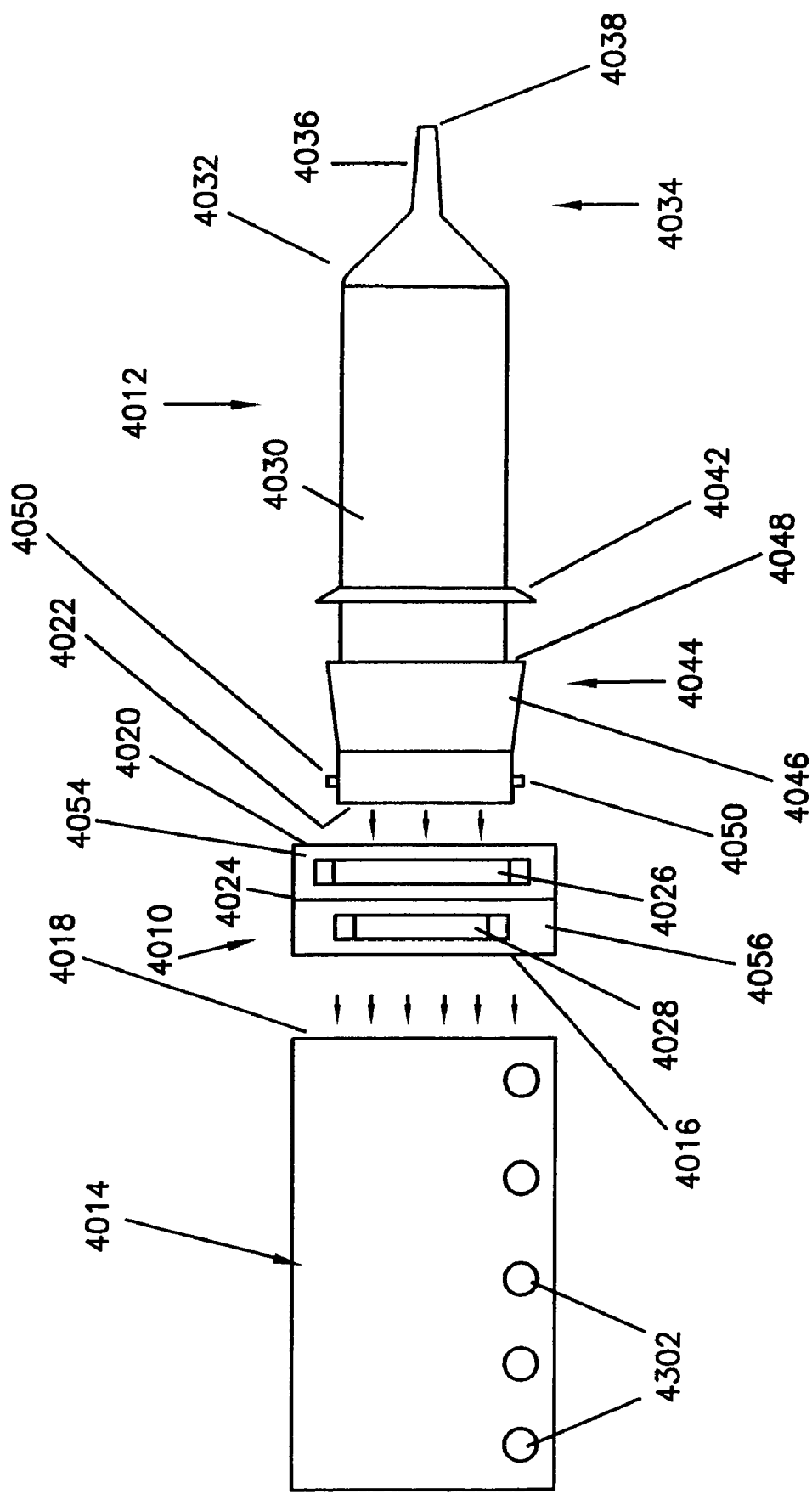
FIG. 55 is a side view schematic illustration of a second preferred embodiment of a front-loading syringe interface and syringe system in accordance with the present invention, illustrating a release mechanism for connecting a syringe to an injector housing.
Figure 56:
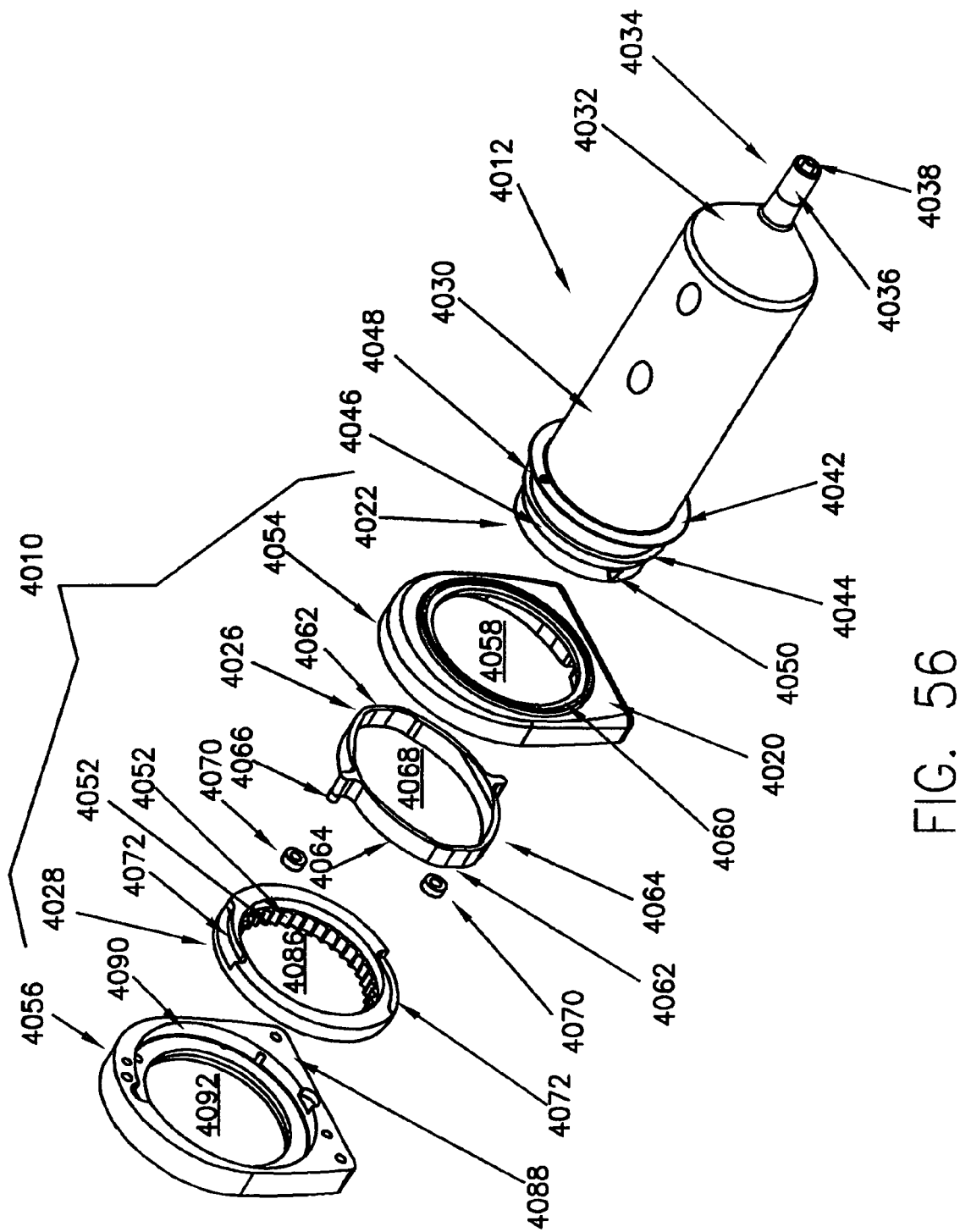
FIG. 56 is an exploded, isometric, front view perspective of the syringe interface and syringe system shown in FIG. 55.
Figure 57:
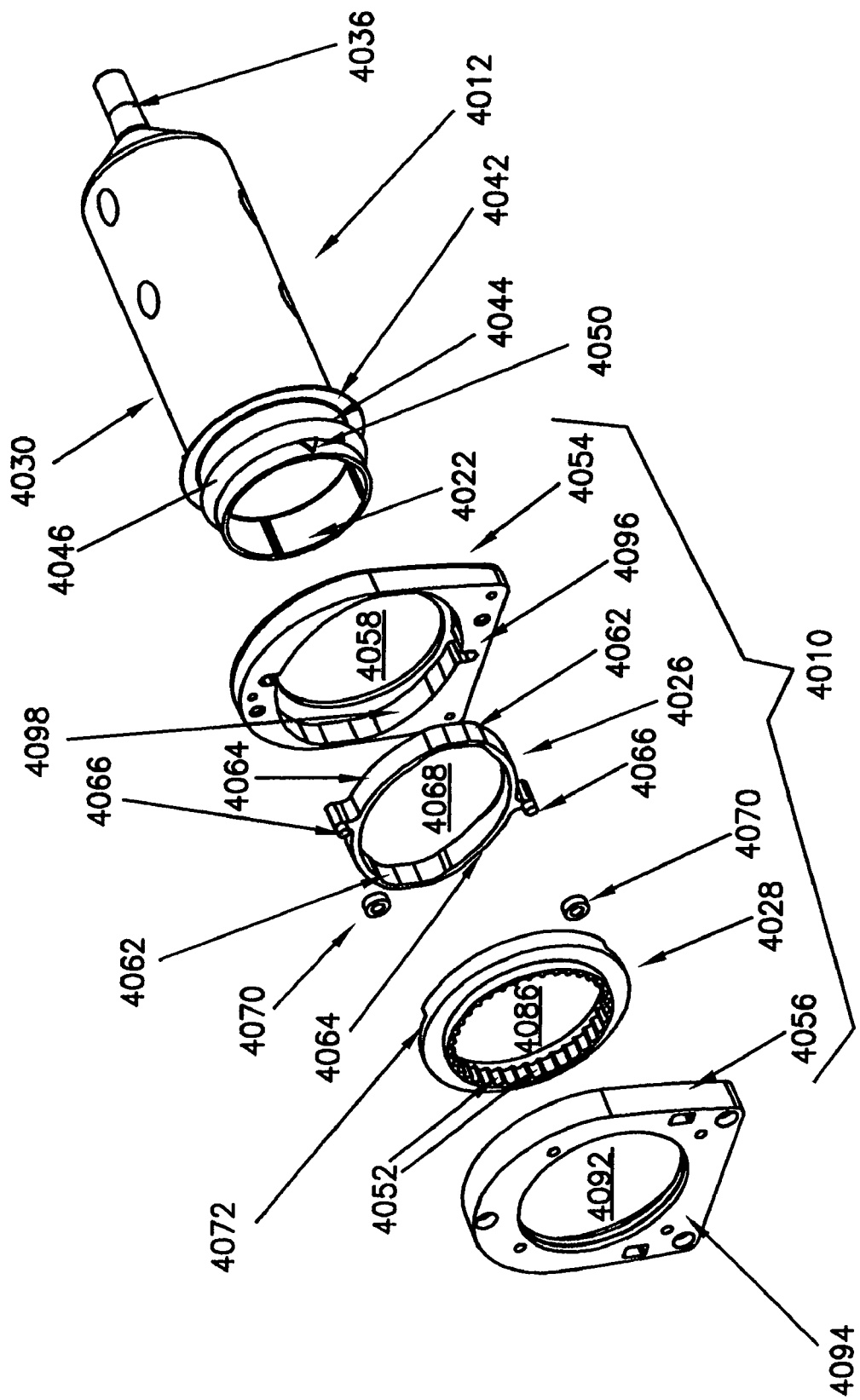
FIG. 57 is an exploded, isometric, rear view perspective of the syringe interface and syringe system shown in FIG. 56.
Figure 82:
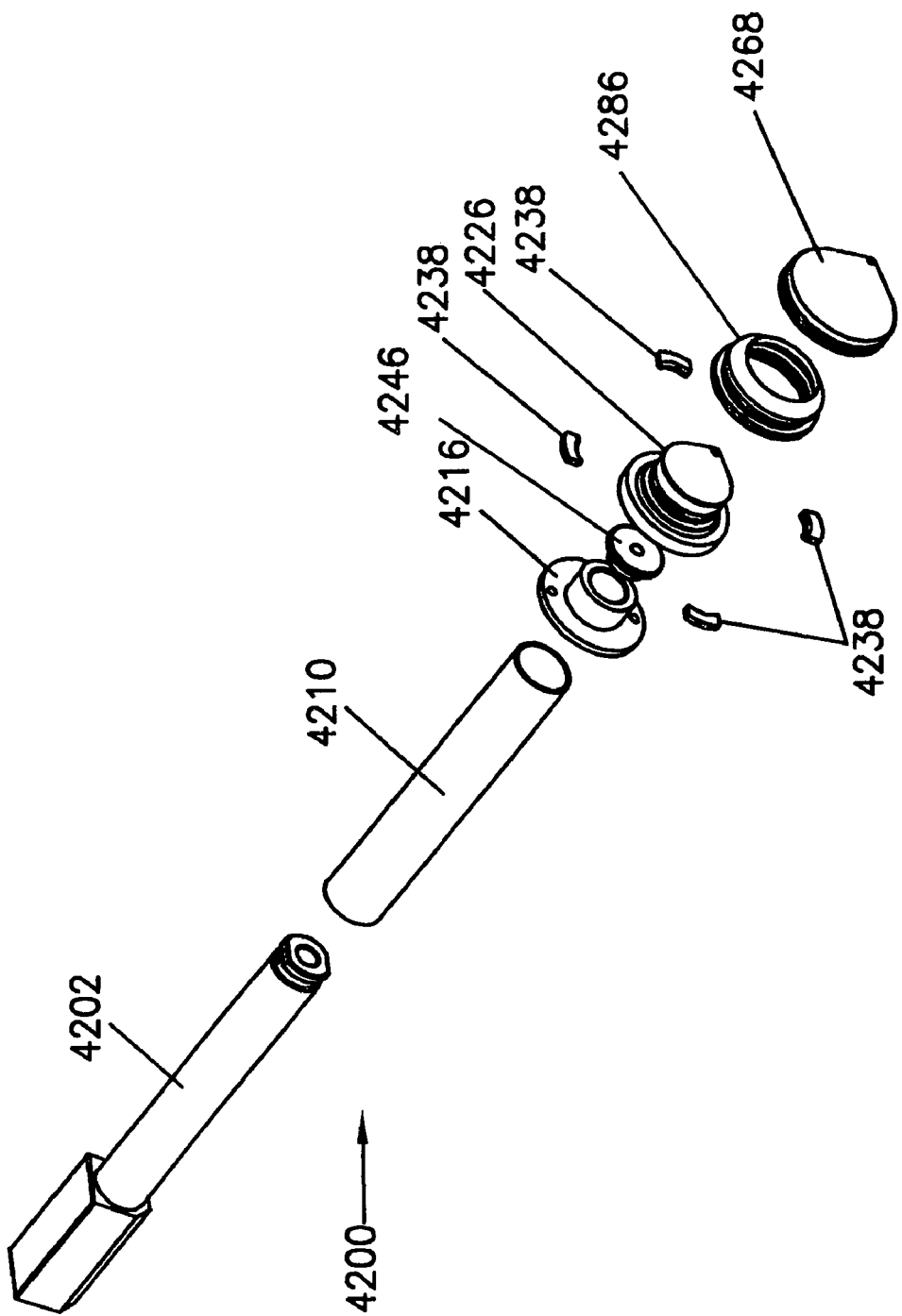
Figure 87:
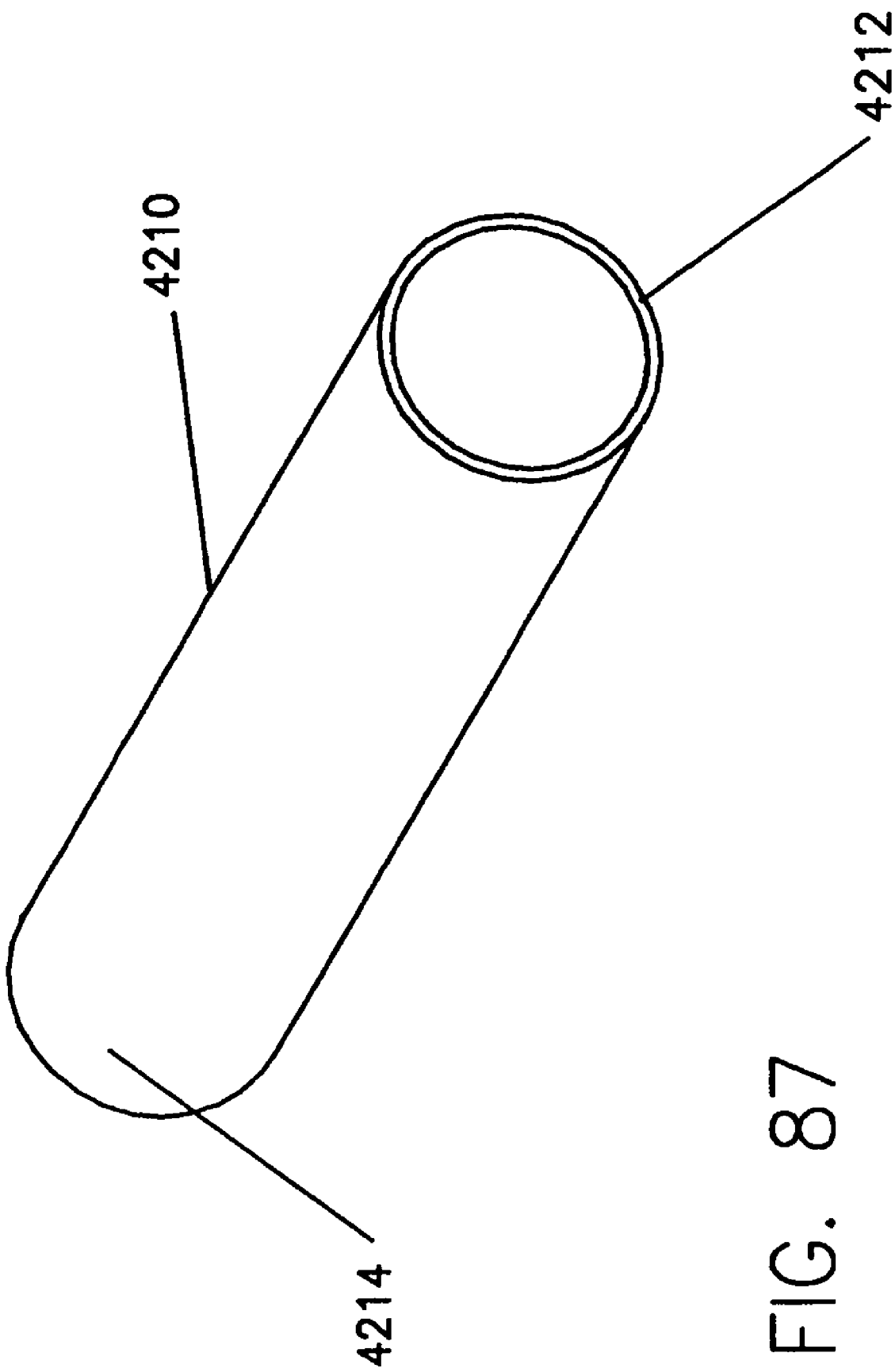
Figure 90:
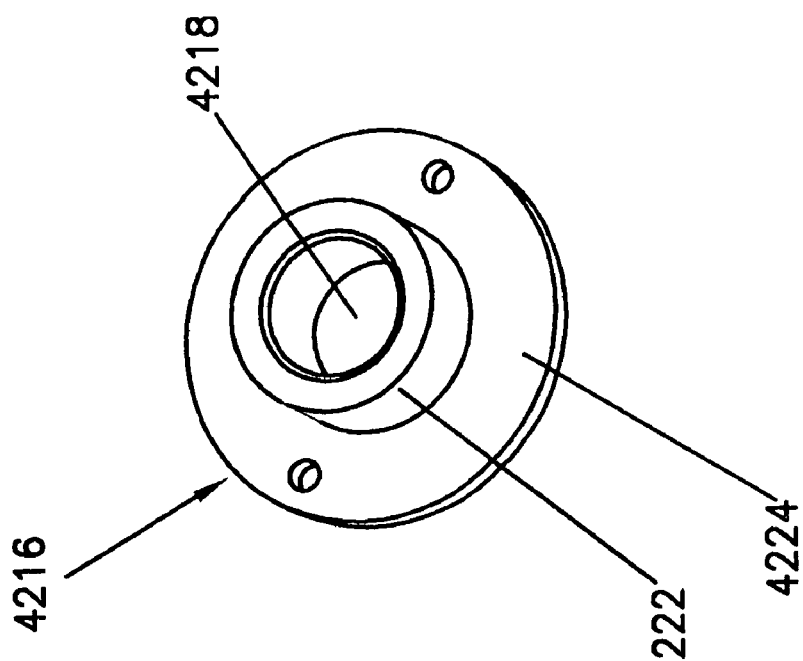
Figure 89:
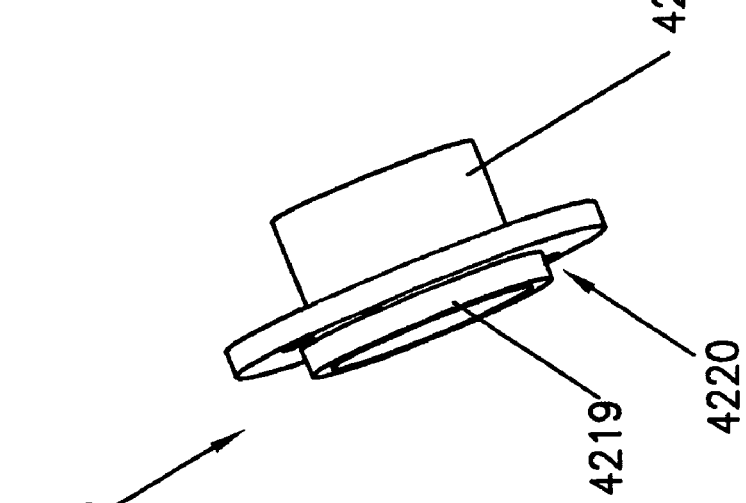
Figure 88:
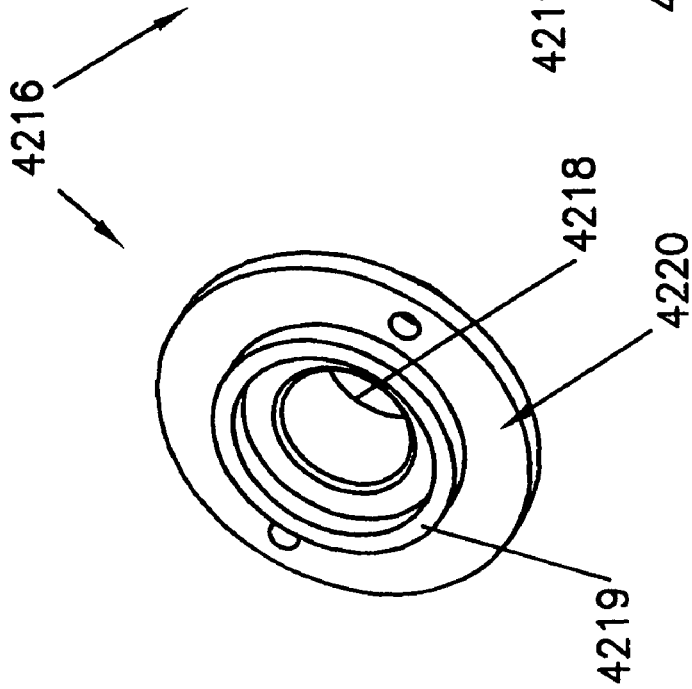
Figure 108:
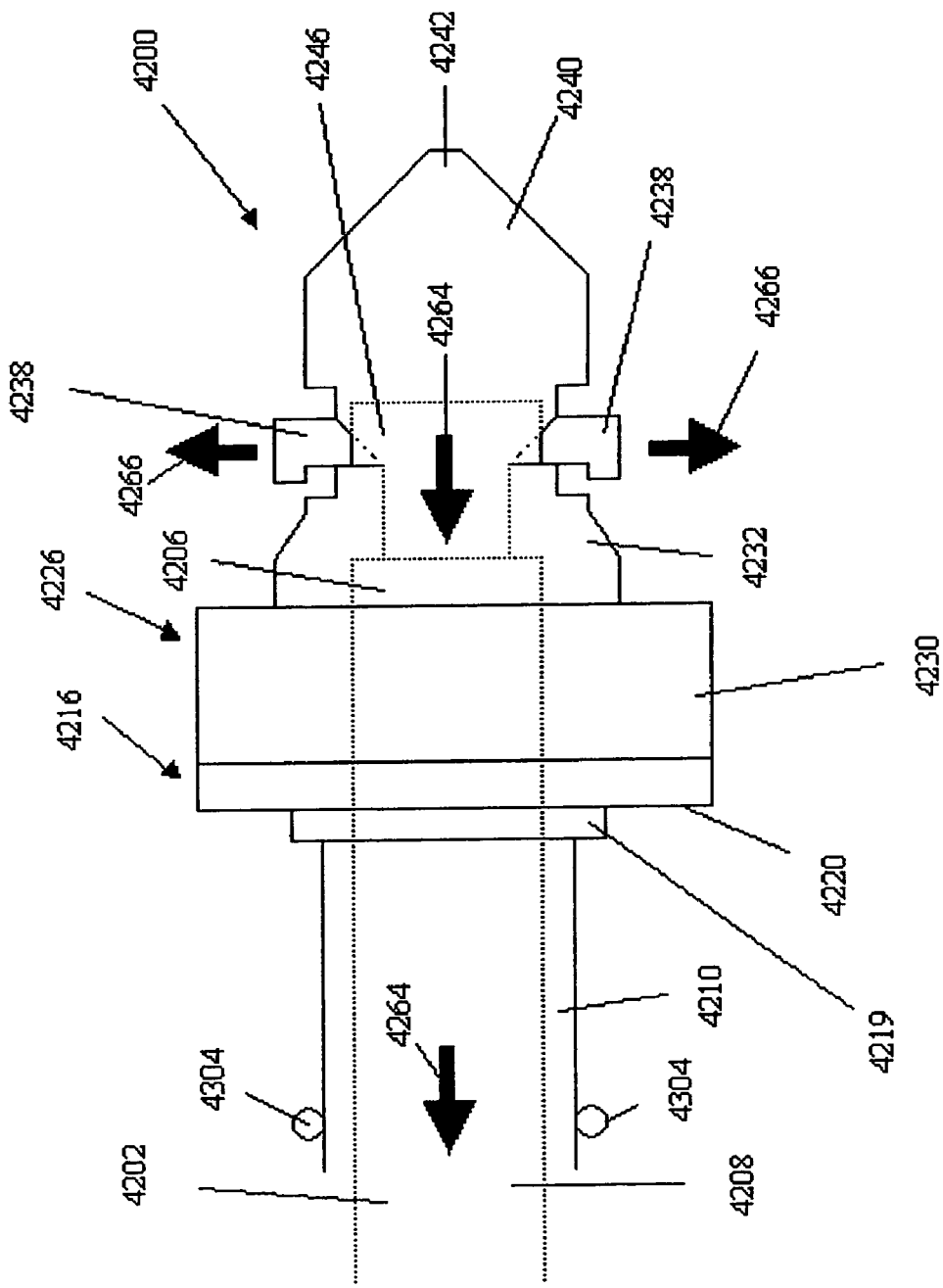
Figure 109:
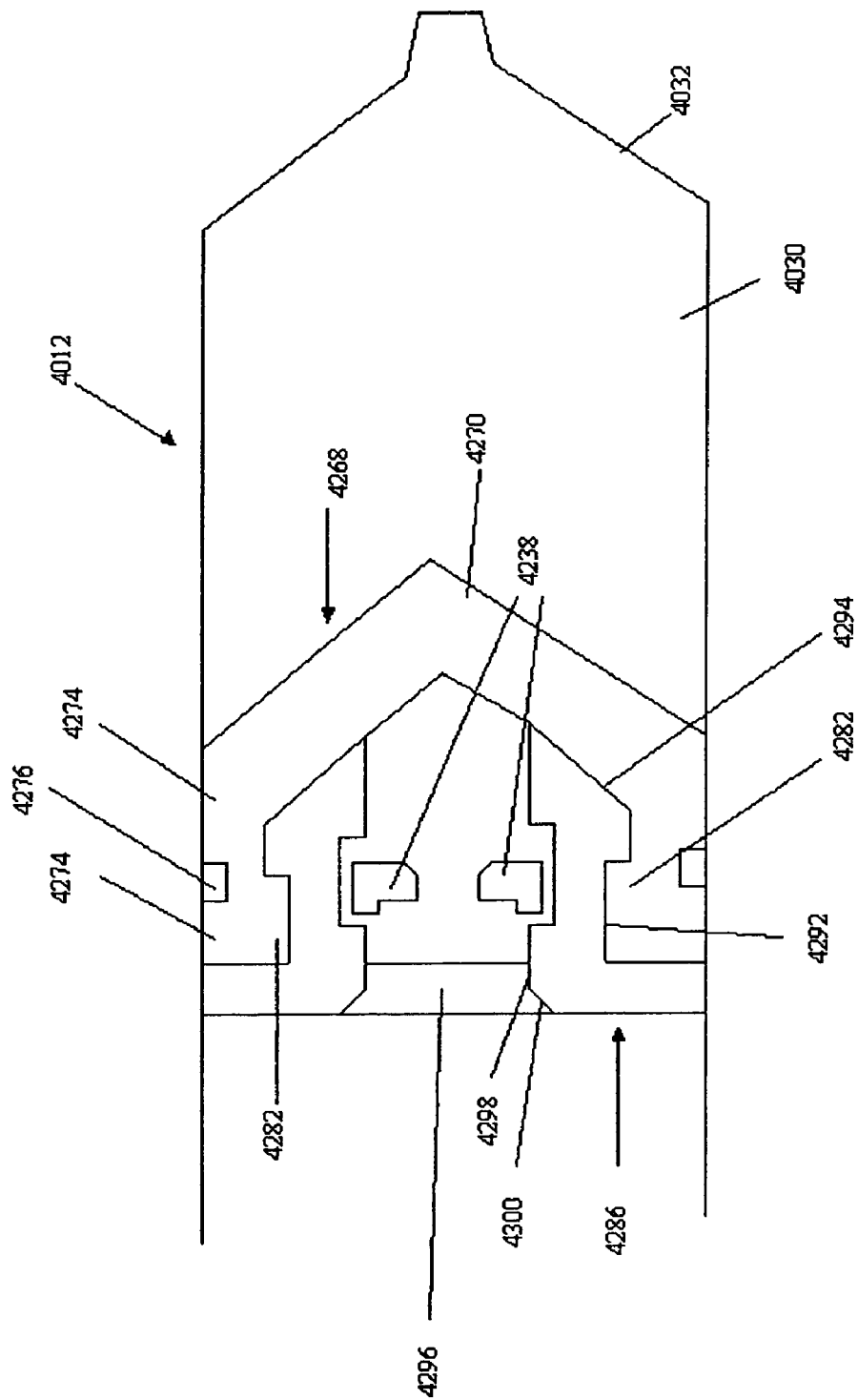
Figure 114:
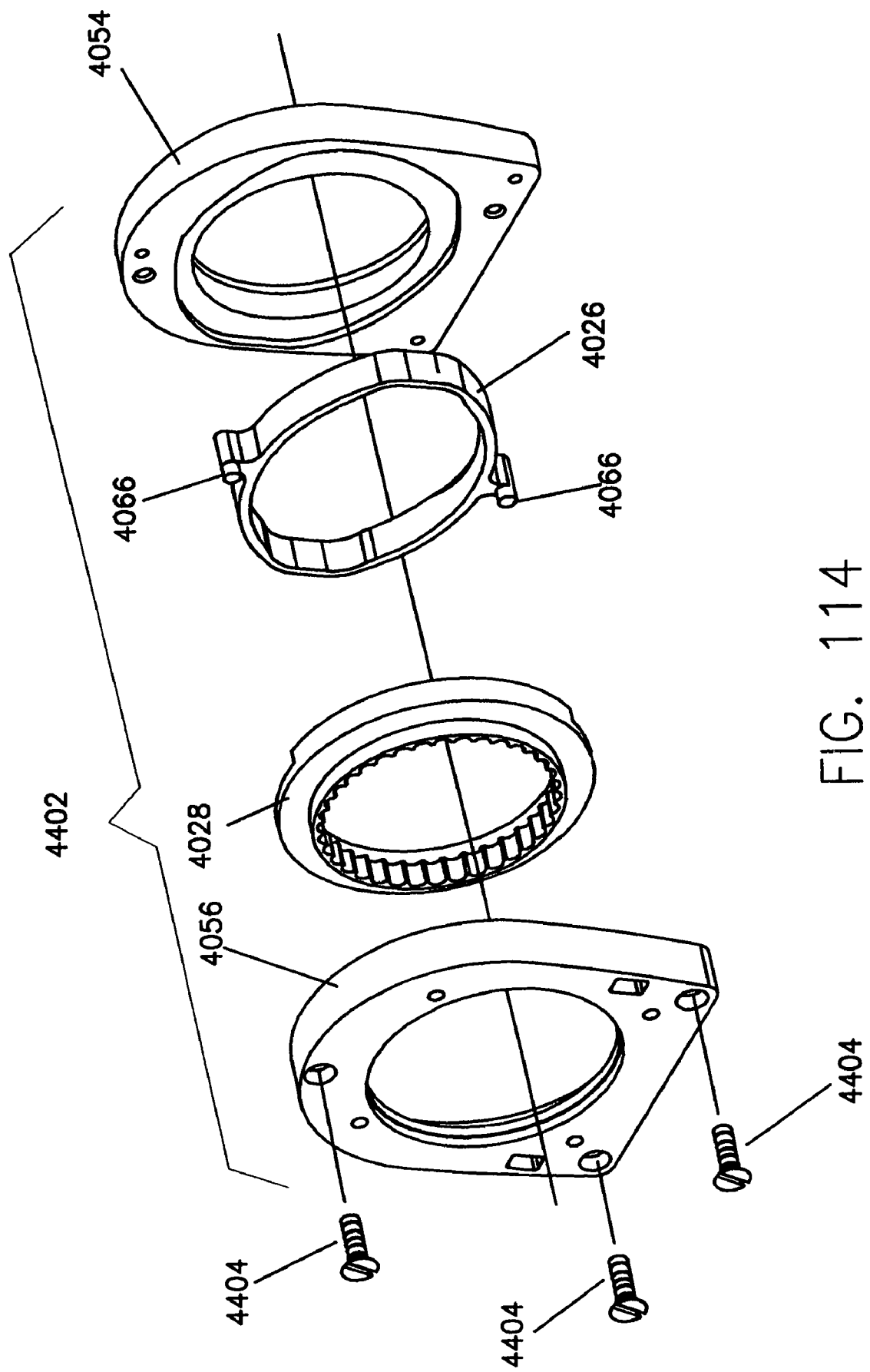
Figure 115:
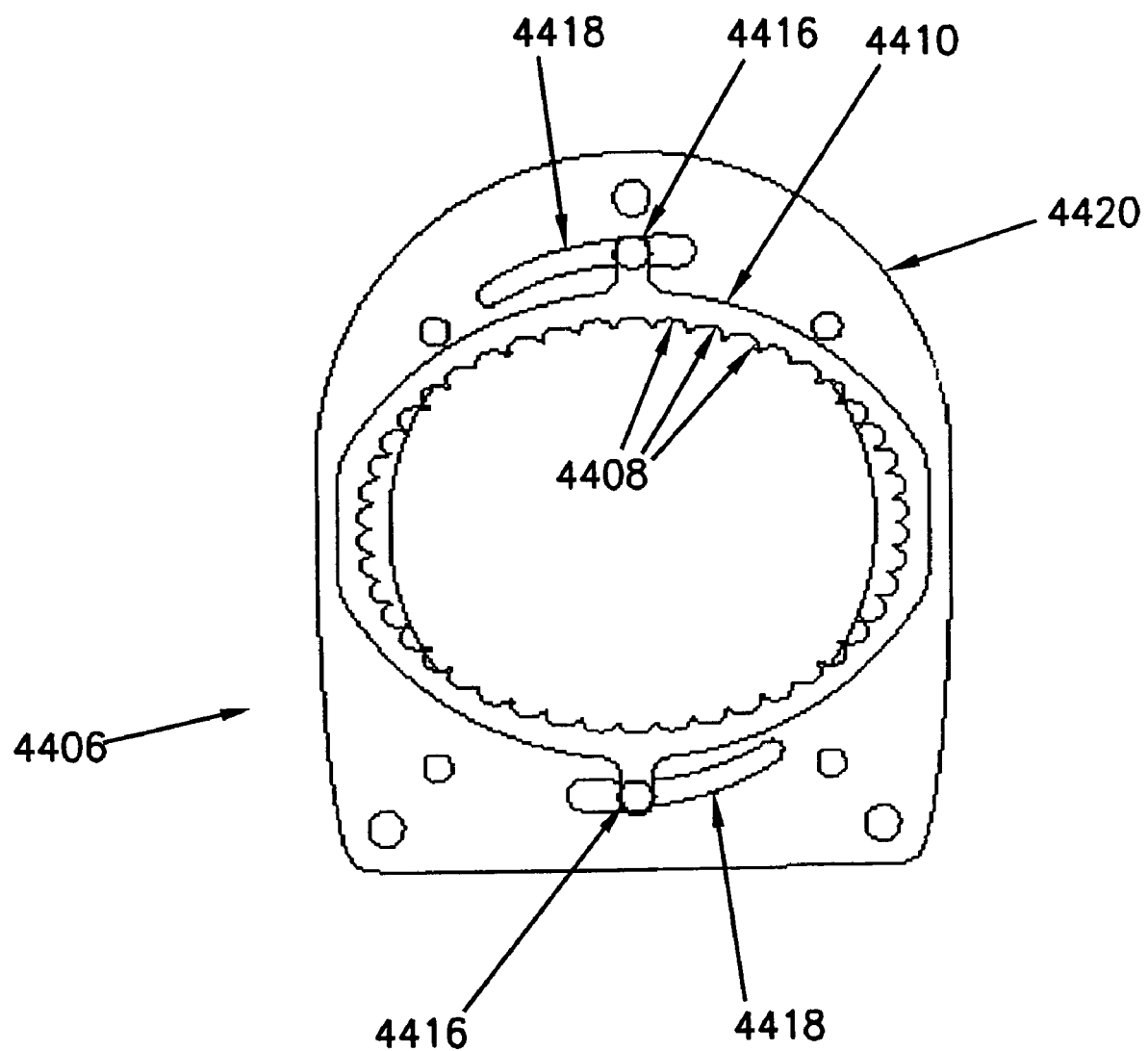
Figure 119:
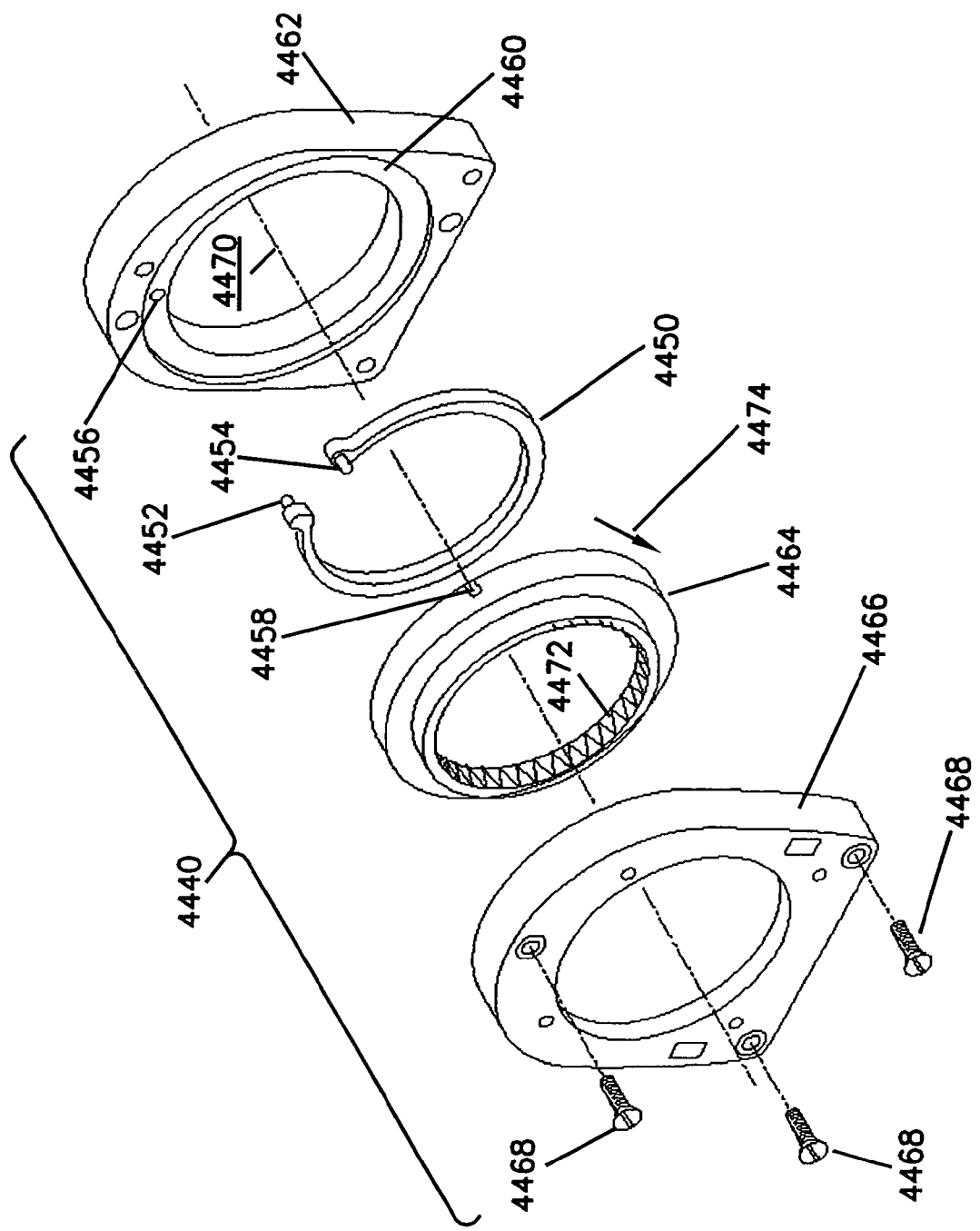
Figure 120:
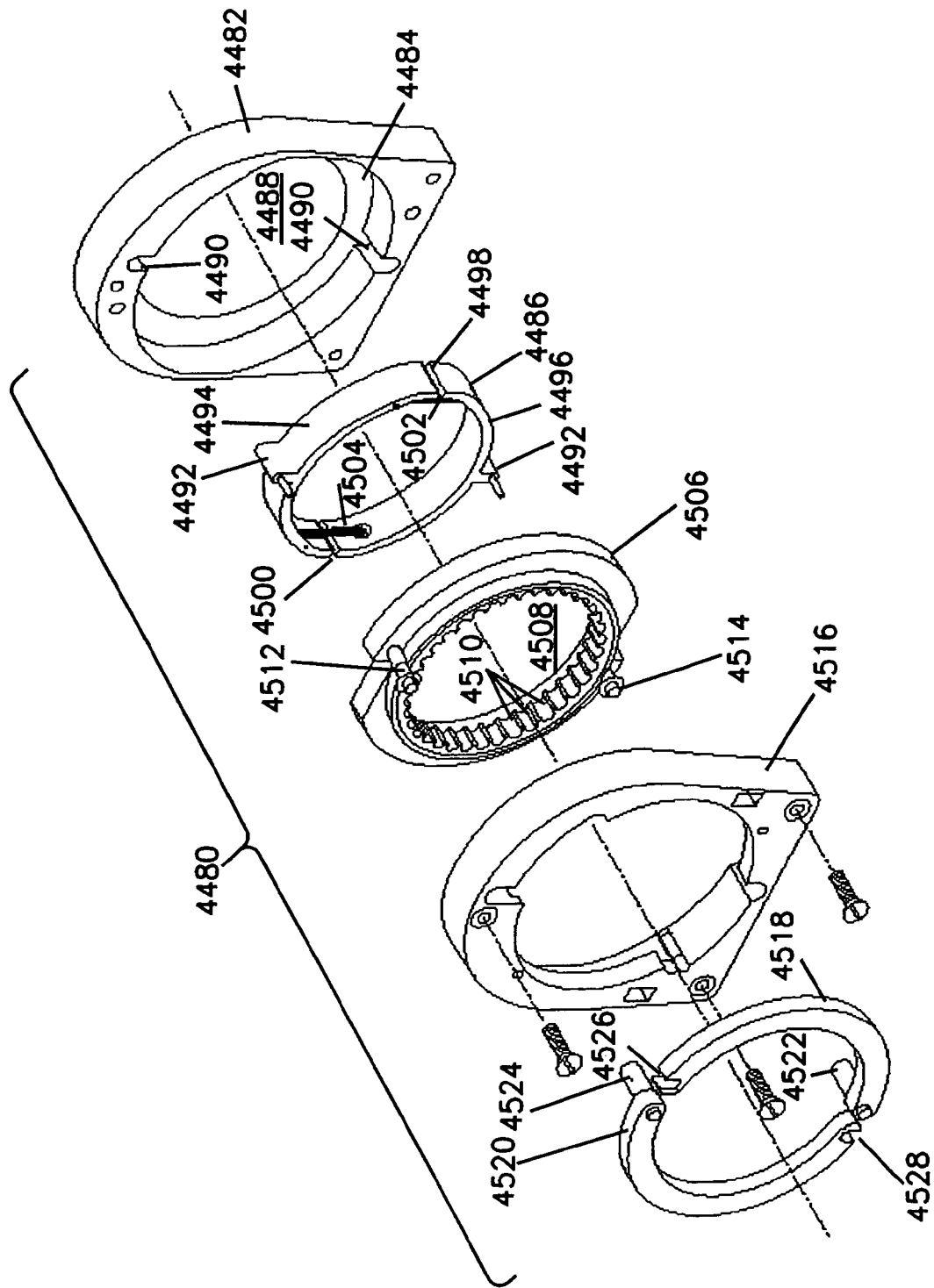
Figure 121:
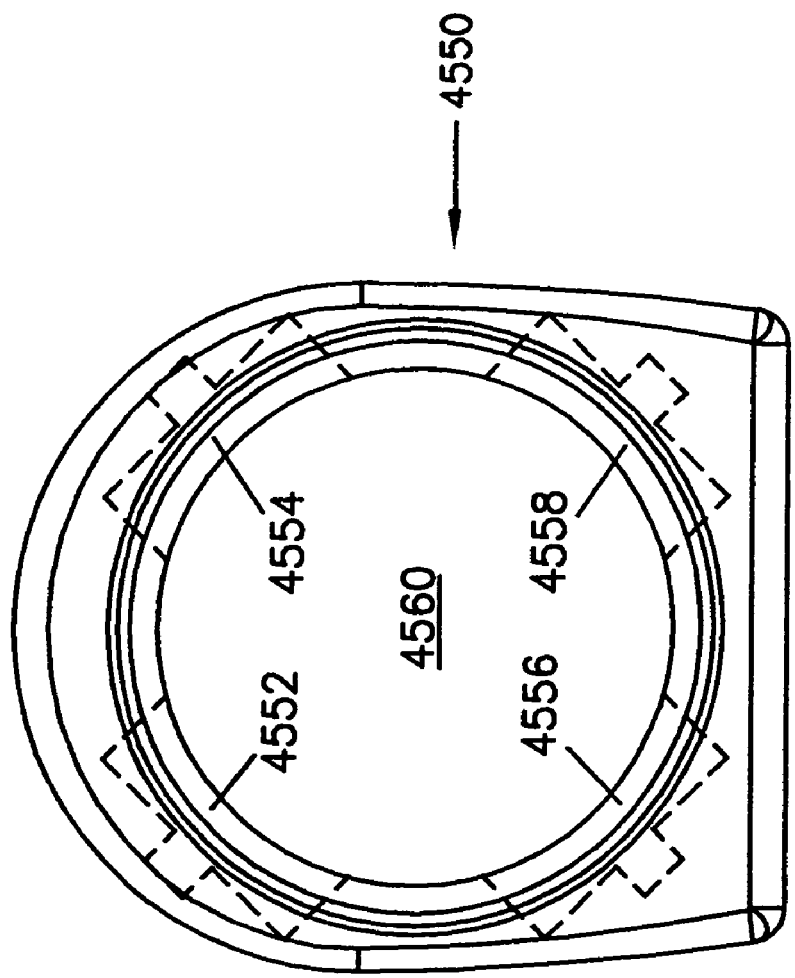
Figure 122:
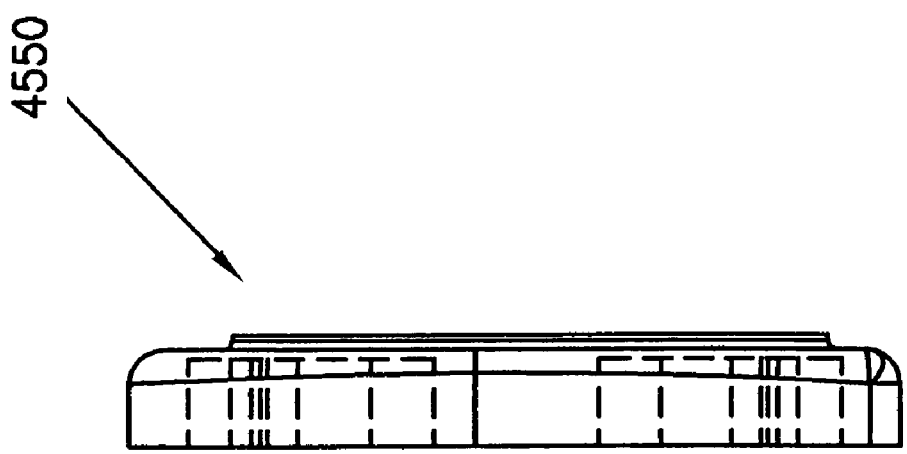
Figure 123:
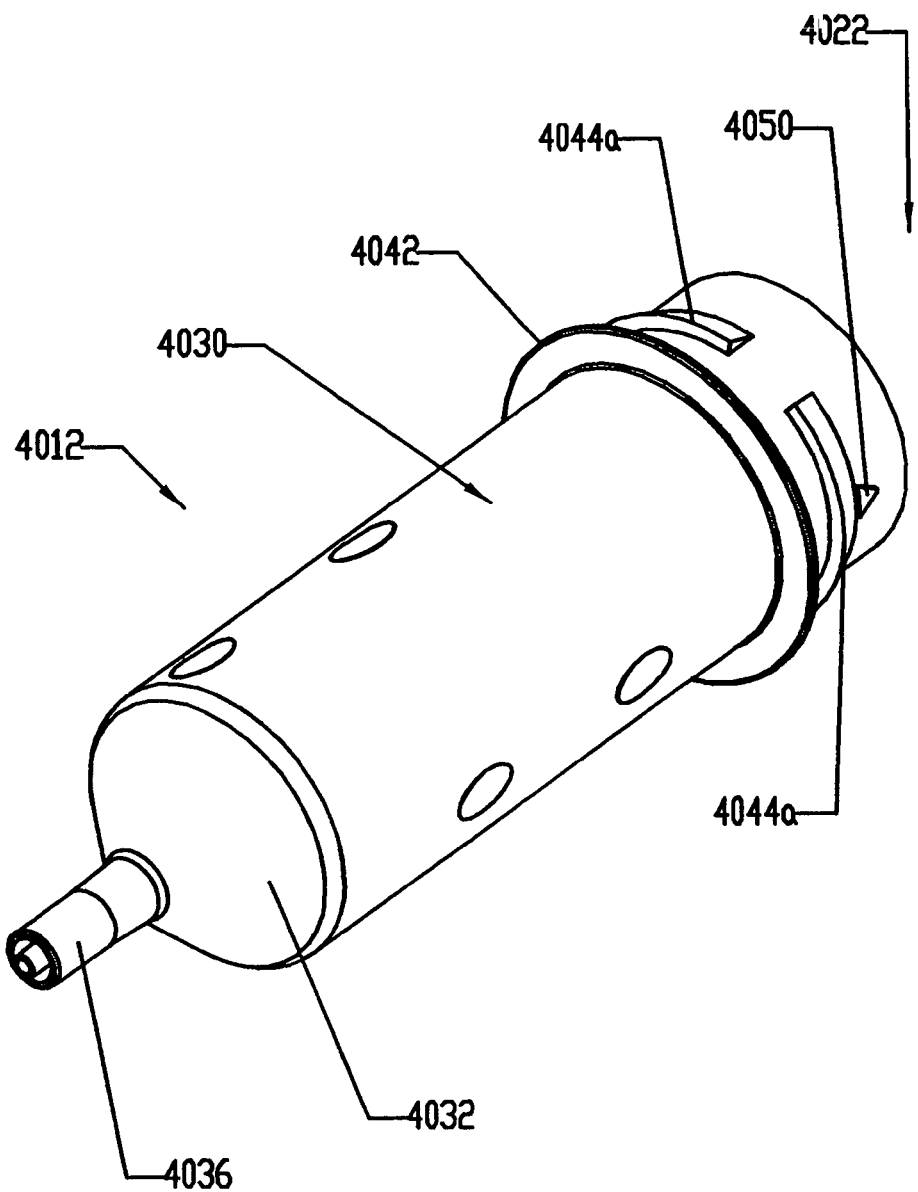
Figure 124:
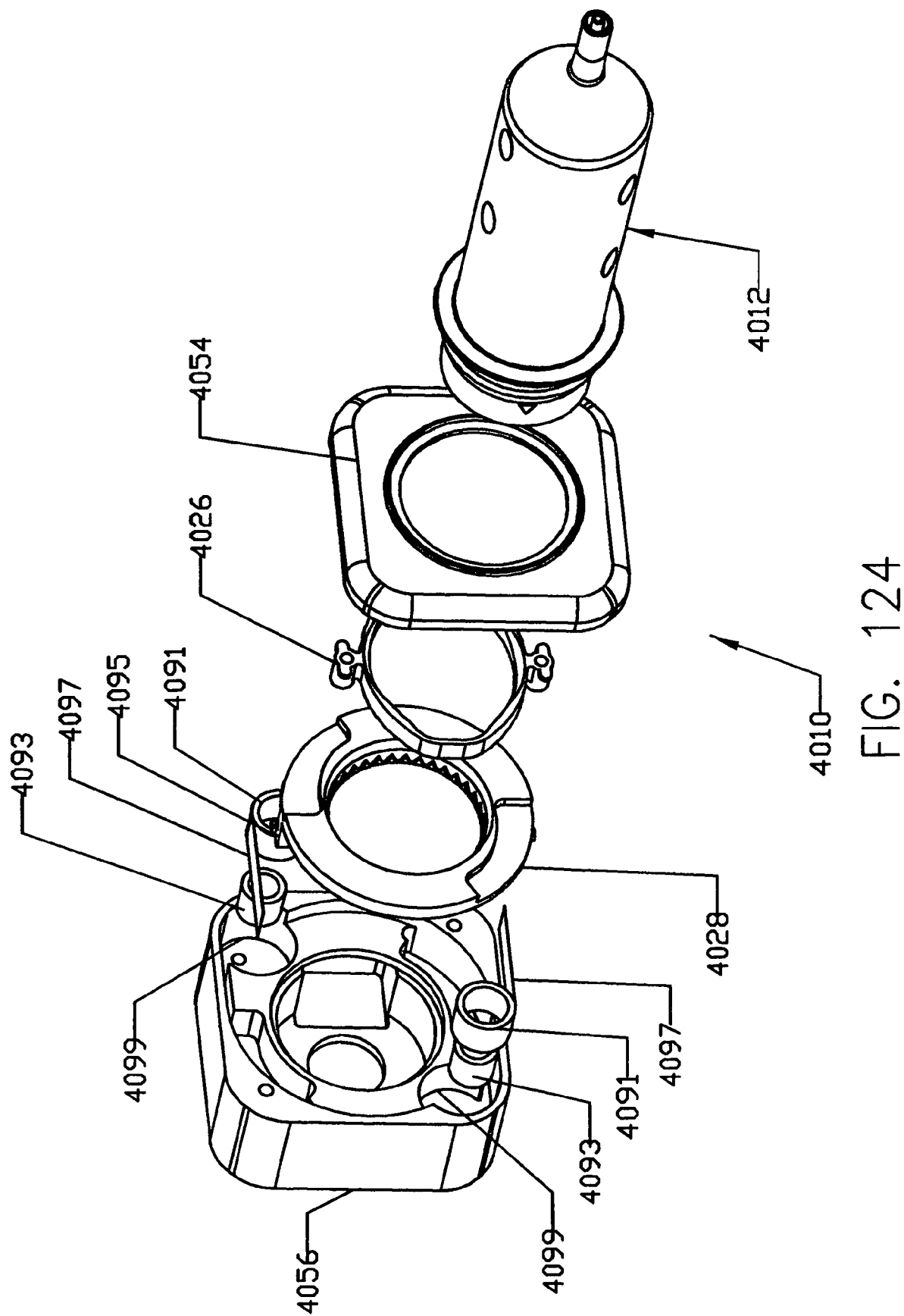
Figure 125:
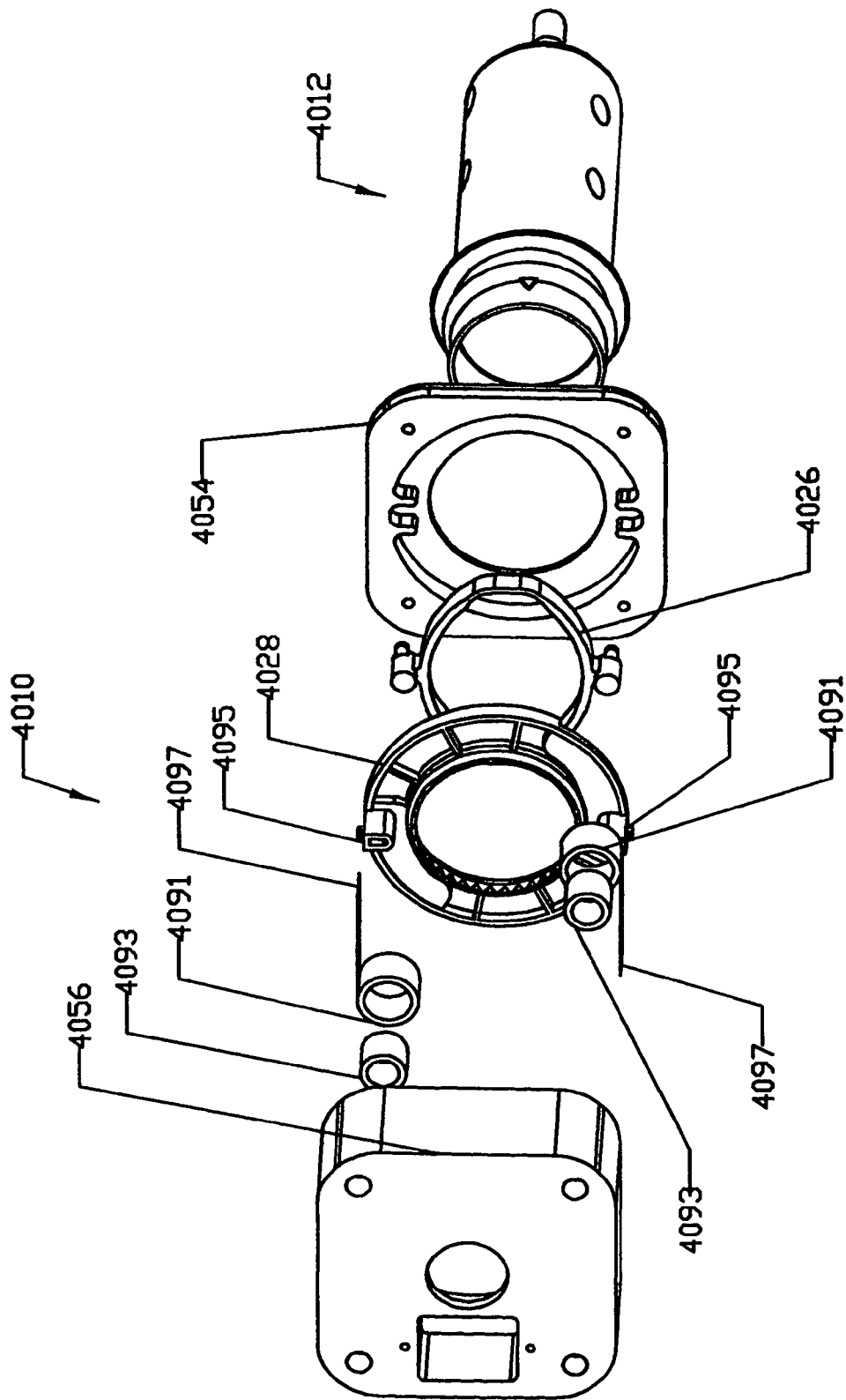
Figure 126:
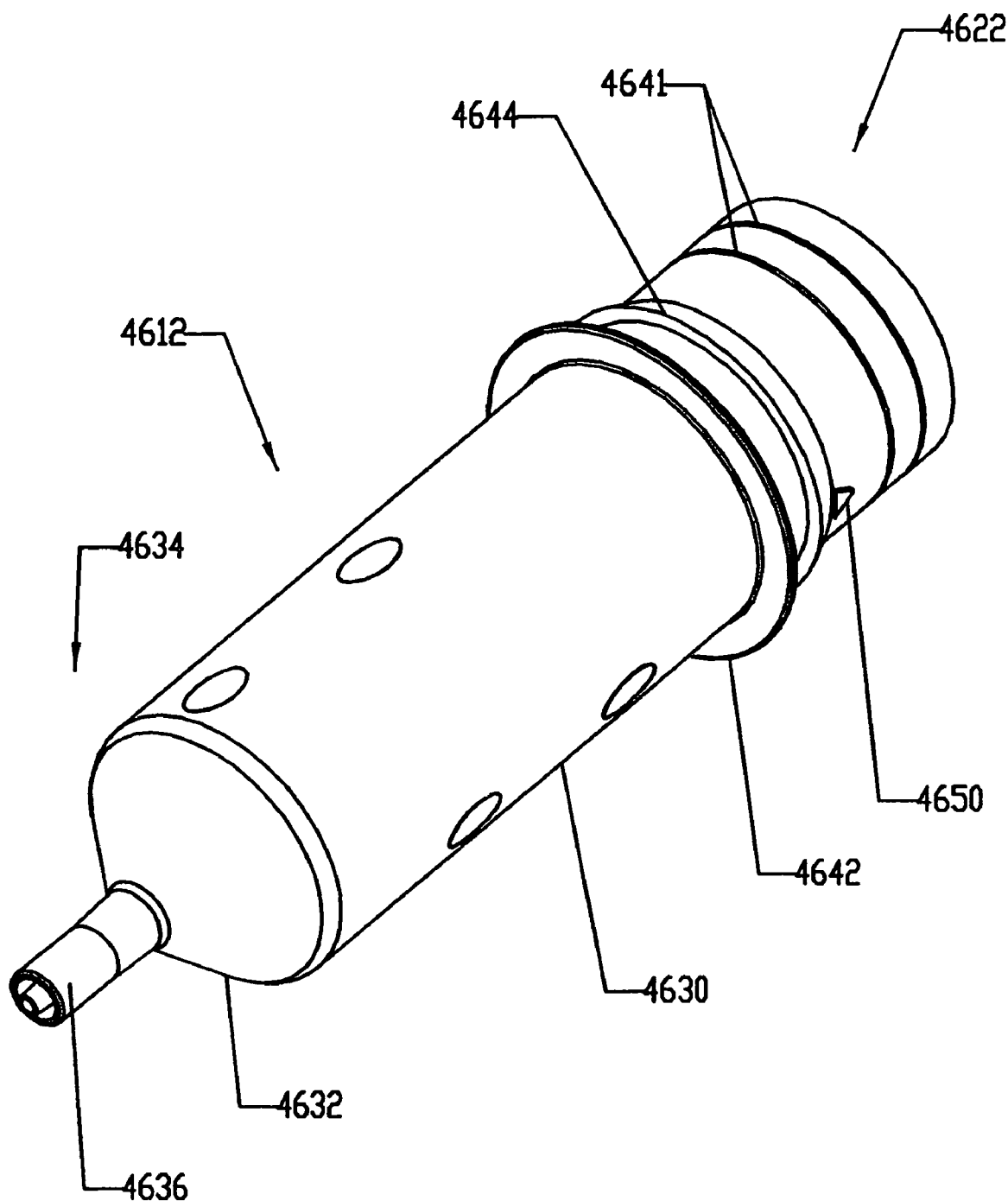
Figure 127B:
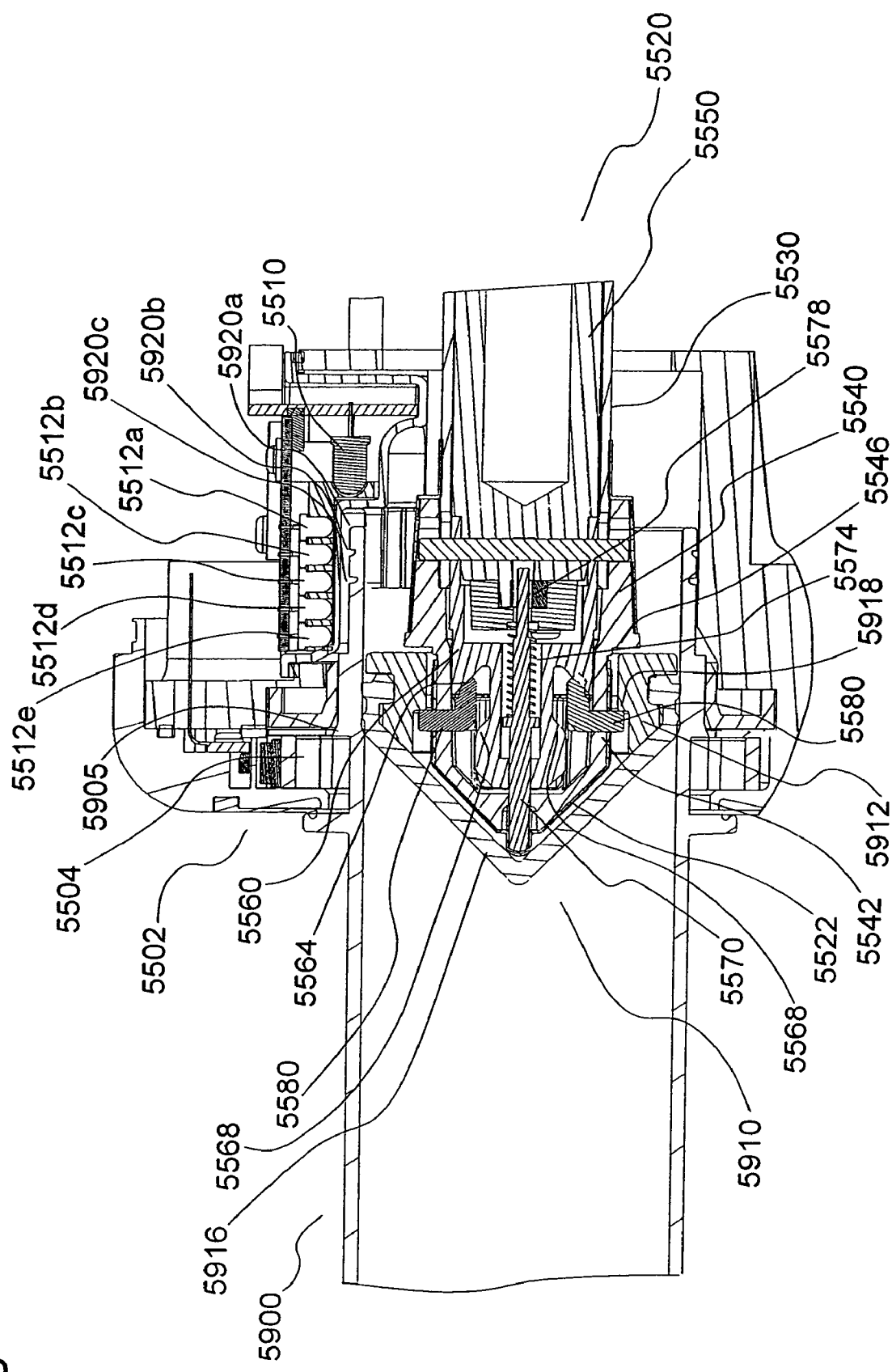
Figure 127C:
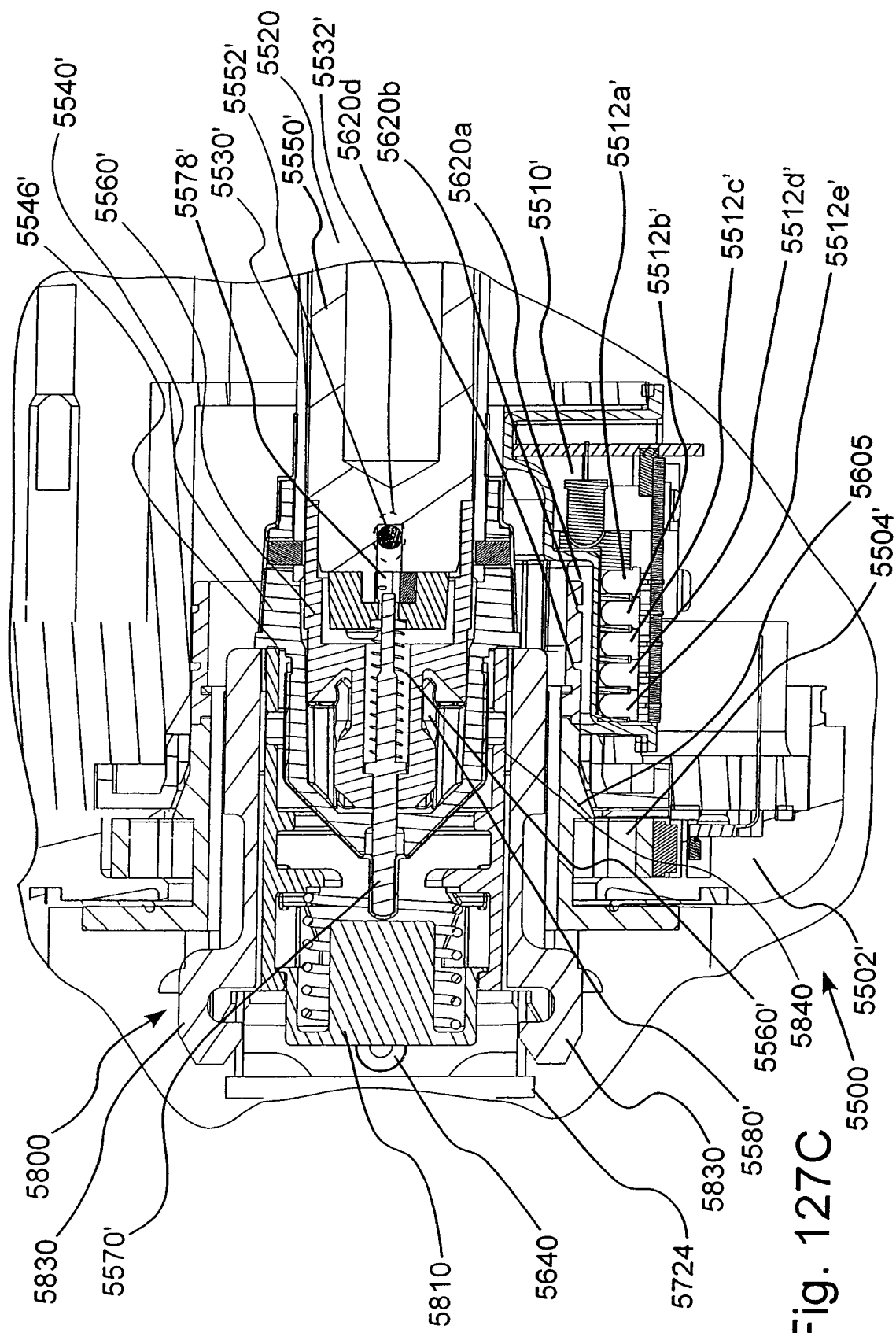
Figure 128A:
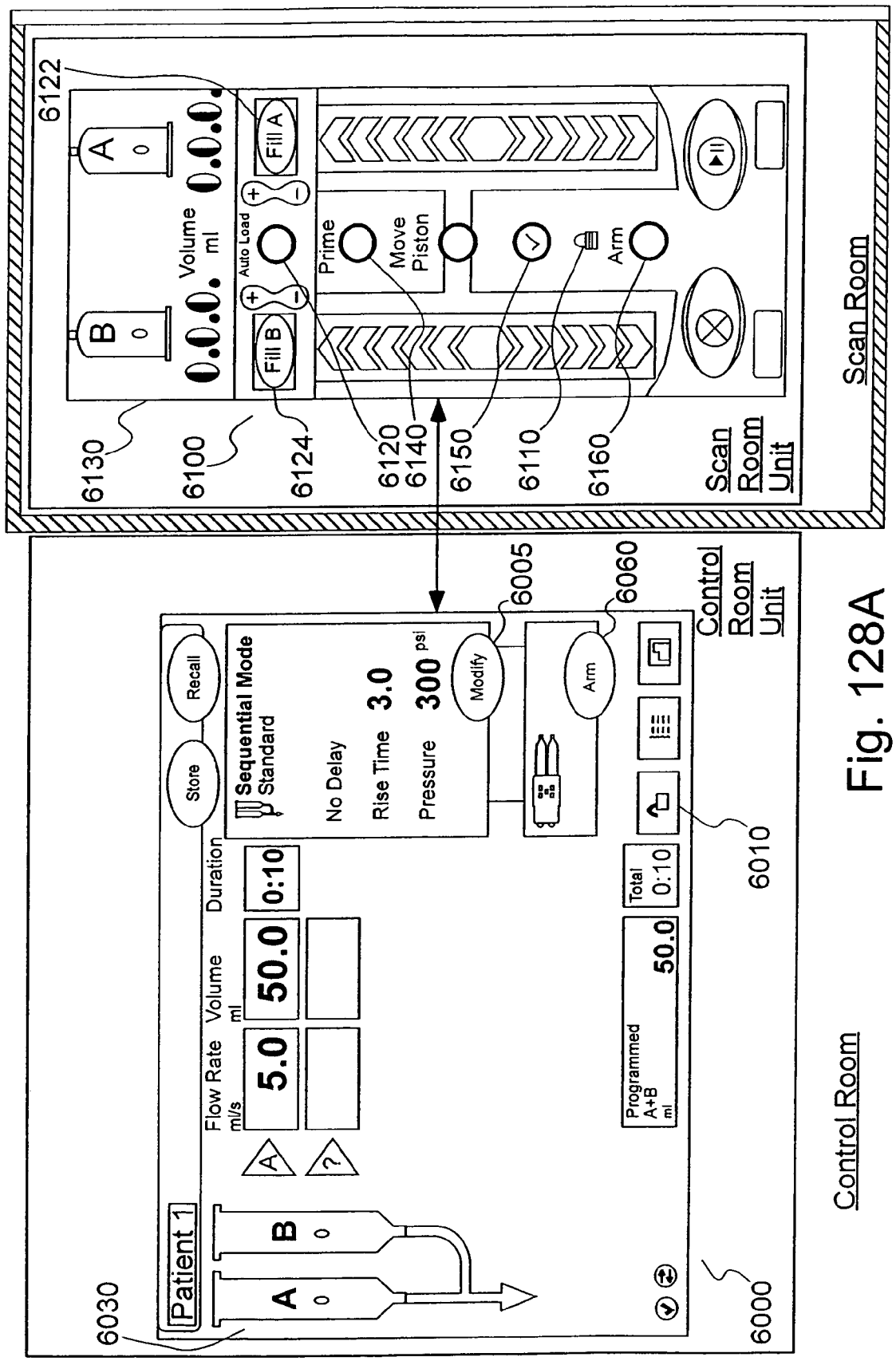
Figure 128B:
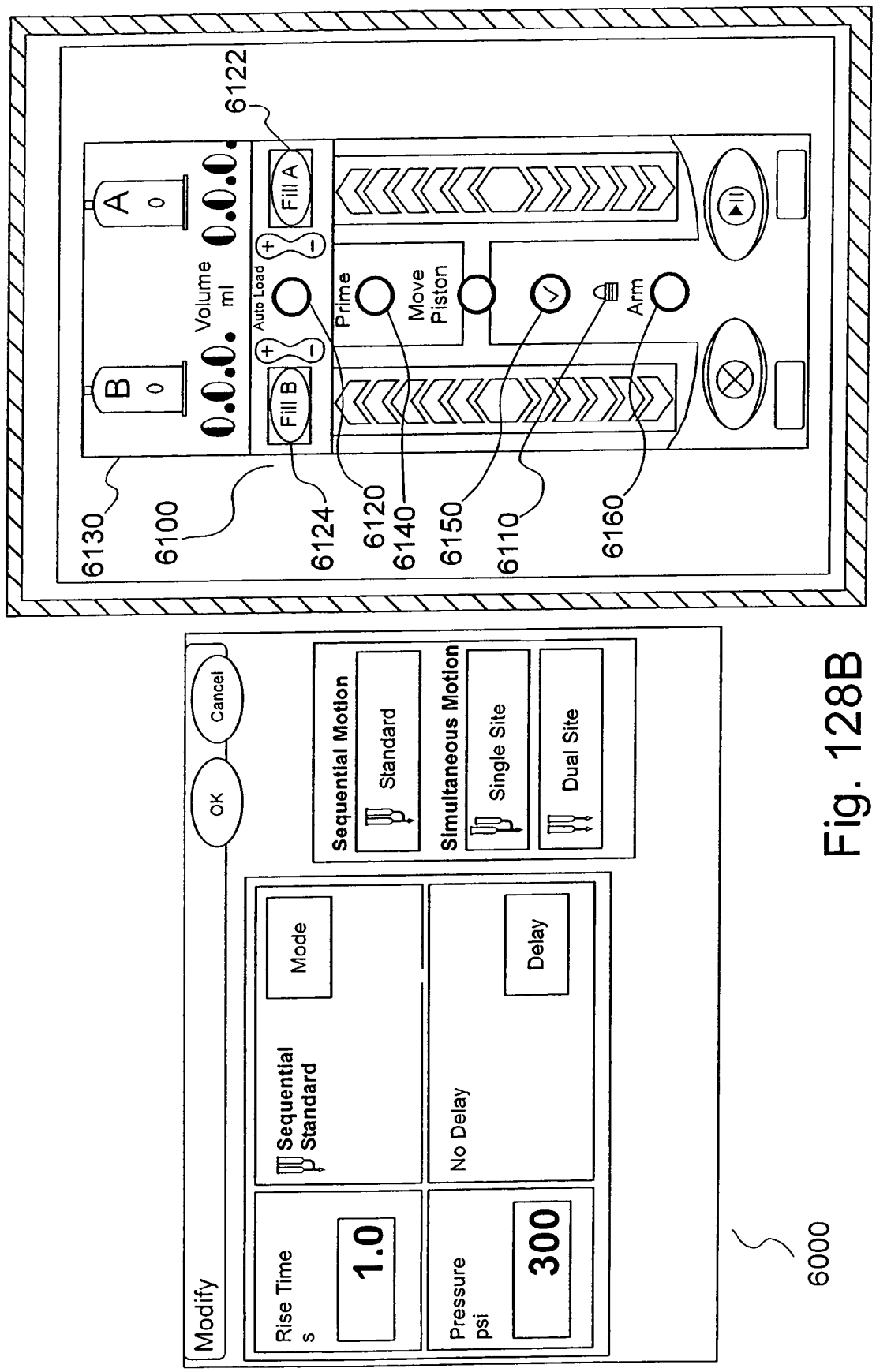
Figure 128C:
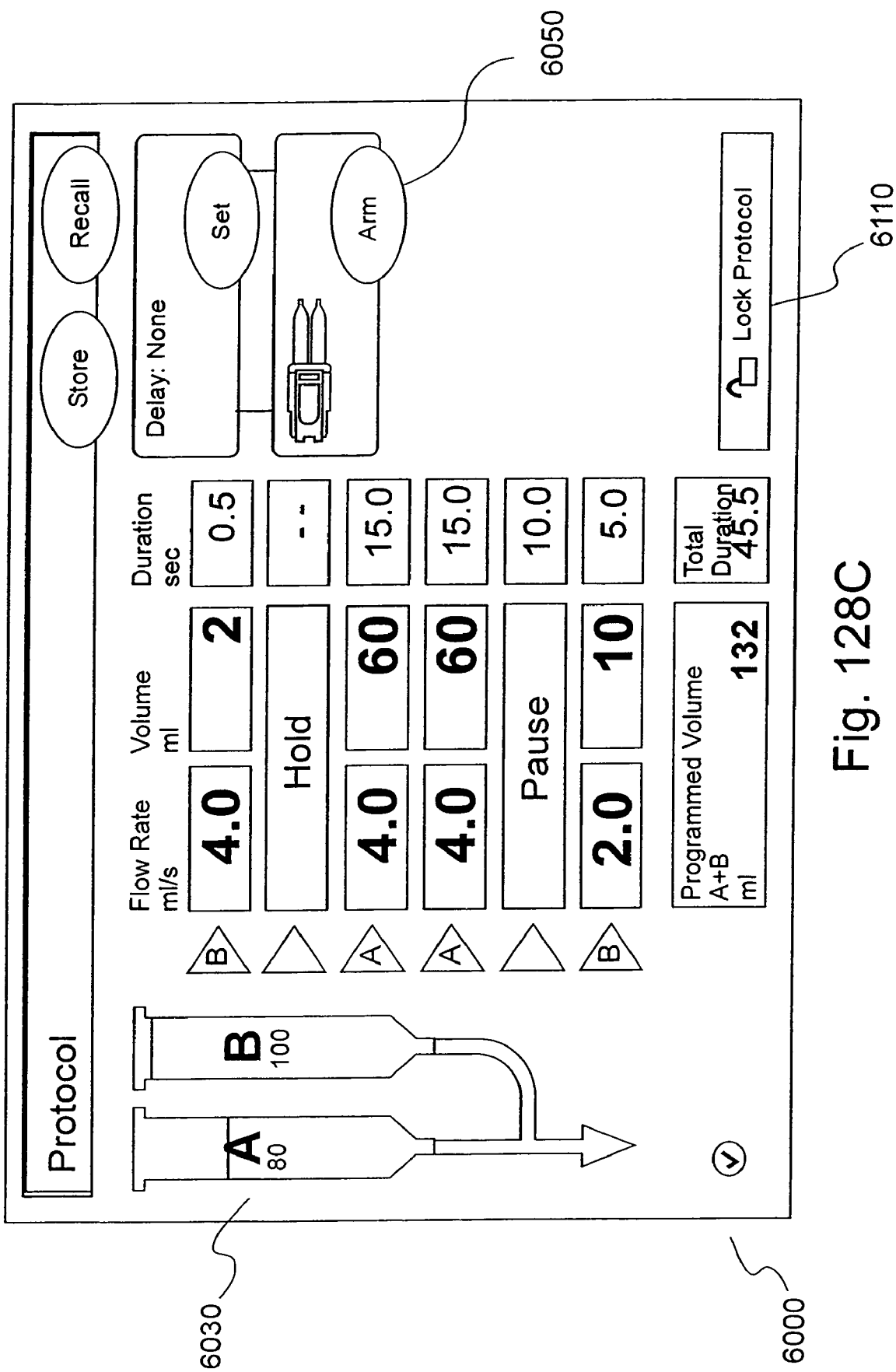
Figure 128D:
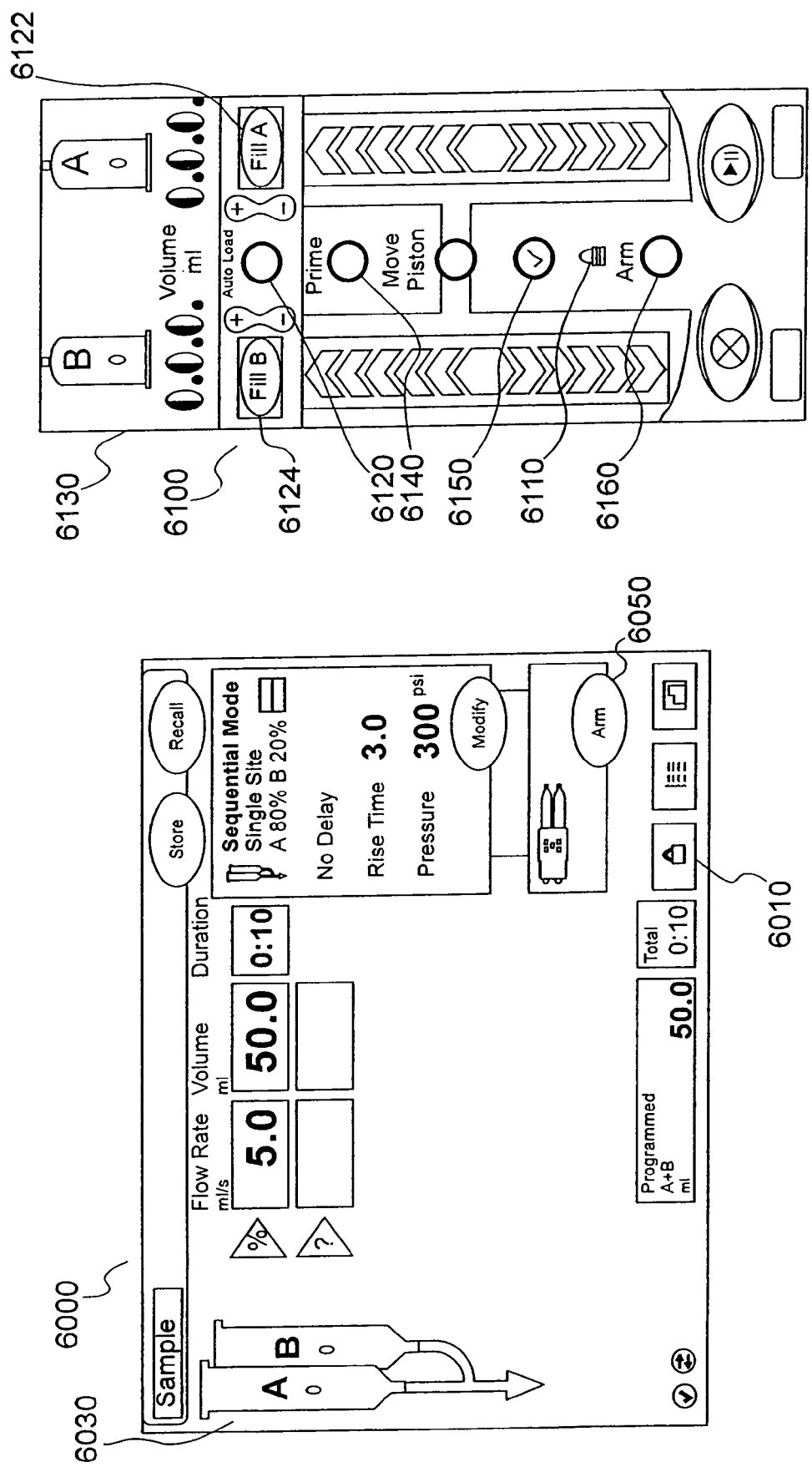
Figure 128E:
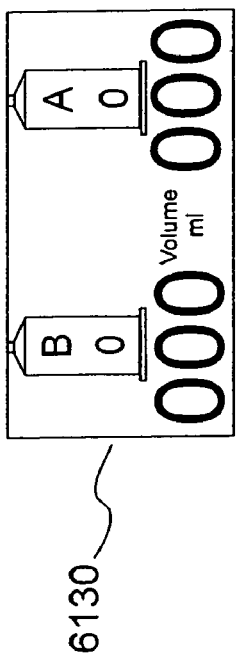
Figure 128F:
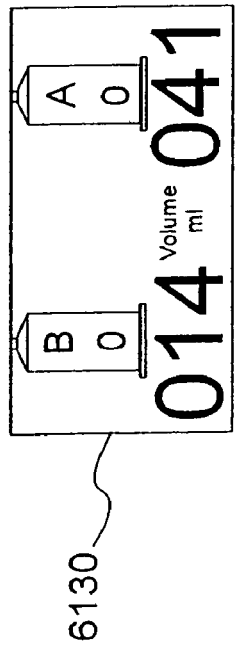
Figure 128G:
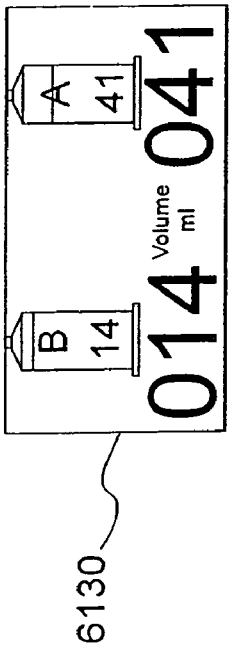
Figure 128H:
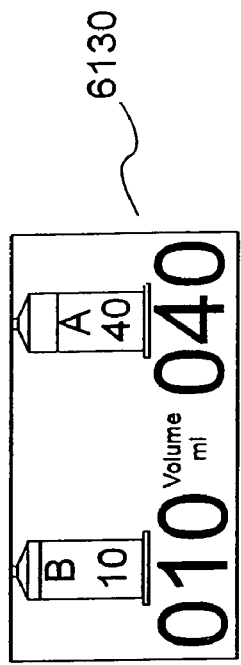
Figure 128I:
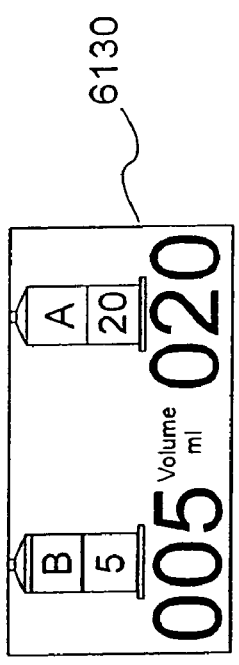
Figure 128J:
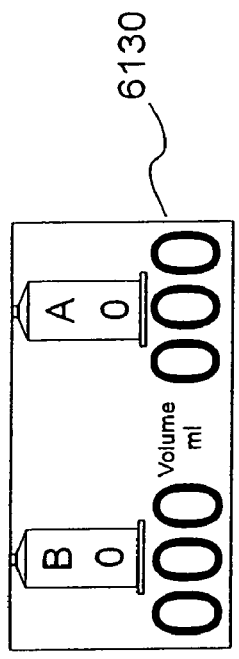
Figure 129A:
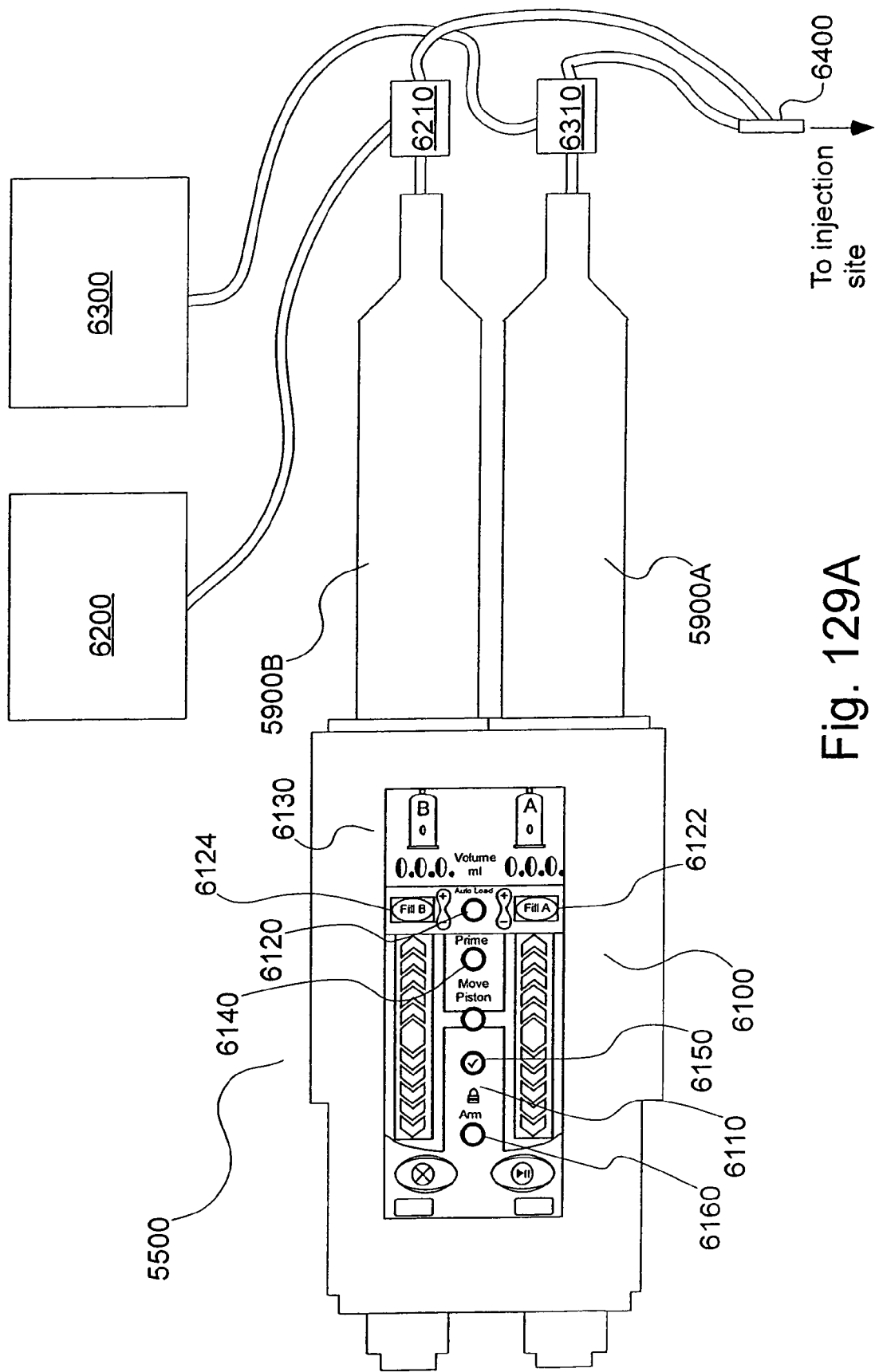
Figure 129B:
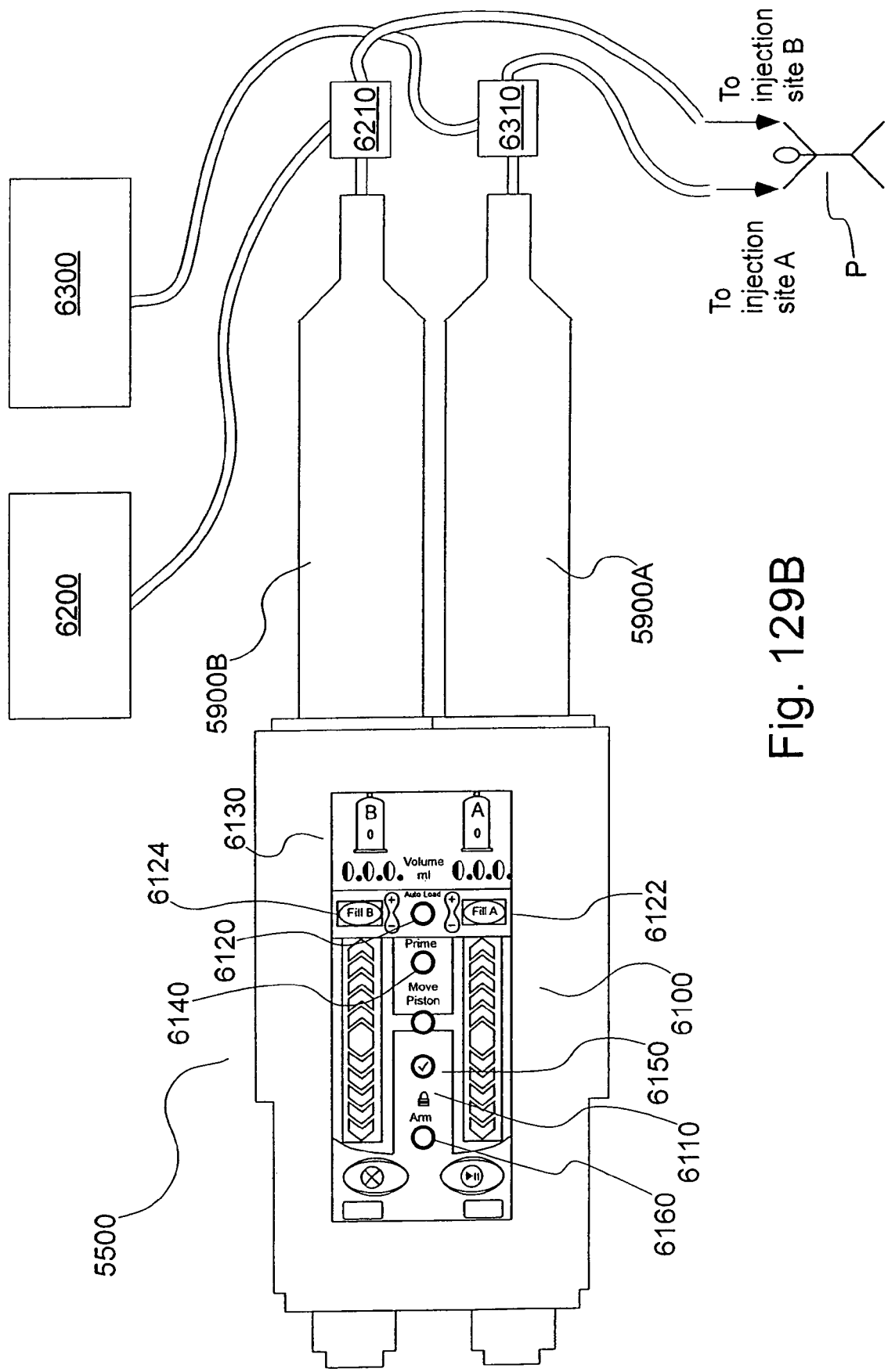

FIG. 83 is an exploded, isometric rear perspective illustration of the front end of the first preferred embodiment of the piston/plunger assembly of the present invention;

FIG. 84 is an exploded, isometric view of the same features of the piston/plunger assembly illustrated in FIG. 83, taken from a slightly different angle from the view shown in FIG. 83;

FIG. 85 is an isometric, front view illustration of the piston from the piston/plunger assembly illustrated in FIGS. 80-82;

FIG. 86 is an isometric, side view illustration of the piston illustrated in FIG. 85;

FIG. 87 is an isometric, front view illustration of the piston sleeve of the piston/plunger assembly shown in FIGS. 80-82;

FIG. 88 is an isometric illustration of the collar element of the piston/plunger assembly shown in FIGS. 80-82;

FIG. 89 is another isometric view of the collar depicted in FIG. 88;

FIG. 90 is a third isometric view of the collar element depicted in FIG. 88;

FIG. 91 is an isometric end view illustration of the gripper expander element of the first preferred embodiment of the piston/plunger assembly of the present invention;

FIG. 92 is a second isometric illustration of the gripper expander depicted in FIG. 91;

FIG. 93 is a third isometric illustration of the gripper expander depicted in FIGS. 91 and 92;

FIG. 94 is a first isometric illustration of one of the support ring grippers of the first preferred embodiment of the piston/plunger assembly of the present invention;

FIG. 95 is a second isometric illustration of the support ring gripper shown in FIG. 94;

FIG. 96 is another isometric illustration of the support ring gripper shown in FIGS. 94 and 95;

FIG. 97 is a first isometric illustration of the plunger cap element of the first preferred embodiment of the piston/plunger assembly of the present invention;

FIG. 98 is a second isometric illustration of the plunger cap shown in FIG. 97;

FIG. 99 is another isometric illustration of the plunger cap shown in FIGS. 97 and 98;

FIG. 100 is a fourth isometric illustration of the plunger cap element shown in FIGS. 97-99;

FIG. 101 is a first isometric illustration of the rubber cover support ring element of the first preferred embodiment of the piston/plunger assembly of the present invention;

FIG. 102 is a second isometric illustration of the rubber cover support ring element shown in FIG. 101;

FIG. 103 is a third isometric illustration of the rubber cover support ring element shown in FIGS. 101 and 102;

FIG. 104 is a fourth isometric illustration of the rubber cover support ring element depicted in FIGS. 101-103;

FIG. 105 is an isometric, side view illustration of the rubber cover of the plunger of the first preferred embodiment of the piston/plunger assembly of the present invention;

FIG. 106 is a second isometric illustration of the rubber cover shown in FIG. 105;

FIG. 107 is a side view schematic illustration of a portion of the first preferred embodiment of the piston/plunger assembly of the present invention, showing the interrelation of the piston, collar, gripper expander, support ring grippers and plunger cap thereof, the illustration showing the relationship of these elements when at rest or when the piston is moved toward the front end of the syringe;

FIG. 108 is a side view schematic illustration of the portion of the piston/plunger assembly depicted in FIG. 107, in this case showing the interrelation of the piston, collar, gripper expander, support ring grippers and plunger cap thereof when the piston is moved/retracted toward the rear end of the syringe;

FIG. 109 is a side view schematic illustration of a portion of the piston/plunger assembly and the syringe, showing the interrelation of the syringe, rubber cover, support ring grippers, and rubber cover support ring when the piston is moved/retracted toward the rear end of the syringe and the support ring grippers engage the rubber cover support ring;

FIG. 110 is an isometric illustration of an alternate embodiment of a rubber cover for use with a plunger of the present invention;

FIG. 111 is a side view illustration of the rubber cover illustrated in FIG. 110;

FIG. 112 is a top view illustration of the rubber cover illustrated in FIG. 110;

FIG. 113 is a cross-sectional illustration of the rubber cover depicted in FIG. 110;

FIG. 114 is an isometric, exploded illustration of an alternate embodiment of the syringe interface/release mechanism of the present invention;

FIG. 115 is an end-view, schematic illustration of another embodiment of the syringe interface/release mechanism of the present invention;

FIG. 116 is a cross-sectional illustration of an end portion of the second preferred embodiment of the syringe according to the present invention;

FIG. 117 is a cross-sectional illustration of an alternate embodiment of the syringe shown in FIG. 116;

FIG. 118 is a schematic representation of three embodiments of grooves that are provided in the rotating ring of the second preferred embodiment of the syringe interface/release mechanism of the present invention;

FIG. 119 is an isometric, exploded illustration of another embodiment of a syringe interface/release mechanism according to the teachings of the present invention;

FIG. 120 is an isometric, exploded illustration of still another embodiment of a syringe interface/release mechanism according to the teachings of the present invention;

FIG. 121 is a front view illustration of yet another embodiment of a syringe interface/release mechanism according to the teachings of the present invention;

FIG. 122 is a side view illustration of the syringe interface/release mechanism illustrated in FIG. 121;

FIG. 123 is an isometric, front view perspective of an alternate embodiment of the syringe shown in FIGS. 55-57;

FIG. 124 is an exploded, isometric, front view perspective of a third preferred embodiment of a front-loading syringe interface and syringe system in accordance with the present invention;

FIG. 125 is an exploded, isometric, rear view perspective of the syringe interface and syringe system shown in FIG. 124;

FIG. 126 is an isometric, front view perspective of a syringe incorporating syringe encoding;

FIG. 127A is a top, cross-sectional view of another embodiment of an injector of the present invention;

FIG. 127B is an enlarged, top cross-sectional view of a first syringe interface and a first piston of the injector of FIG. 127A to which a syringe is attached;

FIG. 127C is an enlarged, top cross-sectional view of a second syringe interface and a second piston of the injector of FIG. 127A to which a syringe adapter is attached;

FIG. 128A illustrates an embodiment of a control interface for a control room control unit and an embodiment of a control interface for a scan room control unit for the injector of FIG. 127A;

FIG. 128B illustrates several modes of injection provided by the control room interface of FIG. 128A;

FIG. 128C illustrates a protocol for a six-step sequential injection;

FIG. 128D illustrates a protocol for simultaneous injection of 40 ml of contrast and 10 ml of saline into a single injection site;

FIG. 128E illustrates the state of a scan room control interface display prior to initiation of auto loading for the protocol of FIG. 128D;

FIG. 128F illustrates the display of FIG. 128E after initiation of auto loading;

FIG. 128G illustrates the display of FIG. 128E after the syringes are filled;

FIG. 128H illustrates the display of FIG. 128E after auto priming;

FIG. 128I illustrates the display of FIG. 128E half way through the injection procedure;

FIG. 128J illustrates the display of FIG. 128E after the injection procedure has been completed;

FIG. 129A illustrates an embodiment of an injector system incorporating the scan room control interface of FIG. 128A;

FIG. 129B illustrates the injector system of FIG. 129A including a fluid path for simultaneous injection from multiple syringes into different injection sites on a patient; and FIGS. 130A-130I are various exploded, perspective and cross-sectional views of an embodiment of a syringe plunger and injector piston interface system of the present invention.

DETAILED DESCRIPTION OF THE INVENTION

Figure 1:
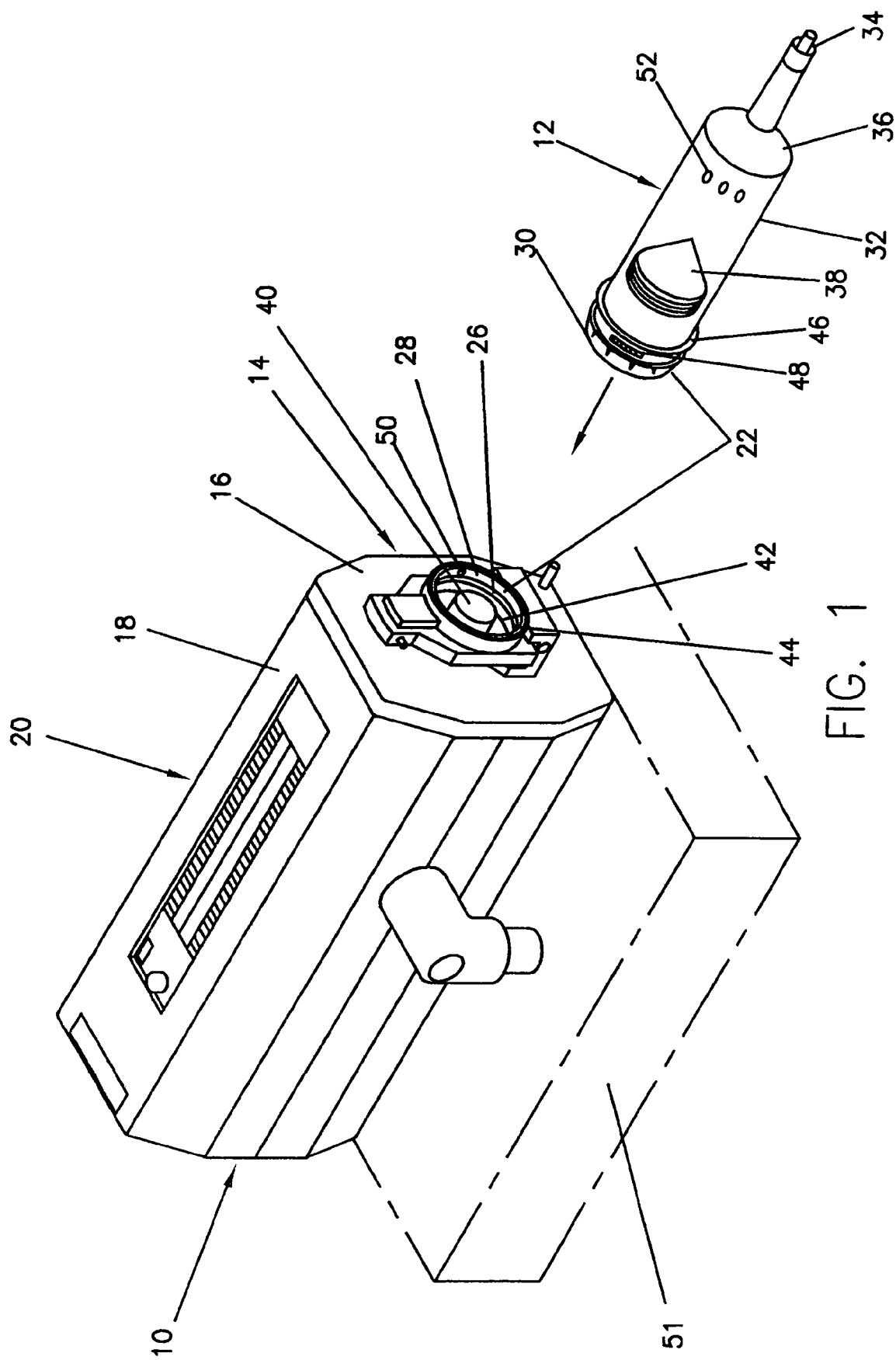
FIG. 1 is a perspective view of an injector apparatus in accordance with the present invention, showing an injector housing and a syringe in a disassembled relationship.

FIG. 1 discloses an injector apparatus 10 of the general type disclosed in U.S. Pat. No. 5,383,858 for injecting a liquid contrast media into a vascular system of an animal. Injector apparatus 10 has a front-loading construction. The apparatus of FIG. 1 utilizes a syringe 12 capable of being front-loaded into a mounting assembly 14 associated with a front wall 16 of a housing 18 of an injector 20 by a first releasable mechanism 22. Syringe 12 is capable of functioning in an injection operation without the use of a pressure jacket (although the syringe may be used in an injector with a pressure jacket, as will be described in greater detail in connection with FIGS. 4 and 5, below). To the extent not inconsistent with this disclosure, the disclosure of the '858 patent, which is assigned to Medrad, Inc., the Assignee of the subject application, is incorporated herein by reference.

With reference to FIG. 1 and the first releasable mechanism 22, the mounting assembly 14 is provided with an essentially cylindrical interface 26 for receiving a rearward end of syringe 12. Interface 26 includes an annular surface 28, which may be cylindrical or conically tapered. As best shown in FIGS. 6 and 7, annular surface 28 includes a distal ledge 29, which is engaged by tabs 30 on the rearward end of syringe 12. Syringe 12 is inserted into cylindrical interface 26 until tabs 30 engage ledge 29 to secure syringe 12 to the injector 20.

Among other things, tabs 30 distribute the attachment force of syringe 12 to ledge 29 equally around the syringe. This helps to maintain a connection between syringe 12 and ledge 29 even if syringe 12 deforms or "ovals" under pressure during use. This overcomes a potential shortfall with conventional front-loading injector systems, which may not function as well if the syringe ovals under pressure during use.

Referring again to FIG. 1, syringe 12 comprises an elongated main tubular body or barrel 32 and a coaxial discharge injection section 34, interconnected by an intermediate conical portion 36. A plunger 38 is slidably positioned within the tubular body 32 and is connectable to a second releasable mechanism 40 on a piston 42 in the injector housing 18. Second releasable mechanism 40 is formed in part by plunger 38 and in part by piston 42, as set forth in greater detail below.

Piston 42 and plunger 38 cooperate to eject fluid contained within syringe 12 in a desired quantity and at a desired rate. Second releasable mechanism 40 is designed to facilitate axial movement of plunger 38 in either direction when actuated. Second releasable mechanism 40 is also designed to engage or disengage plunger 38 from piston 42 no matter where plunger 38 sits in tubular body 32. Further in this connection, the actuating mechanism, which reciprocates the plunger 38 in the syringe tubular body 32, comprises piston 42 or a reciprocable drive member. The drive member or piston 42, while reciprocable, does not need to be rotatable.

Figure 2:
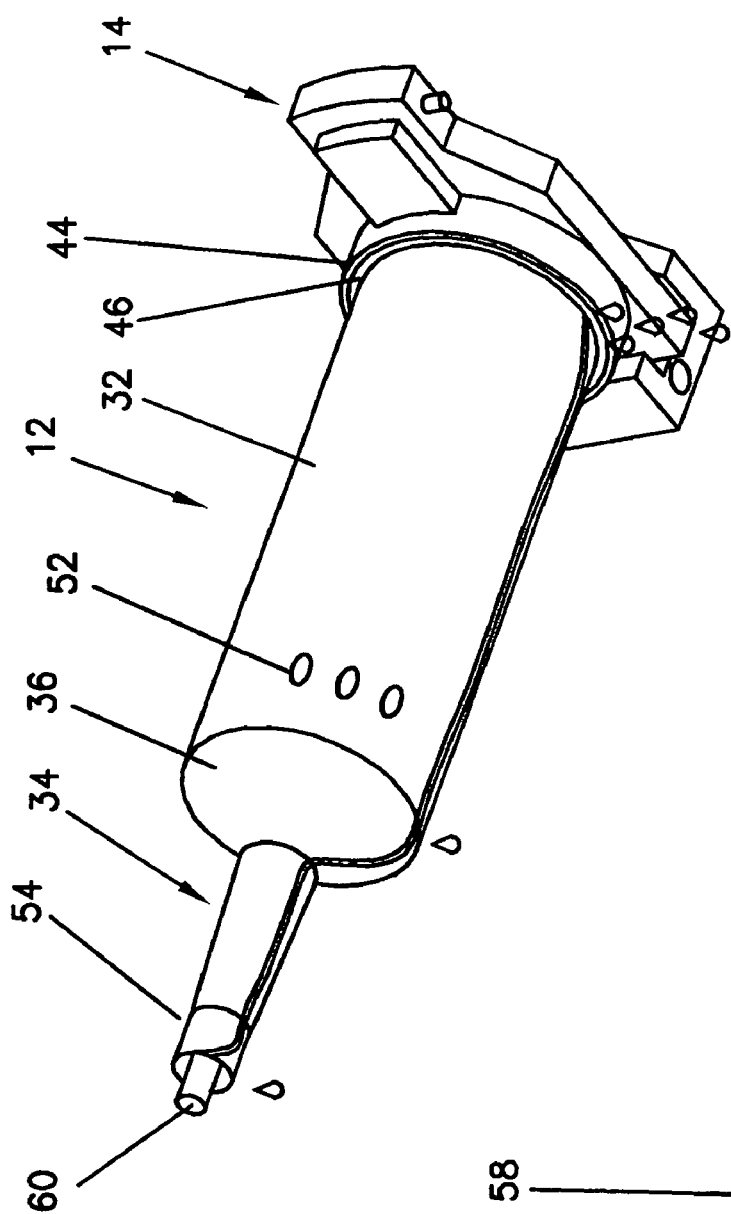
FIG. 2 is an enlarged perspective view of the syringe illustrated in FIG. 1, shown connected to a front wall of the injector housing, illustrating how a flange disposed at a rearward end of the syringe may prevent leaking fluid from entering the injector housing.

With reference to FIG. 1, to be mounted, syringe 32 is inserted into interface 26 in mounting assembly 14. As best shown in FIGS. 6 and 7, tabs 30 initially move past annular surface 28 where they engage ledge 29 to securely hold syringe 12 to mounting assembly 14. As best shown in FIGS. 2 and 7, mounting assembly 14 further includes a forwardly projecting annular ring or collar 44, which functions to assure perpendicular engagement between plunger 38 and piston 42. As explained above, forwardly projecting annular ring or collar 44 also functions as a seal between a flange 46 on syringe 32 and mounting assembly 14.

Resilient annular sealing flange 46 surrounds tubular body 32 of syringe 12 and is disposed forward of tabs 30 a preselected distance essentially equal to a width of annular surface 28. Thus, when syringe 12 is inserted into interface 26 in mounting assembly 14 until sealing flange 46 engages annular ring 44, annular ring 44 and flange 46 create a seal between syringe 12 and mounting assembly 14.

The foregoing mounting arrangement possesses a number of advantages. The attachment of tabs 30 to the periphery of the rearward portion of syringe 12 minimizes wobble of syringe 12 during an injection operation. While minimizing wobble, tabs 30 also permit syringe 12 to rotate freely within interface 26. Tabs 30 also prevent syringe 12 from disengaging from injector 20. The seal between annular ring 44 and flange 46 also prevents contrast media spilled from discharge end 34 of syringe 12 from flowing into injector housing 18 (as illustrated in FIG. 2) and eliminates the need for constructing the respective parts to excessively tight tolerances. To enhance the sealing capability between flange 46 and annular ring 44, a suitable O-ring (not shown) may be provided optionally therebetween.

With further reference to FIG. 1, the apparatus also includes a system for transmitting syringe information from syringe 12 to an injector controller 51. Syringe 12 is provided with an encoding device 48 forward of tabs 30 but rearward of flange 46. Encoding device 48 may be a bar code or any other suitable encoding device known to those skilled in the art. When attaching syringe 12 to the mounting assembly 14, if syringe 12 is rotated after tabs 30 engage ledge 29, a sensor 50 is provided in annular surface 28 to read the encoding device 48. Sensor 50 then forwards the associated signals to injector controller 51, which interprets the signals and modifies the function of the injector 20 accordingly. Examples of the information which could be encoded on encoding device 48 include dimensions of syringe 12, volume of syringe 12, content of syringe 12 (in the case of a pre-filled syringe), manufacturing information such as lot numbers, dates and tool cavity number, recommended contrast media flow rates and pressures, and loading/injection sequences.

As an alternative to encoding device 48 being a bar code, encoding device 48 also could include machine-readable raised or recessed surfaces. The raised or recessed surfaces could then be read by injector sensor 50, mounted in annular surface 28, in a manner similar to that for reading a bar code. In addition to encoding device 48, one might also use a mechanically readable device (e.g. a slot, hole, or projection on the syringe 12 or plunger 38) to register against a switch on the mounting assembly 14. Alternatively, an optically readable device (e.g. characters, dots and other geometric shapes)

could be employed to send information concerning the type of syringe used to the intelligent circuits of injector 20.

In FIG. 1, since syringe 12 is being used in this embodiment without a pressure jacket, for strength and visibility of the contents of syringe 12, the syringe 12 may be formed of a clear PET polyester material. In the alternative, the wall of syringe 12 may be formed of polypropylene reinforced by providing a series of annular ribs on tubular body 32 of syringe 12 in longitudinally spaced relationship. (This arrangement is illustrated in FIG. 5 of the '858 patent.) As discussed in the '858 patent, by suitably spacing the ribs along the length of tubular body 32, such as in equal increments, the ribs also can perform the dual function of serving as volumetric gradations for the purpose of indicating the amount of contrast media in syringe 12.

With reference to FIGS. 1 and 2, tubular body 32 of syringe 12 also may be provided with an indicating mechanism 52 for readily detecting the presence or absence of a liquid contrast media in syringe 12. In this instance, detecting mechanism 52 includes a plurality of integrally molded, textured dots on syringe 12, which provide a visual indication of whether the syringe contains liquid or air. More specifically, when viewed against an air background, dots 52 appear oval-shaped, but when viewed against a liquid contrast media background, which has a different index of refraction than air, dots 52 appear circular. The details of indicating mechanism 52 are described in detail in U.S. Pat. No. 4,452,251, assigned to Medrad, Inc., the Assignee of the subject application. To the extent not inconsistent with the present disclosure, the contents of U.S. Pat. No. 4,452,251 are incorporated herein by reference.

Figure 3:
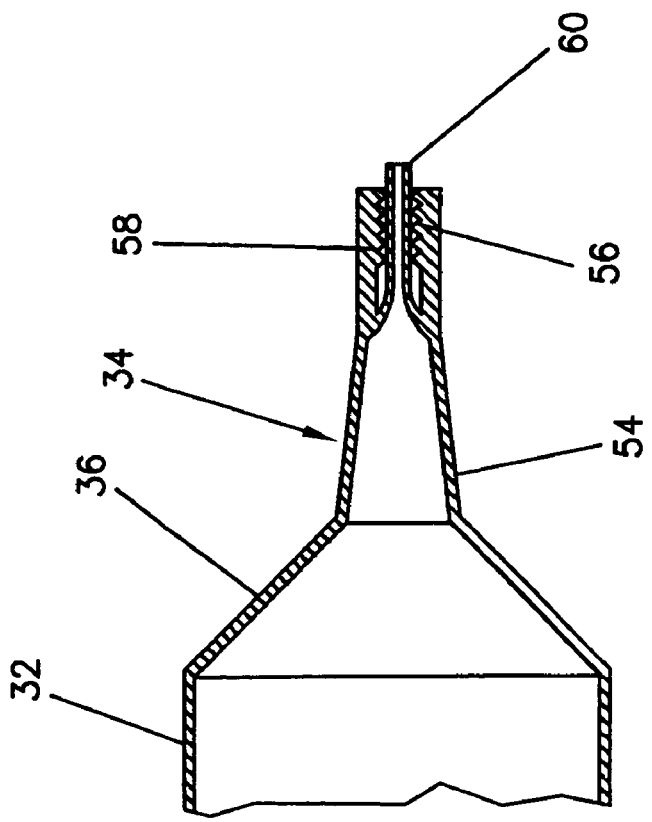
FIG. 3 is an enlarged cross-sectional view of the syringe shown in FIGS. 1 and 2, illustrating the construction of a forward end of the syringe.

FIG. 3 illustrates the internal construction of the syringe discharge end 34. Specifically, while a rearward portion 54 of discharge end 34 is of tapered conical construction, a forward connector portion 56 is of generally cylindrical construction and formed with internal screw threads 58 for attaching a connecting tube to discharge end 34. Further, an injection nozzle 60 of reduced diameter is disposed within the screw-threaded cylindrical connector portion 56 and is integrally molded with tapered rearward portion 54 of discharge end 34 adjacent the point at which the tapered and cylindrical portions merge together.

FIGS. 4 and 5 illustrate an alternate embodiment of the present invention in which a front-loading syringe 112 is mounted on the front of a pressure jacket 170, preferably formed of a strong clear plastic, such as polycarbonate. Pressure jacket 170 is in the form of an elongated tubular member that is suitably mounted at its rearward end in a mounting assembly 124 on housing front wall 116, by fitting the flange of pressure jacket 170 into the collar on the mounting assembly 124. Pressure jacket 170 also has a forward open end 172 for receiving the syringe 112.

In this embodiment, an annular surface 174 with a distal ledge 175 is provided adjacent to the forward open end 172 of the pressure jacket 170. Annular surface 174 is similar in construction to annular surface 28 in the embodiment illustrated in FIGS. 1 and 7. Similarly, a tubular body 132 of syringe 112 includes tabs 180 at a position adjacent its forward end for engagement with ledge 175 when tubular body 132 has been inserted into pressure jacket 170.

In addition, at the forward end of syringe 112, on opposite sides of a discharge end 134, a pair of reinforcing, loop-shaped handles 162, for facilitating handling of the syringe 112, is integrally molded with discharge end 134 and a tapered conical intermediate portion 136. In other respects, while not specifically disclosed and described, it is to be understood that various other features of the embodiment of the invention disclosed in FIGS. 1-3, 6 and 7 may be incorporated into the embodiment of FIGS. 4 and 5, as desired.

In use, the syringe 112 of FIGS. 4 and 5 may be mounted in pressure jacket 170 with piston 142 of injector 120 either in a retracted position, as shown in FIG. 4, or in an advanced position, as shown in FIG. 5. For example, with piston 142 in the retracted position, as shown in FIG. 4, plunger 138 is disposed at the rearward end of syringe 112. Syringe 112 then is inserted into the open end 172 of the forward end of pressure jacket 170 until second releasable mechanism 140 engages with plunger 138.

In FIG. 5, in which piston 142 is in a forward position, the mounting of syringe 112 into pressure jacket 170 is the same as shown in FIG. 4, except that plunger 138 also is in its forward position in syringe 112. In other respects, the mounting of syringe 112 on pressure jacket 170 is essentially the same as previously described with respect to FIG. 4. However, having syringe plunger 138 and piston 142 in their forward positions, as shown in FIG. 5, has several advantages over the rearward position arrangement of FIG. 4. For example, because syringe plunger 138 and piston 142 are already in their forward positions, it is not necessary to move them forward to expel air from the syringe 112 in preparation for a syringe-filling operation. Rather, plunger 138 and piston 142 can immediately be retracted to aspirate fluid into the syringe 112. Similarly, after an injection operation has been completed, additional time is saved by not having to retract plunger 138 and piston 142 in preparation for a next injection operation.

In summary, a new and improved system by which an injection syringe, such as syringe 12 in the embodiment of FIGS. 1-3, can be readily mounted upon and/or removed from injector housing 18, has been disclosed. For this purpose, the first releasable mechanism 22, by which syringe 12 is attached to or removed from injector housing 18, and second releasable mechanism 40, by which plunger 38 of syringe 12 is drivingly connected to or released from piston 42 of injector 20 cooperate to produce their respective connections and disconnections simultaneously and/or independently. Another advantage is that plunger 38 is capable of being placed in a driven or undriven state at any point along its path, whereby syringe 12 may be disengaged from injector 20 without having to retract piston 42, or having to first disconnect syringe 12 from a patient being injected before retracting piston 42.

Other desirable features of the invention include the construction of first releasable mechanism 22, in which syringe 12 is mounted upon injector housing 18 with a secure fit, which is advantageous from the standpoint of minimizing syringe wobble and disengagement during an injection operation, and eliminating the need for excessively tight manufacturing tolerances. Encoding device 48 on syringe 12, in cooperation with sensor 50 on injector 20, also is advantageous from the standpoint of providing "custom programming" of injector 20. Elimination of a pressure jacket also is desirable from the standpoint of better visibility of the contents of syringe 12, better heat transfer to the syringe contents and decreased cleaning and maintenance otherwise needed due to, e.g., scratching or contamination with contrast media of the pressure jacket.

In order to eliminate the need for a pressure jacket, syringe 12 also may be made of a relatively strong clear plastic, or may be provided with annular reinforcing ribs (not shown), which may be spaced to function as volumetric gradations. Further, detection of the presence of air in syringe 12 is facilitated by the indicating mechanism 52 in FIGS. 1 and 2, in the form of dots 52 molded into syringe tubular body 32.

Dots 52 appear visually as either oval-shaped or circular, depending upon whether the tubular body contains air or liquid, respectively. In addition to functioning as a part of first releasable mechanism 22 for syringe 12, syringe resilient annular flange 46 also cooperates with annular ring 44 to create a seal to prevent contrast media spilled from the injection end of syringe 12, from flowing into injector 20, as shown in FIG. 2. The embodiment of the invention shown in FIGS. 4 and 5 provides a system by which various other advantages, including time savings in syringe-filling and syringe-changing operations, can be achieved utilizing a pressure jacket, such as pressure jacket 170 mounted on injector housing front wall 116.

Figure 8:
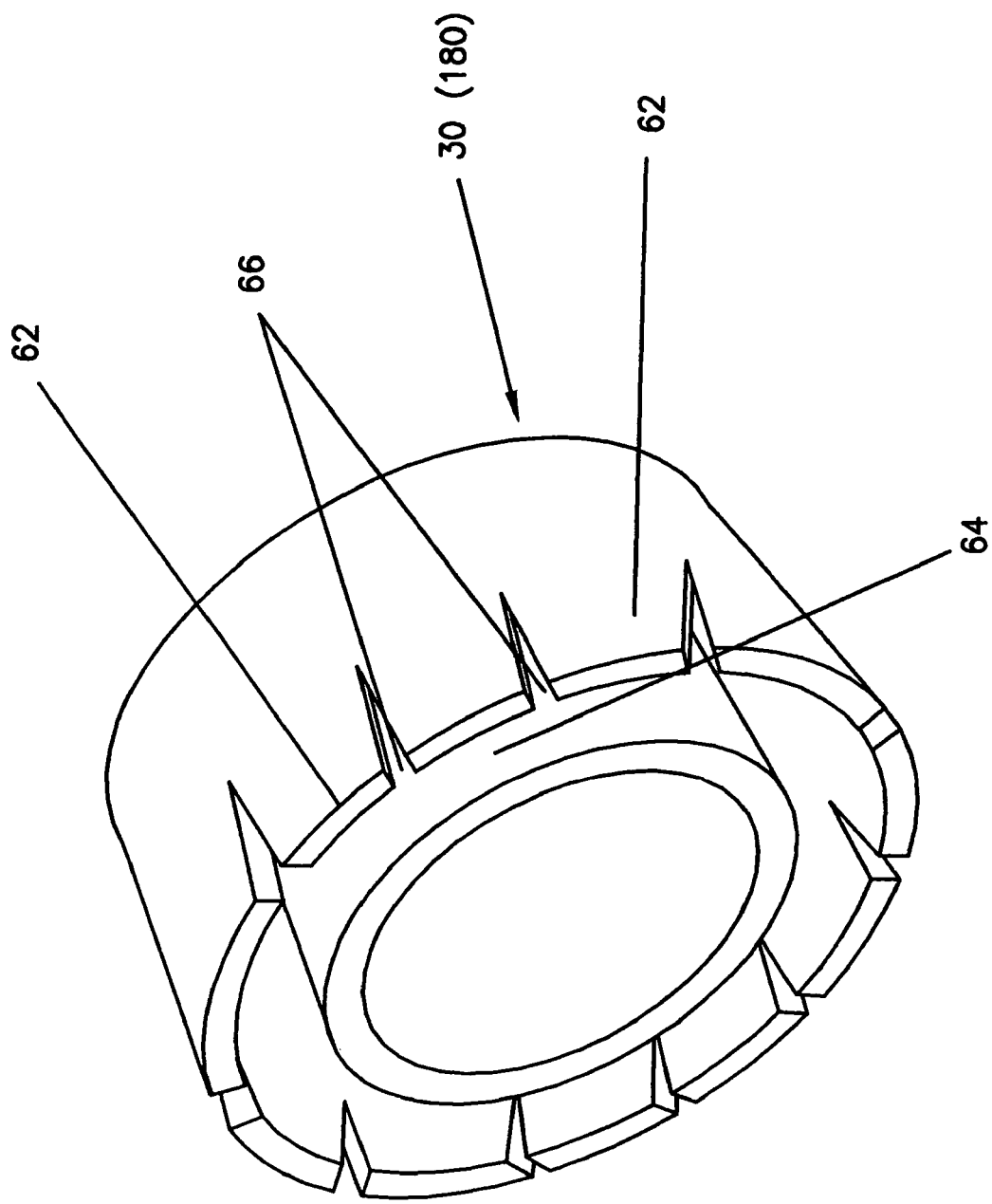
FIG. 8 is an enlarged perspective view of the tabs illustrated in FIG. 7 that are connected to the rearward end of the syringe illustrated in FIG. 1.

FIG. 6 illustrates a cross-section of syringe 12 after it has been inserted into injector 20 so that tabs 30 engage ledge 29. Tabs 30 are preferably substantially V-shaped members that preferably form a ring encircling the rearward end of tubular body 32. Alternately, one or more tabs may be separately disposed around the rearward end of the body 32. Each of tabs 30 on the ring has a first end 62 and a second end 64. (An enlarged, perspective illustration of the ring of tabs 30 is shown in FIG. 8.) As shown in FIG. 8, first ends 62 of tabs 30 engage ledge 29 when syringe 12 is inserted into interface 26 of injector 20. First ends 62 of tabs 30 are separated from one another by gaps 66 around the periphery of tubular body 32 so that they are flexible and can easily compress. Second ends 64 of tabs 30, on the other hand, form a ring that attaches to tubular body 32.

Syringe 12, therefore, is easily connected to the injector 20 simply by inserting the rearward end of tubular body 32 into cylindrical interface 26. During insertion of tubular body 32 into cylindrical interface 26, annular surface 28 compress first ends 62 of tabs 30 until first tabs 62 clear ledge 29. Once first ends 62 clear ledge 29, they spring open and engage ledge 29 to prevent the removal of tubular body 32 from interface 26.

Removal of syringe 12 from housing 20 is enabled by a reciprocating collar 68 that is disposed within injector 20 at a location behind syringe 12 (once inserted into cylindrical interface 26). Reciprocating collar 68 is preferably a cylindrical member that can move in both forward and rearward directions, as illustrated by the arrow in FIG. 7. During an injection operation, reciprocating collar 68 is in its rest position behind tabs 30 so that first ends 62 remain engaged with ledge 29. Upon completion of the injection operation, in order to remove syringe 12 from interface 26, reciprocating collar 68 is pushed forward toward ledge 29 by an actuating mechanism (not shown) or manually so that it compresses first ends 62 so that they can easily slide out from behind ledge 29. Syringe 12 then can be easily removed from injector 20.

Figure 33:
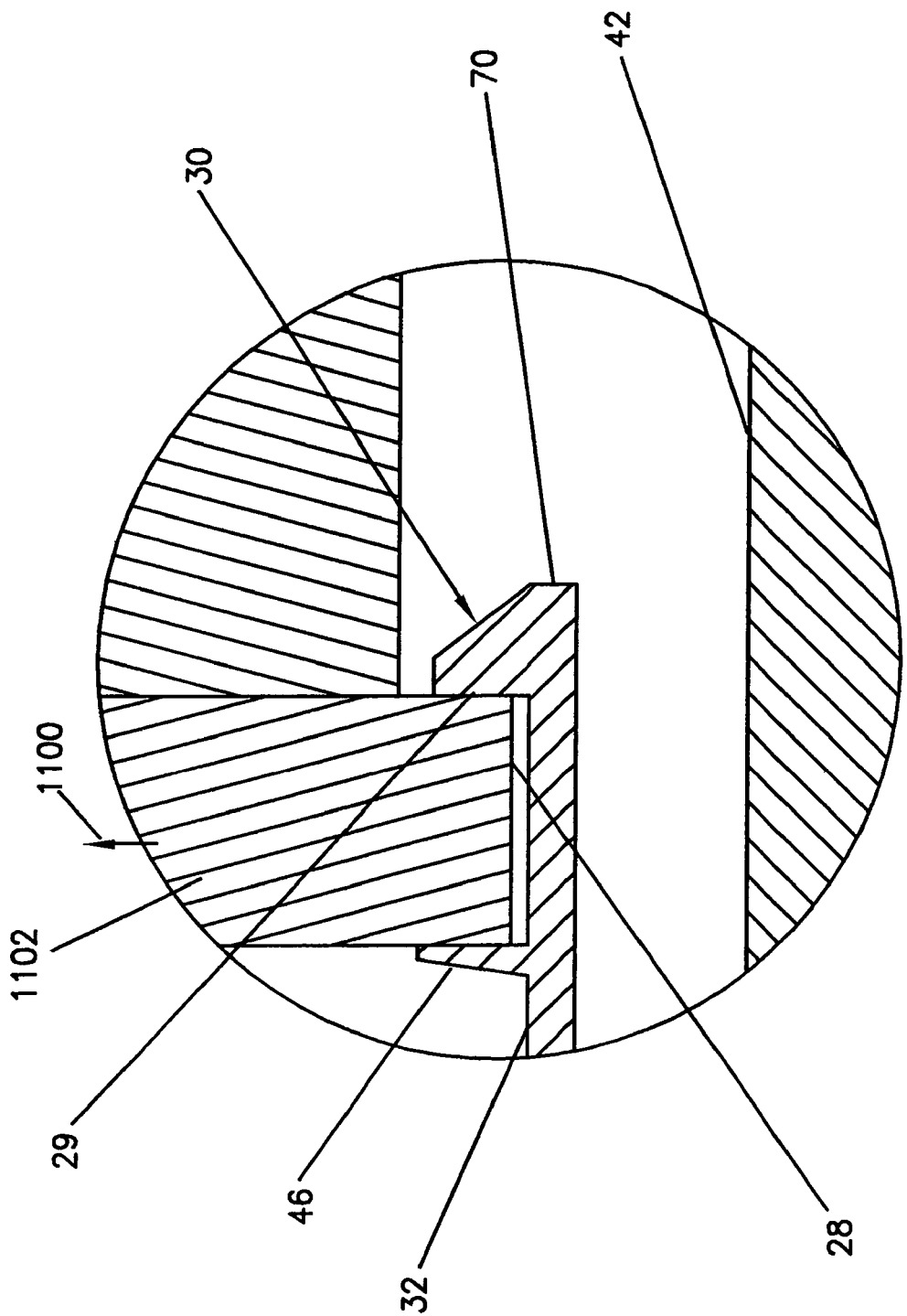
FIG. 33 is an enlarged cross-sectional view of an alternate embodiment of the apparatus shown in FIG. 7.
Figure 34:
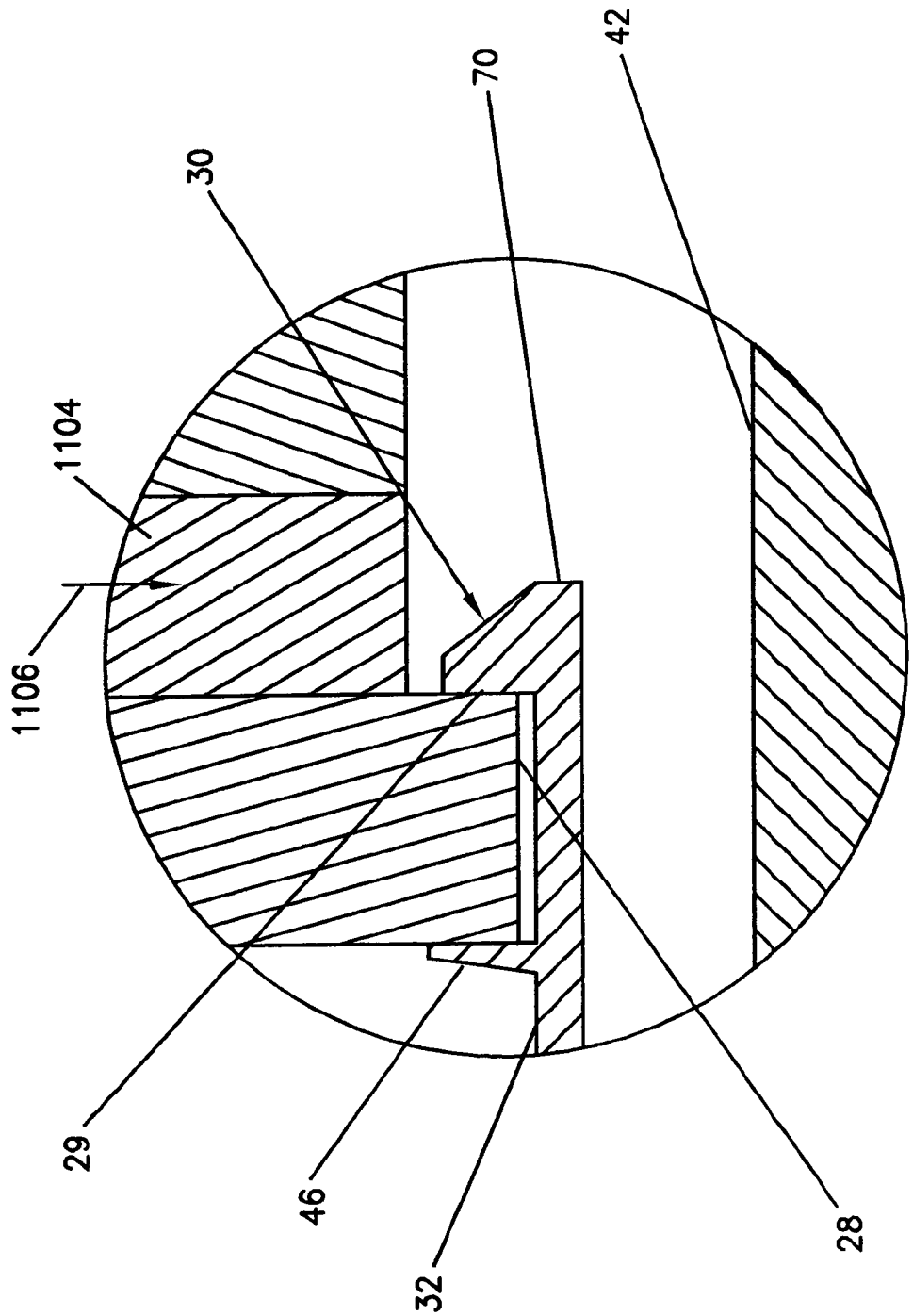
FIG. 34 is an enlarged cross-sectional view of the alternate embodiment of the apparatus shown in FIG. 33.

Alternatively, tabs 30 may be caused to disengage from ledge 29 by retracting annular surface 28 in the direction of arrow 1100 in FIG. 33. To do this, annular surface 28 is made of a number of segments 1102, all of which can retract to release syringe 32. In still another alternative embodiment as illustrated in FIG. 34, a portion of the inner surface 1104 may be moved inwardly in the direction indicated by arrow 1106 to collapse tabs 30 so that syringe 32 may be disengaged from ledge 29. Other embodiments of these two arrangements will be readily understood by those skilled in the art.

In the case where syringe 112 is to be inserted into a pressure jacket 170 (as illustrated in FIGS. 4 and 5), tabs 180 serve the same function as tabs 30, except of course that they are located toward the forward end of syringe 112. In fact, but for the location of tabs 180 on tubular body 132, it is contemplated for the present invention that tabs 180 have the same construction as tabs 30. When tabs 180 are inserted through open end 172 of pressure jacket 170, annular surface 174 compresses first ends 62 of tabs 180 until they clear ledge 175. Syringe 112 is then securely held in place. When it becomes necessary to remove syringe 112 from pressure jacket 170, a reciprocating collar 68 extends forward within the pressure jacket 170 (as described in more detail below) to compress first ends 62 so that they no longer engage ledge 174. Syringe 112 can then be removed from pressure jacket 170.

Figure 9:
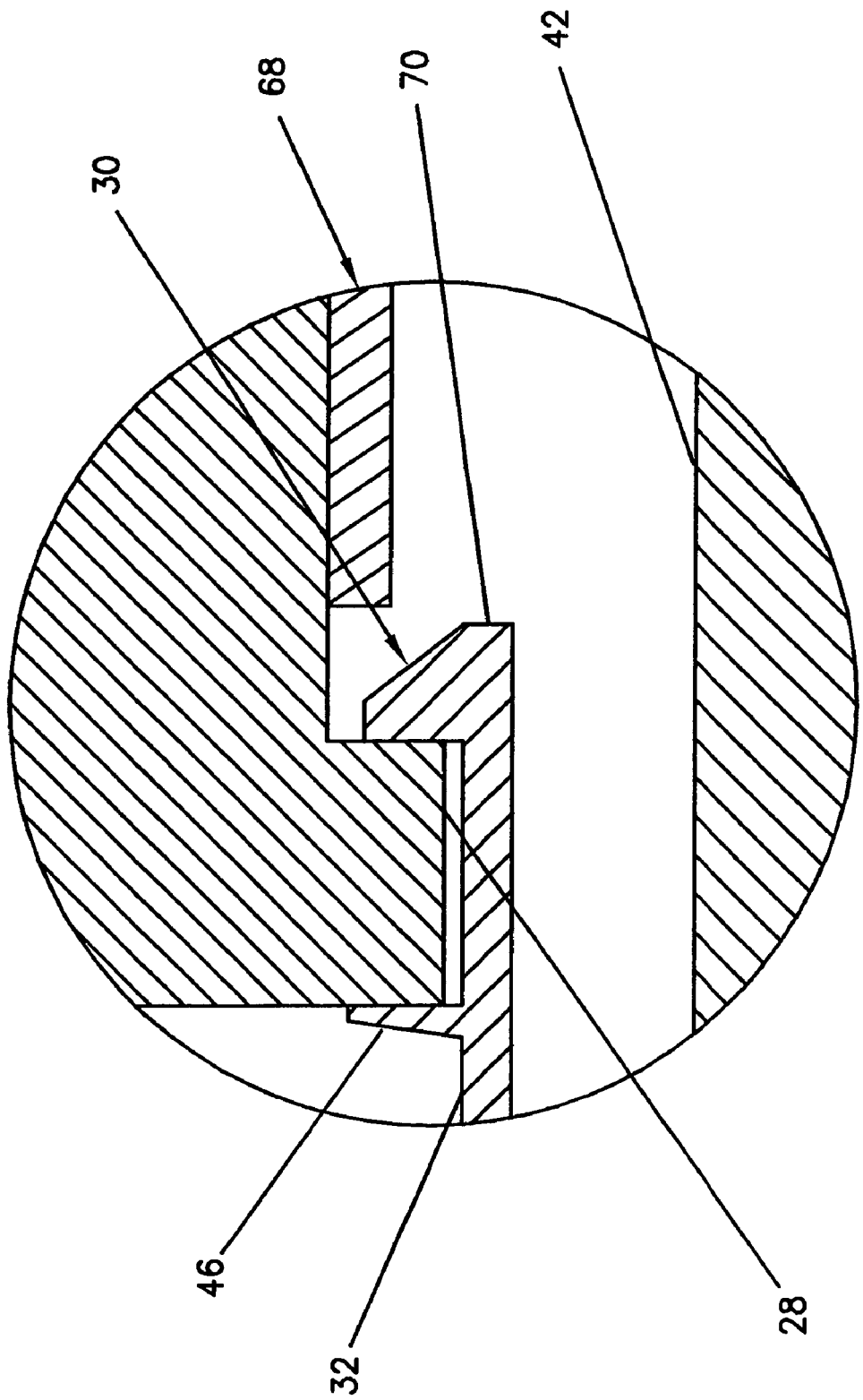
FIG. 9 is an enlarged cross-section of an alternate embodiment of tabs attached at the rearward end of a syringe for engagement with a front wall of an injector, showing essentially the same structures illustrated in FIG. 7.

It is not necessary for tabs 30, 180 to have a V-shaped appearance as illustrated in FIGS. 1 and 4-8, however. It is contemplated for the second embodiment of tabs 30 that they have a b-shaped appearance, as illustrated in FIG. 9. When tabs 30 have a b-shaped appearance, they may be formed integrally with the end of syringe 412. Tabs 30, when they have a b-shaped appearance, have bulbous first ends 70 that extend outwardly from second ends 72, which are separated from adjacent tabs 30 by gaps 71 (as best shown in FIGS. 14 and 15). As with first ends 62, first ends 70 engage ledge 29 when syringe has been inserted into injector housing 18. As with first ends 62, reciprocating collar 68 acts upon first ends 70 to disengage them from ledge 29 when syringe 412 is to be removed from injector 20.

For each of the embodiments of tabs 30 contemplated by the present invention, it is also contemplated that the number of tabs used may be varied while remaining within the scope of the present invention. For example, for syringe 212, illustrated in FIGS. 10 and 11, it is contemplated that only one tab is provided at the end of the syringe. In FIGS. 10 and 11, only one tab 30 with first end 70 and second end 72 is illustrated. It should be understood, however, that tab 30 with first end 62 and second end 64 could be easily substituted therefor.

While a single tab 30 may be used, preferably the syringe has at least two tabs, because the tabs should flex in order to function optimally. Such a syringe 312, with at least two tabs, is illustrated in FIGS. 12 and 13. When two tabs are included on syringe 312, it is contemplated that they be disposed on opposite sides of tubular body 32 to add stability to the secure engagement of syringe 312 to injector 20. The tabs may be appropriately sized and optionally may be of different circumferential dimension.

Figure 32:
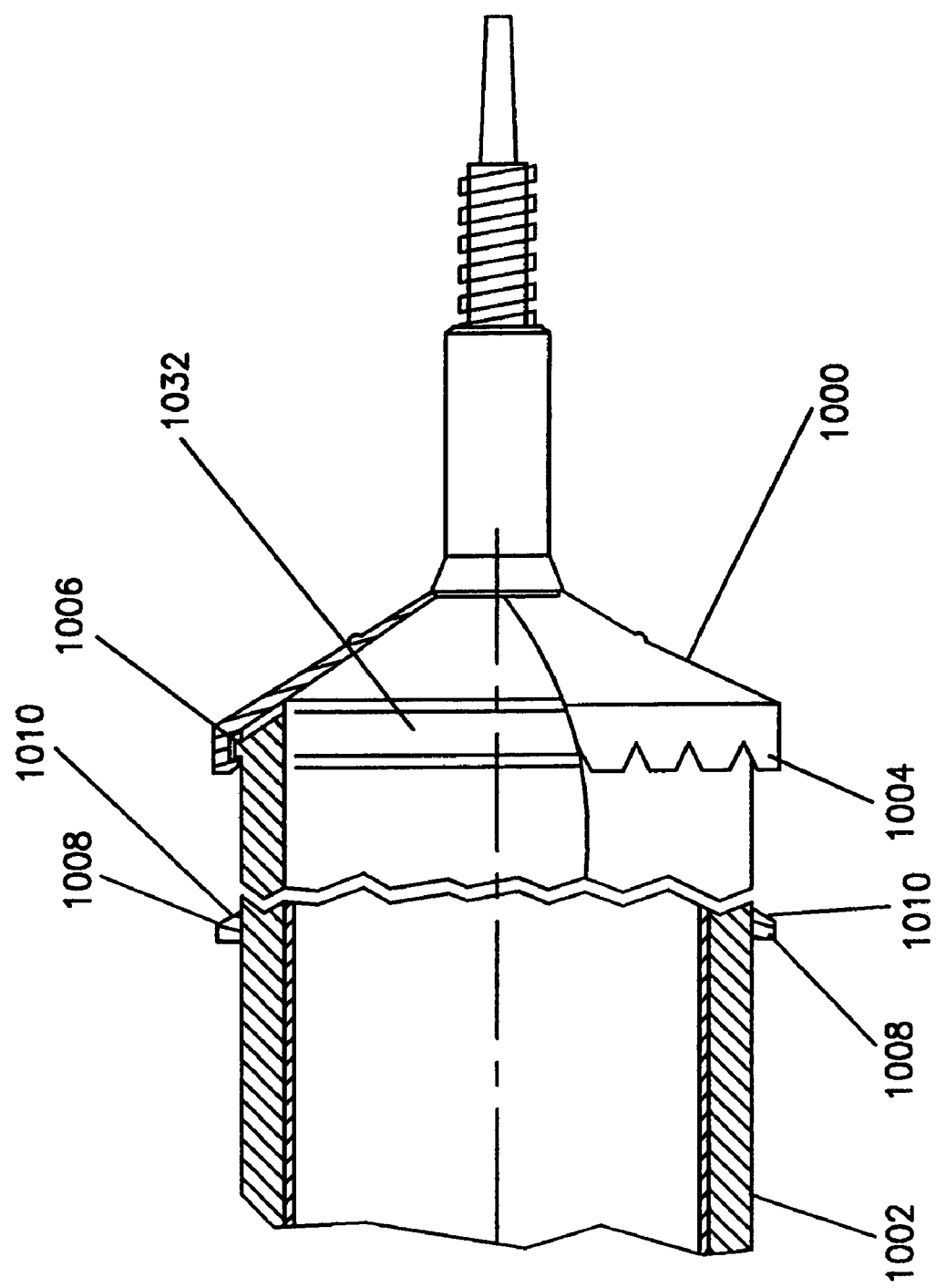
FIG. 32 is a side view illustration of an alternate embodiment of the present invention where tabs are added to a syringe cap that engages the end of a pressure jacket.

In an alternate embodiment of the pressure-jacketed injector system shown in FIG. 32, it is contemplated that a syringe cap 1000 could be provided at the end of the pressure jacket 1002 to hold a syringe 1032 therein. Alternately, cap 1000 could be attached to or molded as a part of syringe 1032 and need not be a separate element. As shown in FIG. 32, pressure jacket 1002 is a modified version of pressure jacket 170 illustrated in FIGS. 4 and 5. According to the teachings of the present invention, cap 1000 includes tabs 1004 about its periphery. Tabs 1004 engage a ridge 1006 that encircles the end of pressure jacket 1002. To disengage tabs 1004 from ridge 1006, a reciprocating ring 1008 slides along the exterior of pressure jacket 1002. Ring 1008 includes a tapered surface 1010 to facilitate removal of tabs 1004 from ridge 1006. The actuator of ring 1008 is not shown. However, those skilled in the art will readily recognize that ring 1008 may be operated either manually, mechanically, or electrically (or in any other fashion suitable to disengage tabs 1004 from ridge 1006).

In another alternate embodiment of the apparatus described in relation to FIG. 32, the tabs could extend from the cap (which could be separate from, attached to, or molded with the syringe) to engage annular member 174 at the end of pressure jacket 170 in the same way that tabs 180 engage annular member 174 in the embodiment illustrated in FIGS. 4 and 5. As with the embodiment illustrated and described in relation to FIGS. 4 and 5, a reciprocating collar should then be positioned within pressure jacket 170 to disengage the tabs from the annular member.

The elements for the releasing mechanism are illustrated in FIGS. 38 and 39. There, reciprocating collar 1402 is shown internal to pressure jacket 170. As illustrated, reciprocating collar 1402 is disposed at the end of at least two supports 1404 that are also within the interior of pressure jacket 170. To accommodate supports 1404, interior wall 1406 of pressure jacket 170 includes at least two tracks 1408 in which supports 1404 slide. When syringe 1032 is to be removed from pressure jacket 170, reciprocating collar 1402 is moved forward within pressure jacket 170 to disengage the tabs on syringe 1032 from engagement with annular member 174.

This arrangement also may be used in connection with the pressure jacket system illustrated and described in connection with FIGS. 4 and 5. When syringe 132 is to be removed from pressure jacket 170, reciprocating collar 1402 is moved forward within pressure jacket 170 to compress tabs 180 so that they no longer engage annular member 174. Once tabs 180 are clear of annular member 174, syringe 132 may be removed from pressure jacket 170.

In the case where syringe 112 is to be inserted into pressure jacket 170 as shown in FIGS. 4 and 5, b-shaped tabs 190 may be added to the forward end of syringe 112 in the same manner that tabs 180 were applied. As shown in FIG. 16, tabs 190 essentially comprise a ring 74 from which second ends 72 of tabs 190 extend in a rearward direction. Ring 74 with tabs 190 form a V-shaped structure in cross-section, as illustrated in FIG. 17. As with tabs 180, when tabs 190 are inserted into pressure jacket 170 (as illustrated in FIGS. 4 and 5), they are compressed until they clear annular surface 174, whereupon they expand to engage ledge 175. Tabs 190 hold syringe 112 securely in pressure jacket 170 until disengaged by reciprocating collar 68.

Figure 18:
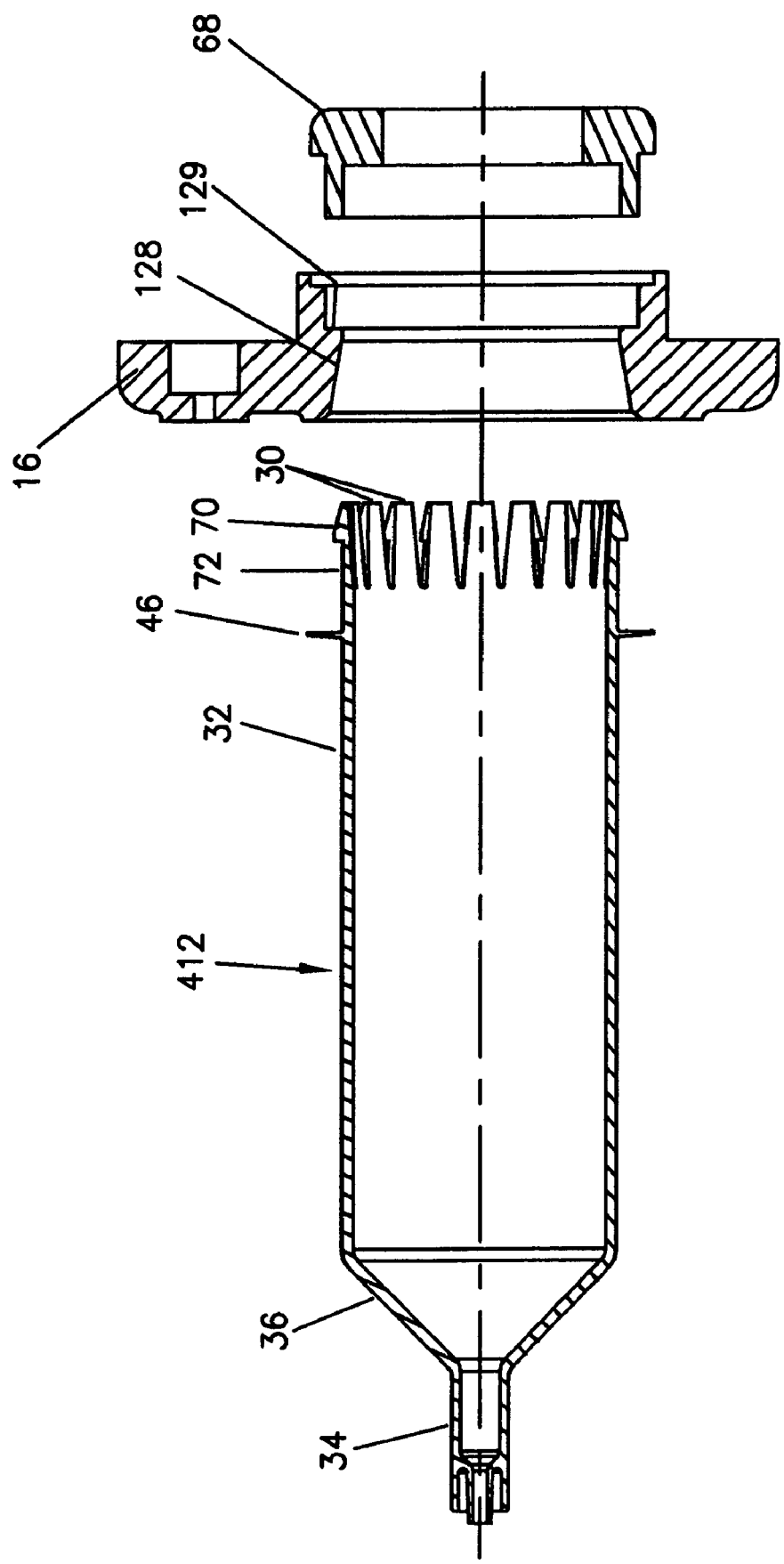
FIG. 18 is a cross-sectional view of the syringe illustrated in FIGS. 14 and 15 with a portion of a front wall of an injector housing, showing a ledge that is securely engaged by tabs at the base of the syringe, and also showing a reciprocating collar that disengages the tabs from the ledge.
Figure 19:
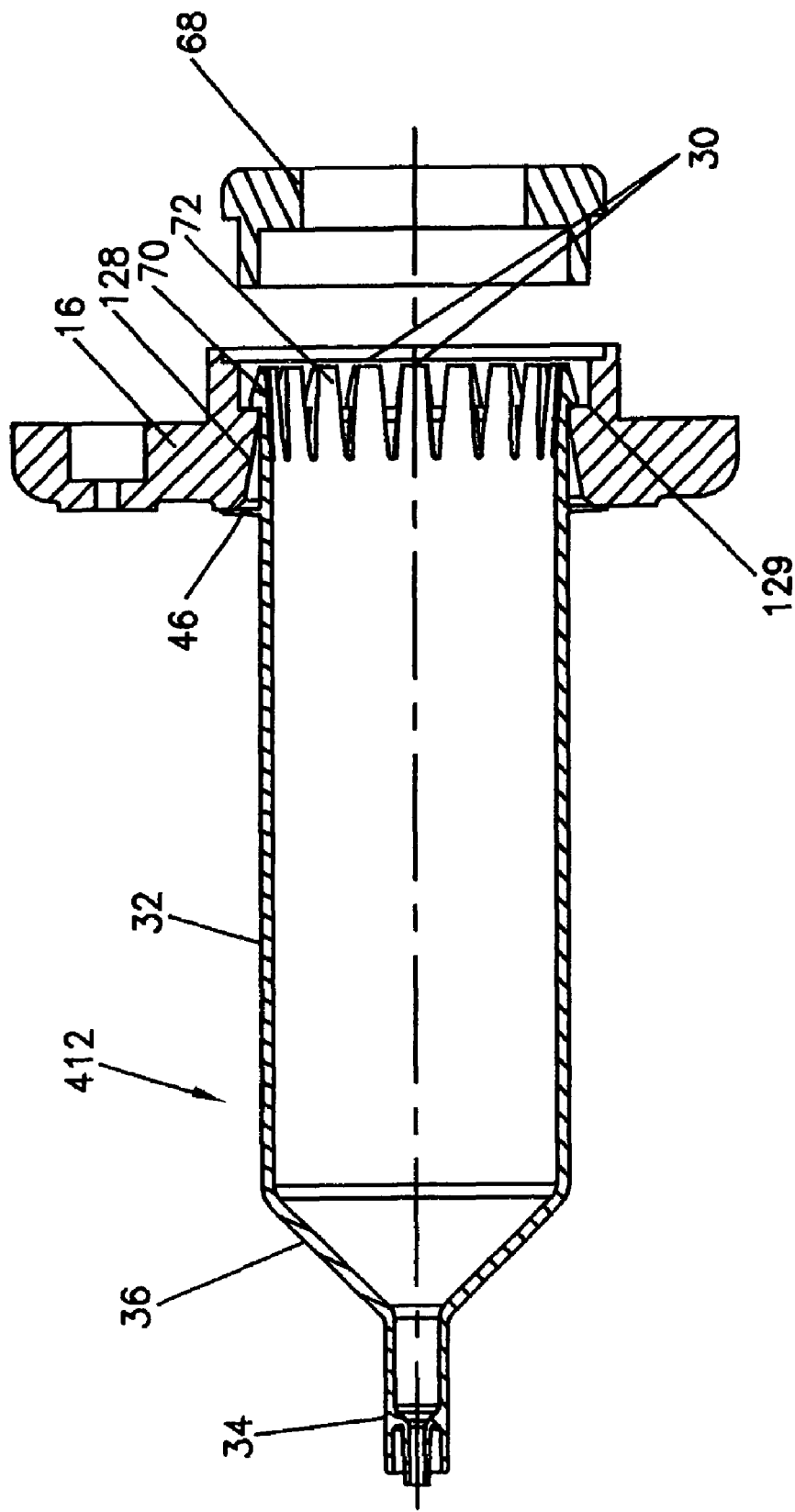
FIG. 19 is a cross-sectional illustration of the embodiment illustrated in FIG. 18, showing the tabs engaging the ledge so that the syringe securely engages the injector housing.
Figure 20:
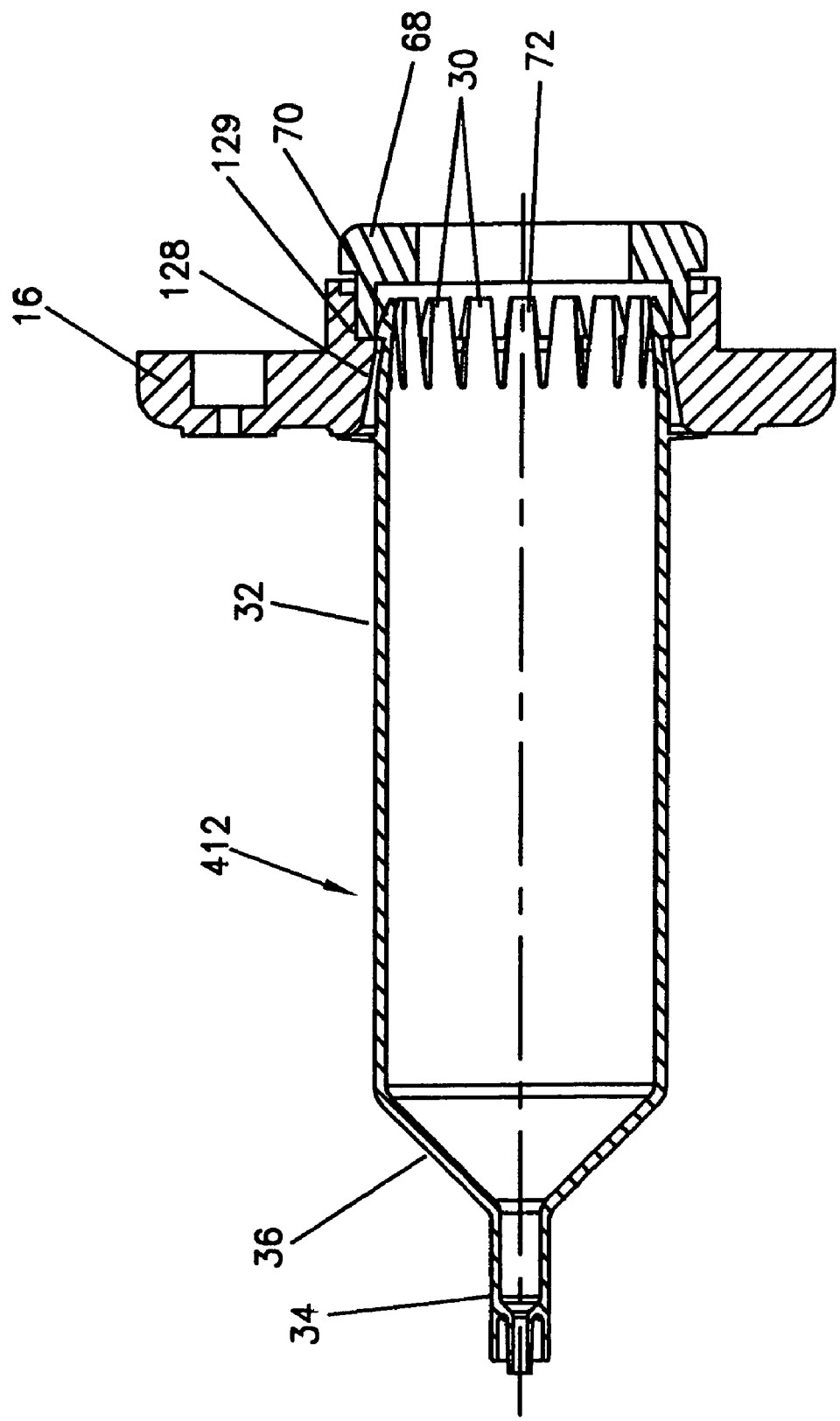
FIG. 20 is a cross-sectional illustration of the embodiment shown in FIGS. 18 and 19, showing the engagement of the reciprocating collar with the tabs to disengage them from the ledge of the injector housing.

The installation and removal of syringe 412 is illustrated in FIGS. 18-20. In FIG. 18, syringe 412 is shown prior to insertion into injector front wall 16. Reciprocating collar 68 is shown in a rest state behind where first ends 70 of tabs 30 will rest after they clear annular surface 128 and rest against distal ledge 129. In this embodiment, annular surface 128 is illustrated with a tapered cross-section rather than the cylindrical cross-section shown in FIGS. 7 and 9. A tapered cross-section may facilitate insertion of syringe 412 into interface 26 because the taper may help to squeeze first ends 70 of tabs 30 during insertion of syringe 412 into injector 20. In addition, annular surface 128, when tapered, acts as a guiding surface for syringe 412 (or any other embodiment disclosed) so that syringe 412 may be inserted into front wall 16 at even greater angular approaches. In other words, syringe 412 may be inserted easily into front wall 16 even when syringe 412 is not oriented exactly with the central axis of interface 26.

Once syringe 412 has been fully inserted into front wall 16, tabs 30 expand to engage ledge 129, as illustrated in FIG. 19. Syringe 412 is then securely held in place. As shown in FIG. 19, reciprocating collar 68 remains in its rest position until after the injection operation is completed.

After the injection operation is completed, reciprocating collar 68 is moved forward to compress first ends 70 of tabs 30 to disengage tabs 30 from ledge 129. FIG. 20 shows reciprocating collar 68 in this forward position. The compression of tabs 30 is also illustrated. The syringe 412 may then be removed from injector 20.

The present invention also contemplates that it may be desirable to connect a syringe to an adapter 500 before connecting the syringe to injector 20. The adapters could be disposable or re-useable, as would be understood by those skilled in the art. The syringe may be of different construction from that disclosed herein, as would be understood by those skilled in the art. An adapter for a syringe is described in U.S. Pat. No. 5,535,746, issued to Hoover et al. on Jul. 16, 1996, the disclosure of which is incorporated herein by reference. Other patents that are exemplary of adapters include U.S. Pat. No. 5,520,653 and WO 97/36635, both of which are assigned to the Assignee of the present application and are incorporated herein by reference.

Figure 21:
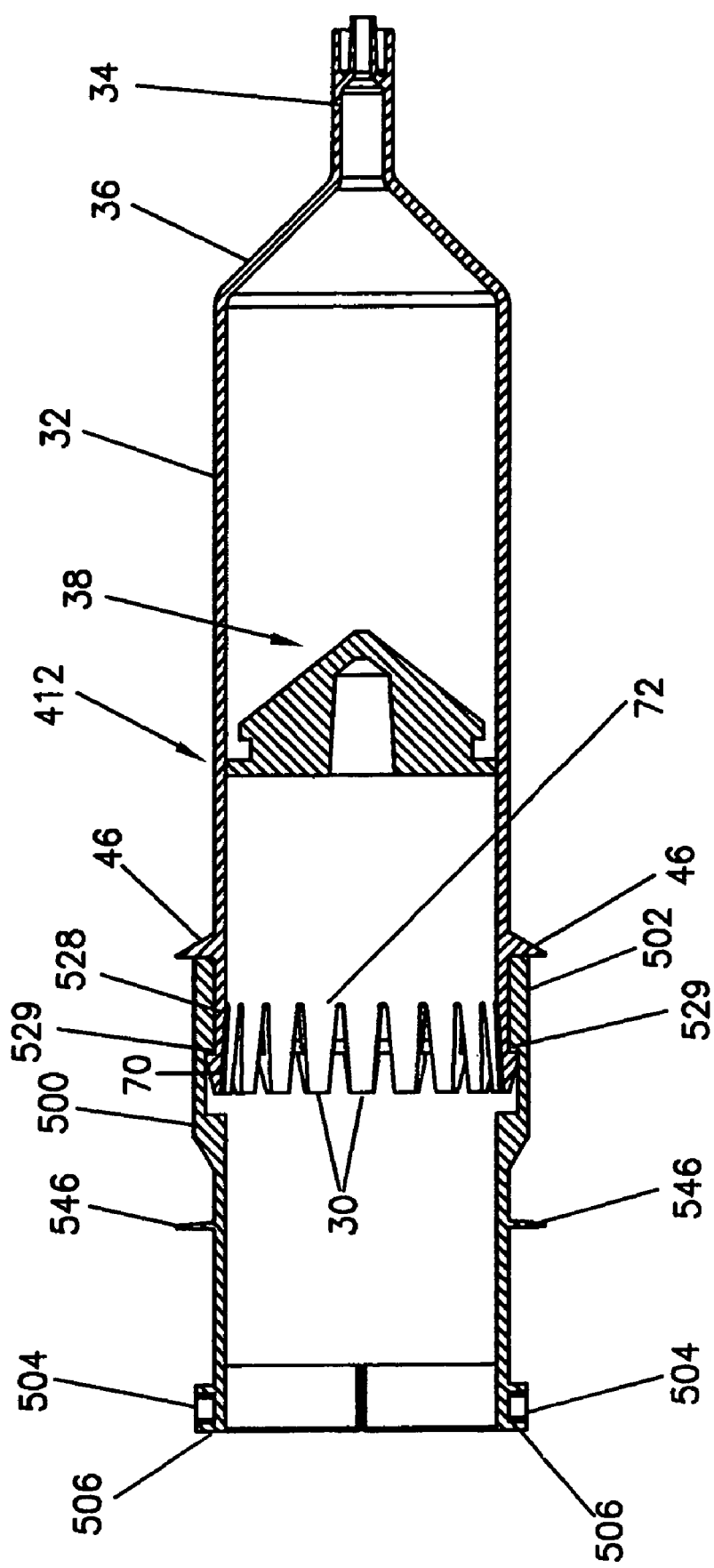
FIG. 21 is a cross-sectional view of an adapter assembly connected to the syringe illustrated in FIGS. 14 and 15.

In the embodiment illustrated in FIG. 21, a syringe 412 with tabs 30 having a b-shaped appearance snap-fits into a forward end 502 of adapter 500. Of course, tabs with the V-shaped cross-section may be substituted therefor. Adapter 500 includes an annular surface 528 with a distal ledge 529 within its forward end 502 to which first ends 70 of tabs 30 engage to hold syringe 412 securely in place. Flange 46 of syringe 412 may or may not be included to engage with forward end 502 of adapter 500 to prevent contrast medium, should it leak, from entering injector housing 18 through adapter 500. The rearward end 504 of adapter 500 also preferably includes a flange 546 that mates with annular ring 44 on mounting assembly 14 of injector 20. Flange 546 serves the same function as flange 46 on syringe 12, namely to prevent contrast medium (or whatever fluid is included in syringe) from entering the injector 20.

If adapter 500 is attached to syringe 32, piston 42 may need to be adapted to accommodate the increased length of the overall construction. If so, a piston extender or adapter (not shown) may be attached to the end of piston 42, as would be understood by those skilled in the art. Alternatively, piston 42 could be constructed so that it is long enough to accommodate syringes 32 of varying lengths.

In this particular embodiment, adapter 500 includes conventional connector elements 506, such as those described in U.S. Pat. Nos. 5,535,746 or 5,383,858. So designed, adapter 500 permits syringe 412 to be connected to an injector that is designed to accept only syringes with conventional connector elements 506.

Figure 22:
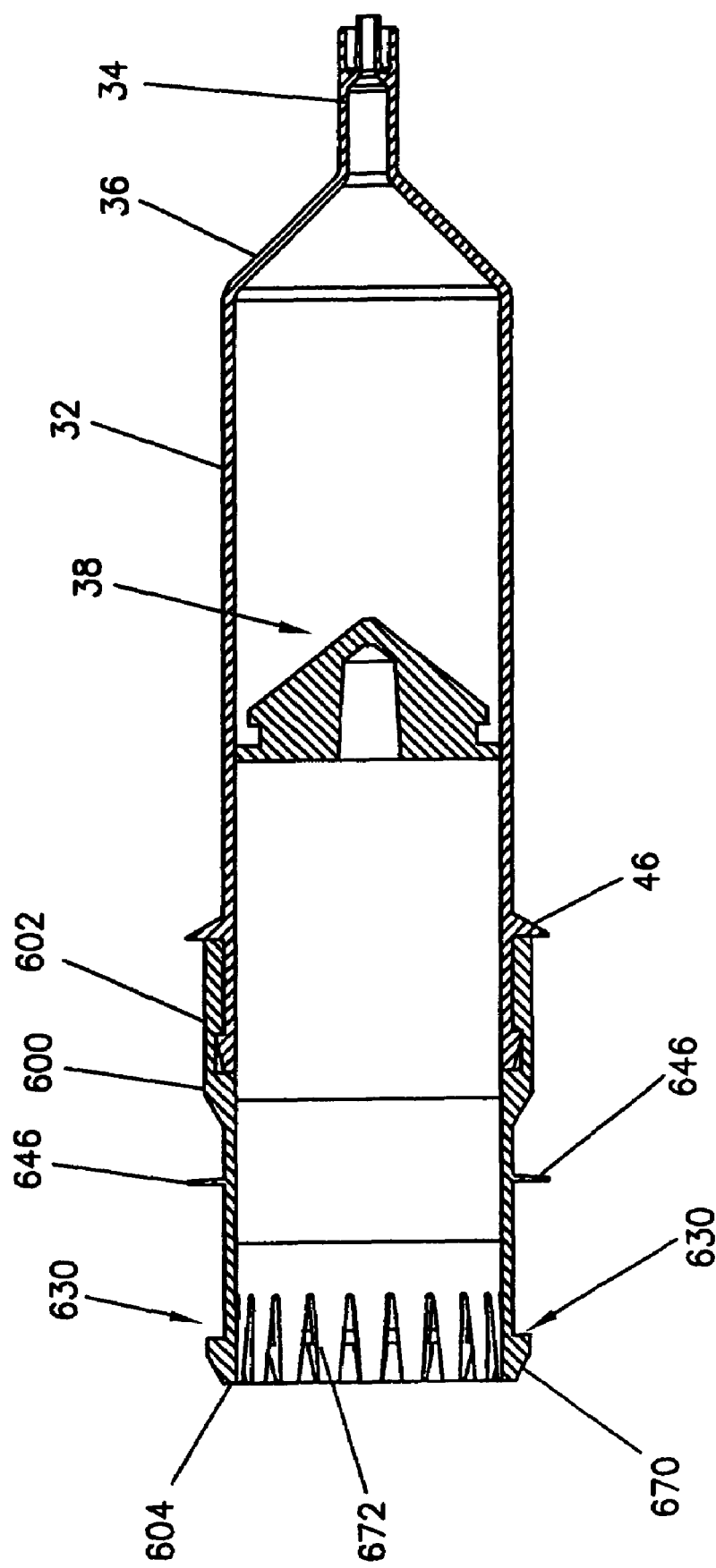
FIG. 22 is a cross-sectional view of an alternate embodiment of the adapter assembly illustrated in FIG. 21, where the adapter includes a tabbed opening for engagement with the injector housing.

As shown in FIG. 22, in an alternate embodiment of the adapter, it may be necessary to adapt a conventional syringe for use in an injector designed to accept the syringes of the present invention. Here, adapter 600 includes tabs 630 at its rearward end 604. Tabs 630 act and function like tabs 30 to secure adapter to housing 18 by engaging ledge 29 on mounting assembly 14. Tabs 630 are disengaged from ledge 29 by reciprocating collar 68. Adapter 600 may also include a flange 646 as in the other embodiments that have been described above. While adapter 600 is shown with a syringe having a ridged end inserted therein, it should be understood that adapter 600 could be easily designed so that its forward end 602 can accept conventional connector elements, such as those described in U.S. Pat. Nos. 5,535,746 or 5,383,858.

FIGS. 23 and 24 illustrate two perspective views of the combination of the syringe 412 and adapter 600. In this embodiment, flange 46 has been omitted. However, as illustrated in FIG. 22, flange 46 may be included. Naturally, as with syringe 212 (shown in FIGS. 10 and 11) and with syringe 312 (shown in FIGS. 12 and 13), the adapter may include only one tab, two tabs, or more than two tabs 630. FIGS. 23 and 24 illustrate adapter 600 with a plurality of tabs.

Figure 25:
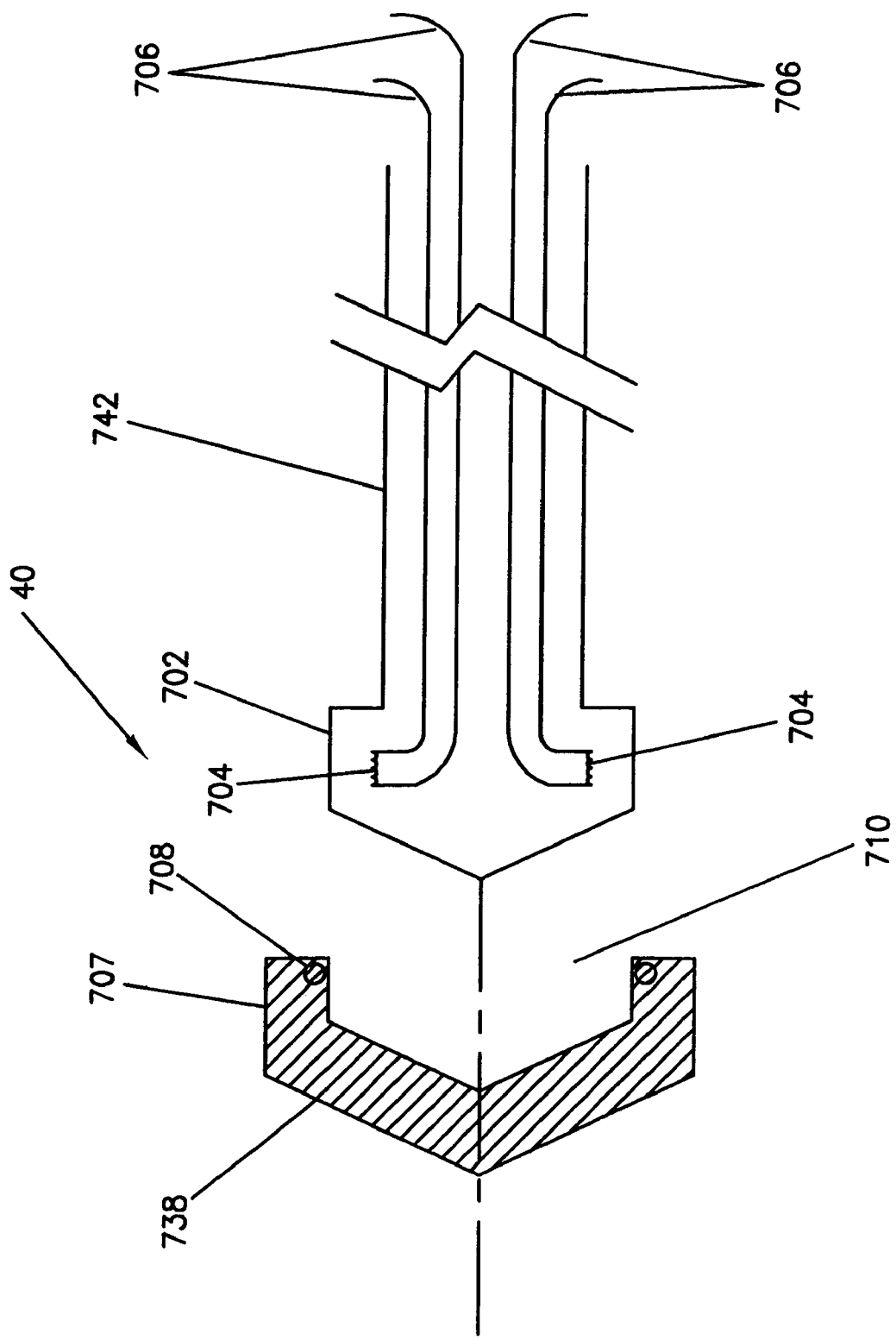
FIG. 25 is a cross-sectional view of an embodiment of a plunger and piston according to the teachings of the present invention, showing an electromagnetic mechanism that causes the plunger and piston to be attracted to one another during operation of the apparatus.
Figure 26:
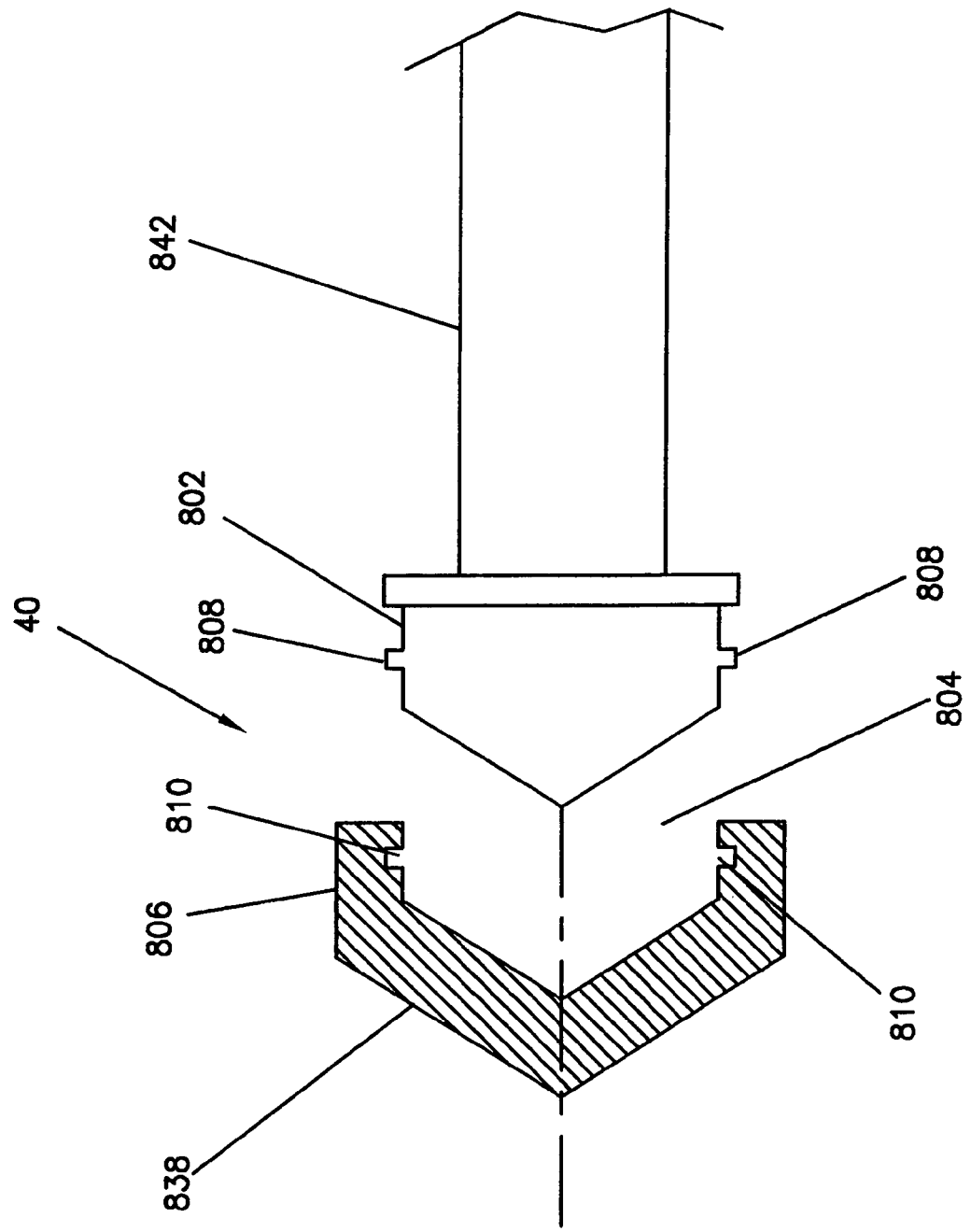
FIG. 26 is a partial cross-sectional view of another embodiment of a plunger and piston, showing an electromechanical mechanism that causes the plunger and piston to be releasably attached to one another during operation of the apparatus.

Two embodiments of second releasable mechanism 40 for engaging and releasing the syringe plunger and the injector piston will now be described with respect to FIGS. 25-29. FIG. 25 illustrates an electromagnetic release mechanism. FIGS. 26-29 illustrate an electromechanical release mechanism.

As shown in FIG. 25, plunger 738 may be releasably connected to piston 742 through an electromagnetic device. A forward end 702 of piston 742 is provided with an electromagnetic coil 704 that can be activated by applying a current through leads 706 that extend through piston 742. At its rearward end 707, plunger 738 includes a magnetically attractive ring 708, made of iron, for example, which is attracted to electromagnetic coil 704 when electromagnetic coil 704 is activated. The cross-sections of forward end 702 of piston 742 and of recess 710 in rearward end 707 of plunger 738 are cylindrical. This permits the engagement of piston 742 with plunger 738 regardless of the orientation of plunger 738 in the syringe.

Second releasable mechanism 40, as illustrated in FIG. 25, operates as follows. When a syringe has been inserted into the interface on the injector housing 18, piston 742 is extended into the syringe until its forward end 702 mates with recess 710 of plunger 738. Electromagnetic coil 704 may then be activated to retract plunger 738. The attraction between magnetically attractive ring 708 and electromagnetic coil 704 holds plunger 738 to the end of piston 742 during rearward movement of piston 742. Alternatively, electromagnetic coil 704 may be activated before piston 742 is extended into the syringe to mate with plunger 738. Once plunger 738 and piston 742 are electro-magnetically attracted to one another, piston 742 may be moved as required within the syringe. To disengage piston 742 from plunger 738, or to retract piston 742 without retracting plunger 738, one need only disengage the power supplied to electromagnetic coil 704. Of course, the piston 742 may advance the plunger 738, for example, during an injection, without activating electromagnetic coil 704.

The second embodiment contemplated for second releasable mechanism 40 involves an electromechanical connection between the piston and the plunger. This embodiment is illustrated in FIGS. 26-29.

Figure 27:
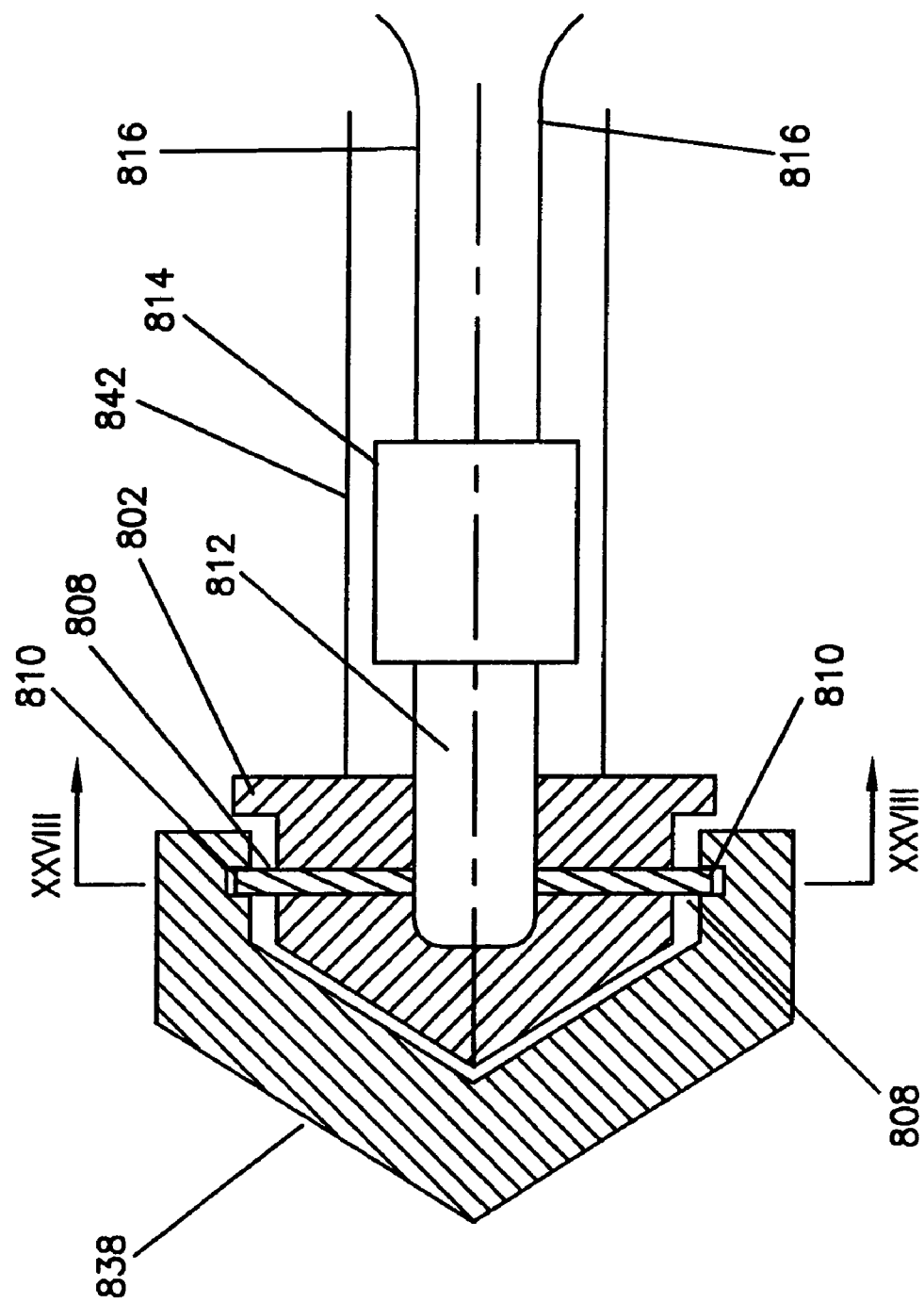
FIG. 27 is an enlarged cross-sectional view of the piston and plunger illustrated in FIG. 26, showing the piston engaging the plunger.

In FIGS. 26-29, piston 842 has a forward end 802 that engages with a recessed area 804 formed in a rearward end 806 of plunger 838. Forward end 802 of piston 842 includes protrusions 808 that retractably extend therefrom. Protrusions 808 engage an indentation or channel 810 formed in the plunger 838, as illustrated in FIG. 27. A member 812 is enclosed by piston 842 and forward end 802. Member 812 is actuated by mechanism 814, also contained within piston 842. Mechanism 814 receives power through leads 816.

Figure 28:
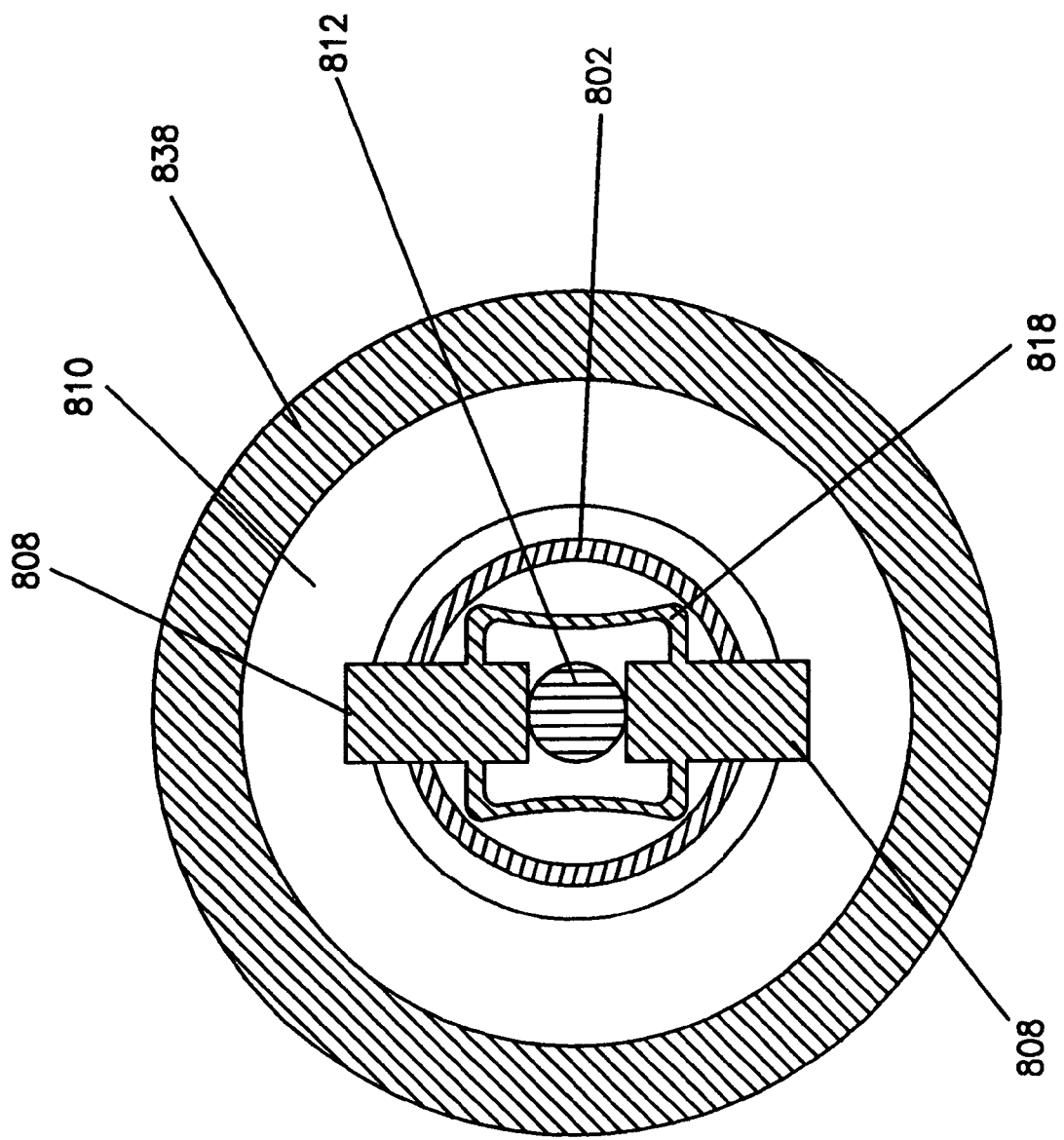
FIG. 28 is a cross-sectional view of the combination of the piston and the plunger shown in FIG. 27, the view taken along line XXVIII-XXVIII, showing two protrusions extended so that the piston engages the plunger.
Figure 29:
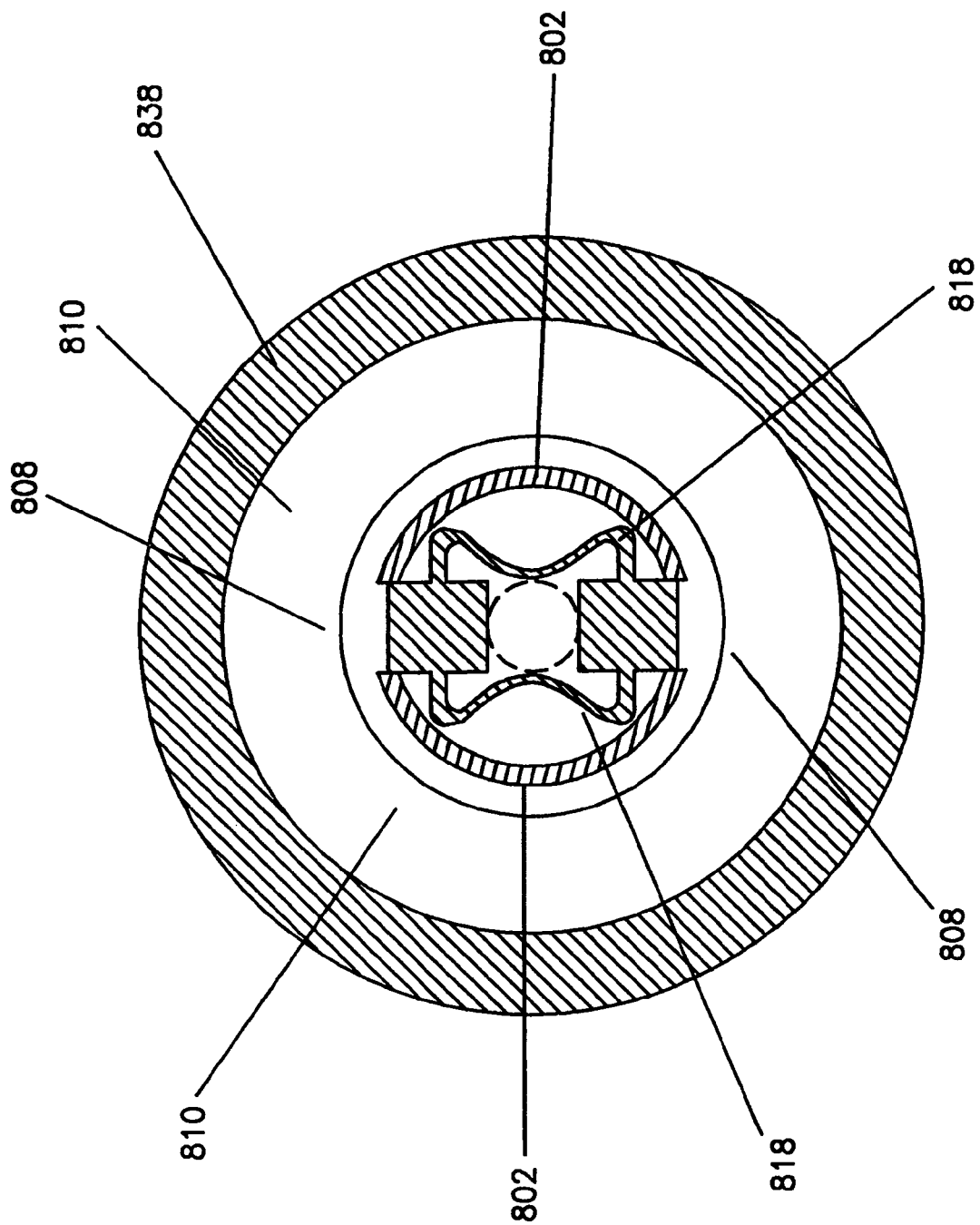
FIG. 29 is a cross-sectional view of the combination of the piston and the plunger shown in FIG. 26-28, with the two protrusions retracted so that the piston can disengage from the plunger.

As shown in FIGS. 28 and 29, protrusions 808 are essentially rectangular. They are connected to one another through resilient members 818. Resilient members 818 bias protrusions 808 so that they do not protrude from forward end 802 of piston 842, as shown in FIG. 29.

The operation of second releasable mechanism 40 will now be described in connection with FIGS. 26-29. When a syringe has been inserted into front wall 16 of injector 20, piston 842 is extended forward to meet with plunger 838. When piston 842 extends forward, mechanism 814 is deactivated so that member 812 is in a retracted condition, as shown in FIG. 29. In other words, member 812 is retracted so that it does not sit between protrusions 808. As a result, resilient members 818 bias protrusions 808 so that they do not extend outside of forward end 802 of piston 842, as shown in FIG. 29.

Once forward end 802 of piston 842 mates with recessed area 804 in plunger 838, mechanism 814 is activated so that member 812 extends forward to sit between protrusions 808, thereby forcing protrusions 808 to extend outside of forward end 802 of piston 842. Protrusions 808, once extended, extend into channel 810 within plunger 838. Once so arranged, piston 842 is connected to plunger 838 so that rearward movement of piston 842 translates directly into a corresponding rearward movement of plunger 838.

When it becomes necessary to disengage the syringe from the injector, or to retract piston 842 without retracting plunger 838, mechanism 814 is activated to withdraw member 812 from between protrusions 808. Once withdrawn, resilient members 818 bias protrusions 808 so that they no longer engage channel 810. Piston 842 may then be withdrawn from plunger 838.

Figure 37:
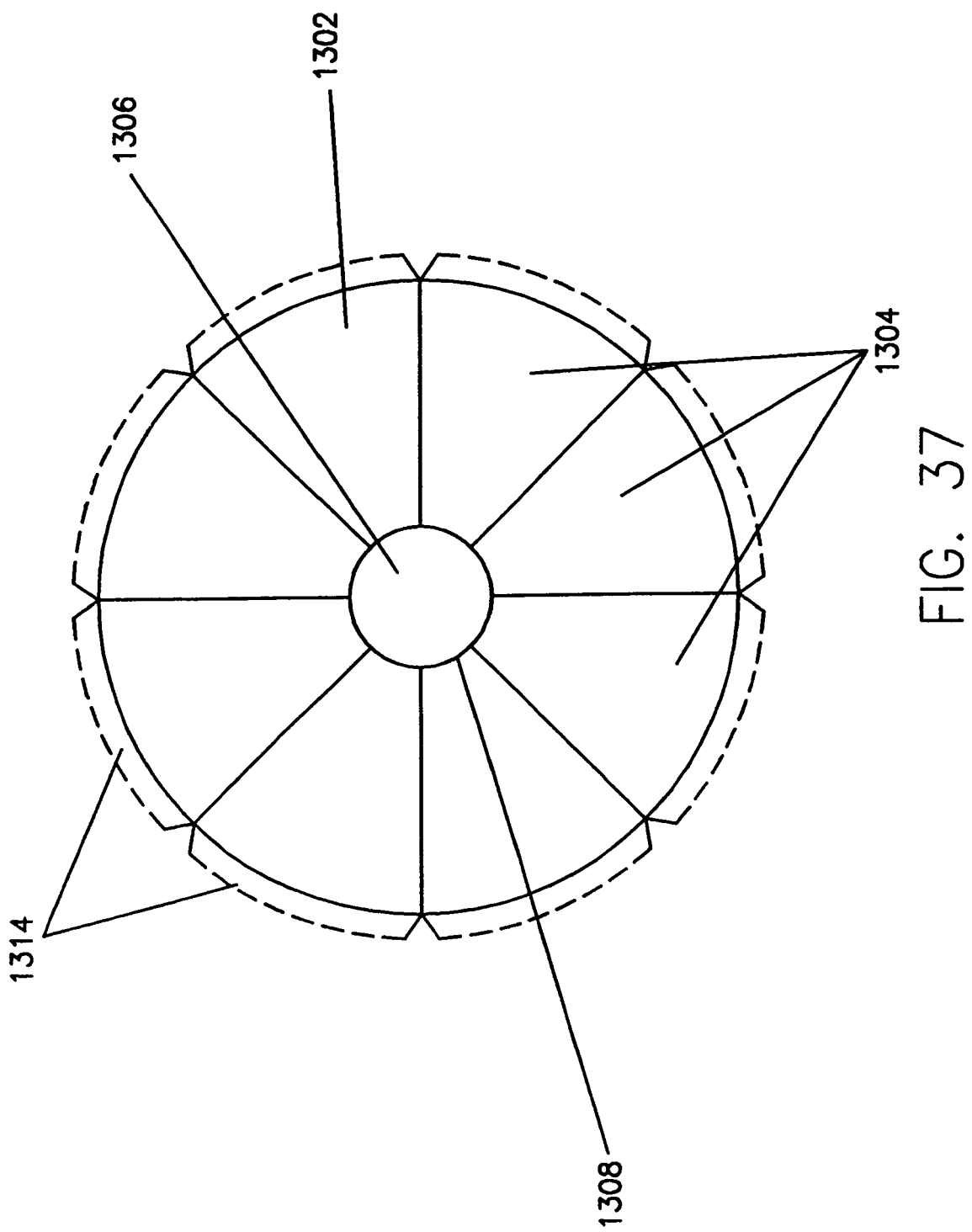
FIG. 37 is an end view illustration of the separable members shown in FIG. 36.

Two additional second releasable mechanisms 40 will now be described with reference to FIGS. 35-37.

Figure 35:
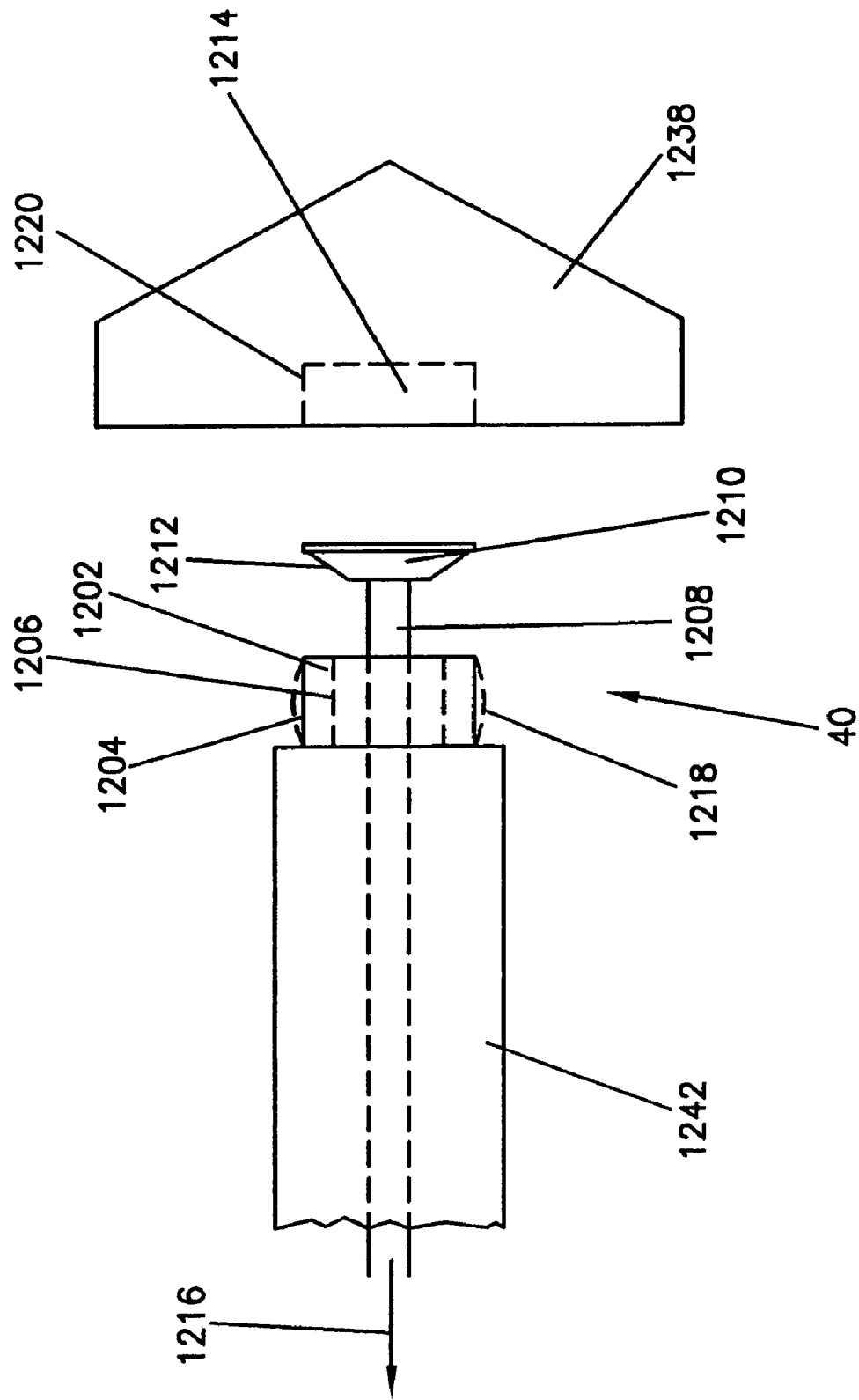
FIG. 35 is a side view illustration of another embodiment of the apparatus that releasably connects the plunger and piston to one another.

In the embodiment illustrated in FIG. 35, plunger 1238 may be releasably connected to piston 1242 through expansion of an elastomeric member 1202 disposed at a forward end thereof. Elastomeric member 1202 is a cylindrical element with external walls 1204 and internal walls 1206. A rod 1208 extends through piston 1242 and connects to an actuator 1210 at a forward end of rod 1208 closest to plunger 1238. Actuator 1210 has a frustoconical shape on a side facing elastomeric member 1202. The frustoconical shape defines an inclined surface 1212 on actuator 1210. The diameter of elastomeric member 1202 is slightly smaller than the diameter of the hole 1214 in plunger 1238. Also, the diameter of actuator 1210 is smaller than the diameter of hole 1214.

The operation of the second releasable mechanism 40 illustrated in FIG. 35 will now be described. Because the diameter of hole 1214 in plunger 1238 is larger than the diameter of elastomeric member 1202 and of actuator 1210, when piston 1242 is pushed forward, elastomeric member 1202 and actuator 1210 easily fit into hole 1214. Plunger 1238 can then be advanced by piston 1242 without a connective engagement existing therebetween. However, once positioned in this manner, to connectively engage the plunger 1238 (e.g., to retract plunger) actuator 1210 is pulled toward elastomeric member 1202 by rod 1208, as shown by arrow 1216 in FIG. 35. The pressure from actuator 1210 compresses elastomeric member 1202 so that external sides 1204 swell or expand from their unstressed condition. The approximate shape of the swelled walls 1218 of elastomeric member 1202 is shown in dotted line format in FIG. 35. Swelled walls 1218 engage walls 1220 of hole 1214 so that piston 1242 releasably engages plunger 1238. Plunger 1238 can now be retracted to, for example, aspirate fluid into the syringe.

The embodiment of second releasable mechanism 40 shown in FIGS. 36-37 will now be described. As shown in FIGS. 36-37, plunger 1338 engages piston 1342 through segmented member 1302. Segmented member 1302 is made of a number of separate elements 1304 as shown in the end view illustration of FIG. 37. Separate elements 1304 may be made from any suitable material, such as an elastomeric material, so long as the material preferably (1) can substantially withstand repeated deformation and (2) returns substantially to its original condition when no longer subject to a deforming stress. Segmented member 1302 is disposed at a forward end of piston 1342. A rod 1306 extends through the middle of piston 1342 and extends at least partially into a central bore 1308 of segmented member 1302.

To releasably connect plunger 1338 with piston 1342, piston 1342 is moved forward until segmented member 1302 is disposed within a hole 1310 formed in plunger 1338. Rod 1306 is then moved forward, in the direction shown by arrow 1312, until rod 1306 is at least partially disposed within segmented member 1302. Since the diameter of rod 1306 is greater than the diameter of bore 1308, the insertion of rod 1306 into bore 1308 pushes segmented members 1304 outwardly until they reach a deformed position 1314 shown in dotted lines in both FIG. 36 and FIG. 37. When deformed, segmented members 1304 engage walls 1316 of hole 1310 in plunger 1338 to create a releasable engagement between plunger 1338 and piston 1342.

For each of the second releasable mechanisms described in FIGS. 25-29 and 35-37, the advantage that the mechanisms provide is that the piston need not be oriented in any specific manner with the plunger in order to facilitate a connection between the piston and plunger. Regardless of the orientation of the piston and the plunger, the two can easily mate with one another and can be easily disengaged from one another.

In addition, if for example a prefilled syringe is mounted on the injector, it may not be necessary to retract the plunger within the syringe to draw fluid within the syringe for subsequent injection. In such a case, the piston may be operated in a "push-only" mode that does not require engagement between the piston and the plunger. If operated in this manner, the engagement mechanism need not be activated at all. Alternatively, if the injector is designed to handle only prefilled syringes, no readily releasable mechanism need be provided.

The plunger of the present invention may also include a pressure sensor like the sensors described in U.S. Pat. No. 5,808,203, issued to Nolan, Jr. et al. on Sep. 15, 1998, and assigned to the Assignee of the present application. The disclosure of U.S. Pat. No. 5,808,203 is incorporated herein by reference, to the extent that it is not inconsistent with the instant disclosure.

Figure 30:
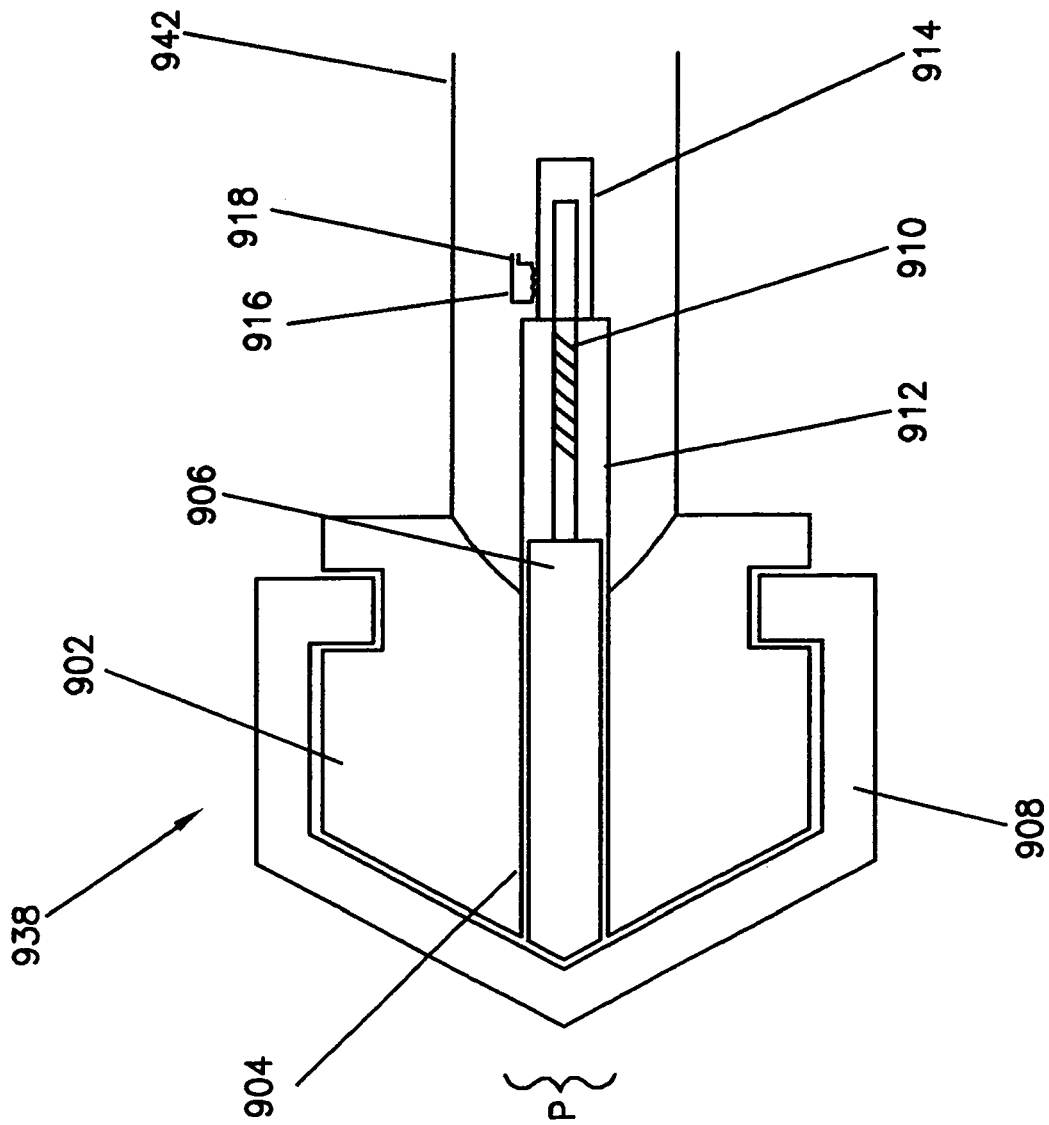
FIG. 30 is an enlarged cross-sectional view of a plunger according to the teachings of the present invention, illustrating the placement of a pressure-sensing device in the plunger.
Figure 31:
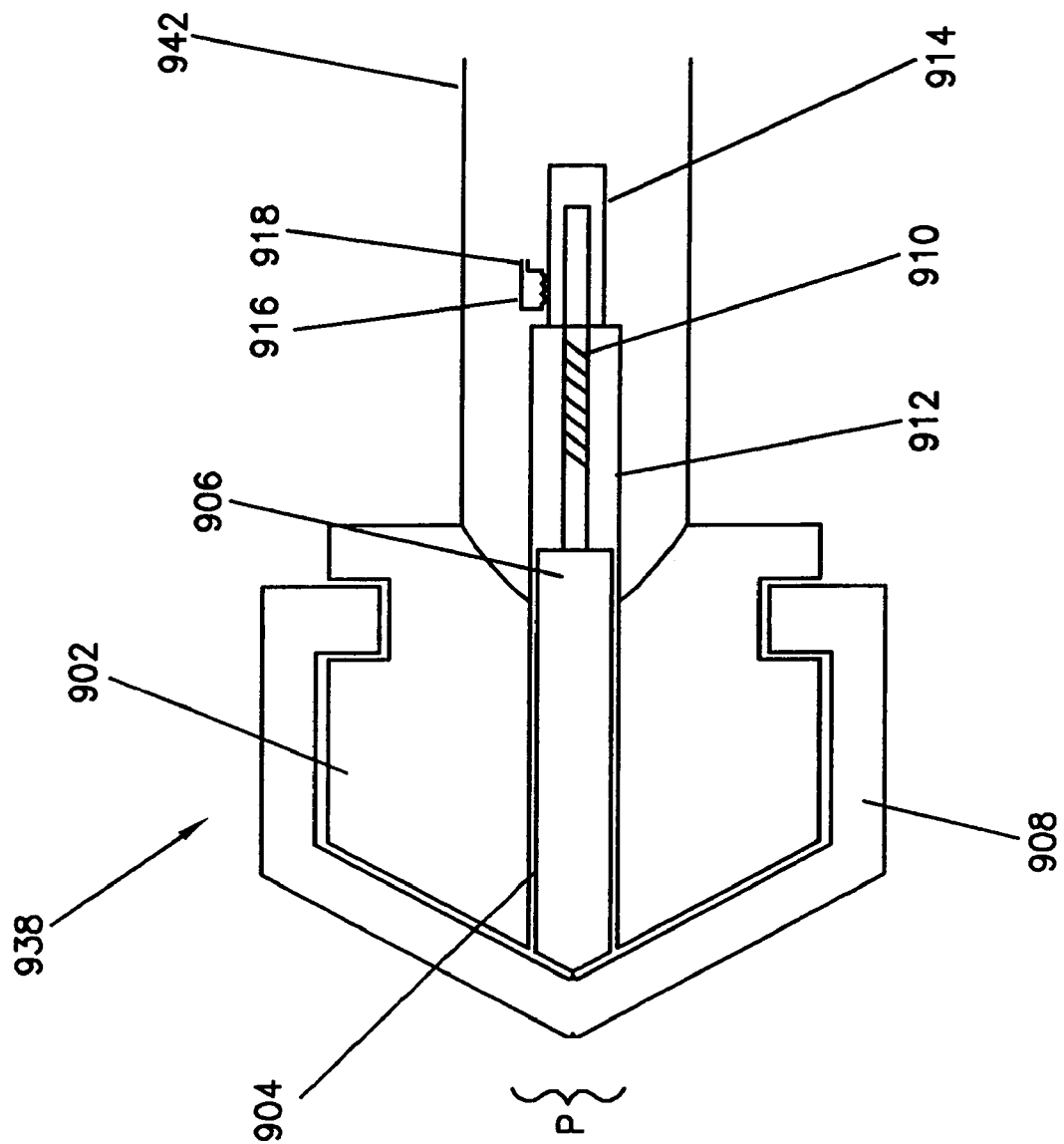
FIG. 31 is an enlarged cross-sectional view of the plunger illustrated in FIG. 30, showing the plunger subjected to a pressure from the fluid contained in a syringe (not illustrated)

FIGS. 30 and 31 illustrate the sensor that can be included in the plunger of the present invention. Plunger 938 preferably comprises a base 902 with a passage 904 therethrough. A sensing member 906 is disposed within passage 904 to be in operative contact with a portion P of contact surface 908. Sensing member 906 is preferably biased forward, for example, via a spring 910. As fluid pressure within the syringe (not shown) increases, portion P of contact surface 908 is deformed as shown in FIG. 31. This deformation of portion P causes sensing member 906 to move rearward through passages 904 and 912 and 914 in piston 942. The movement of sensing member 906 is monitored with a sensor 916 preferably disposed within piston 942. Because the degree of movement of sensing member 906 is a function of the pressure of the fluid medium within the syringe, the pressure of the fluid medium can be determined therefrom. Sensor 916 is preferably connected to a data collection and/or control device via leads 918.

While FIGS. 30 and 31 describe one possible embodiment of a sensor that can be incorporated into the plunger of the present invention, it should be noted that any other suitable sensor might be included. In addition, the sensor need not detect only the pressure of the fluid. As would be understood by those skilled in the art, the sensor may measure a number of different parameters including amount, pressure and density of the fluid in the syringe.

Also, the plunger may contain encoding elements that are read or sensed by the injector or injector piston to identify the syringe and/or its contents. In this embodiment, the encoding elements, such as an integrated circuit, are included on the plunger rather than the syringe. The encoded elements then may be read electronically when the plunger contacts the piston. The plunger may contain information such as the contents and volume of the syringe as well as other information needed for the procedure or for billing purposes. One example of such a system is described in PCT Publication No. WO 99/65548, which is incorporated herein by reference.

The present invention is often shown and described herein in terms of cooperating syringe interfaces and syringes. The terms "syringe interface" and "syringe interfaces" as used herein can be incorporated in or integrated with new medical injectors or configured as syringe adapters mountable on or associated with existing or conventional medical injectors, such as the injector shown and described in U.S. Pat. No. 5,383,858, the contents of which are hereby incorporated by reference, to allow the installation of the syringes of the present invention thereon.

Figure 40A:
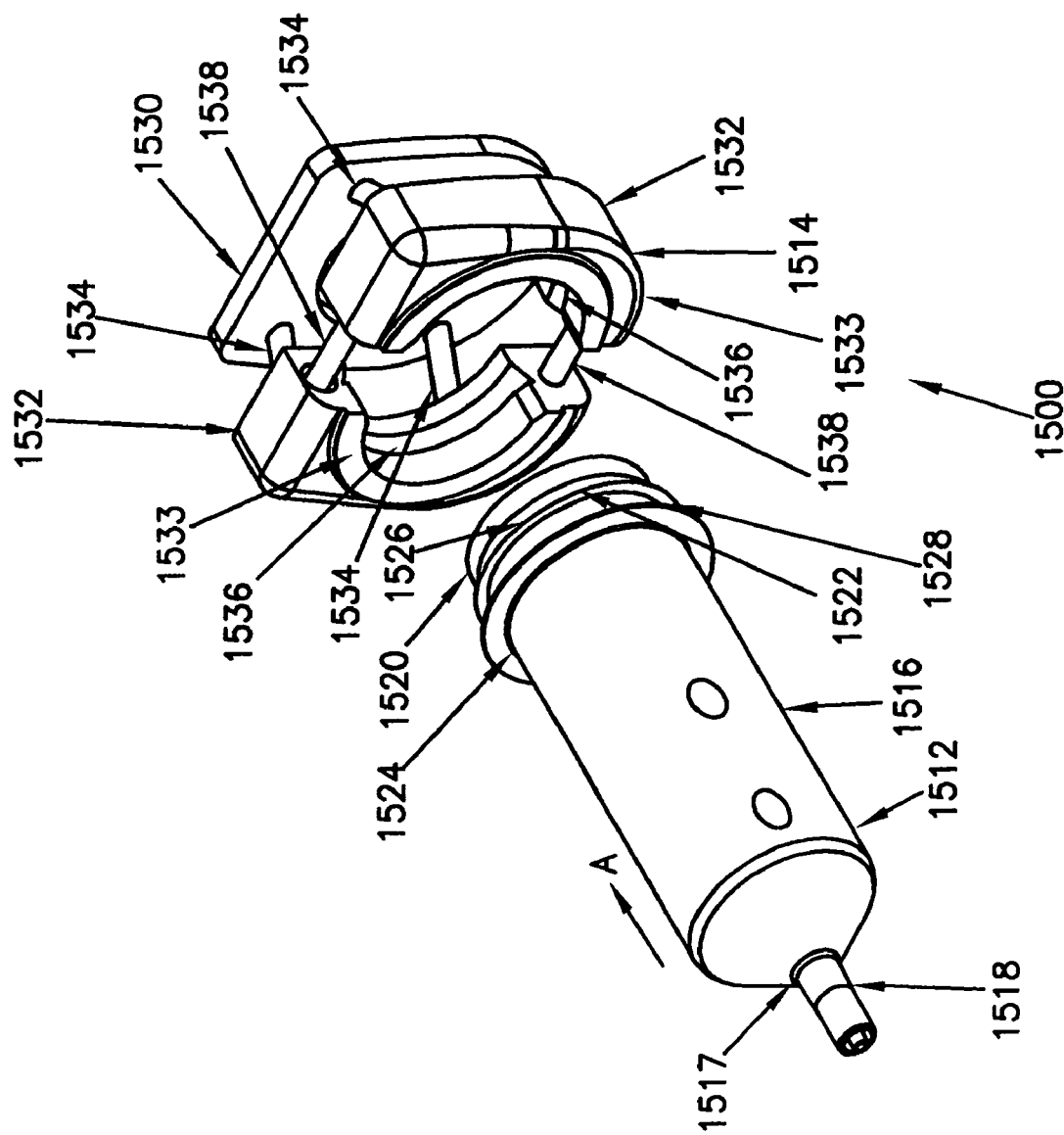
FIG. 40A is an exploded, perspective view of another embodiment of a front-loading syringe interface and syringe system in accordance with the present invention.
Figure 40B:
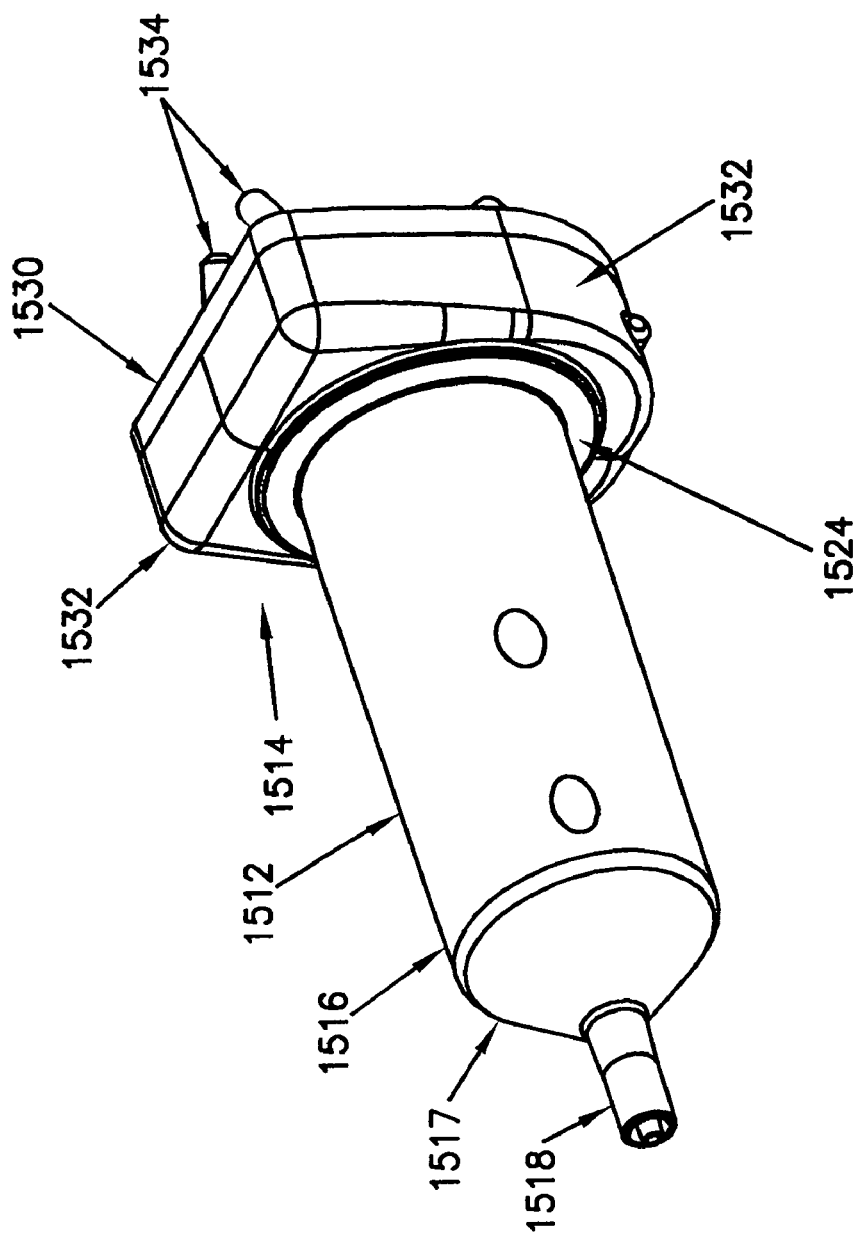
FIG. 40B is a perspective view of the system shown in FIG. 40A in an installed position.
Figure 40C:
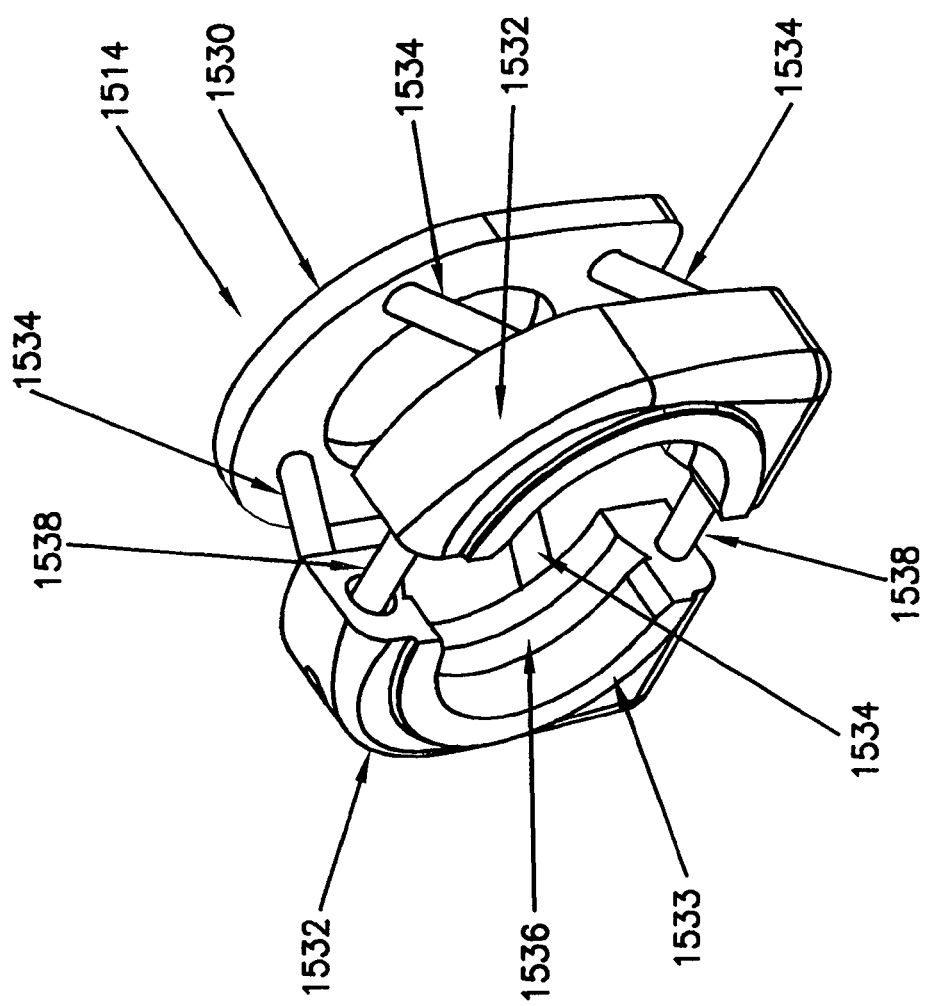
FIG. 40C is a perspective view of the syringe interface shown in FIG. 40A in an open position.

FIGS. 40A-40C illustrate another embodiment of a front-loading syringe interface and syringe system 1500 in accordance with the present invention. The system 1500 includes a syringe 1512 and a syringe interface 1514. The syringe 1512 includes a body or barrel portion 1516 having a rear end 1520 and a front end 1517 defining a fluid discharge end 1518. Preferably, at least one tab or mounting member 1522 is associated with the barrel portion 1516 adjacent to or at the rear end 1520 of the syringe 1512. In addition, a flange 1524 is preferably positioned forward of the mounting member 1522 to facilitate the engagement of the syringe 1512 to the syringe interface 1514 and/or to prevent fluid expelled from the discharge end 1518 of the syringe from entering into the syringe interface 1514 and the injector (not shown), as described in more detail in U.S. Pat. No. 5,383,858.

Preferably, the mounting member 1522 is disposed around the circumference of the barrel portion 1516 and includes an inclined surface 1526 that defines a shoulder 1528. The function of the mounting member 1522 will be described in more detail below. Alternately, the mounting member 1522 may extend around only a portion of the circumference of the barrel portion 1516 or may be formed in discrete segments.

(Unless otherwise noted, the syringe 1512 (and its components parts) described above applies to the remaining embodiments of the present invention discussed and described below with respect to FIGS. 40A-47F.)

As best shown in FIGS. 40A and 40C, the syringe interface 1514 is in an "open" position ready to accept the syringe 1512. The syringe interface 1514 includes a base member 1530 and two cooperating syringe-retaining members 1532. However, in alternate embodiments, three or more retaining members 1532 could be provided. Preferably, each of the retaining members 1532 is associated with the base member 1530 by means of two angled rail members 1534. However, in alternate embodiments, one, three or more members 1534 may be used to associate each retaining member 1532 with the base member 1530.

Further, each retaining member 1532 preferably defines a contact surface 1533 and a channel 1536 to capture and retain the mounting member 1522 on the syringe 1512. In addition, the retaining members 1532 are preferably associated with one another by means of two rail members 1538. Once again, in alternate embodiments, one, three or more rail members 1538 may be used to associate the retaining members 1532 with one another.

To install the syringe 1512 on the syringe interface 1514, the syringe 1512 is moved axially (in the direction of Arrow A in FIG. 40A) into the space defined between the retaining members 1532. When the flange 1524 on the syringe 1512 engages the contact surfaces 1533 on the retaining members 1532, the retaining members 1532 are urged toward the base member 1530 along the rail members 1534. Because the rail members 1534 are angled in toward the center of the base member 1530, the rail members 1534 operate to cause the retaining members 1532 to move toward each other along the rail members 1538 and to "collapse" around the rear end 1520 of the syringe 1512. As the retaining members 1532 collapse on the syringe 1512, the retaining members 1532 cooperate to capture the mounting member 1522 within the channels 1536 to securely engage the syringe 1512 with the syringe interface 1514.

Any suitable type of locking mechanism (not shown), as is known in the art, may be used to secure the retaining members 1532 together to retain the syringe 1512 within the syringe interface 1514. To remove the syringe 1512 from the syringe interface 1514, the lock must first be unlocked and the retaining members 1532 moved apart (e.g., by hand or by means of a lever or any other suitable art-recognized manipulative device) to free the mounting member 1522 from the channels 1536.

Figure 41A:
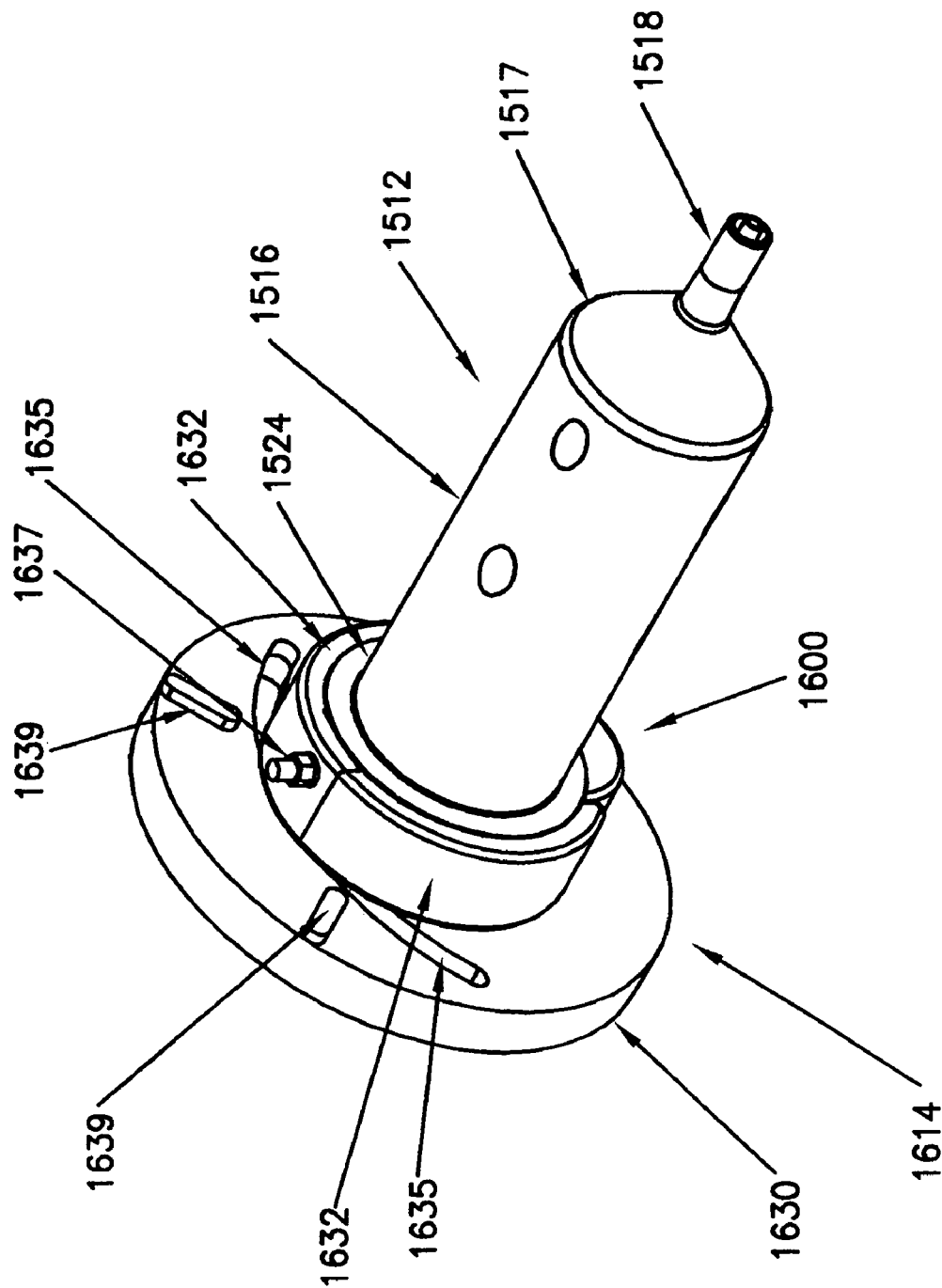
FIG. 41A is an assembled, perspective view of another embodiment of a front-loading syringe interface and syringe system in accordance with the present invention.
Figure 41B:
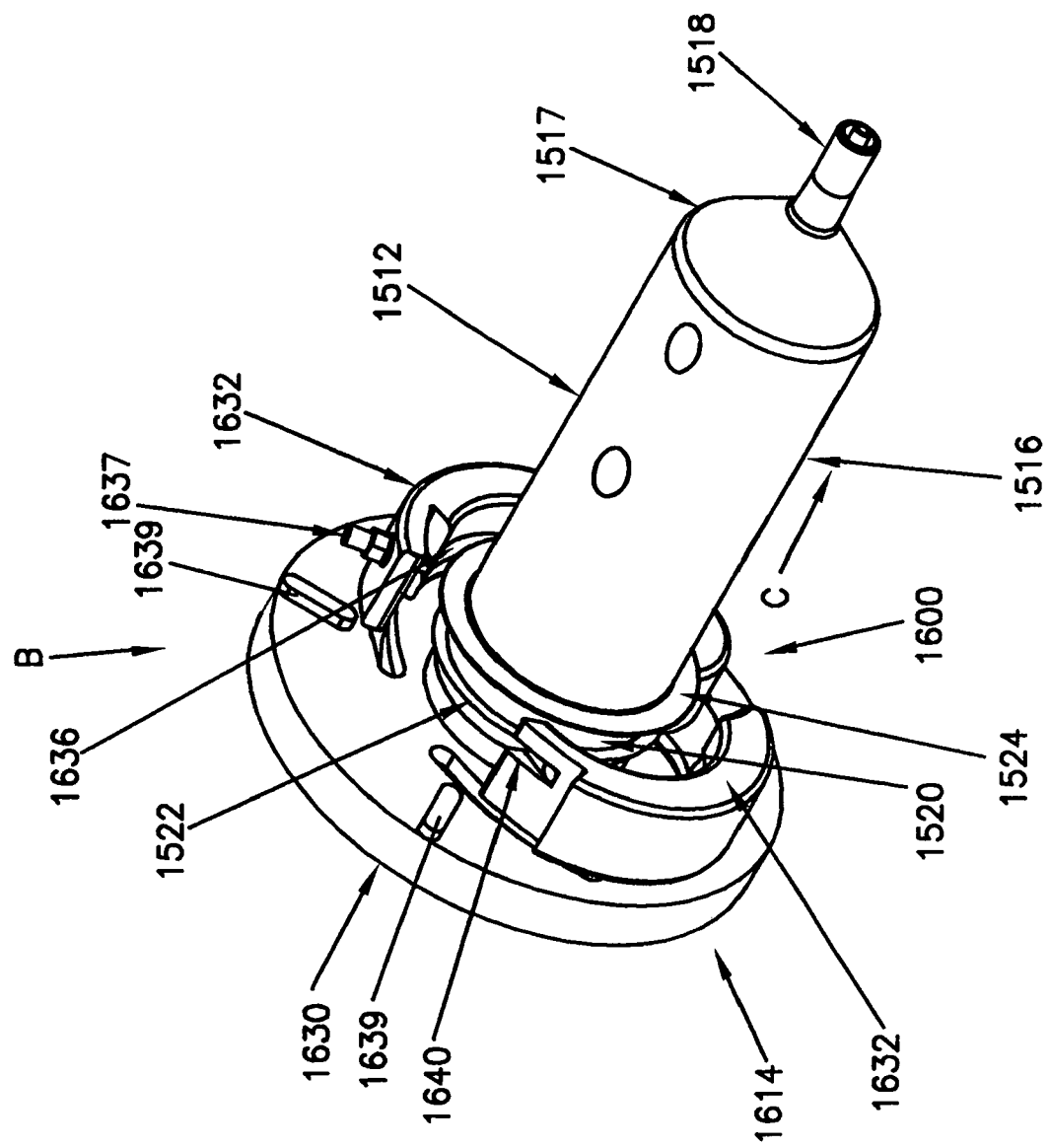
FIG. 41B is a perspective view of the system shown in FIG. 41A in an open position.
Figure 41C:
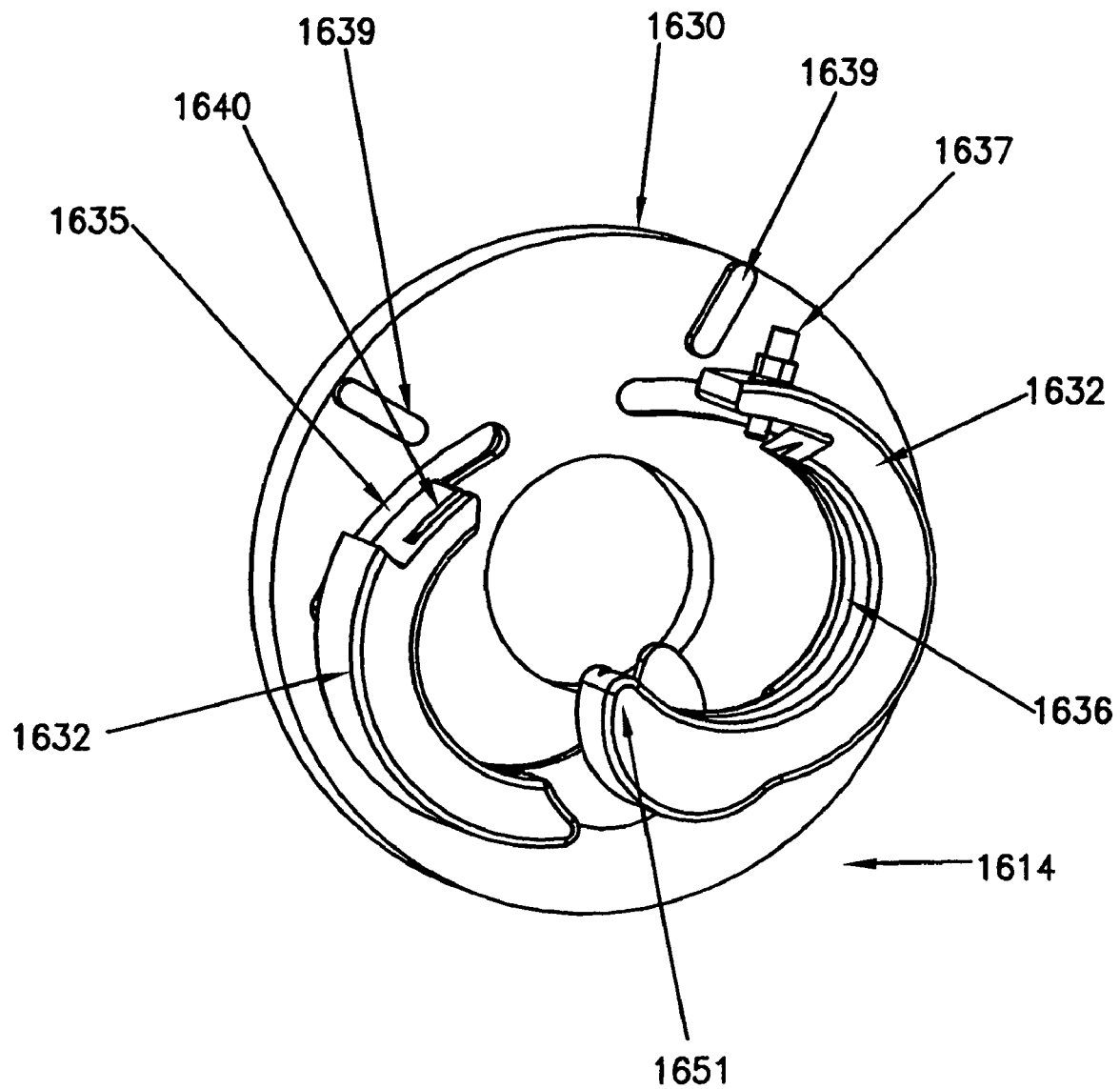
FIG. 41C is a front, perspective view of the syringe interface shown in FIG. 41A in an open position.
Figure 41D:
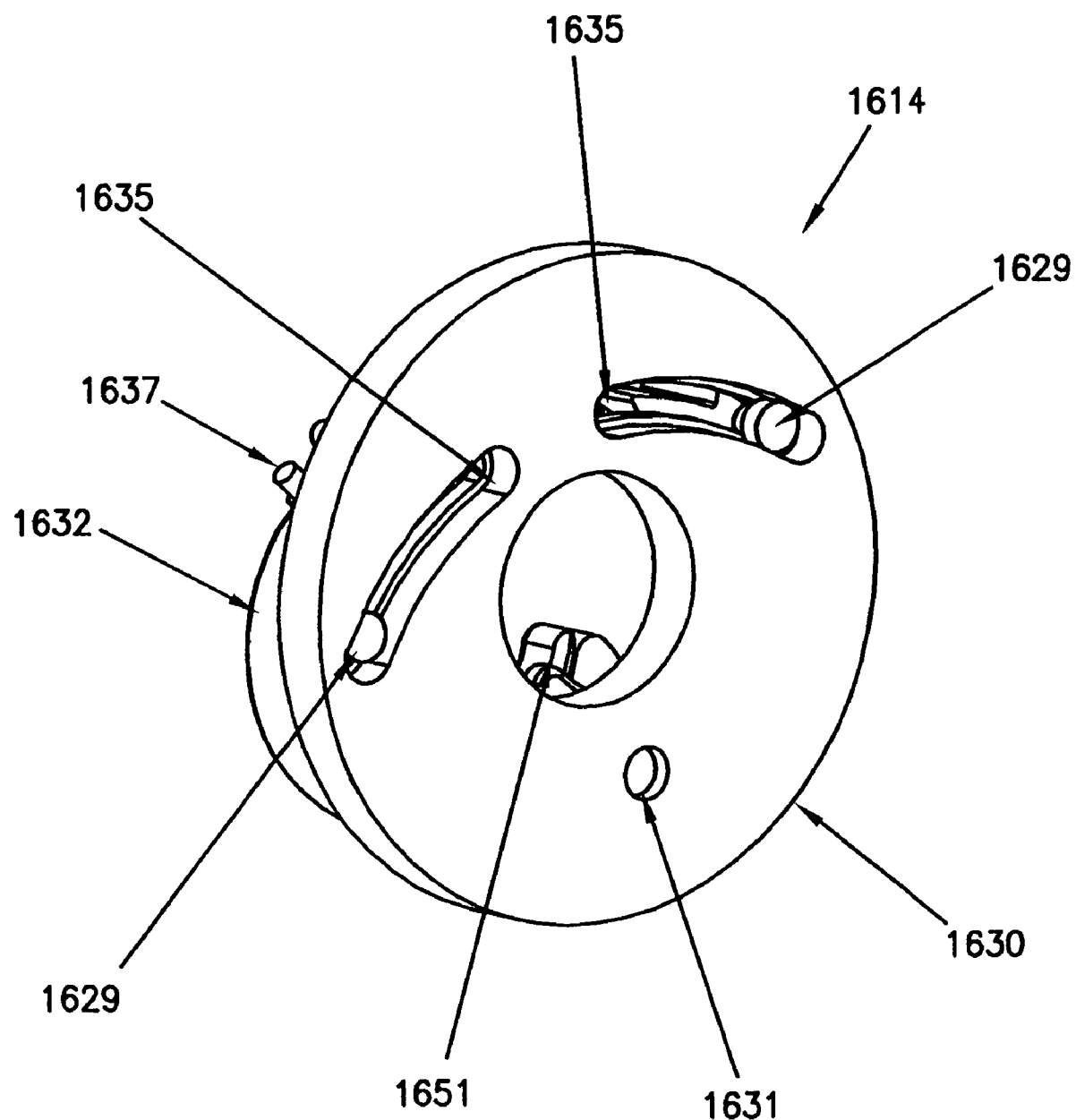
FIG. 41D is a rear, perspective view of the syringe interface shown in FIG. 41A in an open position.

Another embodiment of the syringe interface and syringe system 1600 is shown in FIGS. 41A-41D. The system 1600 includes a syringe 1512 and a syringe interface 1614. As best shown in FIGS. 41B and 41C, the syringe interface 1614 is in an "open" position ready to accept the syringe 1512. The syringe interface 1614 includes a base member 1630 and two cooperating syringe-retaining members 1632. The retaining members 1632 are preferably connected together and associated with the base member 1630 by means of a pivot pin 1631 or other suitable mechanism (see FIG. 41D). In addition, the retaining members 1632 are associated with the base member 1630 by means of pins 1629 (see FIG. 41D) that are associated with the retaining members 1632 and captured within slots 1635 defined in the base member 1630.

Further, each retaining member 1632 preferably defines a channel 1636 to capture and retain the mounting member 1522 on the syringe 1512. As best shown in FIGS. 41B and 41C, a spring pin 1637 (or other suitable locking mechanism) is connected to one retaining member 1632 and a channel with a pin recess 1640 is defined in the other retaining member 1632. In addition, two barrel guide rails 1639 are preferably defined in the base member 1630.

To install the syringe 1512 on the syringe interface 1614, the syringe 1512 is moved downwardly (in the direction of Arrow B in FIG. 41B) into the space defined between the retaining members 1632. The barrel 1516 of the syringe 1512 is guided into position between the retaining members 1632 by the barrel guide rails 1639 in the base member 1630. When the syringe barrel 1516 engages the pivot ends 1651 of the retaining members 1632 (see FIG. 41C), the retaining members 1632 are urged to collapse around the rear end 1520 of the syringe 1512. The pins 1629, riding in slots 1635 defined in the base member 1630, direct and control the arcuate motion of the retaining members 1632 into engagement around the syringe 1512. As the retaining members 1632 collapse on the syringe 1512, the retaining members 1632 cooperate to capture the mounting member 1522 within the channels 1636 to securely engage the syringe 1512 with the syringe interface 1614.

Further, when the retaining members 1632 collapse around the syringe 1512, the spring pin 1637 runs along the channel and locks into the pin recess 1640 to secure the syringe 1512 within the syringe interface 1614. To remove the syringe 1512 from the syringe interface 1614, the spring pin 1637 must be removed from the pin recess 1640 to unlock the retaining members 1632 and the retaining members 1632 moved (e.g., by hand or by any suitable lever means) from engagement with the syringe 1512. At this point, the syringe 1512 can be removed by either moving the syringe 1512 upwardly (in the opposite direction of Arrow B) or axially (in the direction of Arrow C in FIG. 41B).

Figure 42A:
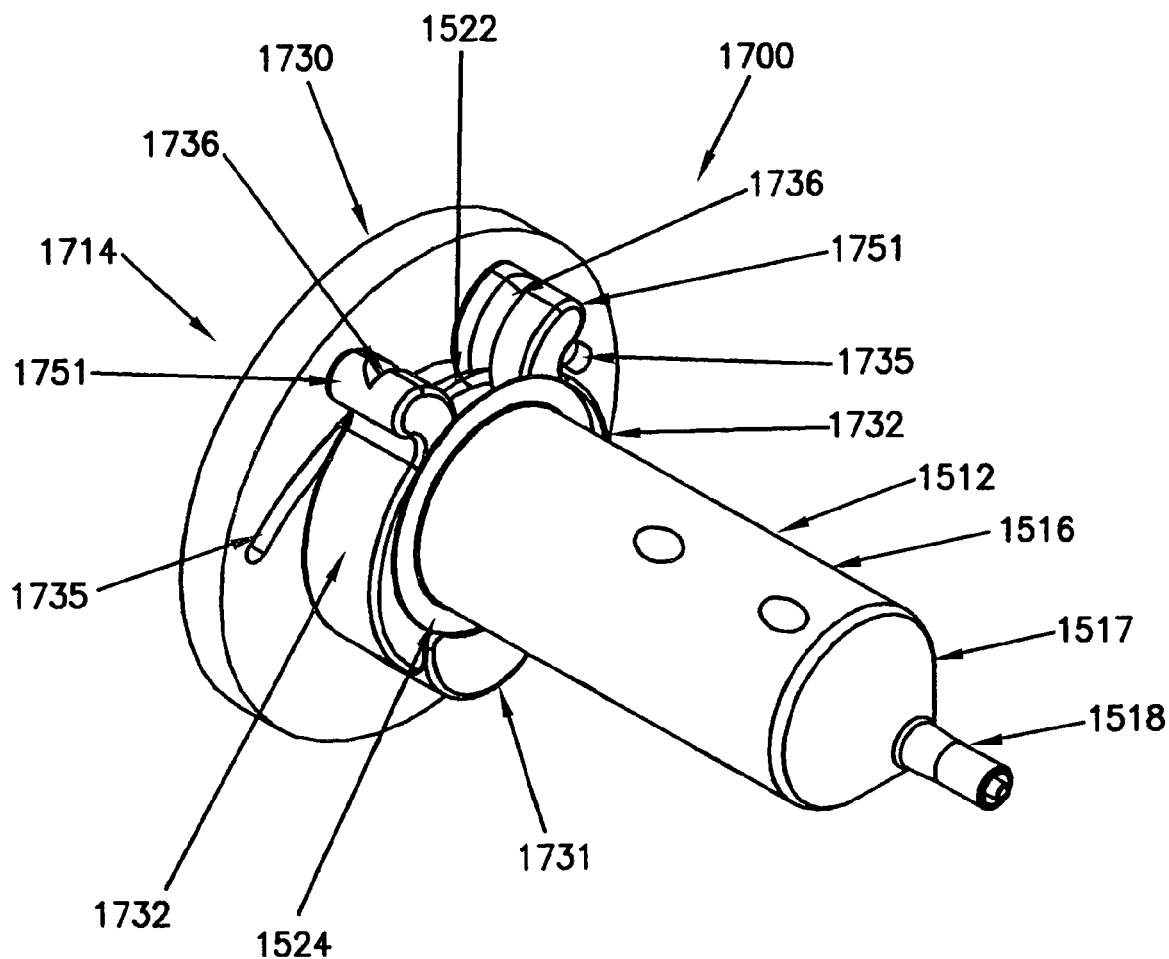
FIG. 42A is an assembled, perspective view of an alternate embodiment of the embodiment of the front-loading syringe interface and syringe system shown in FIGS. 41A-41D.
Figure 42B:
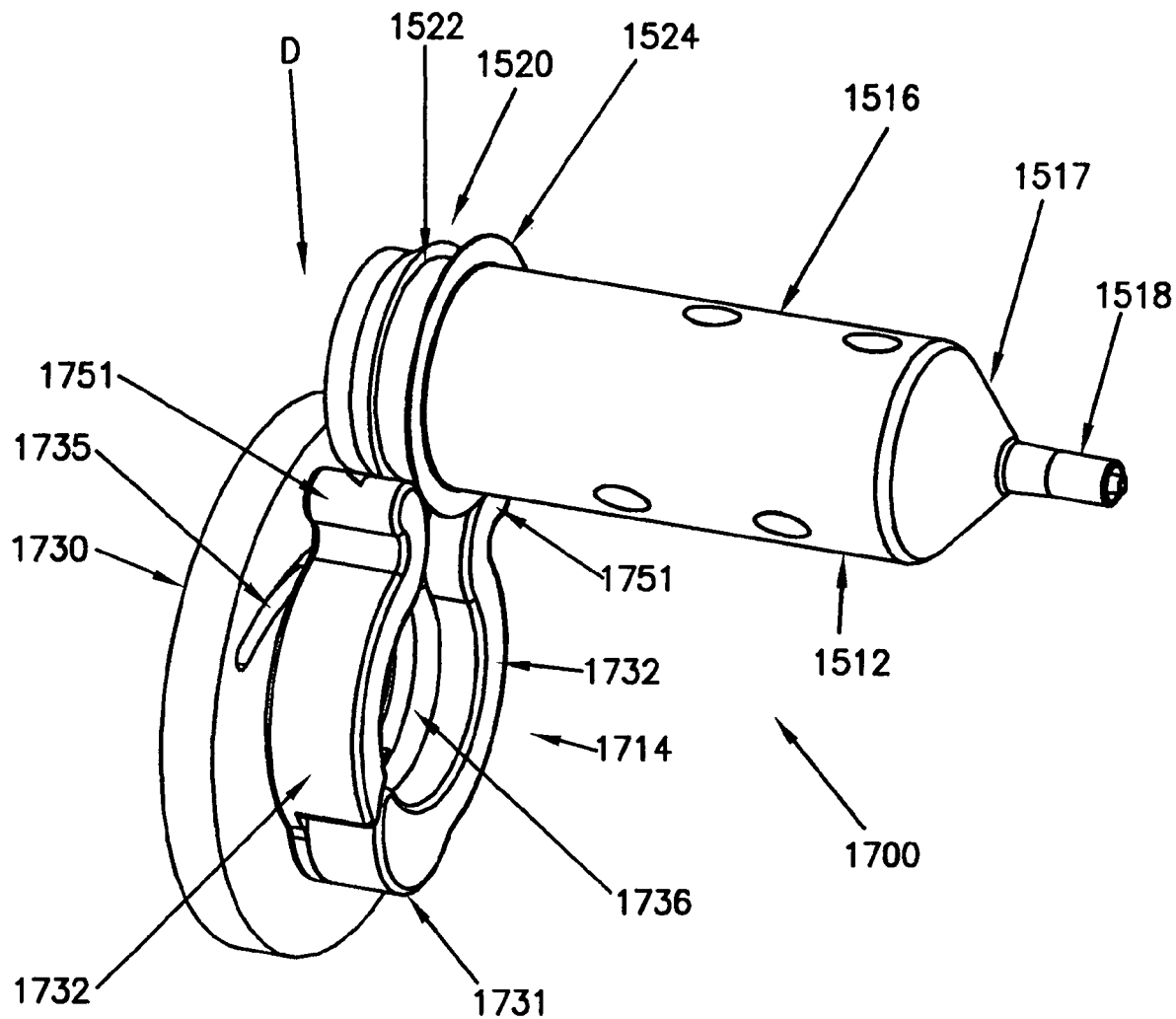
FIG. 42B is a perspective view of the system shown in FIG. 42A in a disengaged position.
Figure 42C:
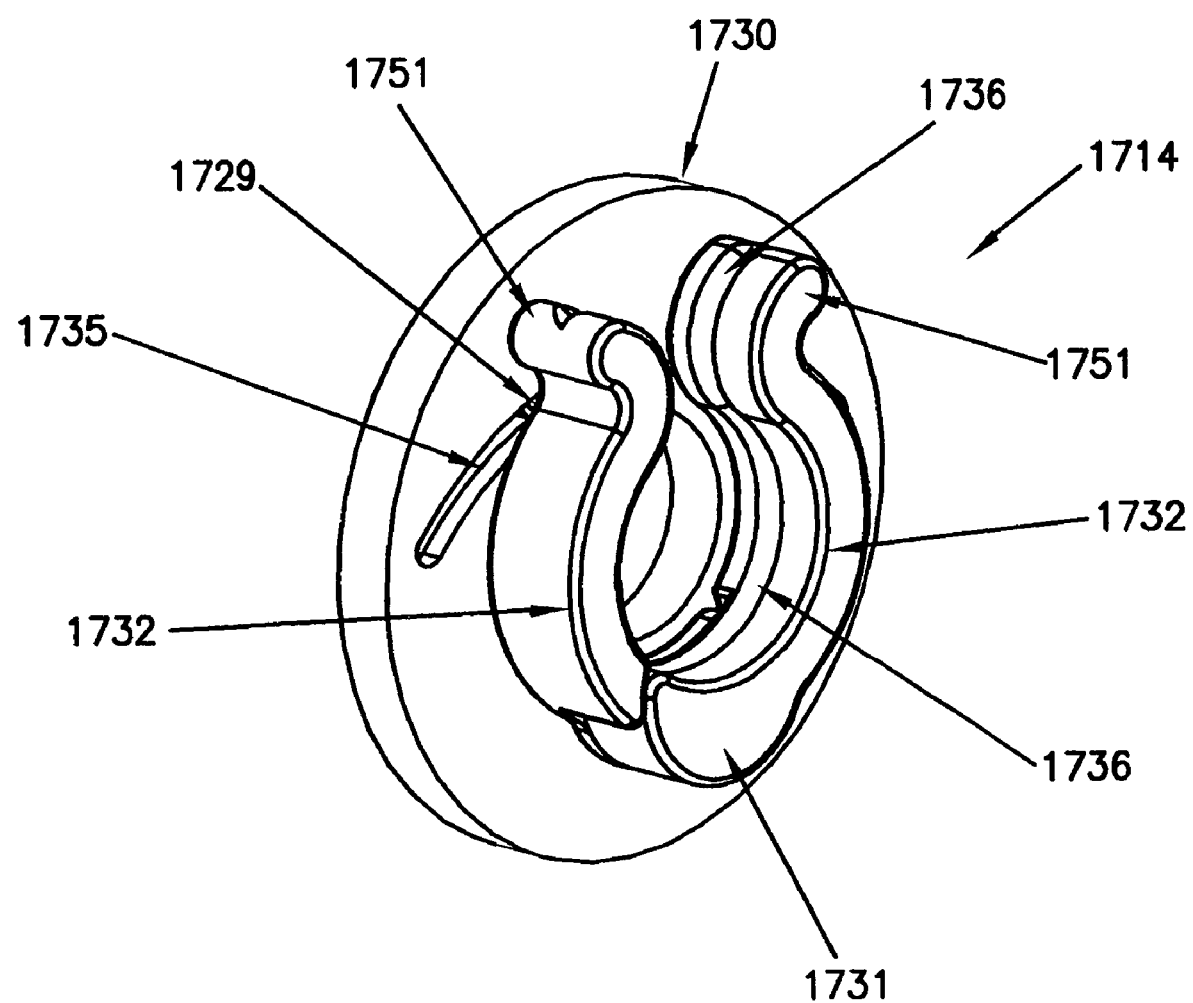
FIG. 42C is a front, perspective view of the syringe interface shown in FIG. 42A in a closed position.
Figure 42D:
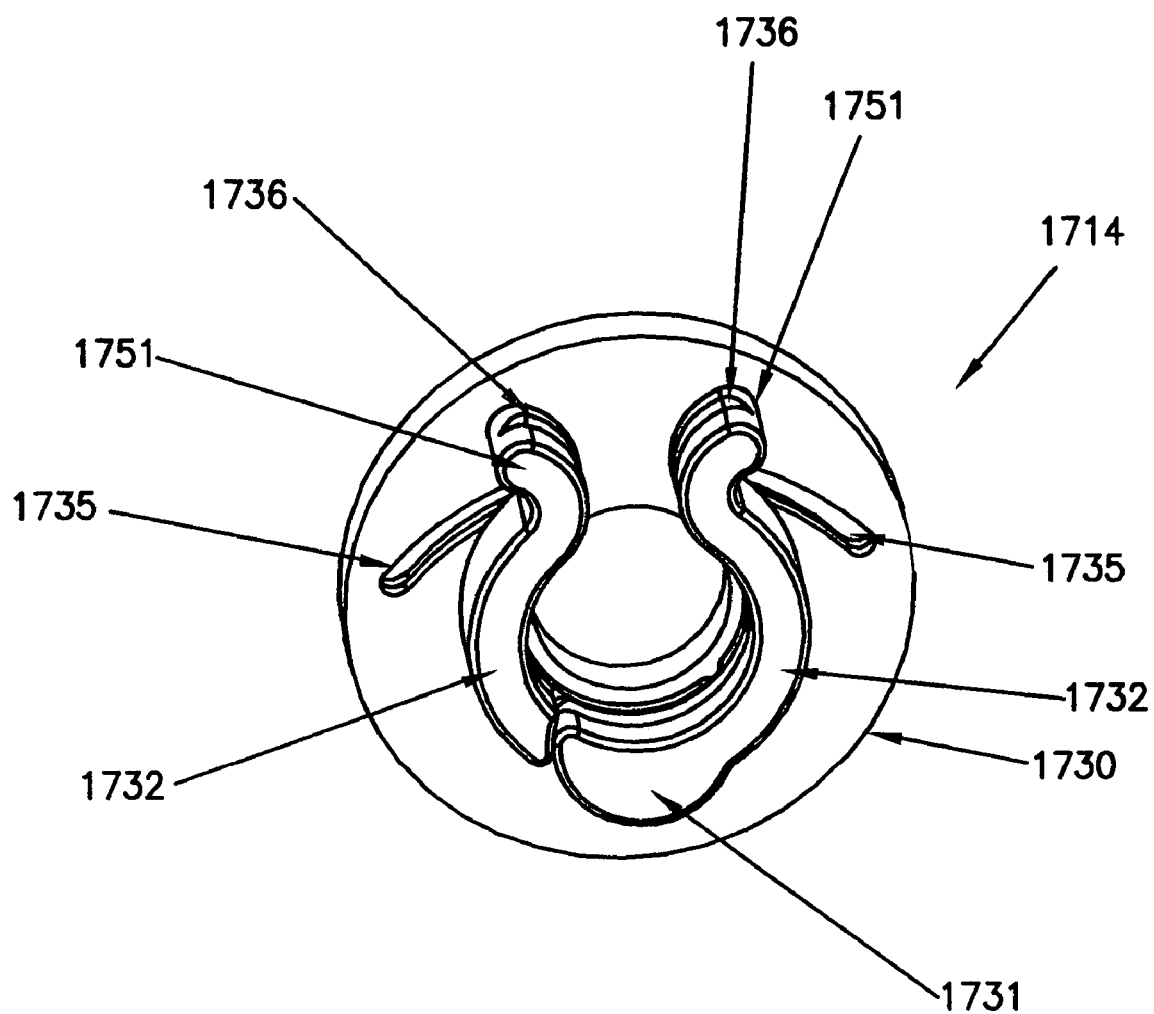
FIG. 42D is a plan, perspective view of the syringe interface shown in FIG. 42A in a closed position.

FIGS. 42A-42D illustrate an alternate embodiment 1700 of the syringe interface and syringe system 1600 shown in FIGS. 41A-41D. The system 1700 includes a syringe 1512 and a syringe interface 1714. The syringe interface 1714, as best shown in FIGS. 42C and 42D, differs from the syringe interface 1614 in FIGS. 41A-41D in that the retaining members 1732 include pivot ends 1751 located at the ends of the retaining members 1732 remote from the pivot pin 1731. Further, the retaining members 1732 are preferably spring-biased in the "closed" or "engaged" position, as best shown in FIG. 42D, to retain the syringe 1512 within the syringe interface 1714.

To install the syringe 1512 on the syringe interface 1714, the syringe 1512 is moved downwardly (in the direction of Arrow D in FIG. 42B) into engagement with the retaining members 1732. When the syringe barrel 1516 engages the pivot ends 1751 of the retaining members 1732, the retaining members 1732 are urged apart against the spring force to allow the syringe barrel 1516 to pass between the pivot ends 1751 and into the space defined between the retaining members 1732. The syringe mounting member 1522 is guided by the channels 1736 defined in the retaining members 1732 to correctly position the syringe 1512 within the syringe interface 1714. Once the syringe 1512 passes the pivot ends 1751, the retaining members 1732 are urged by the spring force to collapse around the rear end 1520 of the syringe 1512. The pins 1729, riding in slots 1735 defined in the base member 1730, direct and control the arcuate motion of the retaining members 1732 into engagement around the syringe 1512. As the retaining members 1732 collapse on the syringe 1512, the retaining members 1732 cooperate to capture the mounting member 1522 within the channels 1736 to securely engage the syringe 1512 within the syringe interface 1714.

To remove the syringe 1512 from the syringe interface 1714, the syringe 1512 is moved upwardly (in the opposite direction of Arrow D) against the pivot ends 1751 of the retaining members 1732. When the upward force on the syringe 1512 overcomes the spring force holding the retaining members 1732 together, the retaining members 1732 will move apart and allow the syringe 1512 to slide free from the syringe interface 1714.

Figure 43A:
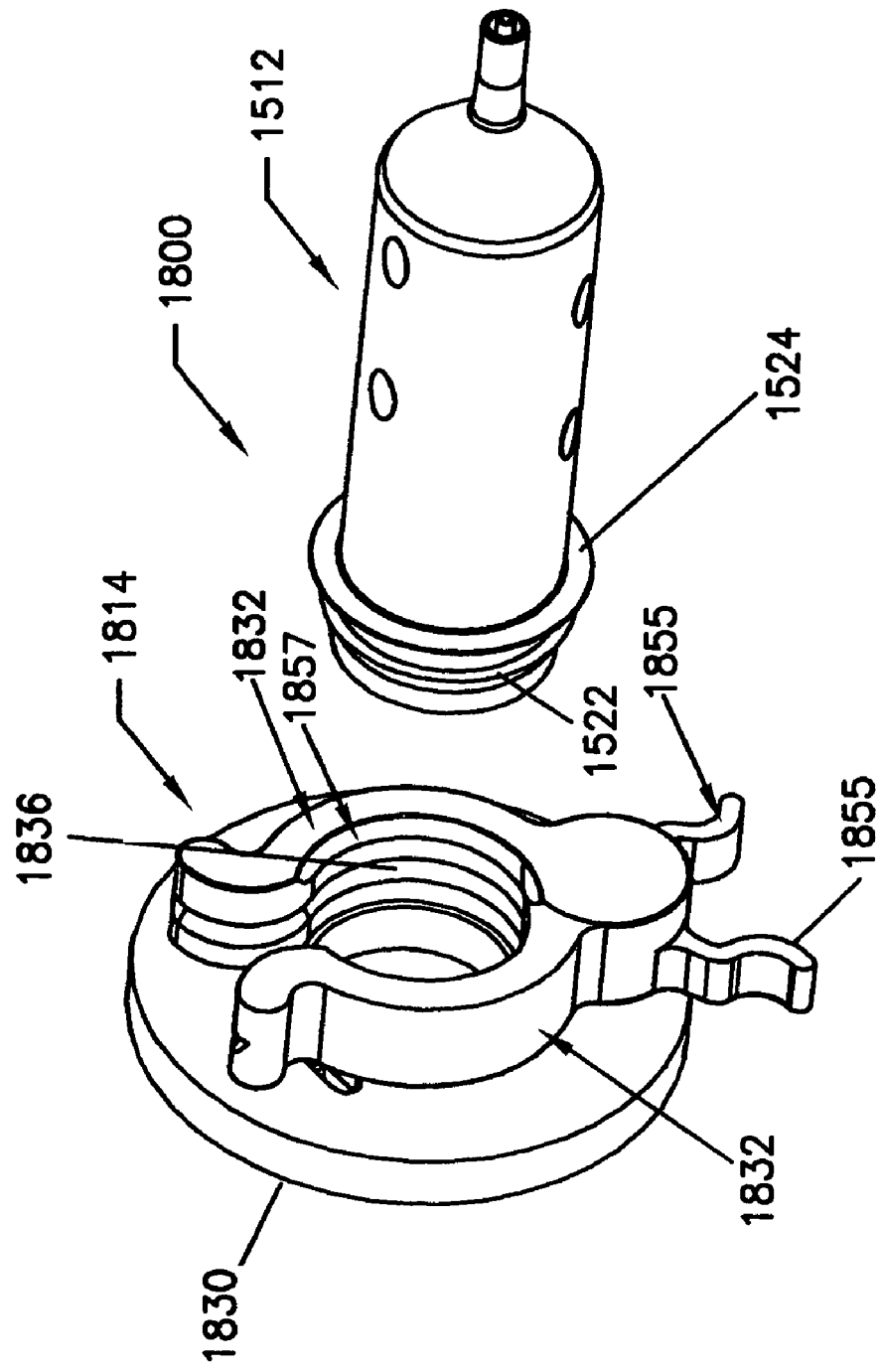
FIG. 43A is an exploded, perspective view of another alternate embodiment of the embodiment of the front-loading syringe interface and syringe system shown in FIGS. 41A-41D.
Figure 43B:
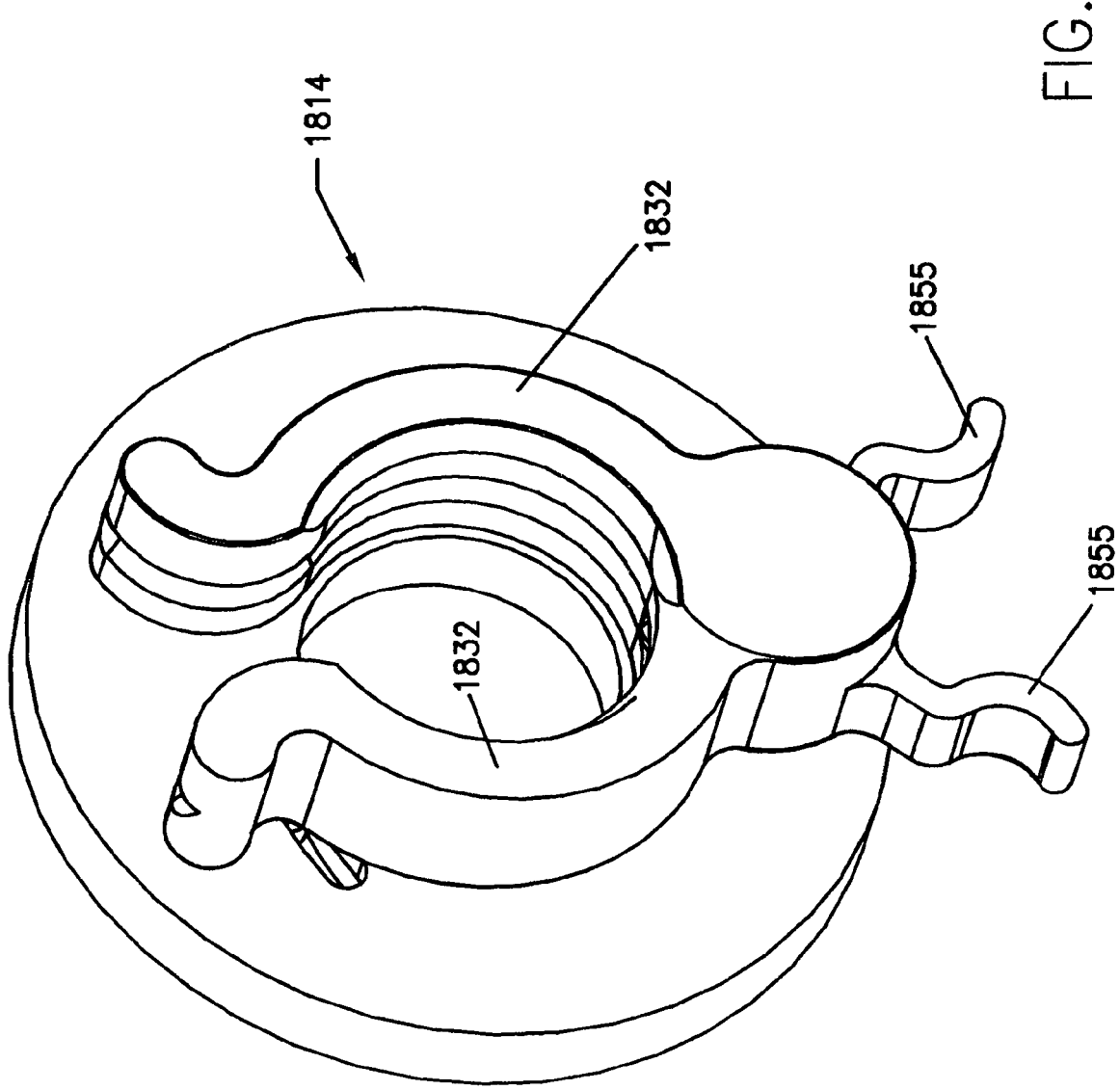
FIG. 43B is a perspective view of the syringe interface shown in FIG. 43A in a closed position.
Figure 43C:
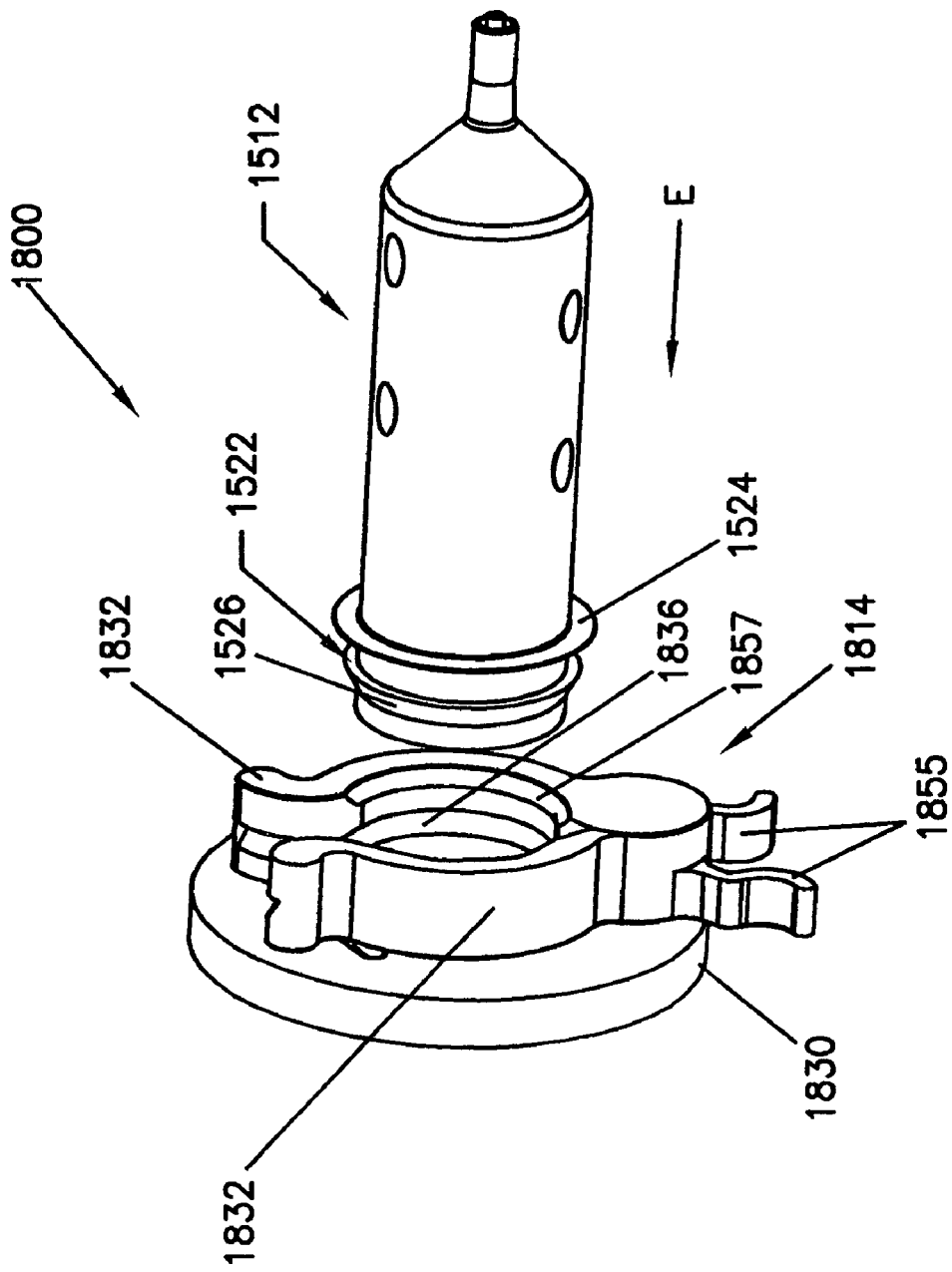
FIG. 43C is a side, perspective view of the system shown in FIG. 43A in a first disengaged position.
Figure 43D:
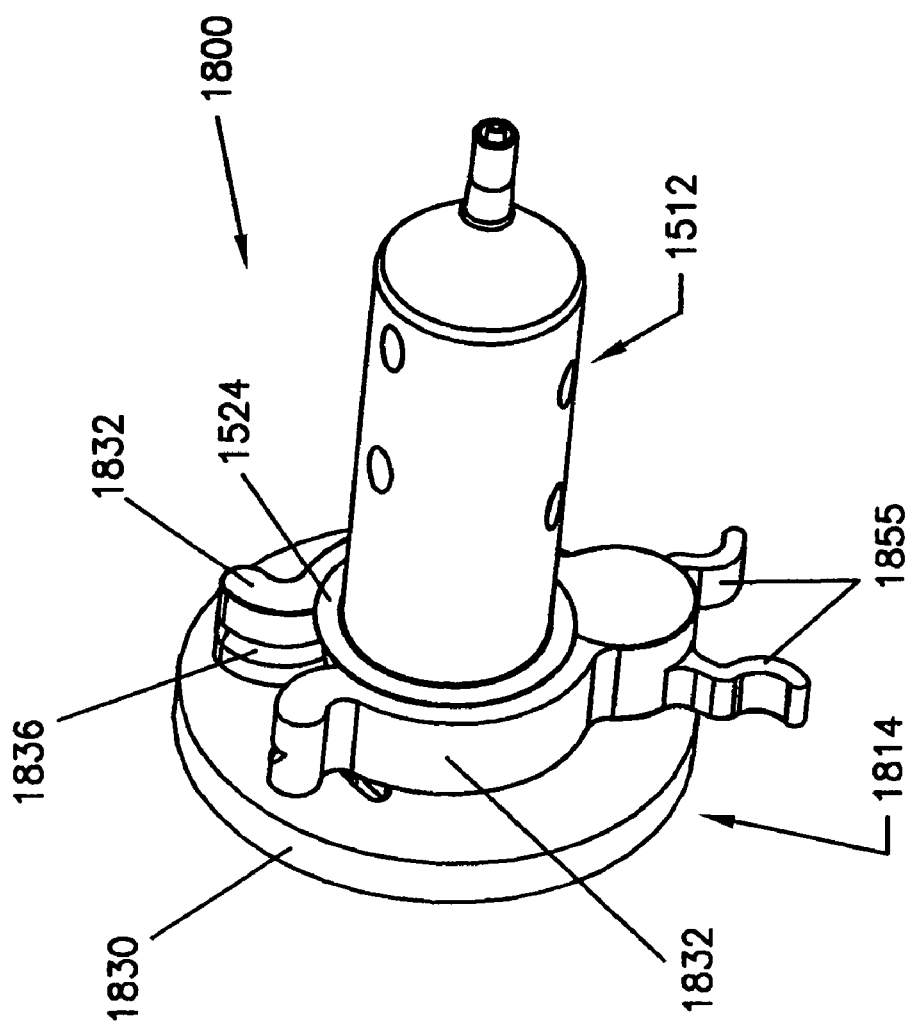
FIG. 43D is a perspective view of the system shown in FIG. 43A in an installed position.
Figure 43E:
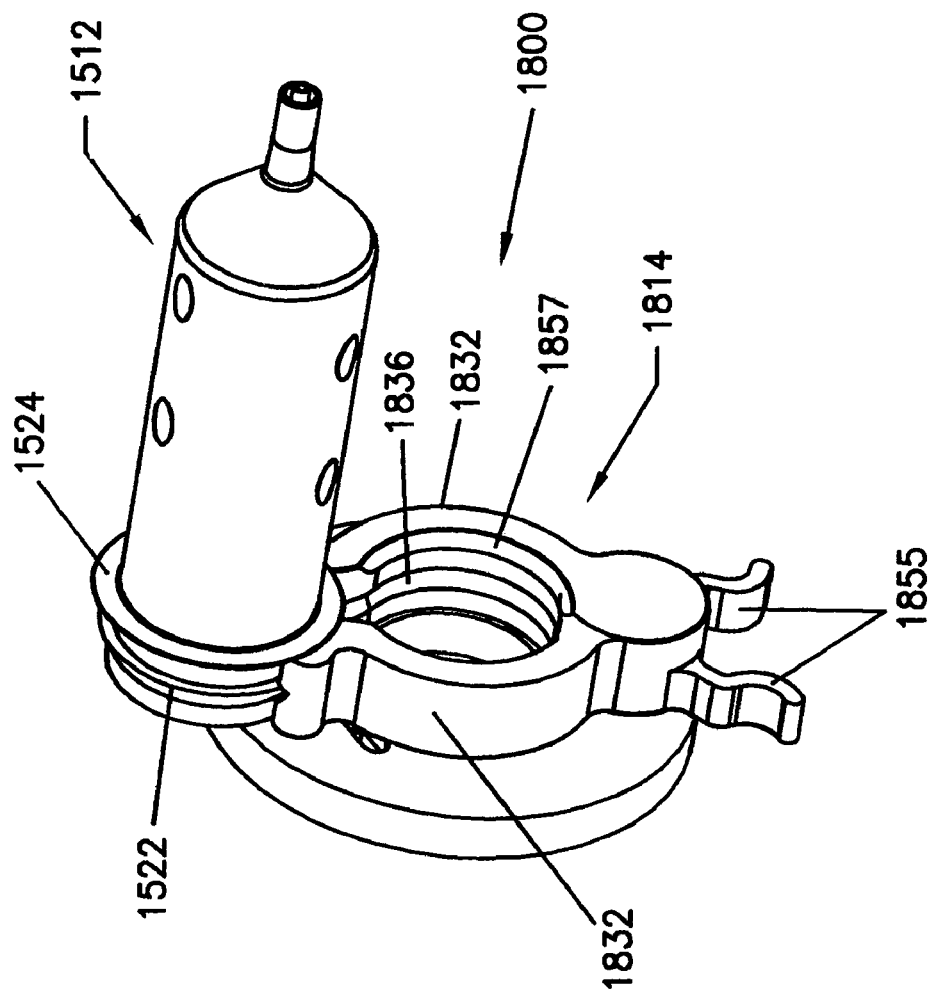
FIG. 43E is a perspective view of the system shown in FIG. 43A in a second disengaged position.
Figure 43F:
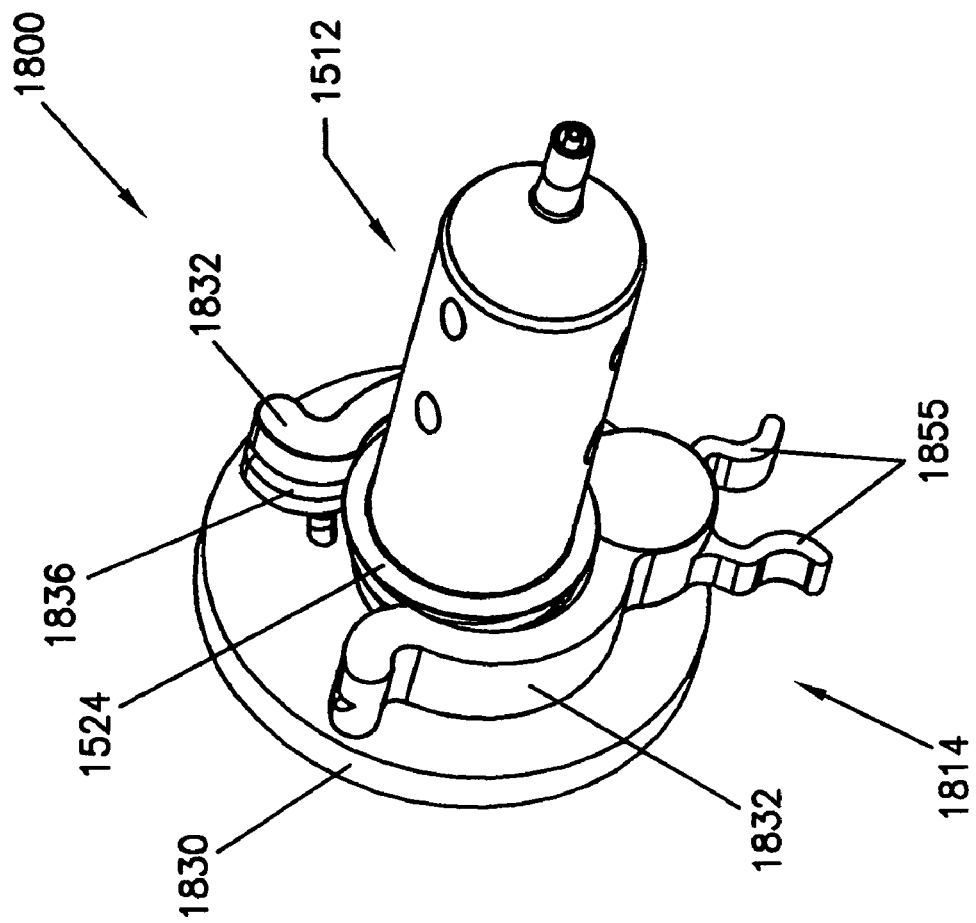
FIG. 43F is a perspective view of the system shown in FIG. 43A in an open position for syringe removal.
Figure 43G:
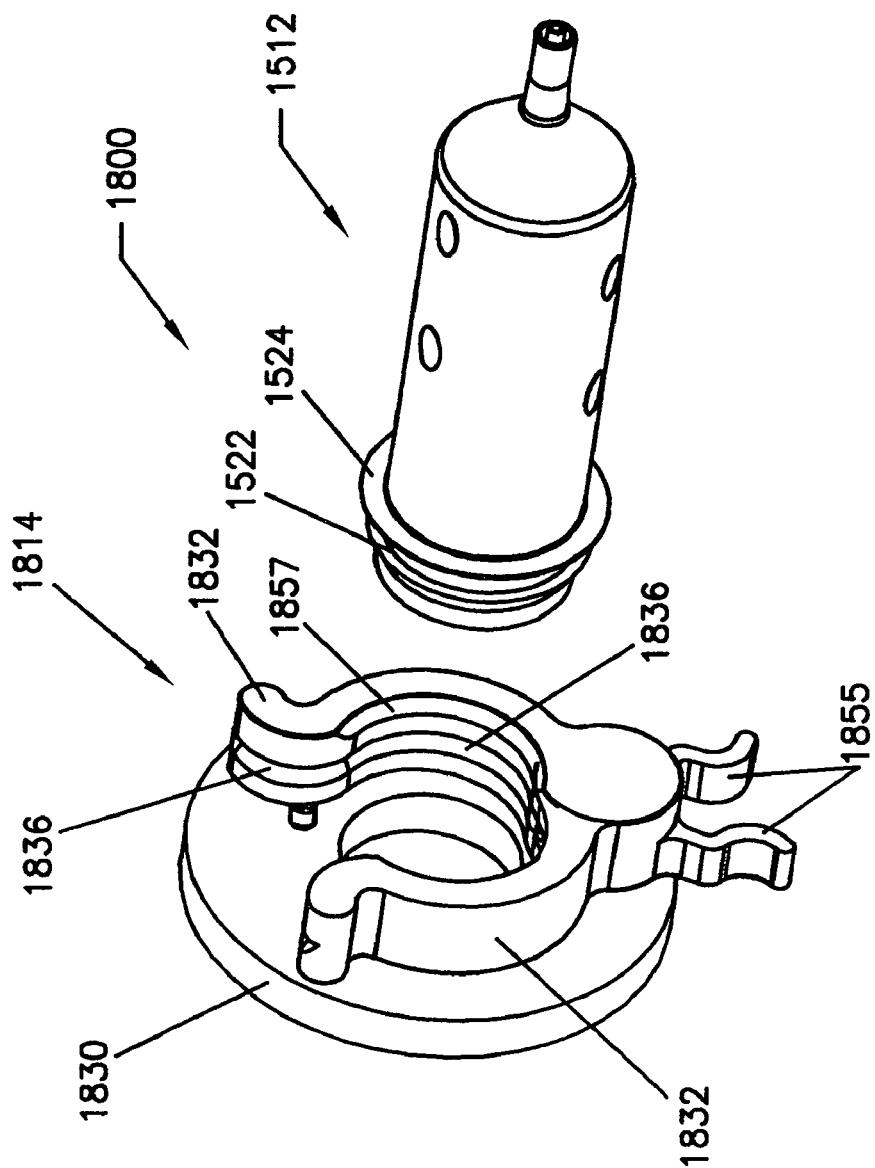
FIG. 43G is an exploded, perspective view of the system shown in FIG. 43A with the syringe interface in an open position.
Figure 43H:
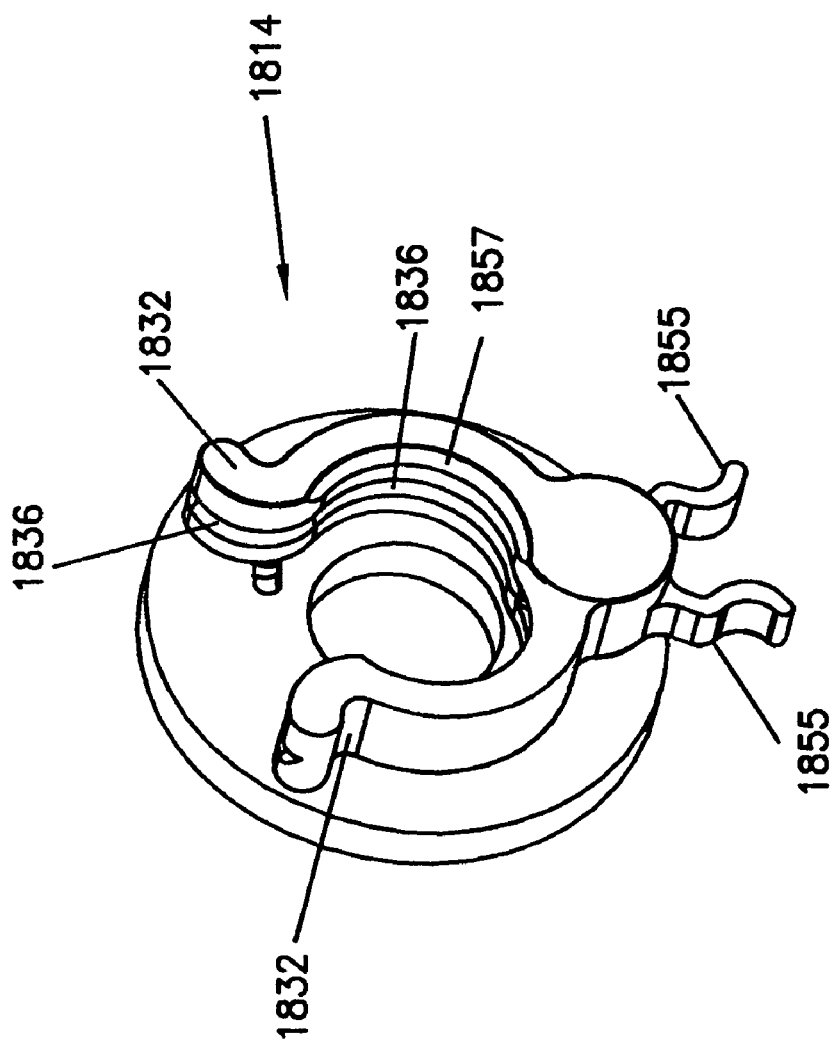
FIG. 43H is a front, perspective view of the syringe interface shown in FIG. 43A in an open position.
Figure 43I:
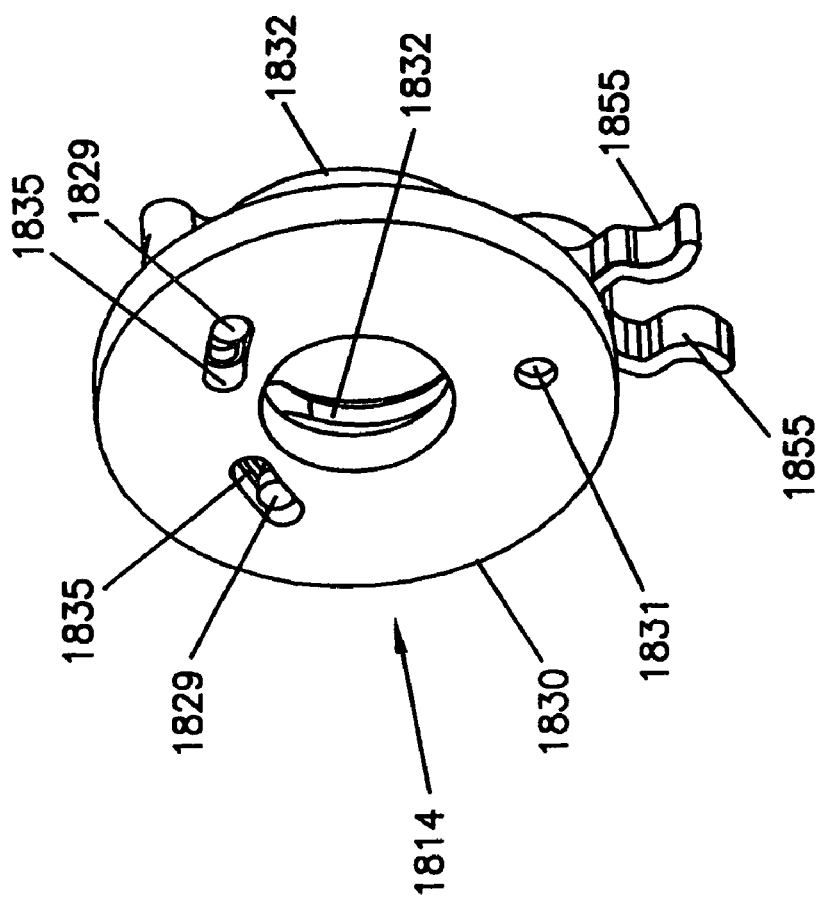
FIG. 43I is a rear, perspective view of the syringe interface shown in FIG. 43A in an open position.

FIGS. 43A-43I illustrate another alternate embodiment 1800 of the syringe interface and syringe systems 1600, 1700 shown in FIGS. 41A-42D. The system 1800 includes a syringe 1512 and a syringe interface 1814. The syringe interface 1814, as best shown in FIGS. 43B and 43H, differs from the syringe interfaces 1614, 1714 in FIGS. 41A-42D in that the retaining members 1832 include extension members 1855 and chamfers 1857. The extension members 1855 preferably are manipulated to move the retaining members 1832 to an open position (i.e., against the spring force holding the retaining members 1832 in the closed position). The chamfers 1857 are operably engaged by the inclined surface 1526 of the mounting member 1522 of the syringe 1512 to open the retaining members 1832 and allow the syringe 1512 to be axially installed (in the direction of Arrow E in FIG. 43C) on the syringe interface 1814. The remaining structure of the syringe interface 1814 is substantially similar or identical to the structure of the syringe interface 1714 described above.

As best shown in FIG. 43E, the syringe 1512 can be installed and removed from the syringe interface 1814 in substantially the same manner as described above with respect to FIGS. 42A-42D. In addition, however, as best shown in FIGS. 43A, 43C, 43F and 43G, the syringe 1512 can be axially installed and removed from the syringe interface 1814. Therefore, the syringe interface 1814 accommodates two methods of installing/removing the syringe 1512.

To axially install the syringe 1512, the syringe 1512 is inserted into the syringe interface 1814 until the mounting member 1522 engages the retaining members 1832. The inclined surface 1526 of the mounting member 1522 engages the chamfers 1857 on the retaining members 1832, thereby forcing the retaining members 1832 apart against the spring force. After the mounting member 1522 clears the chamfered area, the retaining members 1832 collapse around and capture the mounting member 1522 within the channels 1836 to secure the syringe 1512 to the syringe interface 1814.

To axially remove the syringe 1512, the extension members 1855 of the retaining members 1832 may be manipulated (i.e., pressed together) to overcome the spring force and urge apart the retaining members 1832. When the retaining members 1832 have moved apart to such an extent that the mounting member 1522 of the syringe 1512 is cleared from engagement within the channels 1836, the syringe 1512 may be axially removed (in the direction opposite from Arrow E) from the syringe interface 1814.

Figure 44A:
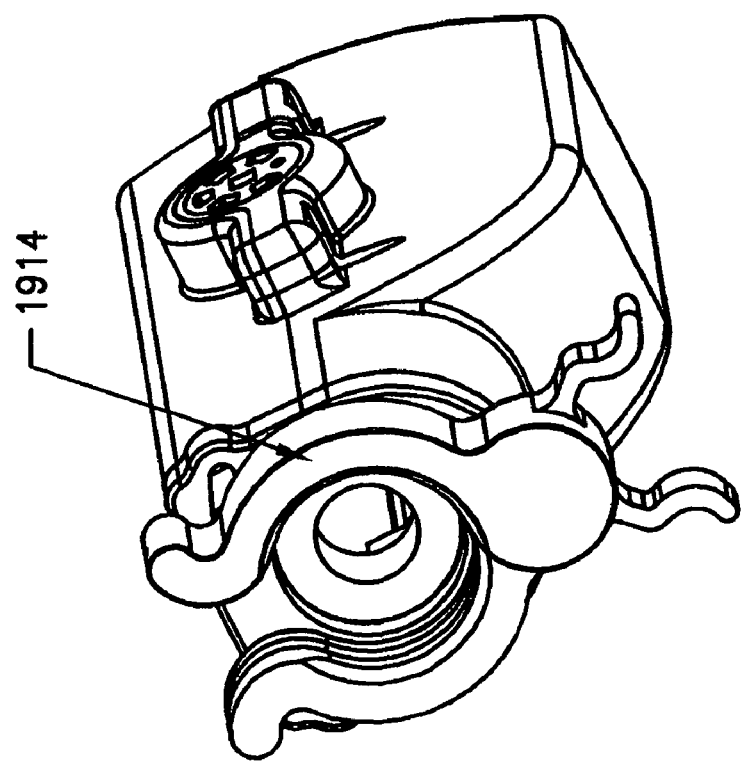
FIG. 44A is a perspective view of a slightly altered version of the syringe interface shown in FIGS. 43A-43I incorporated in or mounted on an injector head.
Figure 44B:
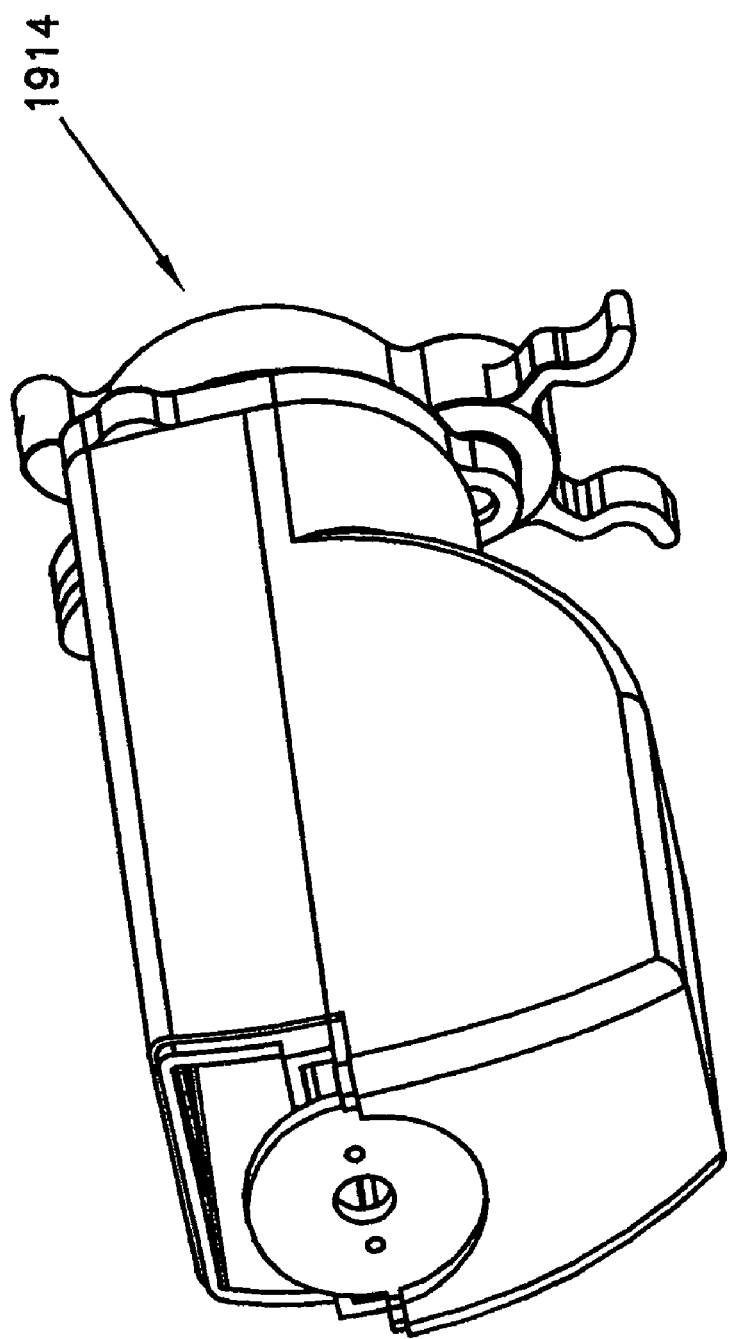
FIG. 44B is a rear, perspective view of the syringe interface and injector head shown in FIG. 44A.

FIGS. 44A and 44B illustrate a first, slightly altered embodiment of the syringe interface 1814 shown in FIGS. 43A-43I incorporated in or mounted on an injector head. The functionality of the syringe interface 1914 is substantially similar or identical to that described above with respect to the syringe interface 1814.

Figure 45A:
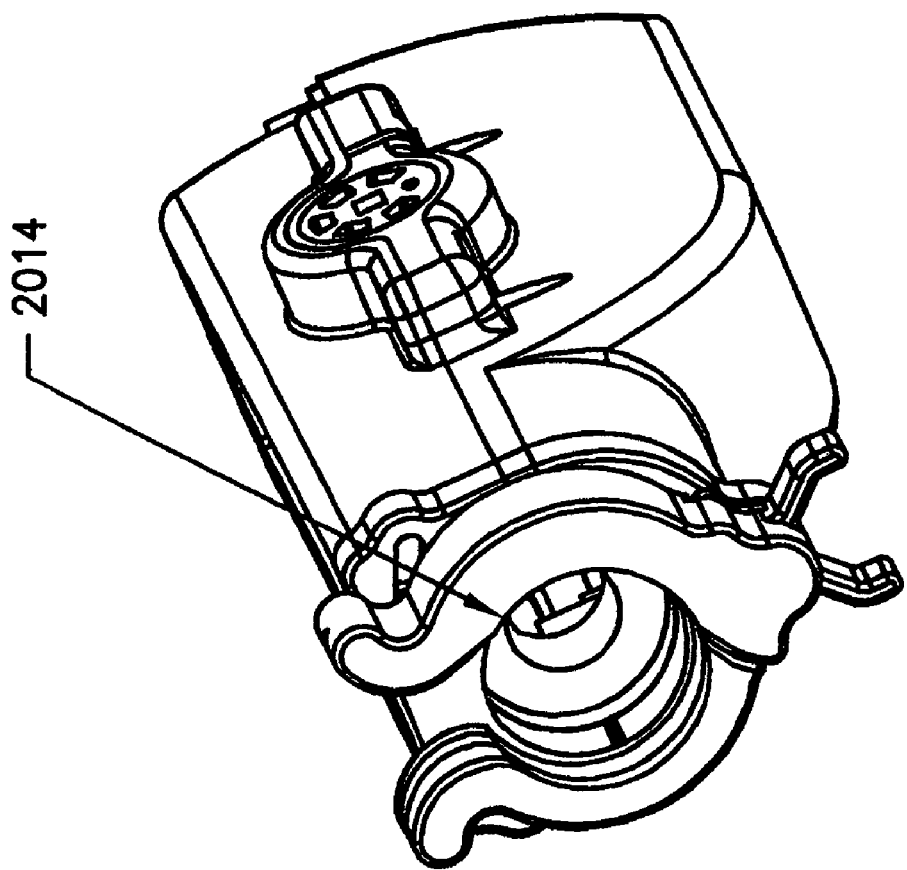
FIG. 45A is a perspective view of a second, slightly altered version of the syringe interface shown in FIGS. 43A-43I incorporated in or mounted on an injector head.
Figure 45B:
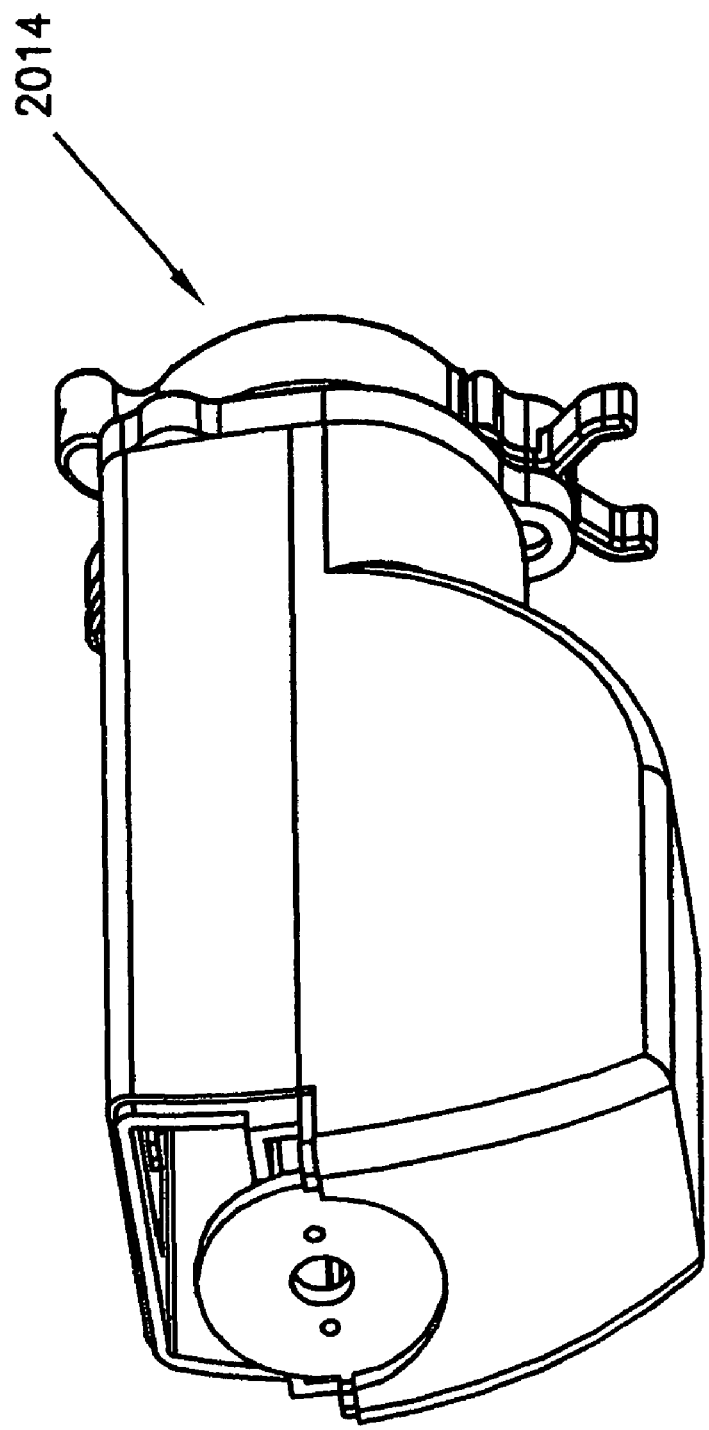
FIG. 45B is a rear, perspective view of the syringe interface and injector head shown in FIG. 45A.

FIGS. 45A and 45B illustrate a second, slightly altered embodiment of the syringe interface 1814 shown in FIGS. 43A-43I incorporated in or mounted on an injector head. The functionality of the syringe interface 2014 is substantially similar or identical to that described above with respect to the syringe interface 1814.

Figure 46A:
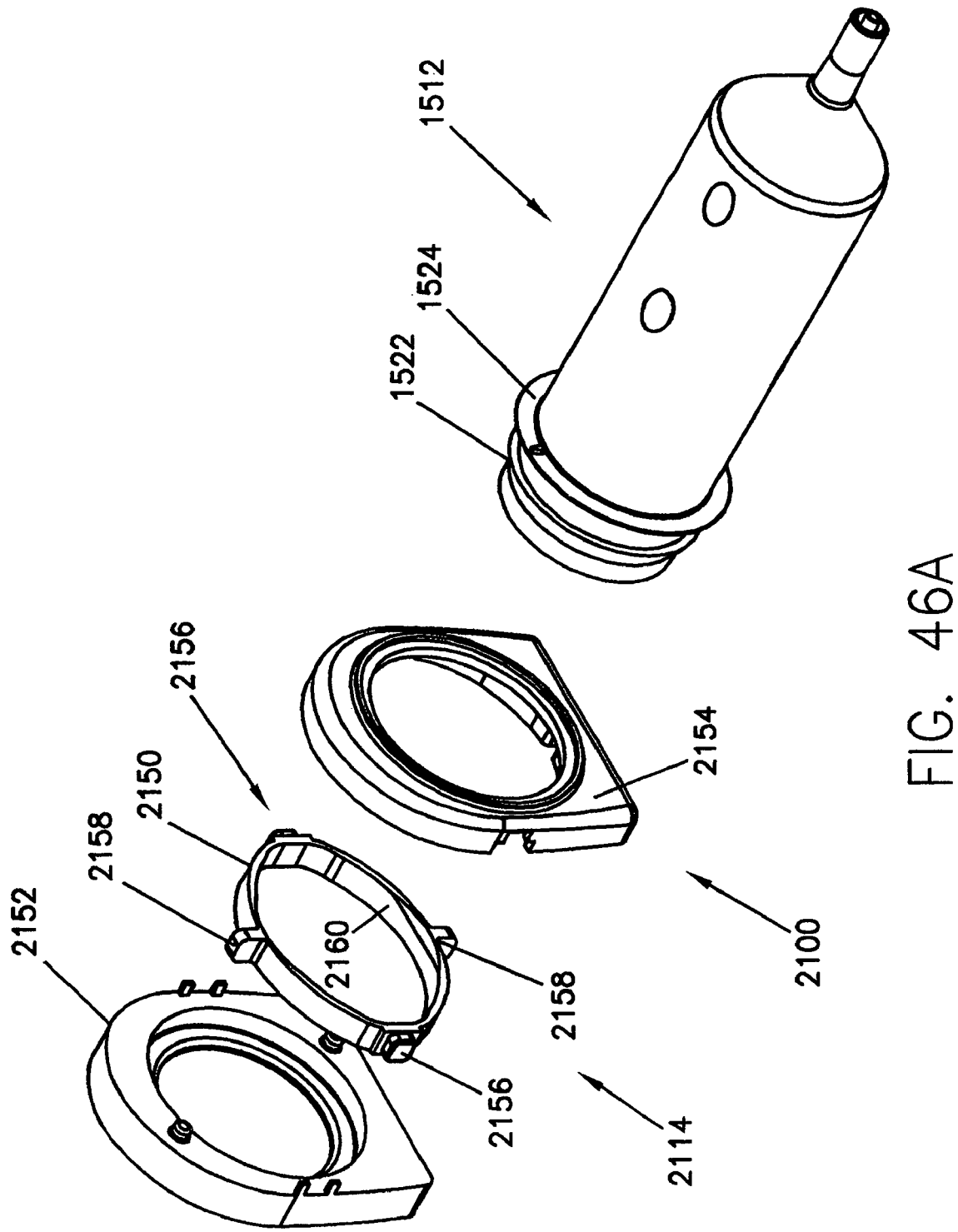
FIG. 46A is an exploded, perspective view of a first preferred embodiment of a front-loading syringe interface and syringe system in accordance with the present invention.

FIGS. 46A-46D illustrate a first preferred embodiment of a front-loading syringe interface and syringe system 2100 in accordance with the present invention. The system 2100 includes a syringe 1512 and a syringe interface 2114. As best shown in FIG. 46A, the syringe interface 2114 comprises a flexible, retaining ring 2150 disposed between a rear plate 2152 and a front plate 2154. The retaining ring 2150 defines a rear ledge 2160 that is adapted to engage the mounting member 1522 of the syringe 1512 when the syringe 1512 is installed in the syringe interface 2114.

Figure 46B:
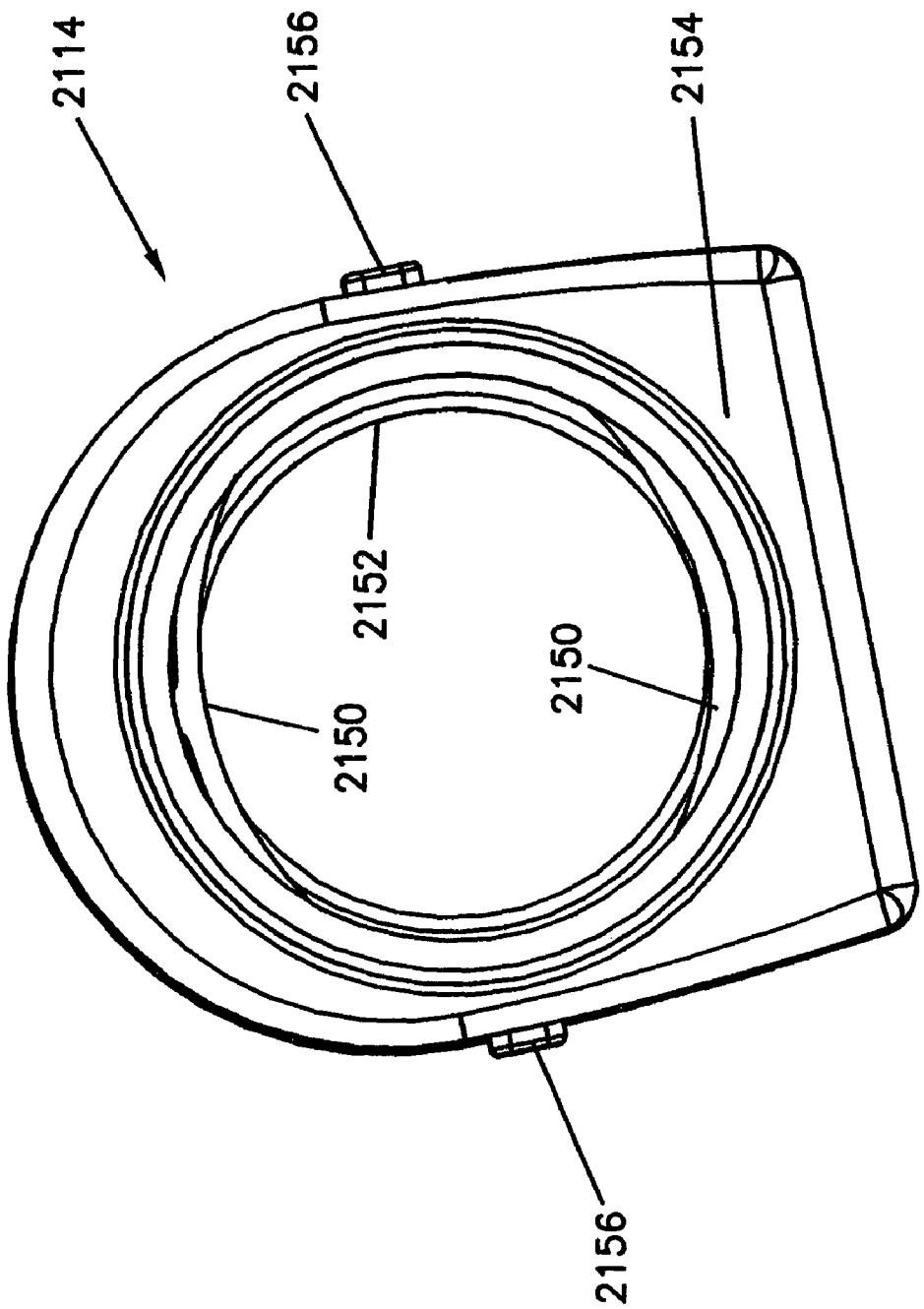
FIG. 46B is an assembled, perspective view of the syringe interface shown in FIG. 46A.
Figure 46C:
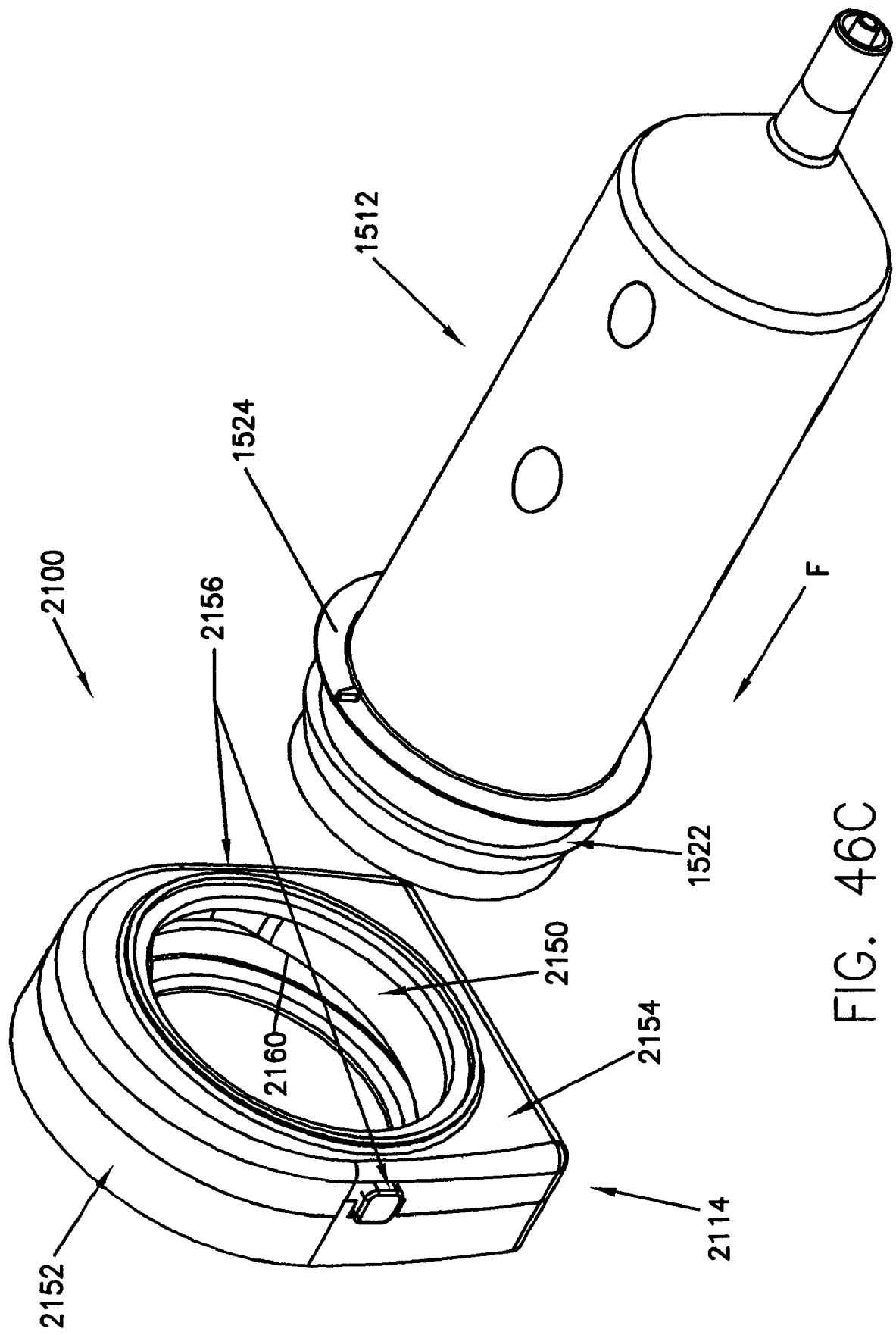
FIG. 46C is a perspective view of the system shown in FIG. 46A in a disengaged position.
Figure 46D:
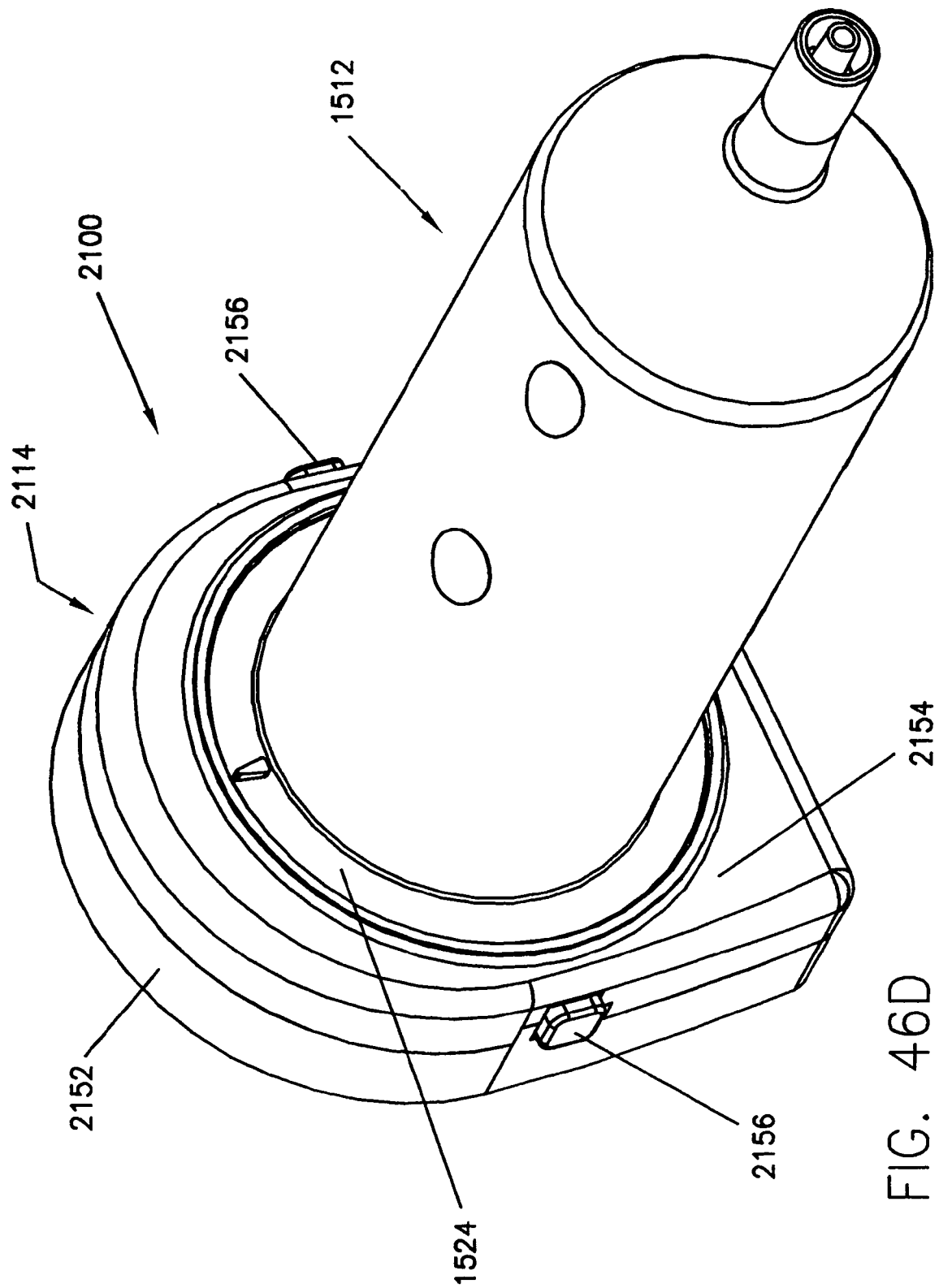
FIG. 46D is a perspective view of the system shown in FIG. 46A in an installed position.
Figure 47A:
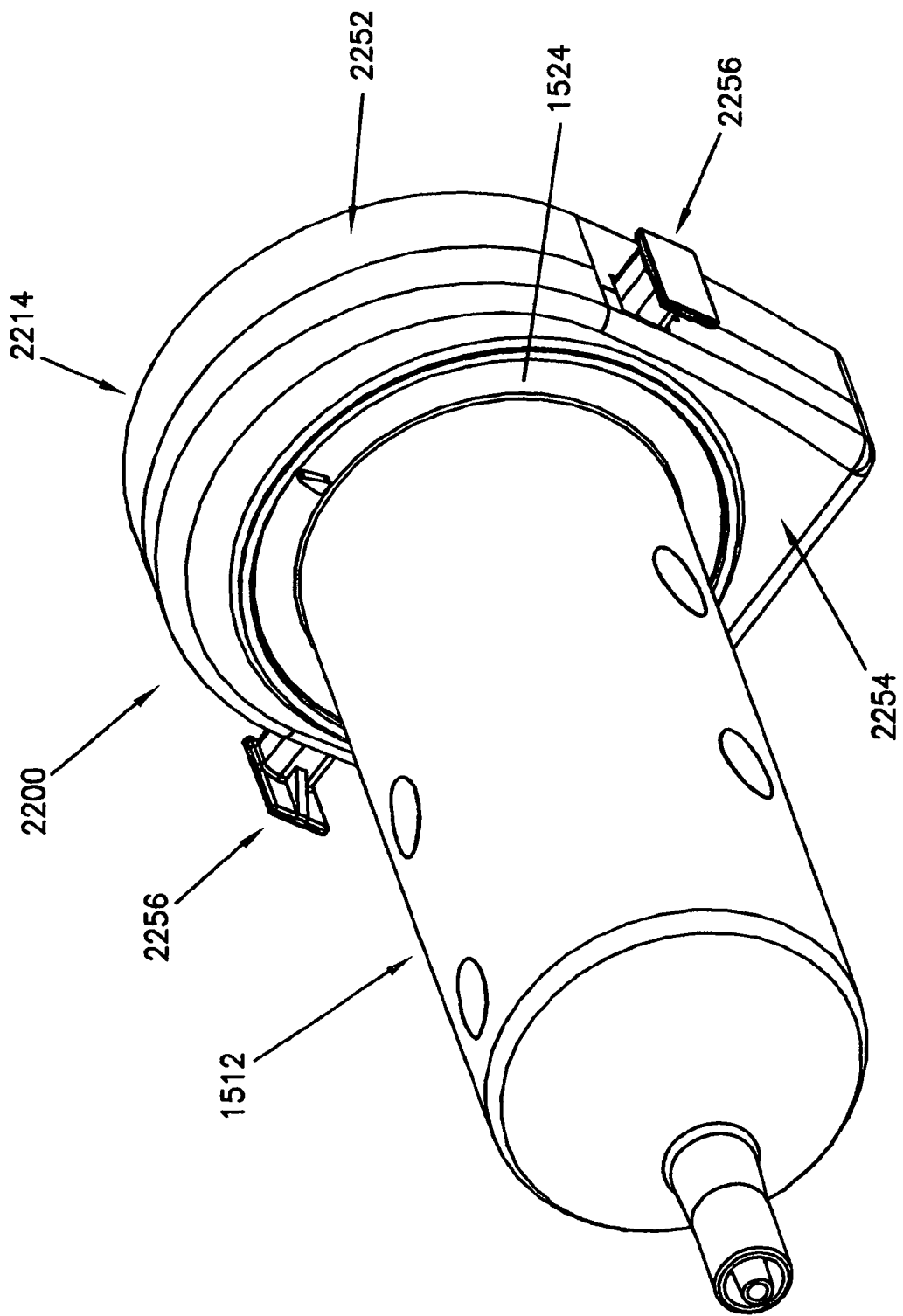
FIG. 47A is a perspective view of an alternate embodiment of the first preferred embodiment of the front-loading syringe interface and syringe system shown in FIGS. 46A-46D in an installed position.
Figure 47B:
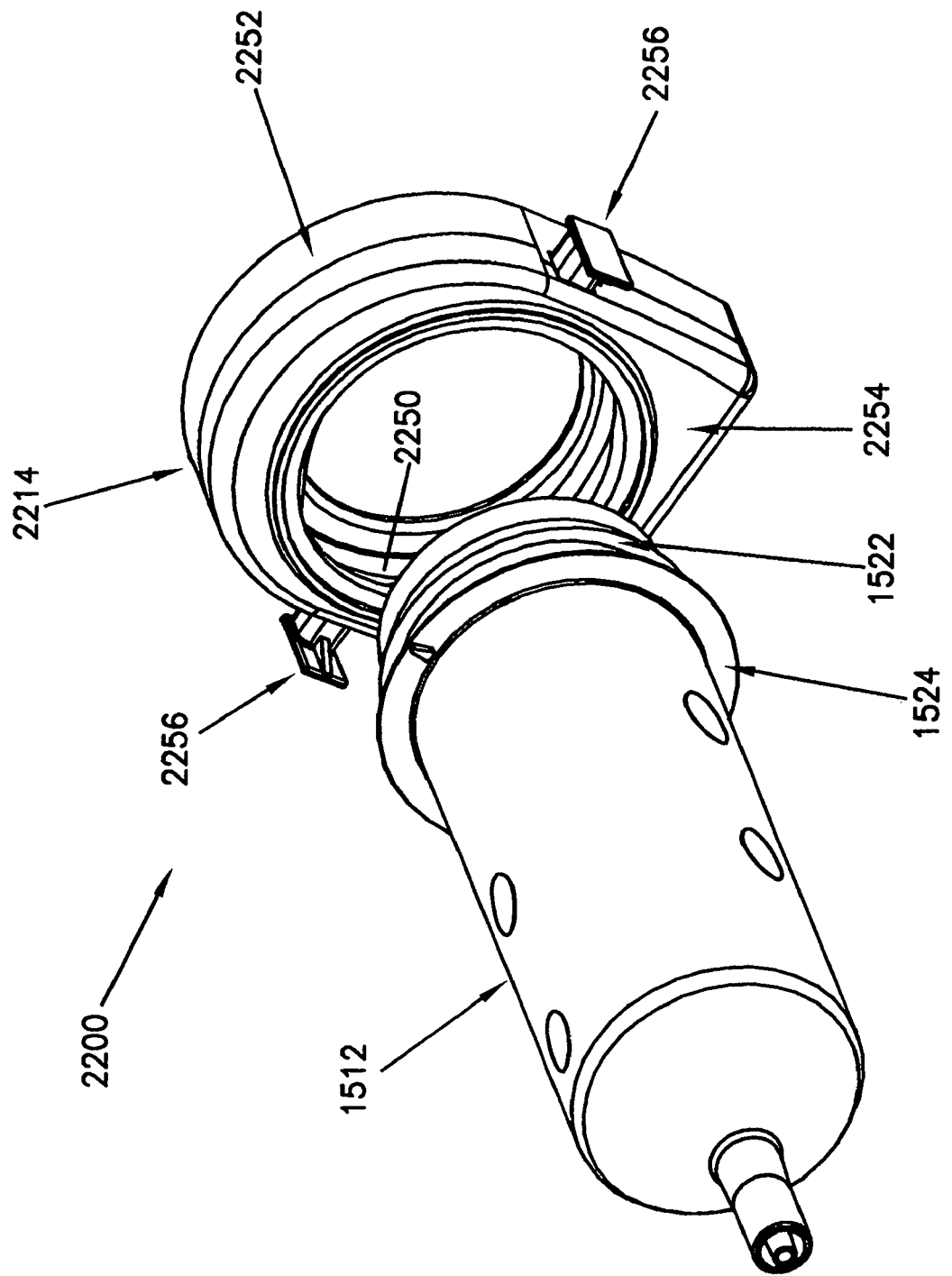
FIG. 47B is a perspective view of the system shown in FIG. 47A in a disengaged position.
Figure 47C:
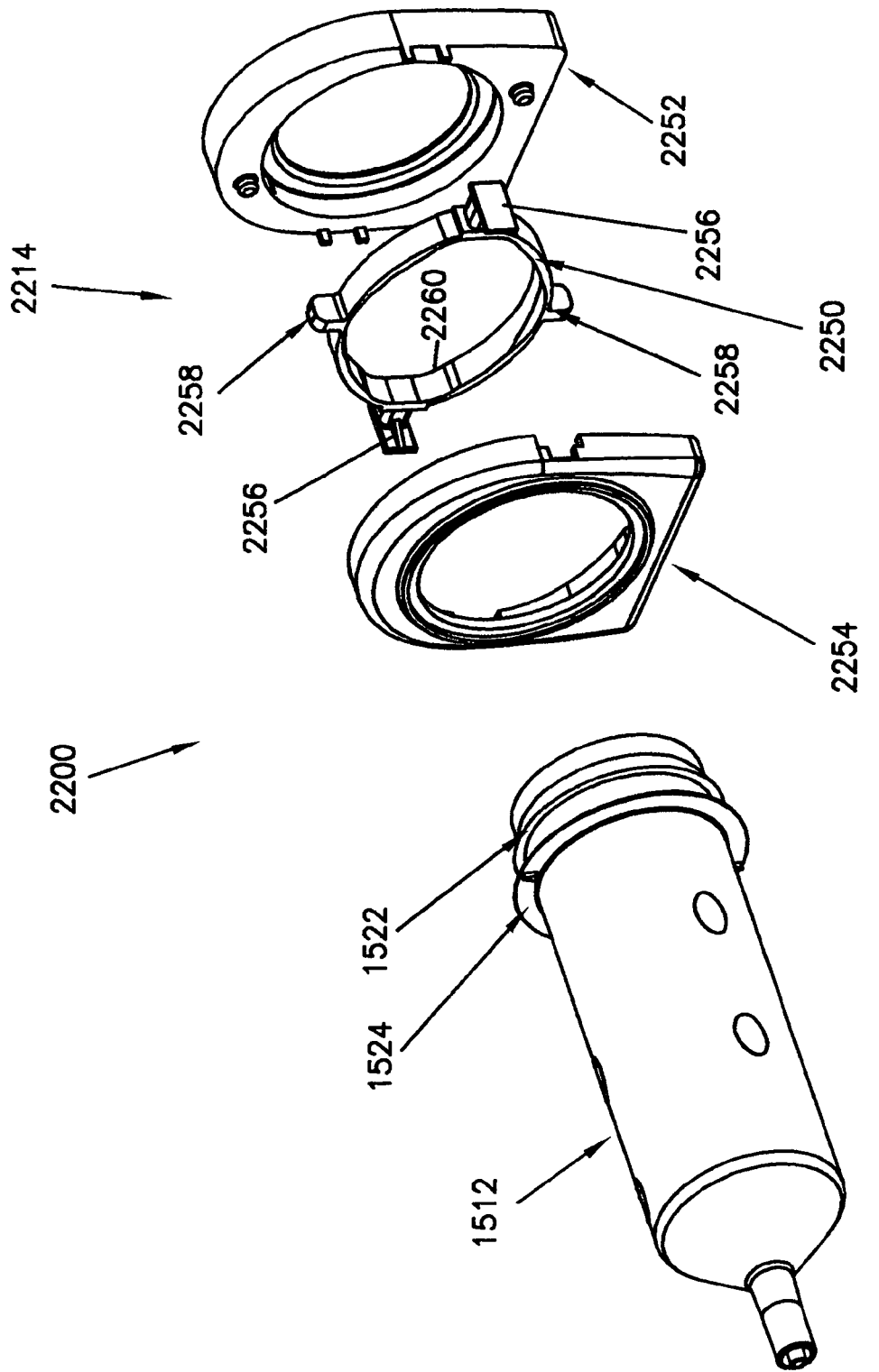
FIG. 47C is an exploded, perspective view of the system shown in FIG. 47A.
Figure 47D:
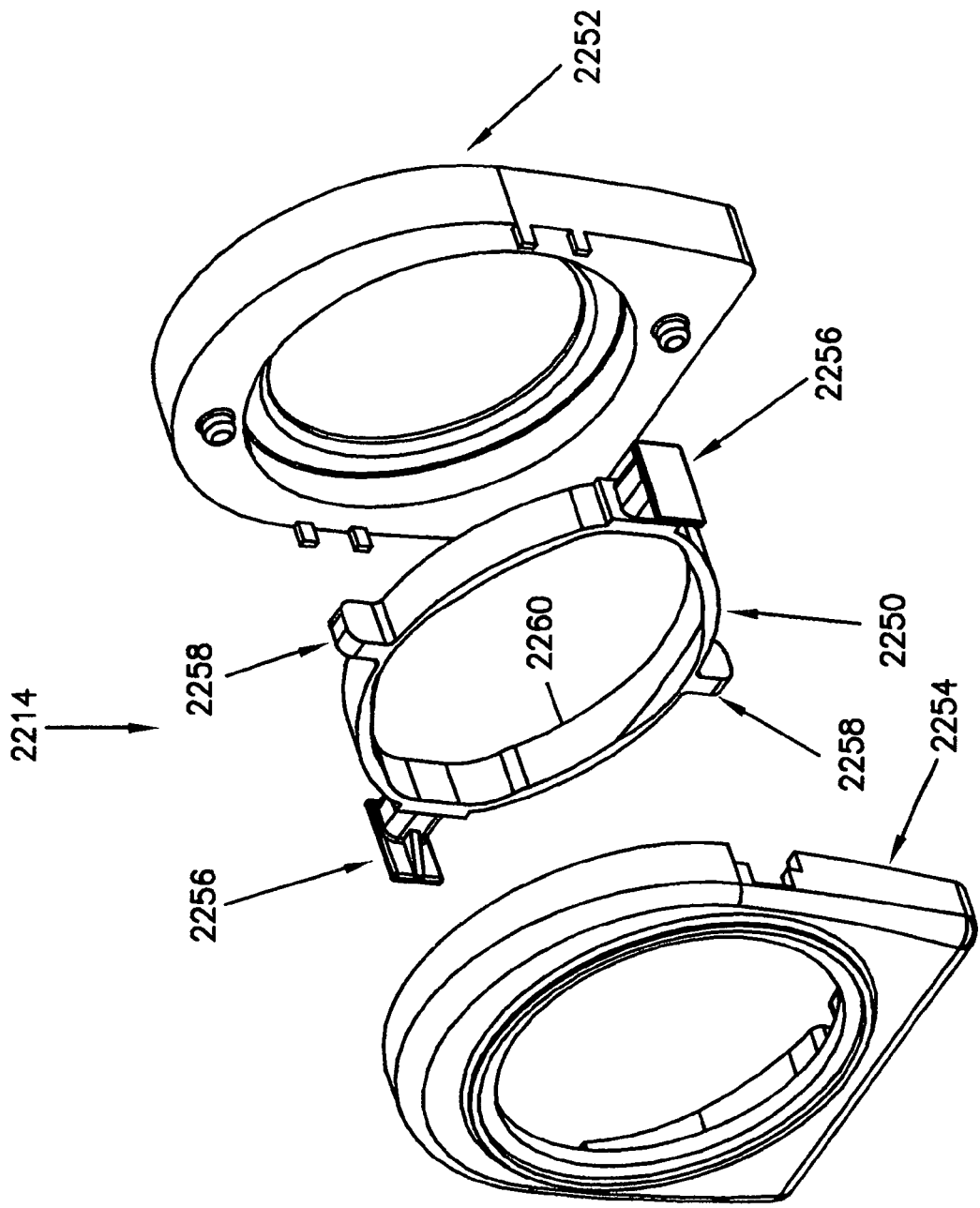
FIG. 47D is an exploded, perspective view of the syringe interface shown in FIG. 47A.
Figure 47E:
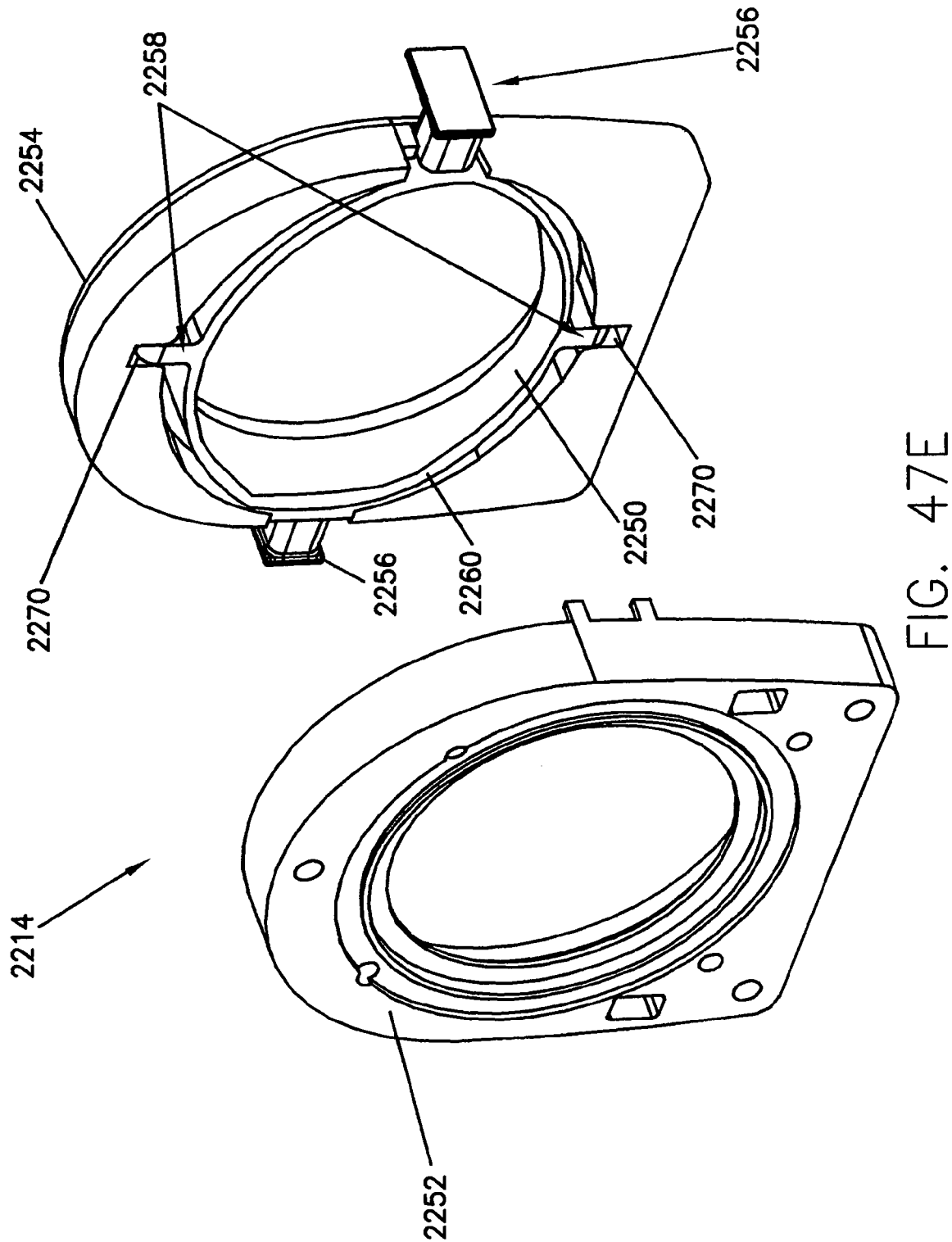
FIG. 47E is a rear, partially assembled, perspective view of the syringe interface shown in FIG. 47A.

The ring 2150 comprises at least one, but preferably two, release members 2156 and at least one, but preferably two, protrusion members 2158. Further, the ring 2150 is preferably elliptical in shape to enable engagement with and disengagement from the mounting member 1522 of the syringe 1512, as described in more detail below. As best shown in FIGS. 46B-46D, the release members 2156 protrude from the rear and front plates 2152, 2154 for manipulation by, for example, an operator to release the syringe 1512 from the syringe interface 2114. Further, the protrusion members 2158 are captured by and slide within channels (not shown) defined in the rear surface (not shown) of the front plate 2154 to allow removal of the syringe 1512 from the syringe interface 2114 when only one release member 2156, instead of both release members 2156, can be manipulated. (The channels are described below with respect to the alternate embodiment of FIGS. 47A-47F and are shown in FIG. 47E.)

To install the syringe 1512 on the syringe interface 2114, the syringe 1512 is moved axially (in the direction of Arrow F in FIG. 46C) into engagement with the syringe interface 2114. When the mounting member 1522 engages the retaining ring 2150, the mounting member 1522 urges the flexible, elliptically-shaped ring 2150 into a more circularly-shaped configuration, thereby allowing the mounting member 1522 to move pass the ring 2150. After the mounting member passes the ring 2150, the ring 2150 returns to its original shape, thereby capturing the mounting member 1522 behind the rear ledge 2160 thereof and securing the syringe 1512 to the syringe interface 2114.

The protrusion members 2158 and the channels (not shown) are provided to control/constrain the motion of the retaining ring 2150 during syringe installation and removal. Specifically, the motion of the ring 2150 during syringe installation and removal (i.e., from substantially elliptical to substantially circular, and back) is directed and controlled by the protrusion members 2158 being able to slide within the channels. Consequently, regardless of the orientation of the syringe 1512 during initial engagement with the retaining ring 2150, the syringe force acting on the ring 2150 and the resulting motion of the ring 2150 is directed to and constrained by the protrusion members 2158 and the channels.

To remove the syringe 1512 from the syringe interface 2114, one or both of the release members 2156 may be pressed inward (i.e., toward the center of the syringe interface 2114), thereby forcing the ring 2150 from engagement with the mounting member 1522 of the syringe 1512. When the release member(s) 2156 is activated, the syringe 1512 may be grasped and moved axially (in the direction opposite from Arrow F in FIG. 46C) to remove the syringe 1512 from the syringe interface 2114.

When the release members 2156 are activated, the protrusion members 2158 slide within the channels (not shown) to direct the motion of the ring 2150 from a generally elliptical configuration to a generally circular configuration to disengage the mounting member 1522 from the rear ledge 2160 of the ring 2150.

As can be appreciated, the present embodiment permits a syringe 1512 to be installed on a syringe interface 2114 with a simple, one-step, axial motion. To remove the syringe 1512, one or both of the release members 2156 may be depressed and the syringe 1512 is simply removed axially from the syringe interface 2114.

FIGS. 47A-47F illustrate an alternate embodiment 2200 of the system 2100 shown in FIGS. 46A-46D. The system 2200 is substantially similar or identical in structure and function to the system 2100 described above in FIGS. 46A-46D, except that the release members 2256 are substantially enlarged for easier and simpler manipulation.

As discussed above with respect to FIGS. 46A-46D, FIG. 47E illustrates the channels 2270 formed in the front plate 2254 and the protrusion members 2258 captured within the channels 2270.

Figure 48A:
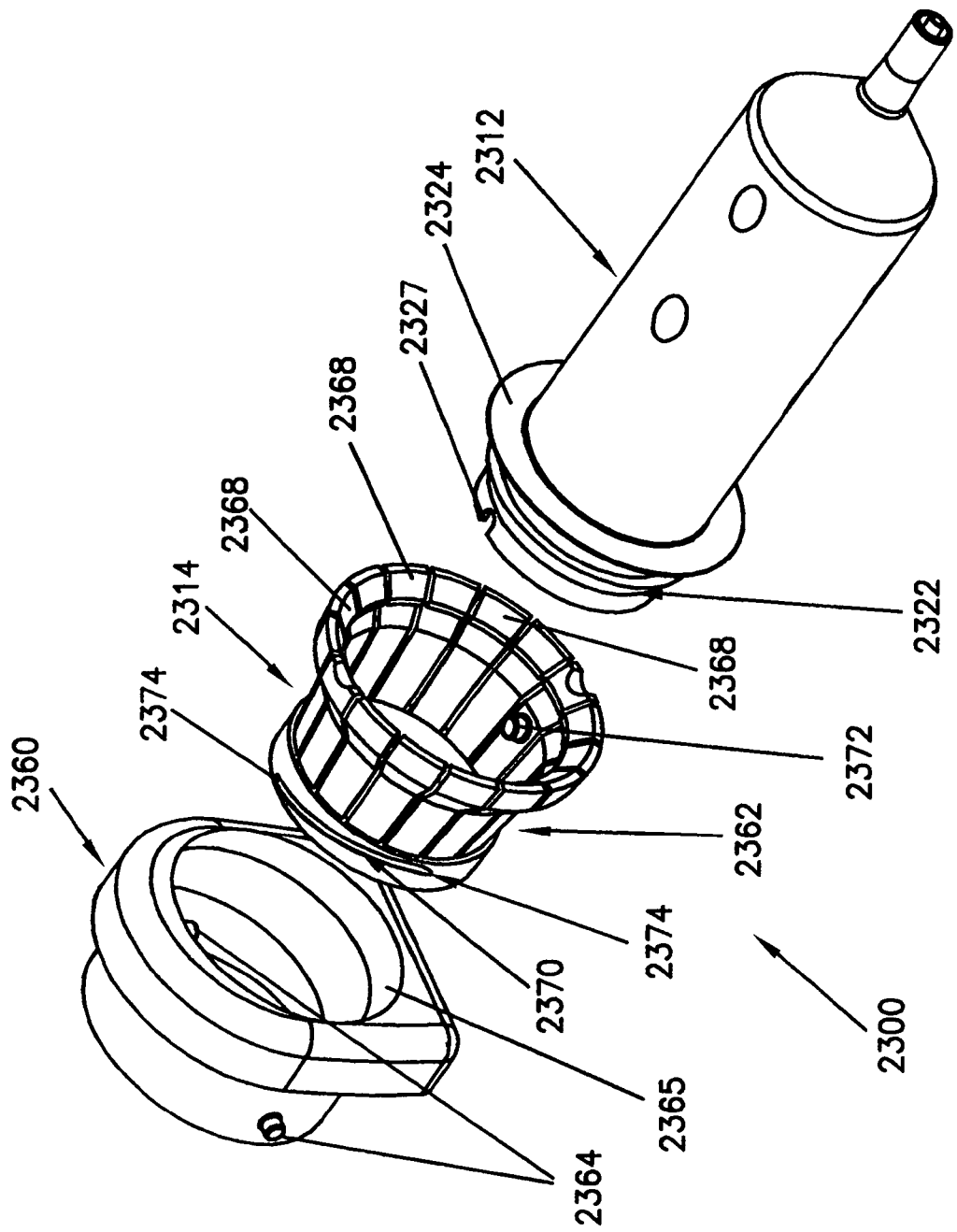
FIG. 48A is an exploded, perspective view of still another embodiment of a front-loading syringe interface and syringe system in accordance with the present invention.
Figure 48B:
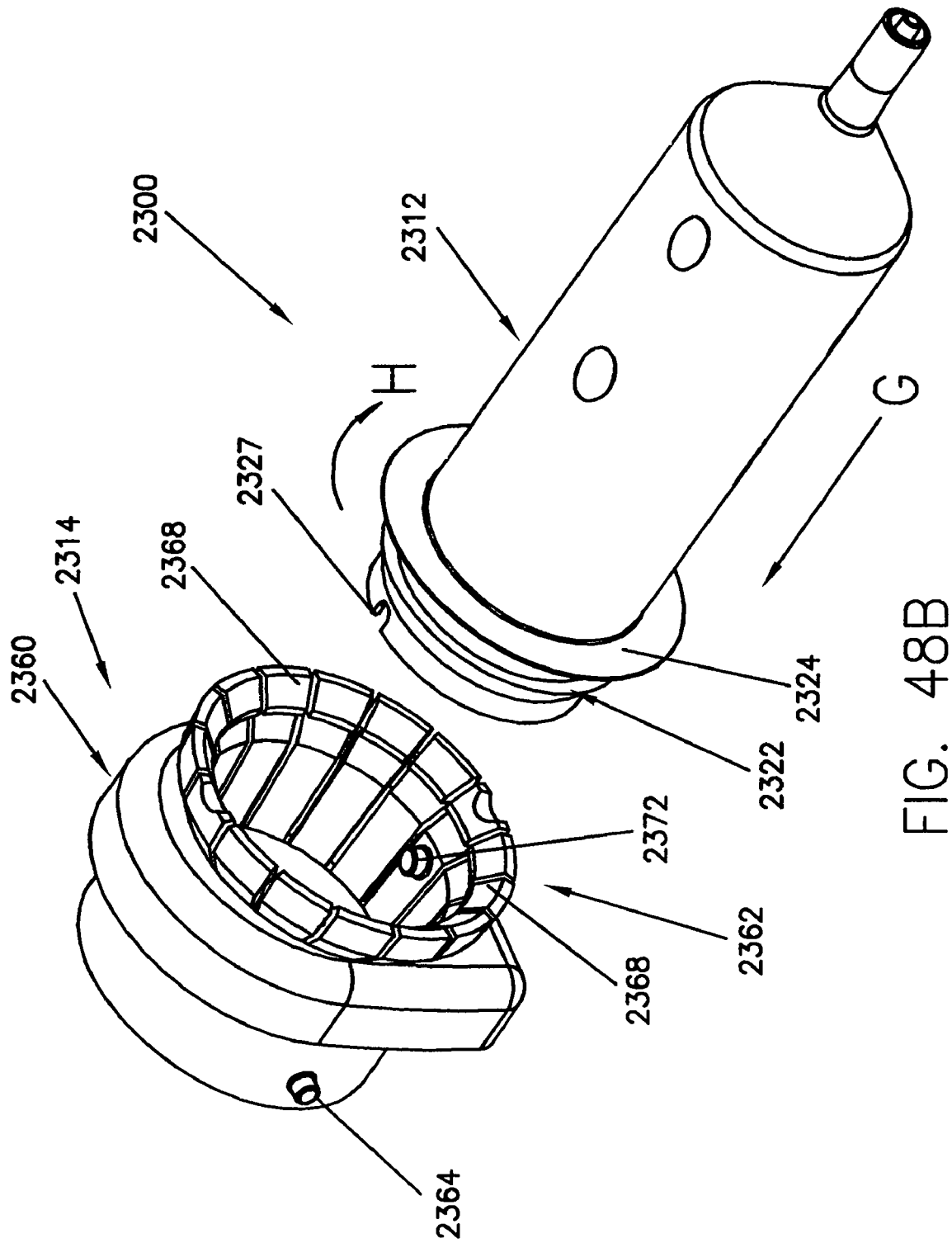
FIG. 48B is a perspective view of the system shown in FIG. 48A in a disengaged position.
Figure 48C:
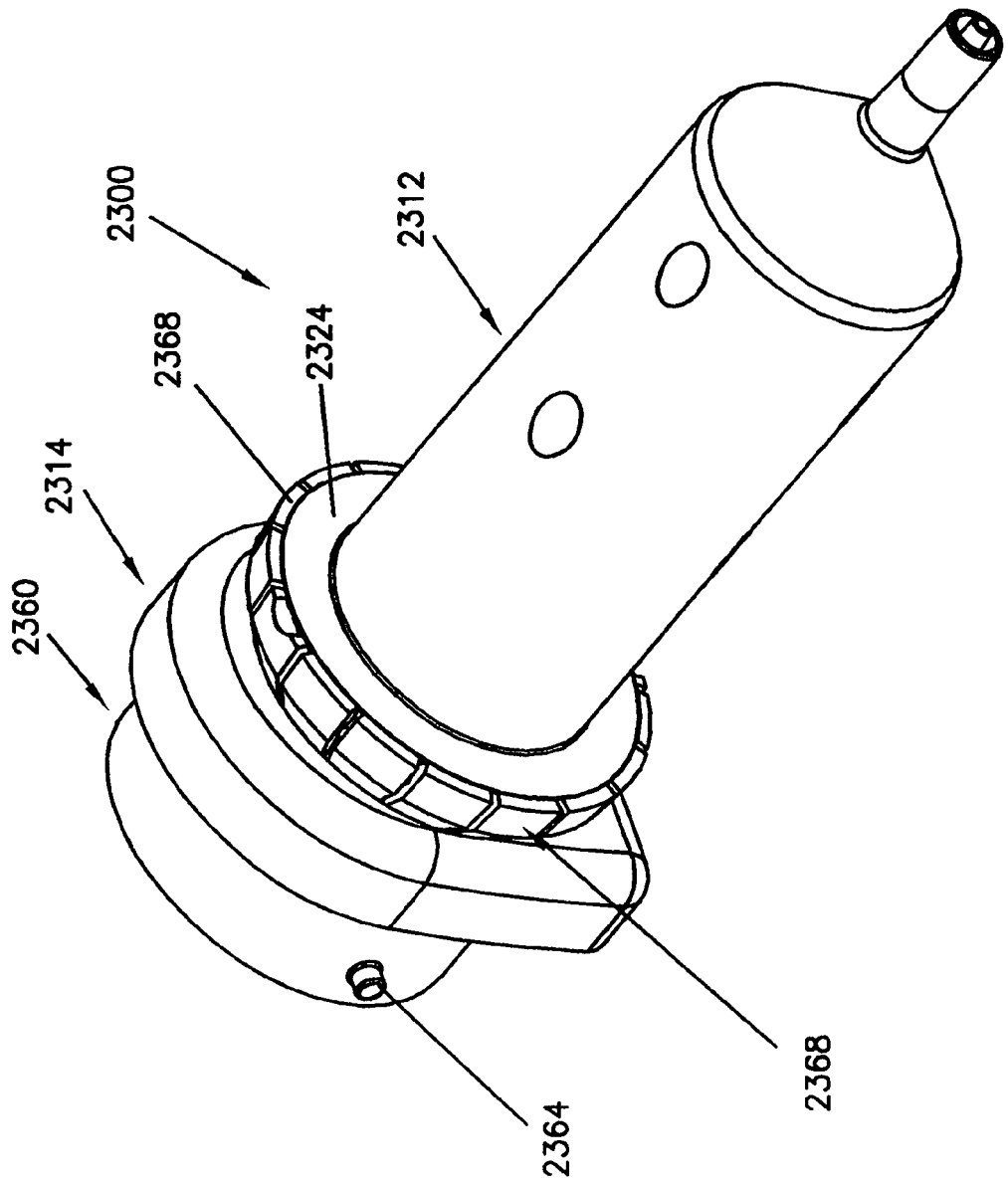
FIG. 48C is a perspective view of the system shown in FIG. 48A in an installed position.

FIGS. 48A-48C illustrate still another embodiment of a front-loading syringe interface and syringe system 2300 in accordance with the present invention. The system 2300 includes a syringe 2312 and a syringe interface 2314. Unlike the syringe 1512 discussed and described above with respect to the other embodiments of the syringe interface and syringe system of the present invention illustrated in FIGS. 40A-47F, the syringe 2312 preferably comprises (in addition to the other components of syringe 1512) two notches 2327 defined in the rear thereof. Alternately, one, three or more notches 2327 may be defined in the syringe 2312.

The syringe interface 2314 preferably comprises a base member 2360 and a collet member 2362 rotatably mounted in the base member 2360. As described in more detail below, the base member 2360 preferably comprises two dowel pins 2364 inserted therein. The collet member 2362 comprises a plurality of segmented members or tangs 2368 formed therein, a helical track 2370 defined in a rear end thereof and at least two posts 2372 operable to engage the notches 2327 in the syringe 2312. Preferably, for reasons described below, small detents 2374 may be formed at suitable locations within (e.g., at or adjacent to terminal ends of) the helical track 2370. The collet member 2362 is held within the base member 2360 by means of the dowel pins 2364, which are captured by and ride within the helical track 2370 in the collet member 2362.

To install the syringe 2312 on the syringe interface 2314, the notches 2327 on the syringe 2312 are aligned with the posts 2372 on the collet member 2362 and the syringe 2312 is inserted axially (in the direction of Arrow G in FIG. 48B) into the collet member 2362 until the notches 2327 engage the posts 2372. The syringe 2312 is then rotated (preferably in a clock-wise direction according to Arrow H in FIG. 48B and approximately 90°) relative to the initial syringe position to complete the installation. As the syringe 2312 is rotated, the engagement between the posts 2372 on the collet member 2362 and the notches 2327 on the syringe 2312 cause the collet member 2362 to rotate with the syringe 2312 within the base member 2360.

As the collet member 2362 rotates with the syringe 2312, the dowel pins 2364 riding within the helical track 2370 cause the collet member 2362 to be pulled into the base member 2360. As the collet member 2362 is pulled into the base member 2360, each tang 2368 is urged by the inclined surface 2365 of the base member 2360 into engagement with the mounting member 2322 of the syringe 2312, thereby securing the syringe 2312 within the syringe interface 2314. As can be appreciated, the "post and notch" engagement prevents syringe rotation relative to the collet member 2362 and the "tang and mounting member" engagement prevents axial syringe translation.

When the syringe 2312 (and collet member 2362) are fully rotated into place in the base member 2360, the dowel pins 2364 snap into place in the small detents 2374 to provide the operator with a tactile, and possibly audible, feedback that the syringe 2312 is completely and securely installed in the syringe interface 2314.

To remove the syringe 2312 from the syringe interface 2314, the syringe 2312 (and collet member 2362) is rotated (preferably in a counter-clockwise direction opposite from the direction of Arrow H) within the base member 2360. To initiate the rotation, sufficient force must be applied to the syringe 2312 (and collet member 2362) to cause the dowel pins 2364 to escape the detents 2374 and ride along the helical track 2370. The syringe 2312 is then rotated until the dowel pins 2364 snap into place in the detents 2374 at the opposite end of the helical track 2370. (The tactile (and possibly audible) feedback of the pins 2364 snapping into place will alert the operator that the syringe 2312 may be removed from the collet member 2362.) As the collet member 2362 rotates out of the "closed" position within the base member 2360, the tangs 2368 release the mounting member 2322 of the syringe 2312 and the syringe 2312 may be removed axially (in the opposite direction of Arrow G) from the syringe interface 2314.

Figure 49A:
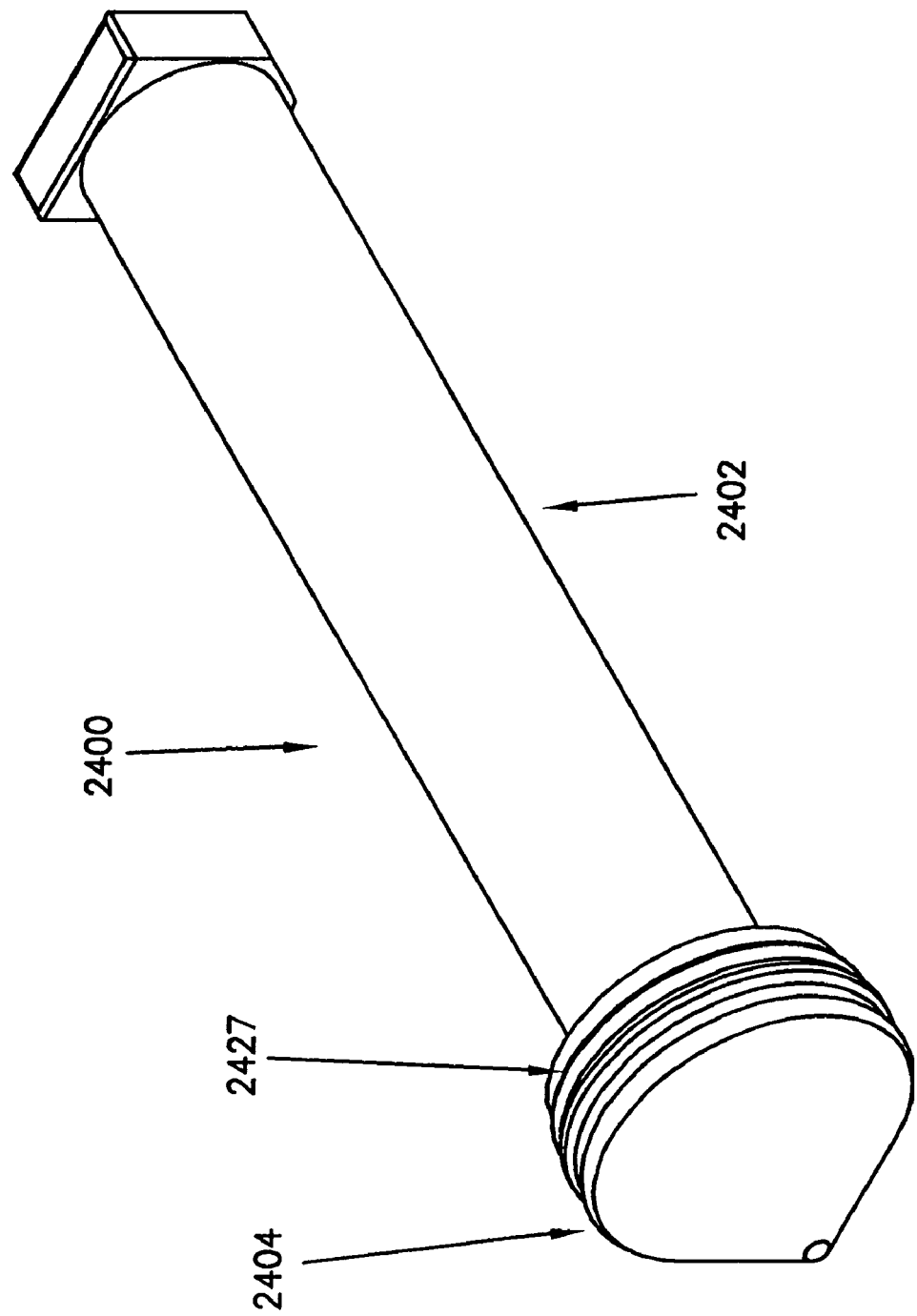
FIG. 49A is an assembled, perspective view of another embodiment of an injector piston and syringe plunger interface system of the present invention.
Figure 49B:
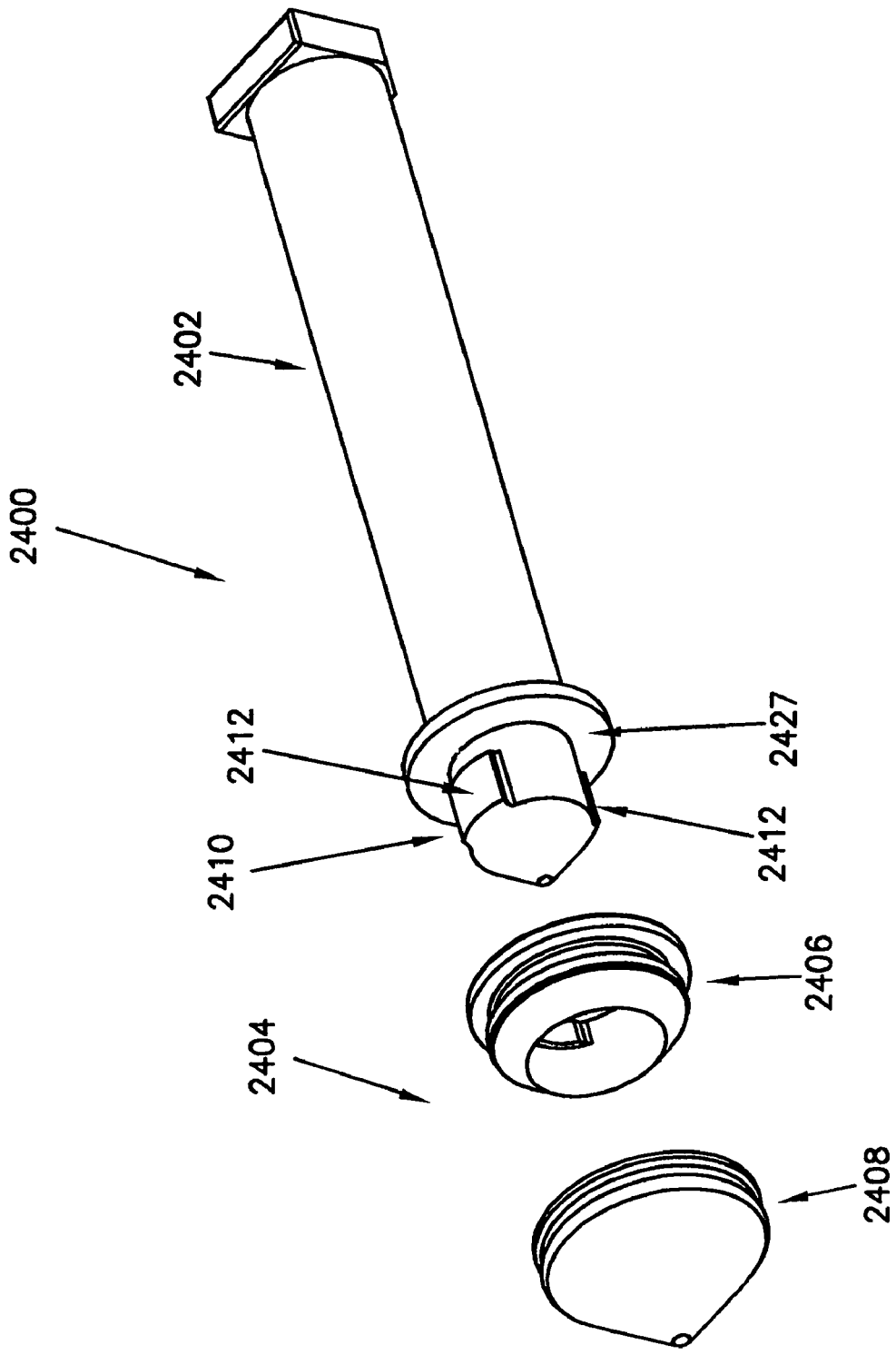
FIG. 49B is an exploded perspective view of the piston/plunger system shown in FIG. 49A.
Figure 49C:
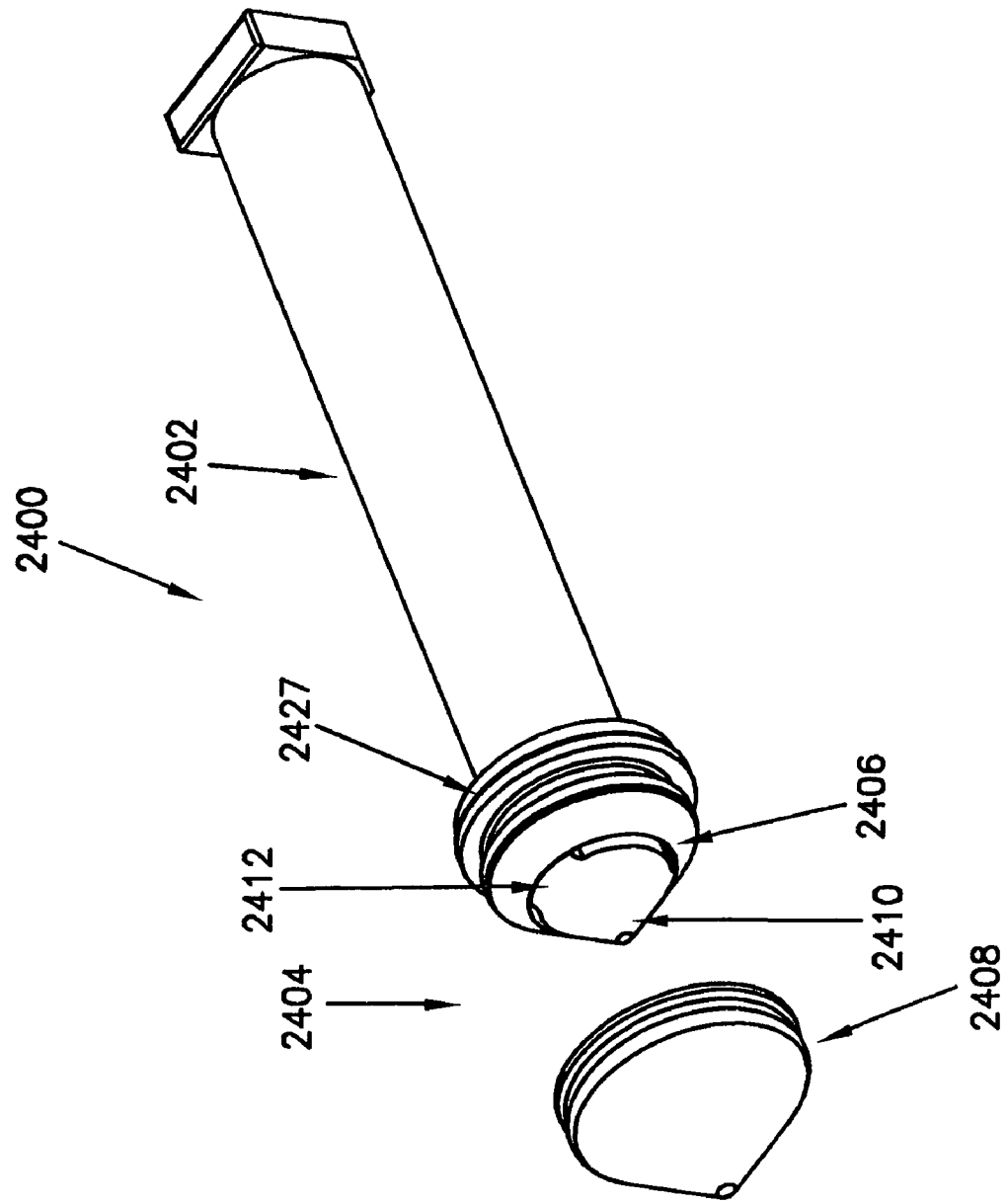
FIG. 49C is a perspective view of the piston/plunger system shown in FIG. 49B with the plunger base separated from the plunger cover and associated with the piston.
Figure 49D:
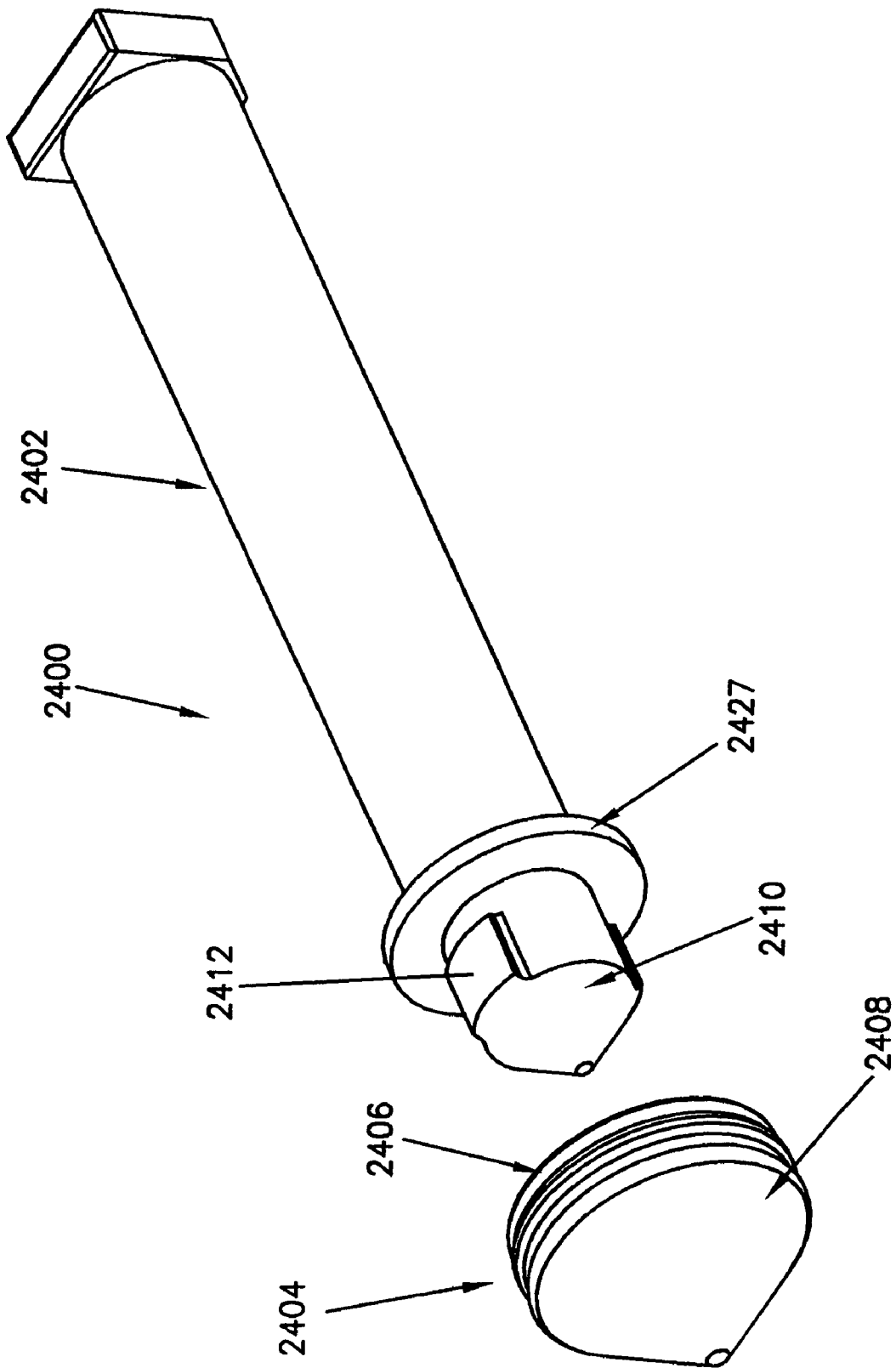
FIG. 49D is a perspective of the piston/plunger system shown in FIG. 49B with the plunger, including the plunger base and the plunger cover, separated from the piston.

FIGS. 49A-49F illustrate another embodiment of an injector piston and syringe plunger interface system 2400 of the present invention. The system 2400 may be incorporated in the syringe interface and syringe systems described above. The system 2400 comprises an injector piston 2402 having a piston head 2410 and a syringe plunger 2404 preferably comprising a plunger base 2406 and a plunger cover 2408. As best shown in FIG. 49F, the plunger base 2406 and the plunger cover 2408 (which may be formed of rubber) are preferably interconnected by means of a mechanical connection.

As described below, the piston head 2410 and the plunger base 2406 preferably engage one another by means of a bayonet-type, interlocking mechanism. As in know in the art, the piston 2402 is preferably disposed within an injector (not shown) and the plunger 2404 is preferably disposed within a syringe, such as the syringes 1512, 2312 described above.

Figure 49E:
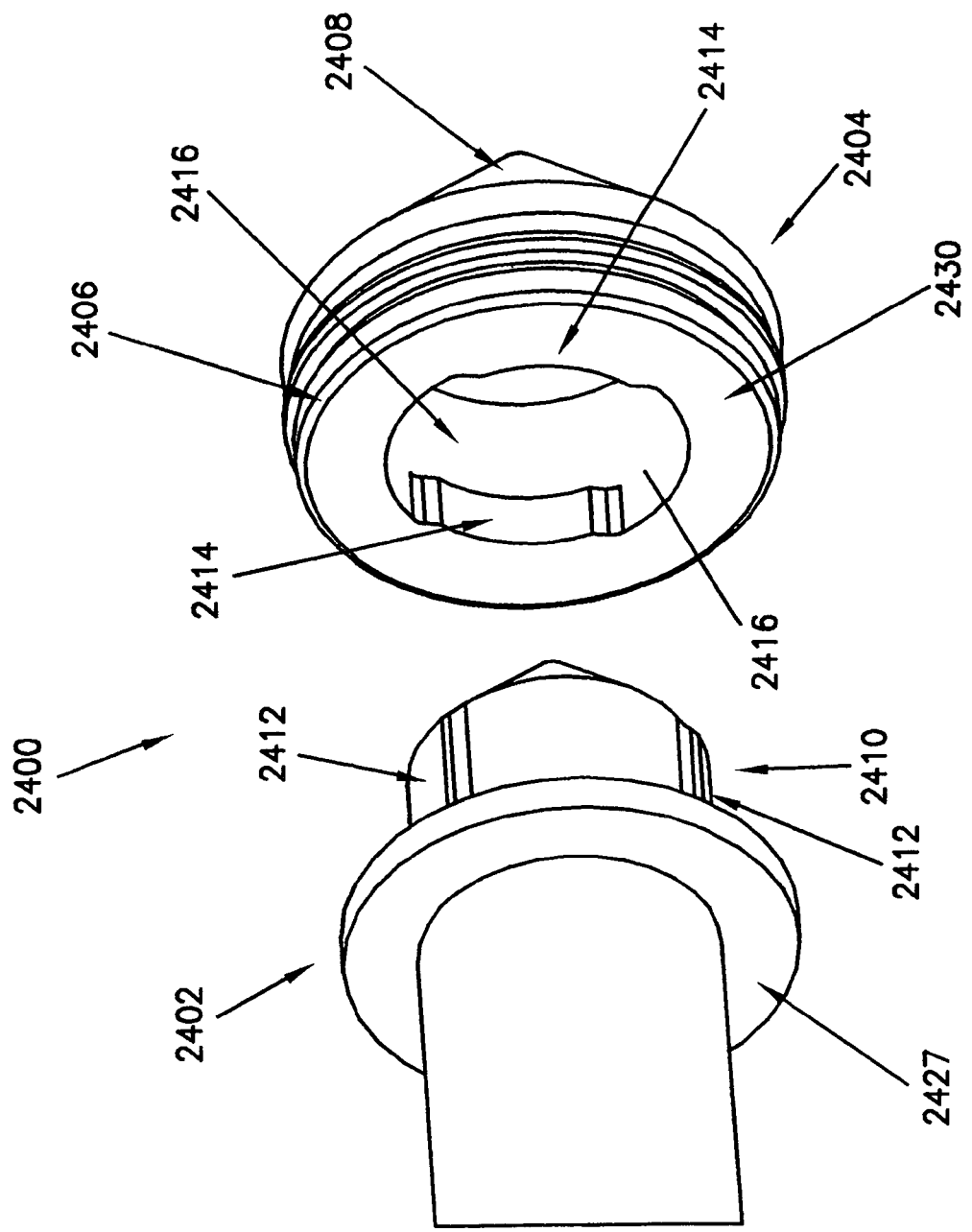
FIG. 49E is a rear, perspective view of the piston/plunger system shown in FIG. 49A in a disengaged position.

The piston head 2410 preferably comprises a pair of extending flanges 2412 and, as best shown in FIG. 49E, the plunger base 2406 preferably comprises a pair of retaining flanges 2414 separated by channels 2416. To connect the piston 2402 and the plunger 2404, the extending flanges 2412 on the piston head 2410 are inserted along the channels 2416 into the plunger 2404. When the extending flanges 2412 clear the retaining flanges 2414, which is preferably indicated by the flange 2427 on the piston 2402 engaging the contact surface 2430 on the plunger 2404, either the piston 2402 or the plunger 2404 is rotated to cause the retaining flanges 2414 to be captured behind the extending flanges 2412. To disconnect the piston 2402 from the plunger 2404, the reverse steps are preferably taken by the operator.

As can be appreciated by one skilled in the art, the piston 2402 and the plunger 2404 may be engaged by translating and rotating the plunger 2404 (disposed within a syringe) into engagement with the piston 2402 (disposed within an injector), or vice-versa. Alternately, the translational and rotational motions can be alternated between the plunger 2404 and the piston 2402 to interconnect the two members.

Figure 50A:
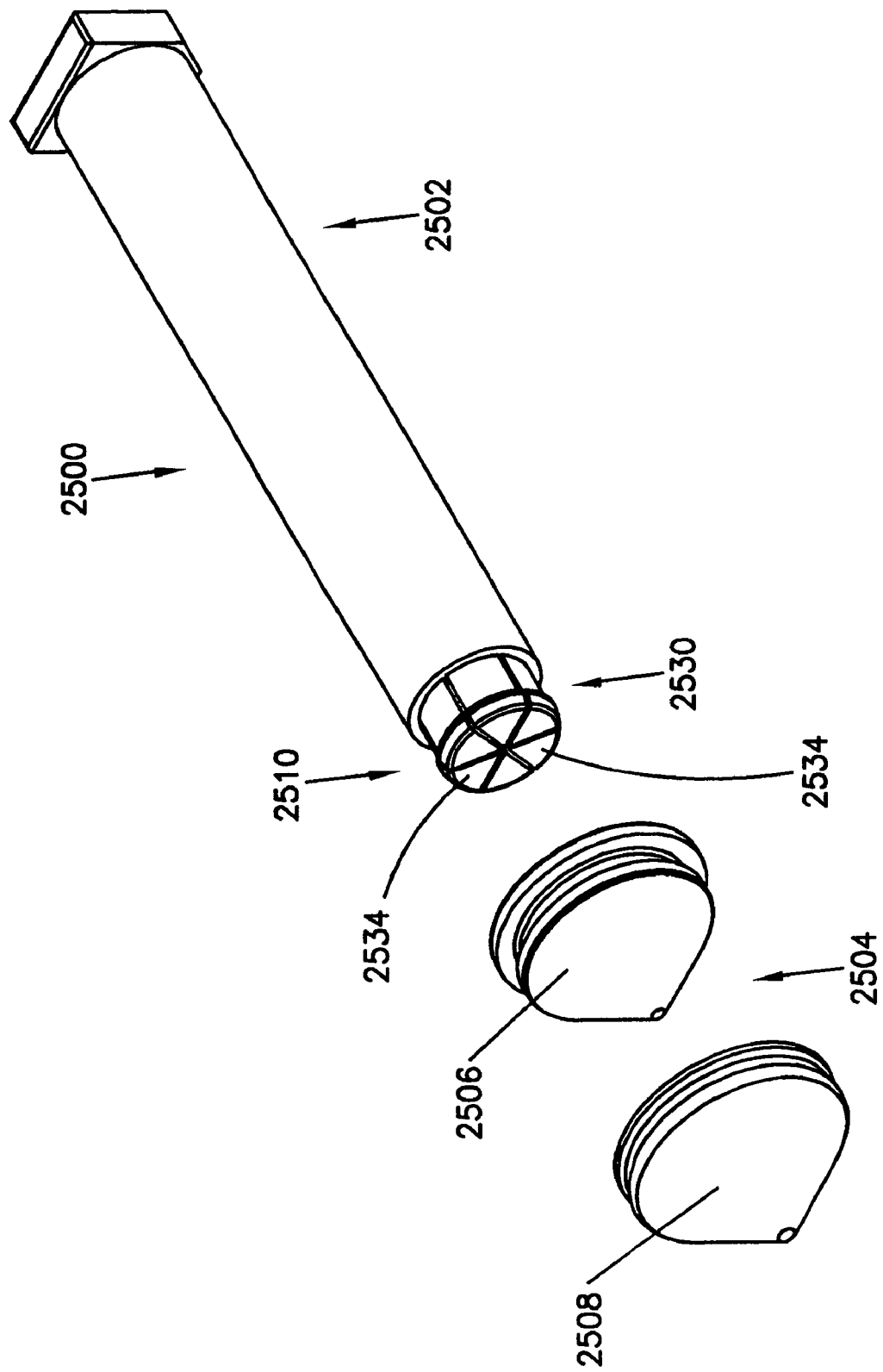
FIG. 50A is an exploded, perspective view of another embodiment of an injector piston and syringe plunger interface system of the present invention.

FIGS. 50A and 50B illustrate another embodiment of an injector piston and syringe plunger interface system 2500 of the present invention. The system 2500 preferably comprises a piston 2502 and a plunger 2504. The plunger 2504 is preferably configured as shown and described above with respect to FIGS. 49A-49F. The piston 2502 preferably comprises a piston head 2510 having a collet-type mechanism 2530. The collet 2530 is preferably comprised of a plurality of flexible segment members or tangs 2534.

To connect the piston 2502 and the plunger 2504, the collet mechanism 2530 is inserted into the plunger 2504. When the tangs 2534 pass the plunger undercut 2536 (as best shown in FIG. 50B), preferably a rod or pin member (not shown) is driven through the center of the collet mechanism 2530 to radially force apart the tangs 2534 into locking engagement with the plunger undercut 2536. To disconnect the piston 2502 from the plunger 2504, the rod or pin member (not shown) is retracted from the center of the collet mechanism 2530, thereby causing the tangs 2534 to disengage the plunger undercut 2536.

Due to the symmetrical nature of the collet mechanism 2530, no particular alignment between the piston 2502 and the plunger 2504 is required for the piston 2502 and the plunger 2504 to engage and/or disengage one another. This feature simplifies the installation and removal of a syringe from a syringe interface.

As can be appreciated by one skilled in the art, the piston 2502 and the plunger 2504 may be engaged by translating the plunger 2504 (disposed within a syringe) into engagement with the piston 2502 (disposed within an injector), or vice-versa.

Figure 51A:
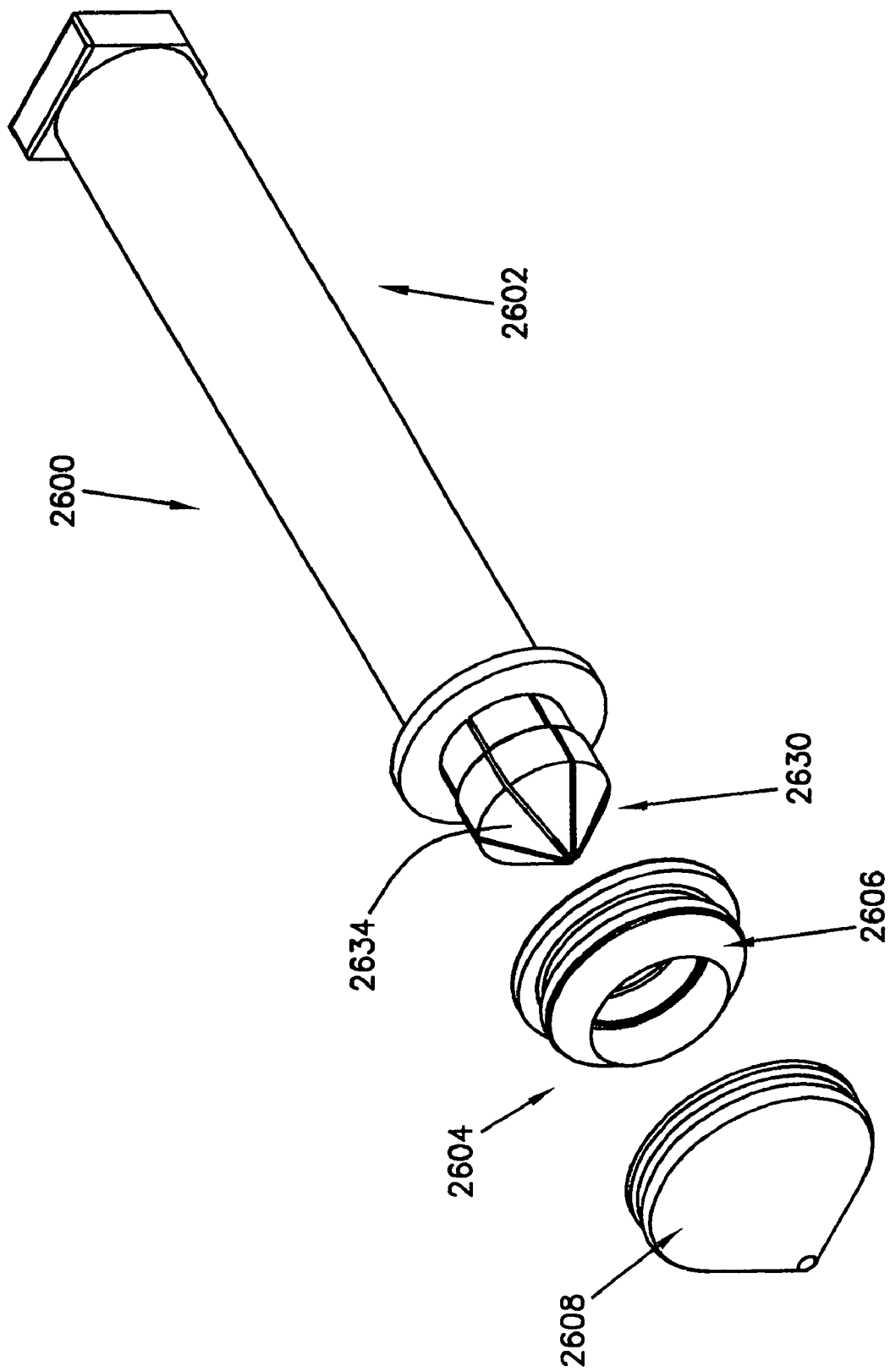
FIG. 51A is an exploded, perspective view of an alternate embodiment of the injector piston and syringe plunger interface system shown in FIGS. 50A and 50B.

FIGS. 51A-51C illustrate an alternate embodiment 2600 of the injector piston and syringe plunger interface system 2500 shown in FIGS. 50A and 50B. The structure and function of the system 2600 is substantially similar or identical to the system 2500 shown in FIGS. 50A and 50B, except that the collect mechanism 2630 is configured to be complementary in shape to the plunger cover 2608 to support the plunger cover 2608 during an injection procedure and to provide, for example, fluid pressure monitoring through the plunger 2604, as described in U.S. Pat. No. 5,808,203, the contents of which are hereby incorporated by reference.

Figure 52A:
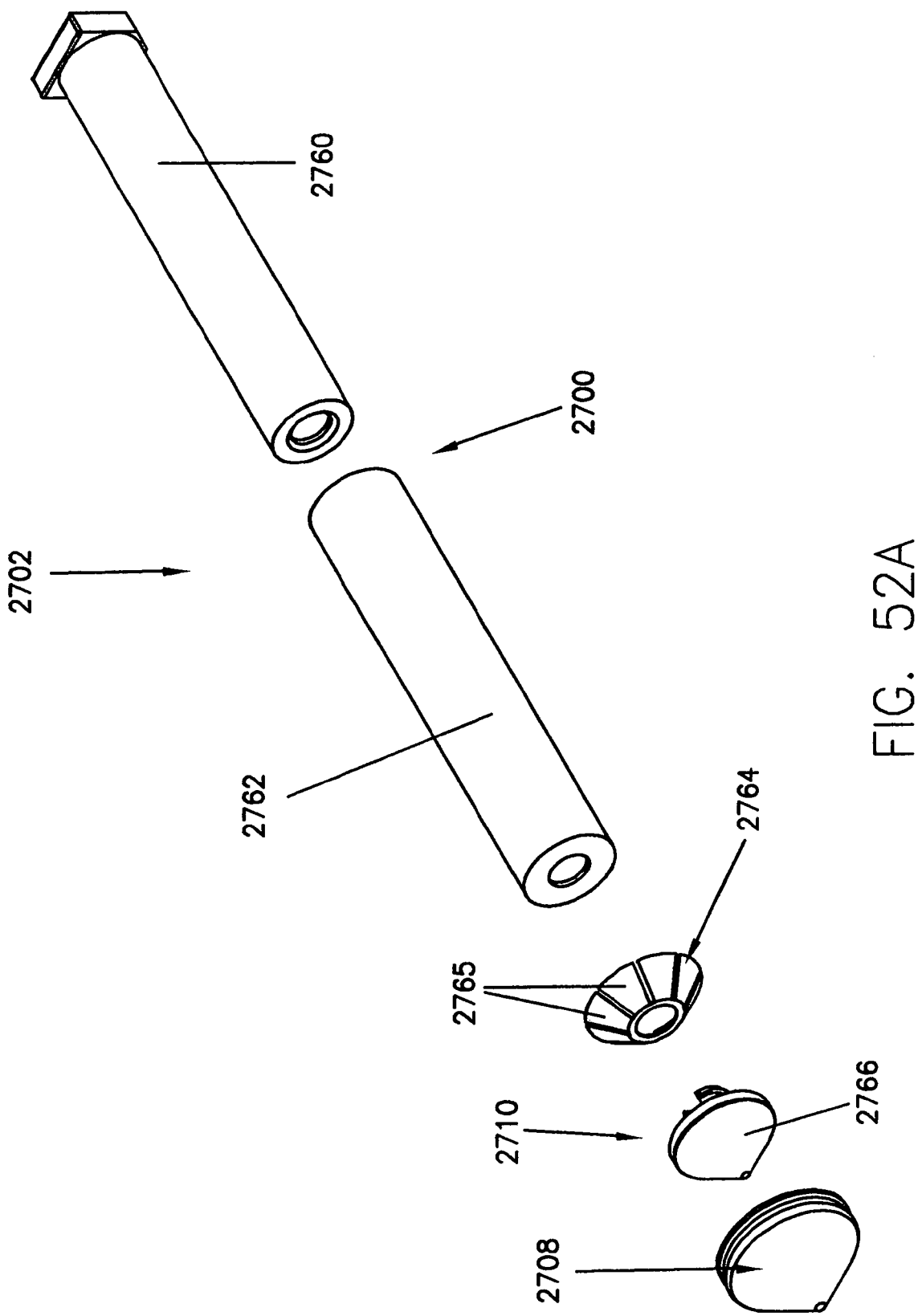
FIG. 52A is an exploded, perspective view of still another embodiment of an injector piston and syringe plunger interface system of the present invention.
Figure 52C:
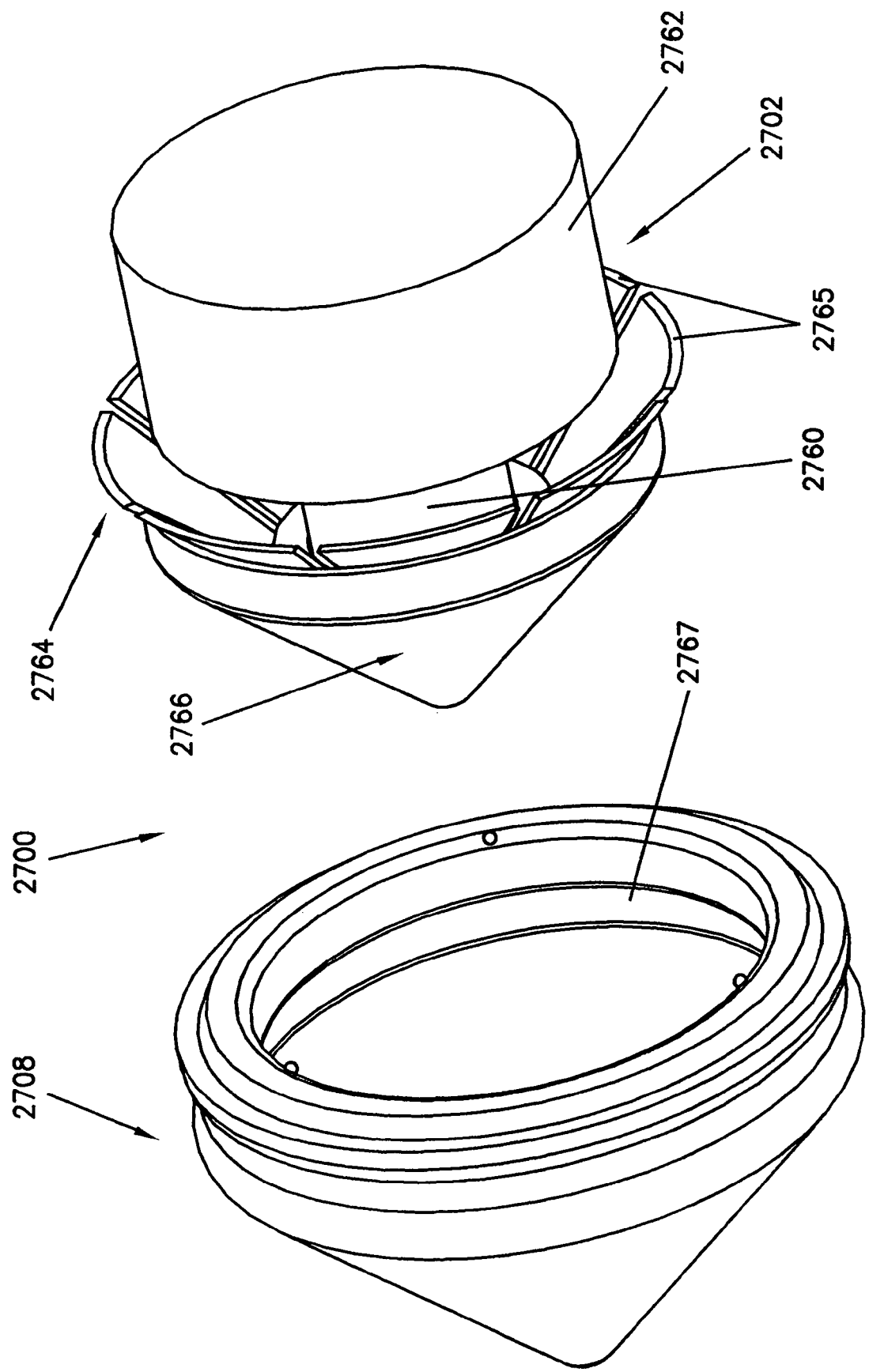
FIG. 52C is a rear, perspective view of the piston/plunger system shown in FIG. 52A in a disengaged position.

FIGS. 52A-52C illustrate still another embodiment of an injector piston and syringe plunger interface system 2700 of the present invention. The system 2700 comprises a piston 2702 and a plunger cover 2708. In contrast to the above embodiments, a plunger base is not present in the plunger 2704. Rather, the piston head 2710 is configured to be complementary in shape to the plunger cover 2708 to support the plunger cover 2708 during a fluid injection.

Preferably, as best shown in FIG. 52A, the piston 2702 comprises a base member 2760, a sleeve 2762, a segmented flap member 2764 and a piston cap 2766. During forward movement of the piston 2702 (e.g., during a fluid injection), the piston 2702 preferably contacts and moves the plunger cover 2708 without connectively engaging or locking thereto. Upon retraction of the piston 2702 (i.e., base member 2760, flap member 2764 and cap 2766), the sleeve 2762 moves (in the direction of Arrow I in FIG. 52B) into contact with the segmented flap member 2764 and urges the flaps 2765 radially outward into engagement with an undercut 2767 formed in the plunger cover 2708 (as best shown in FIG. 52C) to connect the piston 2702 and plunger cover 2708 together. Retraction of the piston 2702 and plunger cover 2708 together is useful, for example, in aspirating fluid into a syringe for subsequent injection into a patient.

FIGS. 53A-53D illustrate an alternate embodiment 2800 of the injector piston and syringe plunger interface systems 2600, 2700 shown in FIGS. 51A-51C and 52A-52C. The function of the system 2800 is substantially similar or identical to that of the systems 2600, 2700, but there are different structural components that are explained below.

Figure 53A:
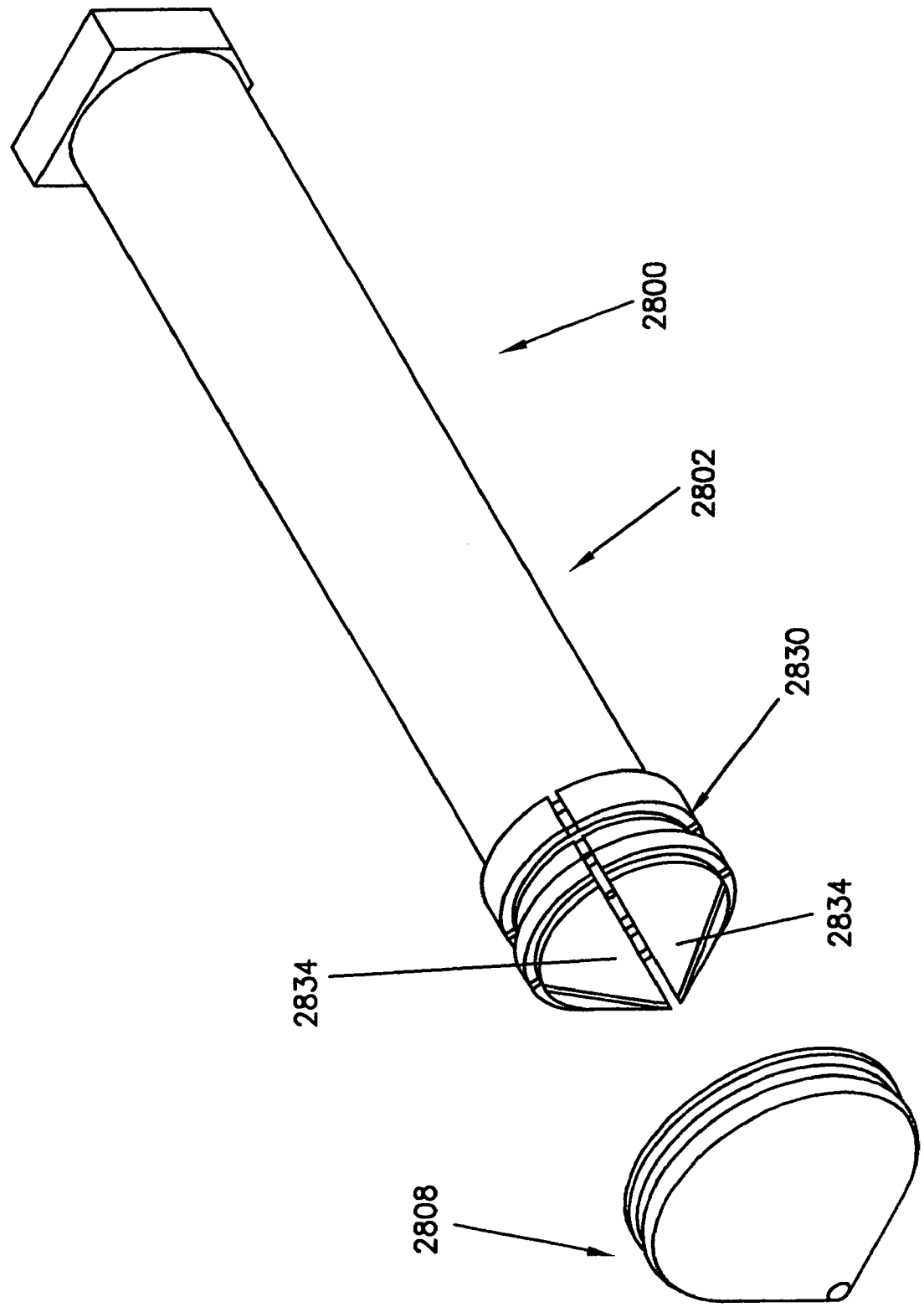
FIG. 53A is an exploded, perspective view of an alternate embodiment of the injector piston and syringe plunger interface systems shown in FIGS. 51A-51C and 52A-52C.
Figure 53C:
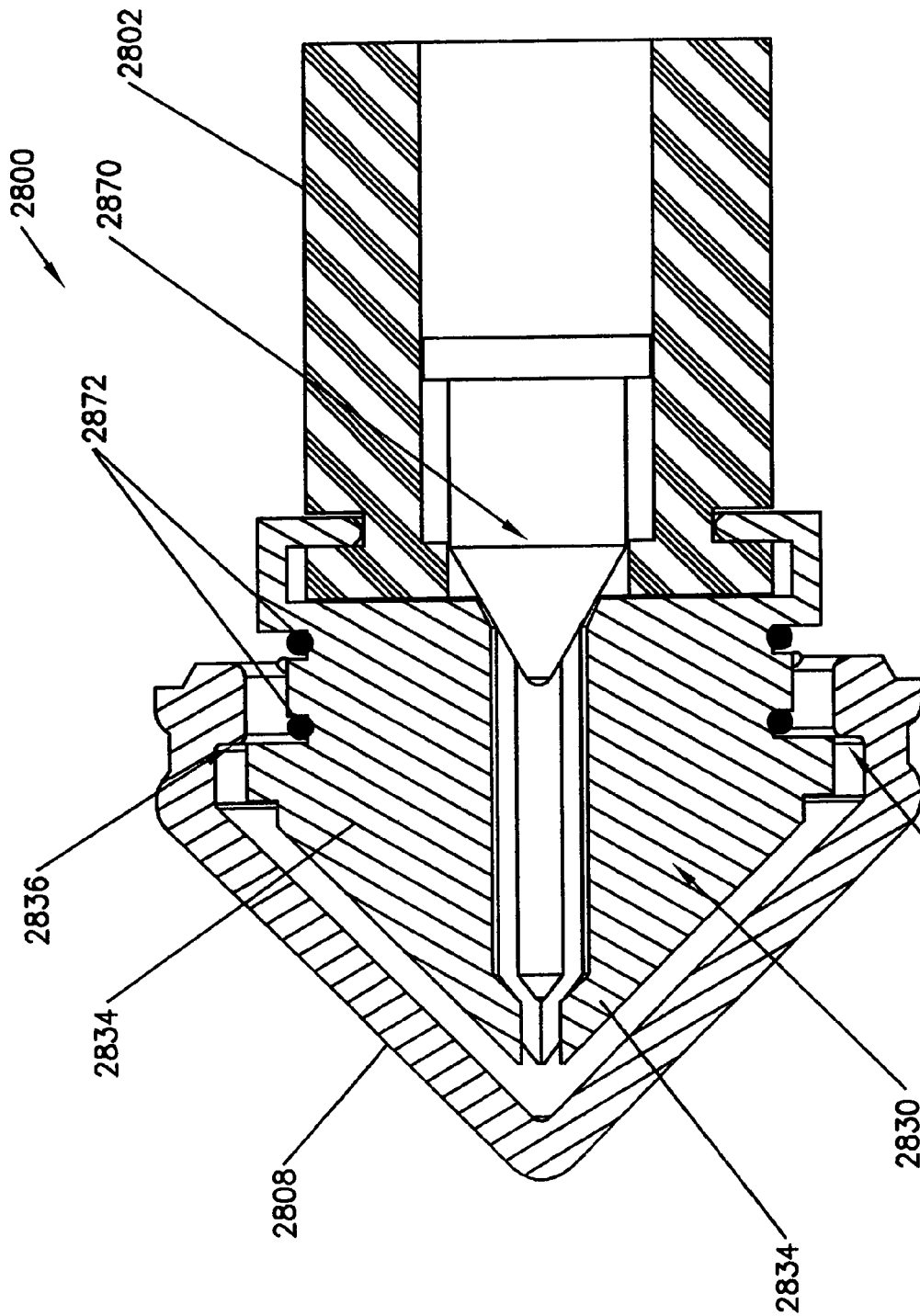
FIG. 53C is a cross-sectional view of the piston/plunger system shown in FIG. 53A.
Figure 53D:
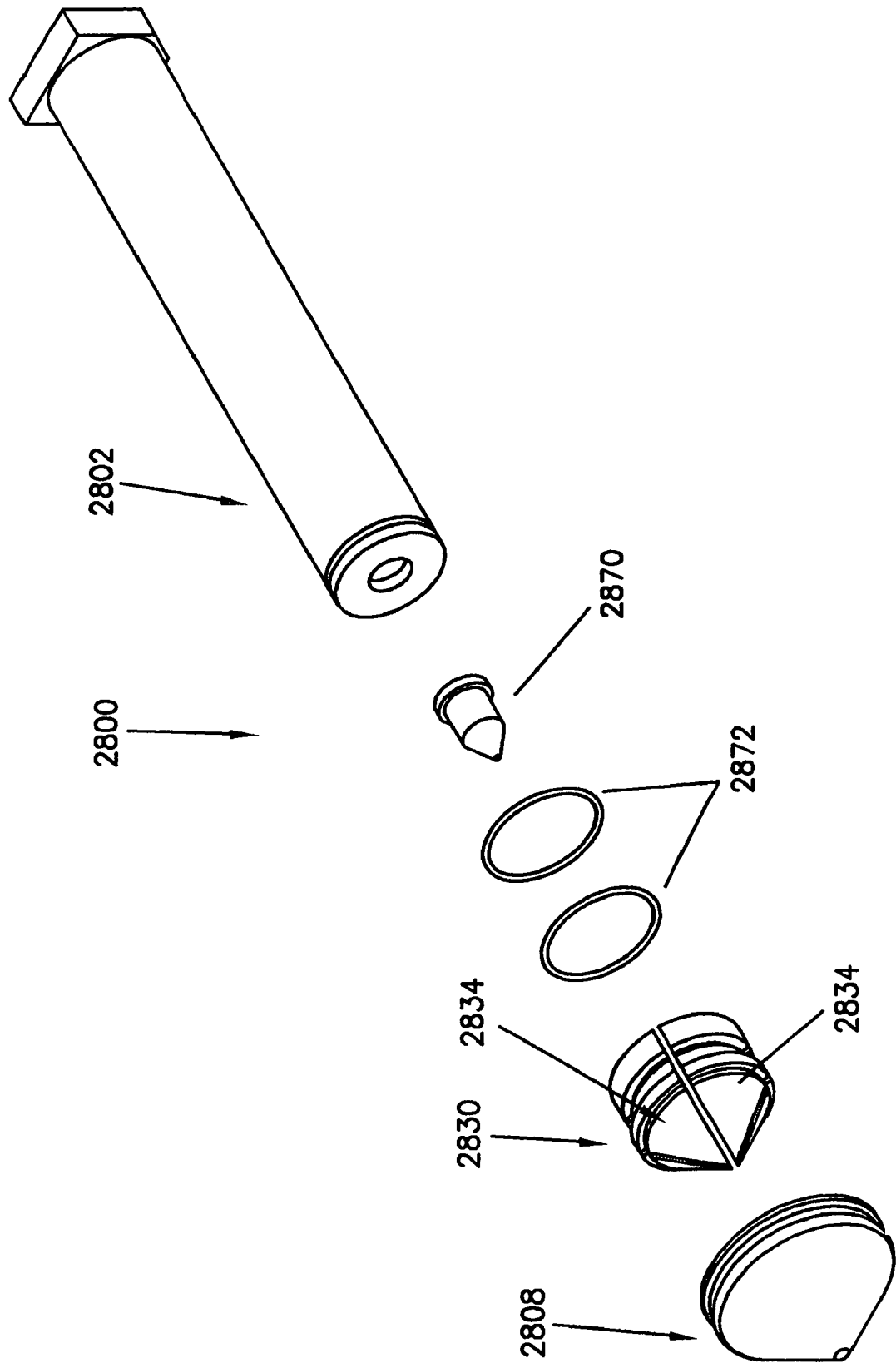
FIG. 53D is an exploded, perspective view of the piston/plunger system shown in FIG. 53A.

As best shown in FIGS. 53C and 53D, the collet mechanism 2830 is acted upon by an actuator 2870 disposed within the piston 2802 to urge the tangs 2834 radially outward into engagement with an undercut 2836 formed on the plunger cover 2808 to interconnect the piston 2802 and the plunger cover 2808. The collet mechanism preferably includes spring retention members 2872, such as O-rings, to hold the tangs 2834 together and to spring-bias the tangs in a "disengage" position.

Figure 54A:
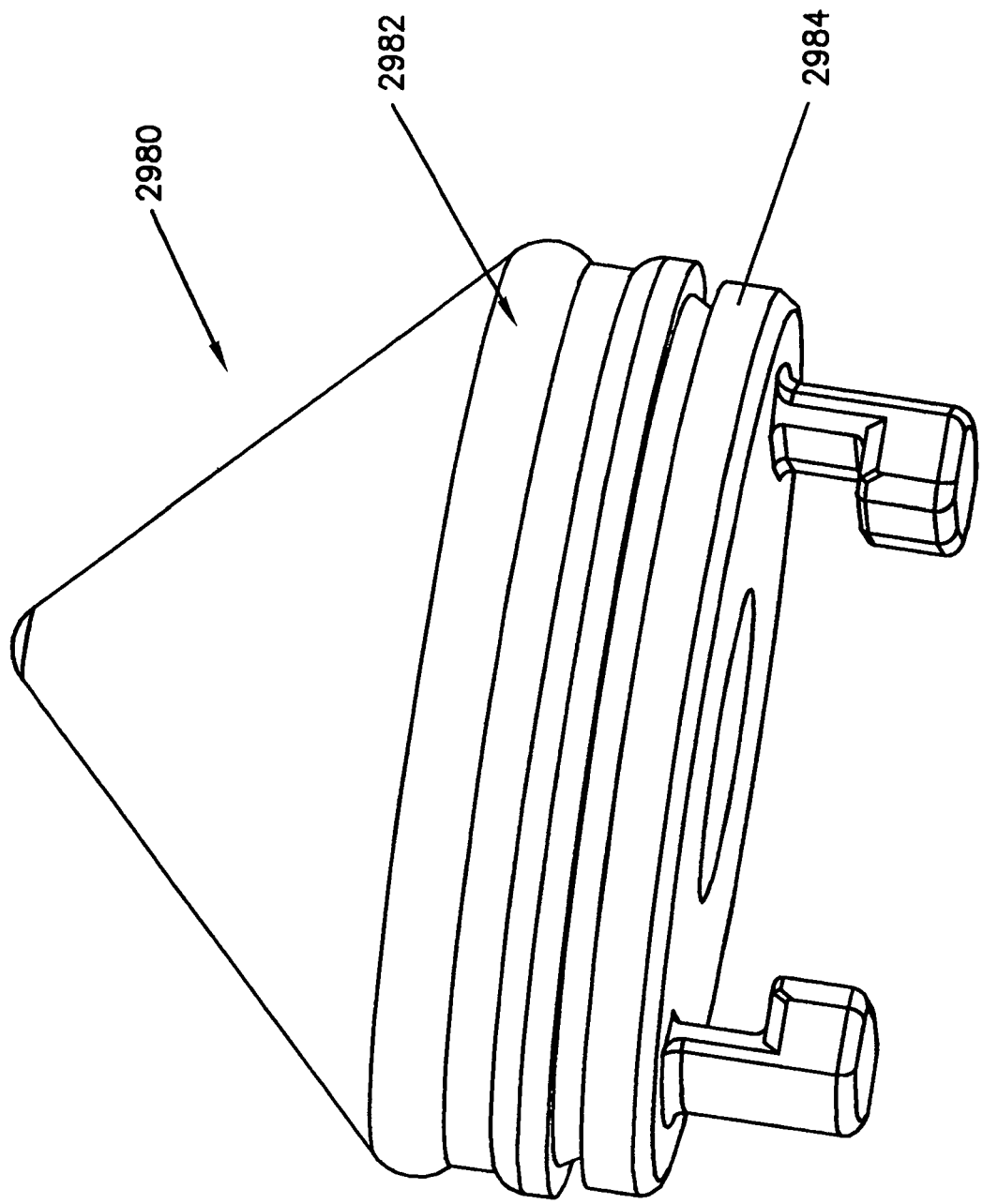
FIG. 54A is a perspective view of a current syringe plunger.
Figure 54B:
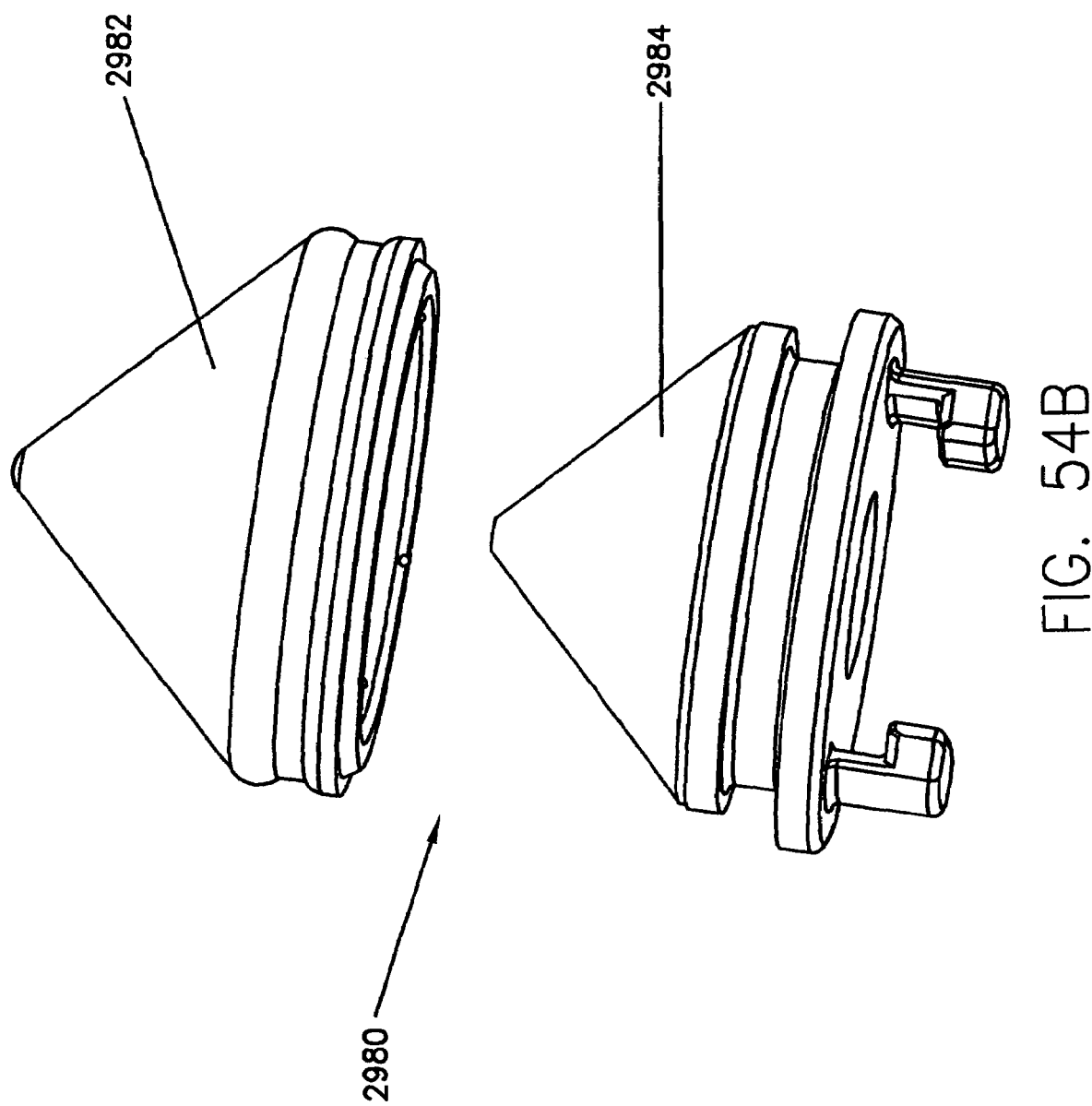
FIG. 54B is an exploded, perspective of the plunger shown in FIG. 54A.

FIGS. 54A and 54B illustrate a current syringe plunger 2980, which comprises a plunger base 2984 and a mechanically-connected plunger cover 2982.

Figure 54D:
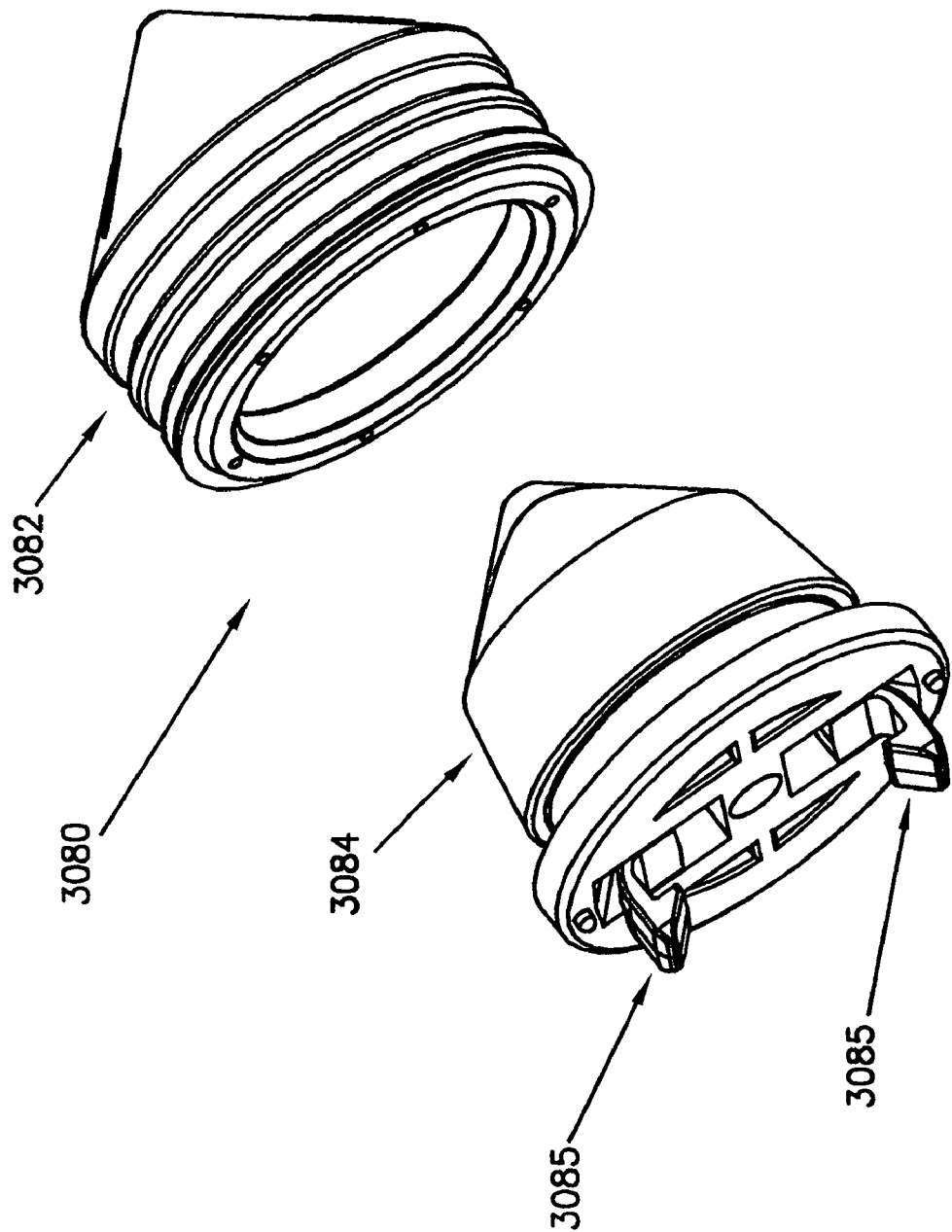
FIG. 54D is an exploded, perspective of the plunger shown in FIG. 54C.

FIGS. 54C and 54D illustrate an embodiment of the plunger 3080 of the present invention. The plunger 3080 comprises a plunger cover 3082 having a larger syringe contact region (than the plunger cover 2982 shown in FIGS. 54A and 54B) and a least three sealing elements 3083. The plunger base 3084 comprises at least two flexible, piston-retention members 3085, as shown and described in PCT Publication No. WO 98/20920, the contents of which are hereby incorporated by reference. The plunger cover 3082 is preferably mechanically connected to the plunger base 3084, as best shown in FIG. 54D.

Figure 54E:
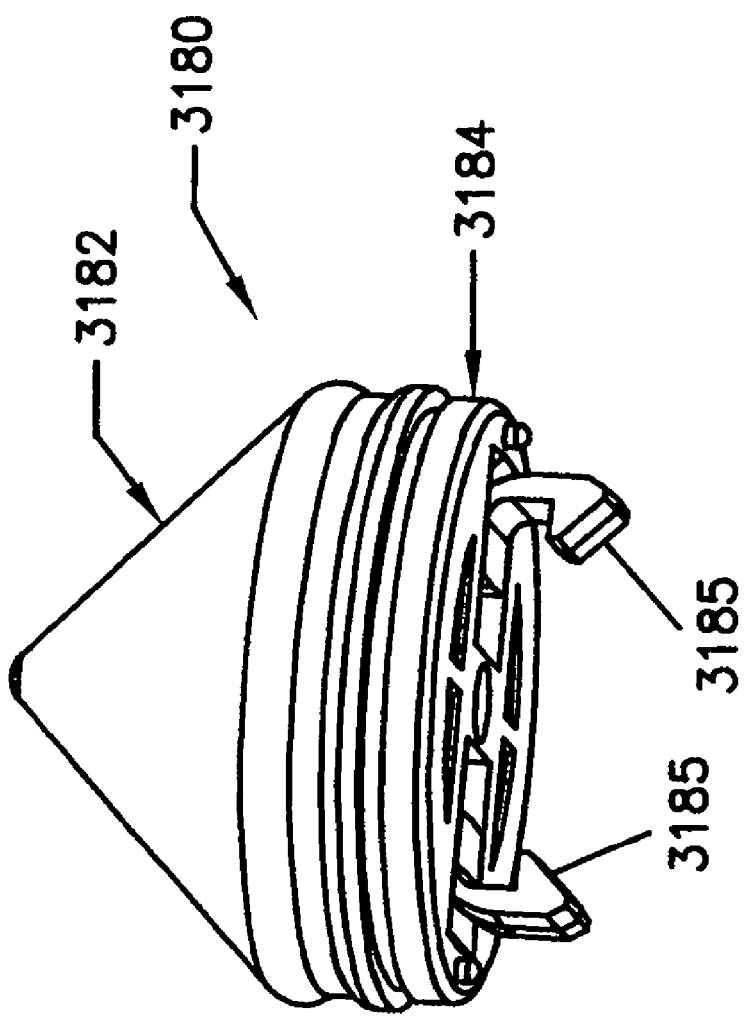
FIG. 54E is a perspective view of another embodiment of a syringe plunger of the present invention.

FIGS. 54E and 54F illustrate another embodiment of the plunger 3180 of the present invention. The plunger cover 3182 is substantially similar or identical to the plunger cover 2982 shown in FIGS. 54A and 54B. The plunger base 3184 comprises at least two flexible, piston-retention members 3185.

Figure 54G:
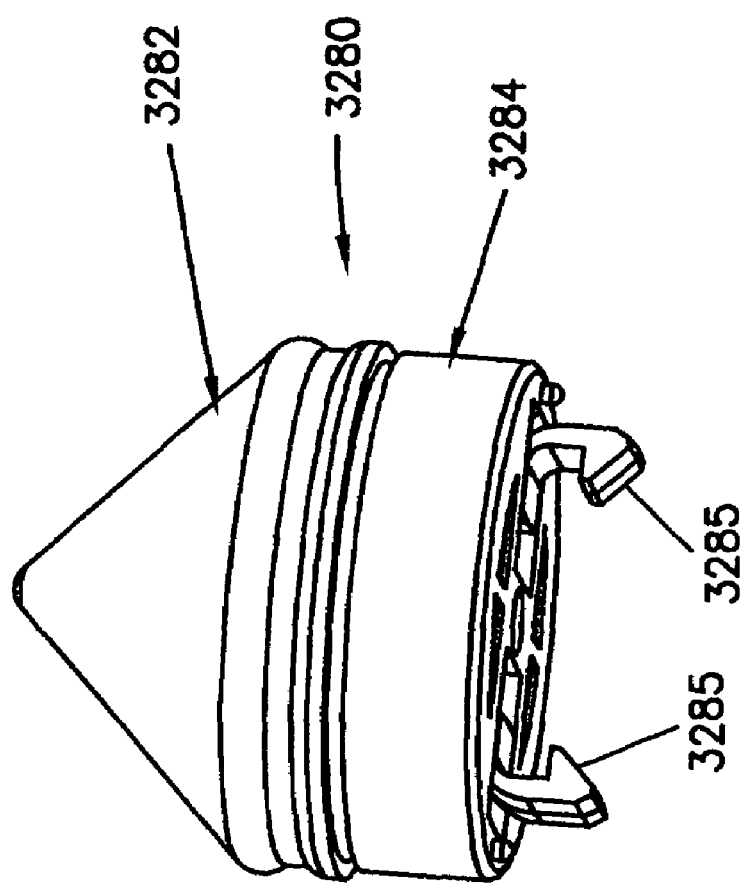
FIG. 54G is a perspective view of yet another embodiment of the syringe plunger of the present invention.
Figure 54H:
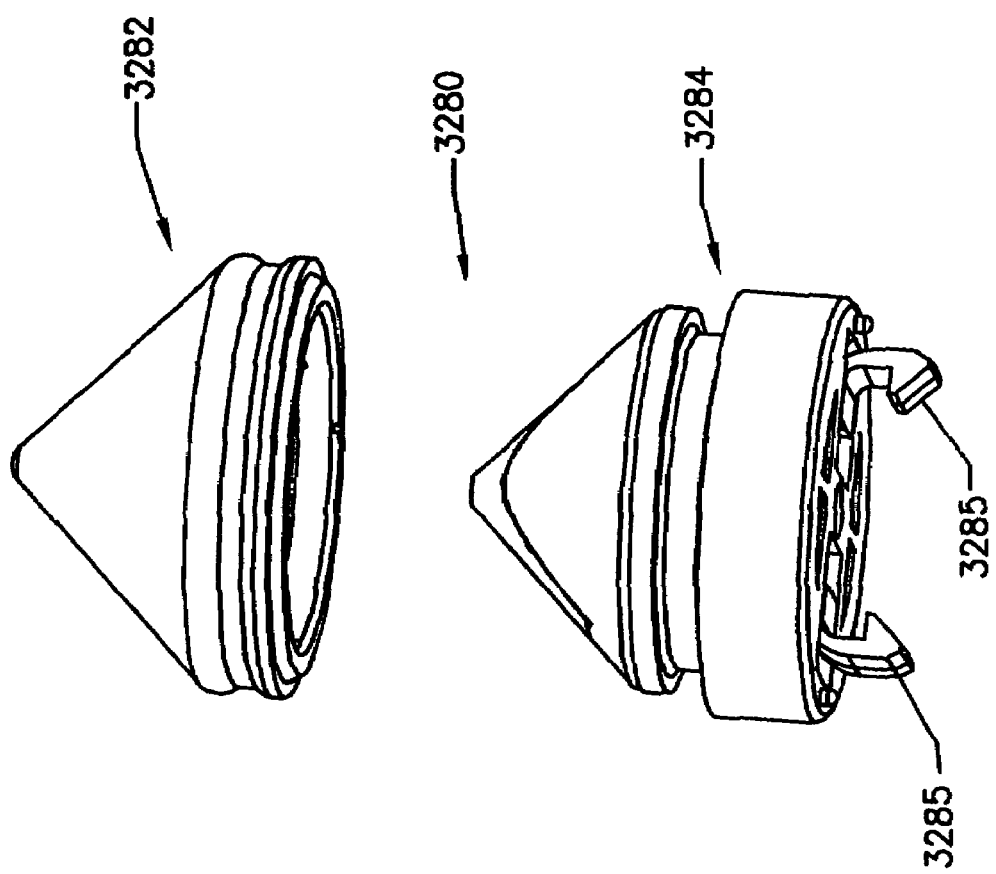
FIG. 54H is an exploded, perspective view of the syringe plunger shown in FIG. 54G.

FIGS. 54G and 54H illustrate an alternate embodiment of the plunger 3280 of the present invention. The plunger cover 3282 is substantially similar or identical to the plunger cover 2982 shown in FIGS. 54A and 54B. The plunger base 3284 comprises a longer base region and at least two flexible, piston-retention members 3285.

As can be appreciated, the plungers 2980, 3080, 3180, 3280 shown and described above may be incorporated in the syringes 1512, 2312 described herein.

The most preferred embodiments of the present invention will be described in connection with FIGS. 55-109. Of these drawings, FIGS. 55-78 concern the second preferred embodiment of the syringe interface/release mechanism that releasably secures the syringe to the injector housing. FIG. 79 illustrates the efficacy of the flange assembly associated with the syringe of a related art medical injector assembly, which applies equally to the function of the flange on the syringe of the present invention. FIGS. 80-109 illustrate the first preferred embodiment of the injector piston and syringe plunger interface system/assembly of the present invention that cooperates to axially move the plunger within the syringe.

Among other features (as illustrated in FIGS. 55-57), the second preferred embodiment of the syringe interface of the present invention encompasses a release mechanism 4010 for connecting a syringe 4012 to an injector 4014.

Specifically, the second preferred embodiment of the present invention provides a mechanism by which a syringe 4012 may be connected quickly to an injector 4014 without the requirement (present in the prior art) for any particular orientation of the syringe 4012 to the injector 4014 during installation. The release/connector mechanism 4010 of the present invention also provides an audible "click" when the syringe 4012 fully engages the connector/release mechanism 4010. Additionally, the present invention provides an audible "click" when the syringe 4012 has been disengaged from the release/connector mechanism 4010. The audible "click" for connection and removal of the syringe 4012 from the release/connector mechanism 4010 is a particularly useful feature because it provides the operator with an audible confirmation of proper engagement and disengagement of the syringe 4012 from the release/connector mechanism 4010.

FIG. 55 illustrates generally the syringe interface/release mechanism 4010 (hereinafter, release or connector mechanism 4010, for brevity) of the present invention. A rear surface 4016 of release mechanism 4010 attaches to a front surface 4018 of injector 4014. A front surface 4020 of release mechanism 4010 is adapted to receive a rear end 4022 of syringe 4012.

Release mechanism 4010 may be affixed to front surface 4018 of injector 4014 in any suitable manner known to those skilled in the art. For example, release mechanism 4010 may be attached by means of screws (not shown) extending from the front surface 4018 of injector 4014. As would be appreciated by those skilled in the art, any suitable alternative connection may be employed. For example, release mechanism 4010 may be affixed by means of tabs or other suitable connectors that permit release mechanism 4010 to be removed from injector 4014 for cleaning of the components contained therein. In addition, release mechanism 4010 may be adapted to mount to conventional injectors to allow syringes of the present invention to be used therewith.

The second preferred embodiment of the syringe interface/release mechanism 4010, which is illustrated in FIGS. 55-78, includes a connector housing 4024. Connector housing 4024 contains within it at least two elements that facilitate connection of syringe 4012 to injector 4014. The first of the two elements is a flex ring 4026, which is disposed within release mechanism 4010 near front end 4020. The second of the two elements is a rotating ring 4028, which is disposed within release mechanism 4010 near rear end 4016. Flex ring 4026 and rotating ring 4028 are adapted to cooperate with one another, as described in greater detail below, to permit connection and release of syringe 4012 to and from release mechanism 4010 (and, accordingly, to and from injector 4014).

FIGS. 56 and 57 illustrate release mechanism 4010 and syringe 4012 in an exploded perspective view to facilitate an understanding of this aspect of the present invention. Syringe 4012 includes a cylindrical body 4030 with a tapering conical portion 4032 at a front end 4034. Conical portion 4032 is integrally connected to a discharge end 4036. Discharge end 4036 is provided with a luer lock 4038 that may be connected to a tube (not shown) that is connected ultimately to the patient (also not shown).

As would be understood by those skilled in the art, syringe 4012 may be made from any suitable material, such as a polymeric material. Specifically, syringe 4012 may be made of PET (polyethylene terephthalate). Alternatively, syringe 4012 may be constructed from polymethylpentene (which is made by Mitsui Plastics under the tradename "TPX").

At rear end 4022, syringe 4012 includes a flange 4042, which, when syringe 4012 is connected to release mechanism 4010, helps to prevent contrast medium that may leak from, for example, discharge end 4036 or luer lock 4038 from entering release/connector mechanism 4010. FIG. 79, which illustrates a related art syringe, helps to illustrate the advantages provided by flange 4042 on syringe 4012.

As shown in FIGS. 55-57, a ridge 4044 is integrally formed on syringe 4012 behind flange 4042 toward rear end 4022 of syringe 4012. Alternately, as shown in FIG. 123, the ridge may be segmented into two or more sections 4044a instead of a single continuous member. However, the sections 4044a must collectively provide sufficient surface area and strength to retain the syringe 4012 on the injector 4014.

As shown in FIGS. 55-57, ridge 4044 includes two parts, a sloping section 4046 and a shoulder section 4048 that is essentially perpendicular to the exterior surface of cylindrical body 4030. At least one, and preferably two or more, extending tabs or projections 4050 are provided at rear end 4022 of syringe 4012. Tabs 4050 engage grooves 4052 provided in ring 4028. Alternatively, as would be understood by those skilled in the art, slots, recesses or divots, etc. could be provided in rear end 4022 of syringe 4012 and tabs or projections could be provided on the interior surface of rotating ring 4028.

In addition, to mount conventional syringes on the syringe interface 4010 of the present invention, a syringe adapter incorporating the structural components (e.g., ridge 4044, tabs 4050 and/or flange 4042) of the rear end 4022 of syringe 4012 could be fashioned to fit to a conventional syringe for mounting on the injector of the present invention. Of course, to properly engage the conventional syringe, the adapter would preferably include structural components complementary to the mounting elements of the conventional syringe.

Release/connector mechanism 4010 includes a front plate 4054 and a rear plate 4056. Front plate 4054 and rear plate 4056 are preferably constructed of aluminum coated with a fluoropolymer (such as Tufram™, which is the product name of a fluoropolymer manufactured by the General Magna Plate Company). The fluoropolymer coating provides improved resistance to wear and also provides lubricity to the exterior surfaces of front plate 4054 and rear plate 4056. Lubricity is particularly advantageous because, when contrast medium crystallizes on the exterior surface of front plate 4054 or rear plate 4056, it easily flakes off of the surface when the surface is coated with the fluoropolymer. Of course, any suitable alternative coating material may be used on the exterior surface of front plate 4054 or rear plate 4056.

In still another alternative embodiment, a coating may not need to be applied to the surface of front plate 4054 or rear plate 4056 if either plate is made of a suitable material. For example, if front plate 4054 and rear plate 4056 are constructed of a high density plastic (an acetyl copolymer, for example) the material itself may provide the same resistance to caking of contrast media as does the fluoropolymer coating on aluminum.

As shown in FIGS. 56 and 57, front plate 4054 includes a hole 4058 therethrough. A lip 4060 extends around the periphery of hole 4058 through front plate 4054. In one preferred embodiment, when syringe 4012 engages release/connector mechanism 4010, flange 4042 and lip 4060 mate with one another to minimize any leaked contrast medium from entering the interior of connector mechanism 4010 through hole 4058. FIG. 72 is particularly illustrative of the mating engagement between lip 4060 and flange 4042. Alternatively, syringe 4012 may be constructed so that it does not include flange 4042, as would be understood by those skilled in the art. In addition, some alternative structure may be provided on either syringe 4012 or front plate 4054 to minimize ingress of contrast medium into the interior of release/connector mechanism 4010.

In the embodiment described and illustrated throughout FIGS. 55-78, flange 4042 also serves an additional function as a mechanical stop when it engages with front surface 4020 of front plate 4054.

Contrast medium of the type typically used within syringe 4012 may interfere with the operation of connector/release mechanism 4010. Accordingly, it is advantageous to include some structure, such as flange 4042 (see FIG. 79), to minimize the ingress of contrast medium into the interior of connector mechanism 4010. However, it is believed that connector/release mechanism 4010 will operate even if fouled with some contrast medium, which is usually unavoidable.

Figures 66, 67:
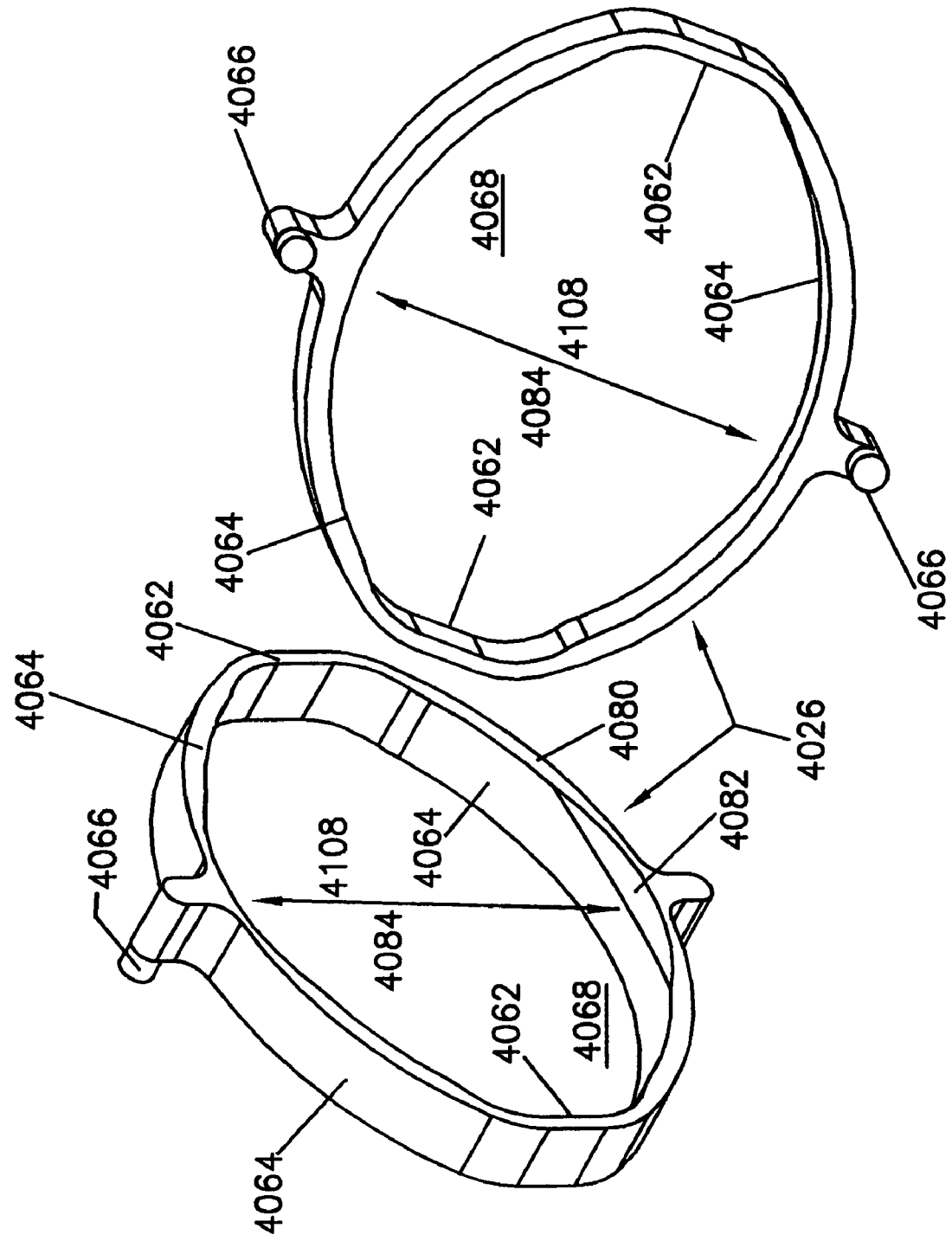
FIG. 66 is an isometric, front view perspective illustration of the flex ring element of the release mechanism of the second preferred embodiment of the present invention, detailing several aspects thereof.
FIG. 67 is an isometric, rear view perspective illustration of the flex ring shown in FIG. 66.

Flex ring 4026 is a substantially elliptically shaped member that is disposed behind front plate 4054 of release/connector mechanism 4010. Flex ring 4026 may be made from an acetal copolymer or any other suitable material. As best shown in FIGS. 66 and 67, flex ring 4026 includes, on either side, a linear or flattened portion 4062 that is integrally connected to two curved portions 4064. From approximately the midpoint of the curved portions 4064, posts 4066 extend toward rear plate 4056. As shown, flex ring 4026 includes a hole 4068 therethrough. As shown in FIG. 66, on a front side 4080 of flex ring 4026, a chamfered surface 4082 is provided. As explained below, chamfered surface 4082 facilitates insertion of rear end 4022 and ridge 4044 of syringe 4012 therethrough.

In the embodiment illustrated in FIGS. 56 and 57, posts 4066 extending rearward from flex ring 4026 are provided with bearings 4070. (Flex ring 4026 is illustrated in detail in FIGS. 66 and 67.) Bearings 4070 preferably are composite bearings (for example, metal and plastic) having inner and outer races with roller bearings disposed therebetween. Alternatively, bearings 4070 may be plastic elements that surround posts 4066 and rotate with respect thereto. Bearings 4070 engage grooves or cam tracks 4072 on rotating ring 4028. As would be appreciated by those skilled in the art, however, bearings are not required for the operation of release/connector mechanism 4010. FIG. 114 illustrates one alternate embodiment of the present invention where bearings 4070 are omitted, which simplifies construction of connector mechanism 4402 and, accordingly, reduces the cost of its manufacture.

Figure 61:
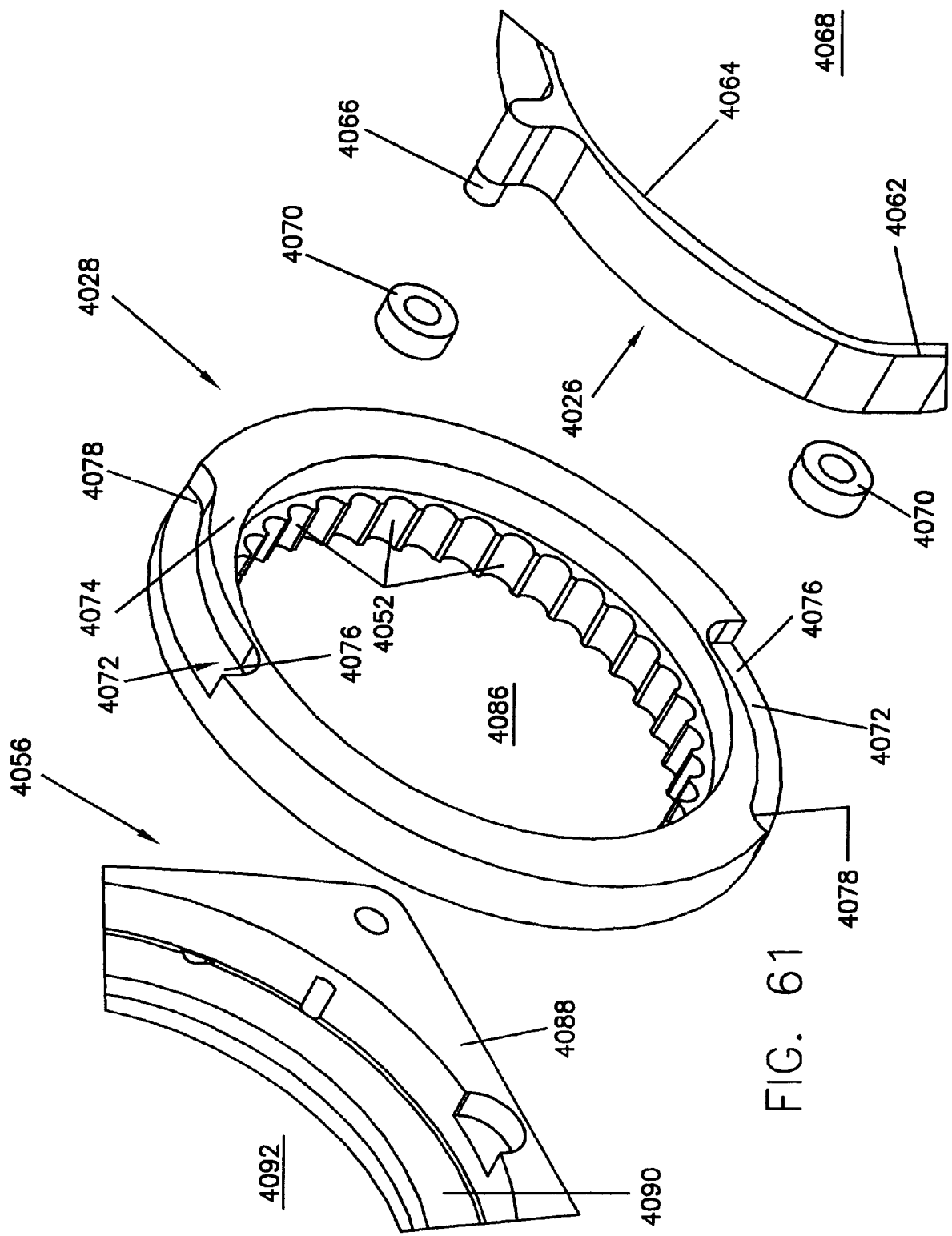
FIG. 61 is an exploded, isometric, front view perspective illustration of the portion of the present invention as shown in FIG. 59, detailing the front of the rotating ring and a portion of the flex ring thereof.
Figures 62, 63:
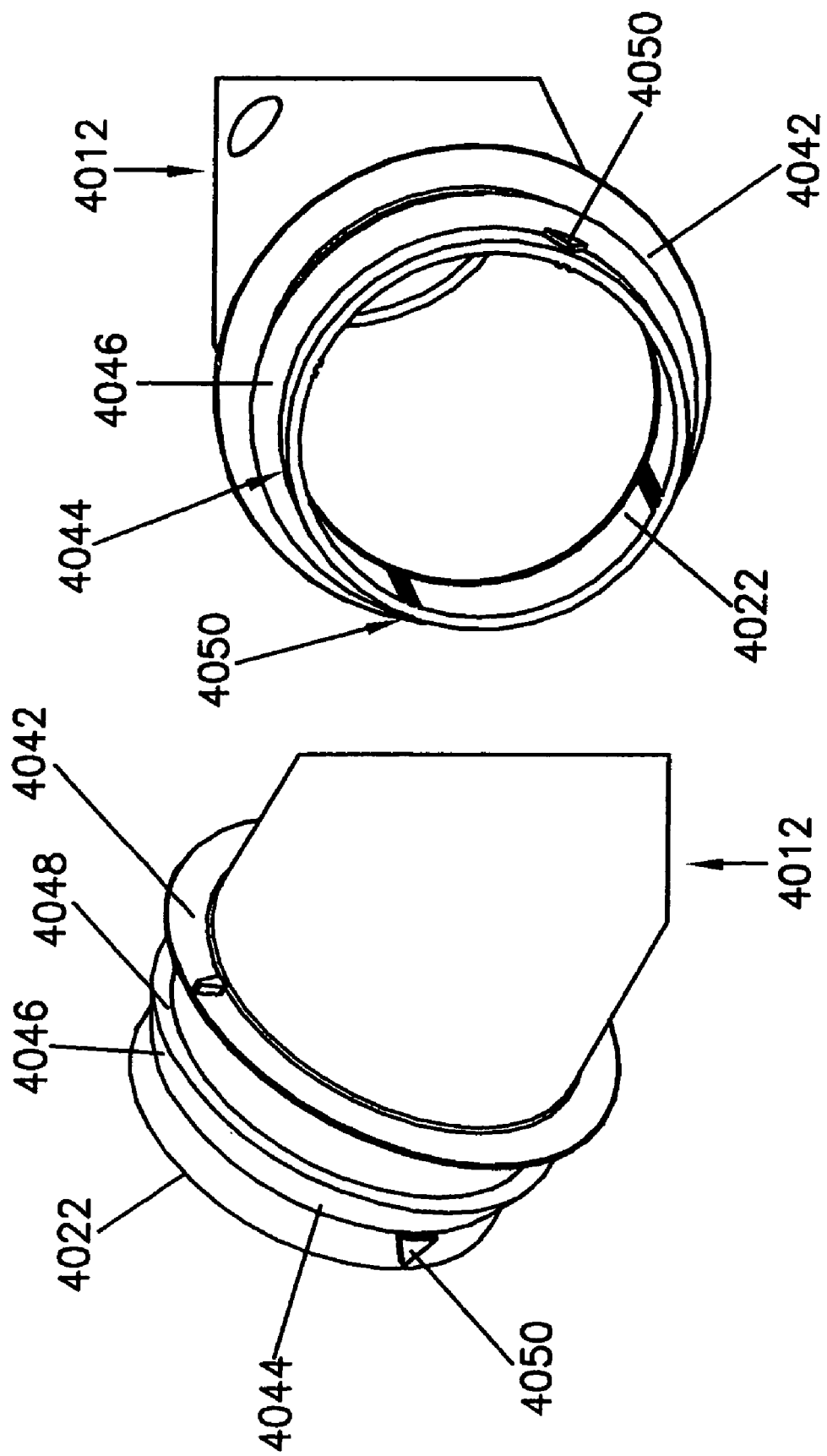
FIG. 62 is a partial, isometric, front view, perspective illustration of the rear portion of the syringe of the second preferred embodiment of the present invention, detailing the ridge and flange structure thereof.
FIG. 63 is a partial, isometric, rear view, perspective illustration of the syringe shown in FIG. 62.

Rotating ring 4028, which is disposed to the rear of flex ring 4026 within housing 4024, includes two grooves or cam tracks 4072 on a front surface 4074 thereof. As best shown in FIGS. 61, 68 and 69, cam tracks 4072 are shaped such that the outer surface 4074 increases in diameter along its arc from the closest point 4076 to the center of rotating ring 4028 to the farthest point 4078 from the center of ring 4028. Grooves 4072 engage posts 4066 through bearings 4070 and, when syringe 4012 is rotated while engaging rotating ring 4028 (e.g., to disengage syringe 4012 from release/connector mechanism 4010), force posts 4066 apart to stretch flex ring 4026 in a direction indicated by arrow 4084 in FIGS. 66 and 67. As shown, flex ring 4026 has a hole 4068 through its center to accommodate rear end 4022 of syringe 4012 therein or therethrough.

Rotating ring 4028, which is shown in detail in FIGS. 68 and 69, is disposed within an indentation or recess 4090 formed in front surface 4088 of rear plate 4056. (Rear plate 4056 is shown in detail in FIGS. 70 and 71.) Rear plate 4056 has a hole 4092 therethrough for accommodating rear portion 4022 of syringe 4012. Rotating ring 4028 is disposed in indentation 4090 so that ring 4028 may freely rotate therein. Rear plate 4056 has a rear surface 4094, which is illustrated in FIGS. 57 and 71.

Figure 58:
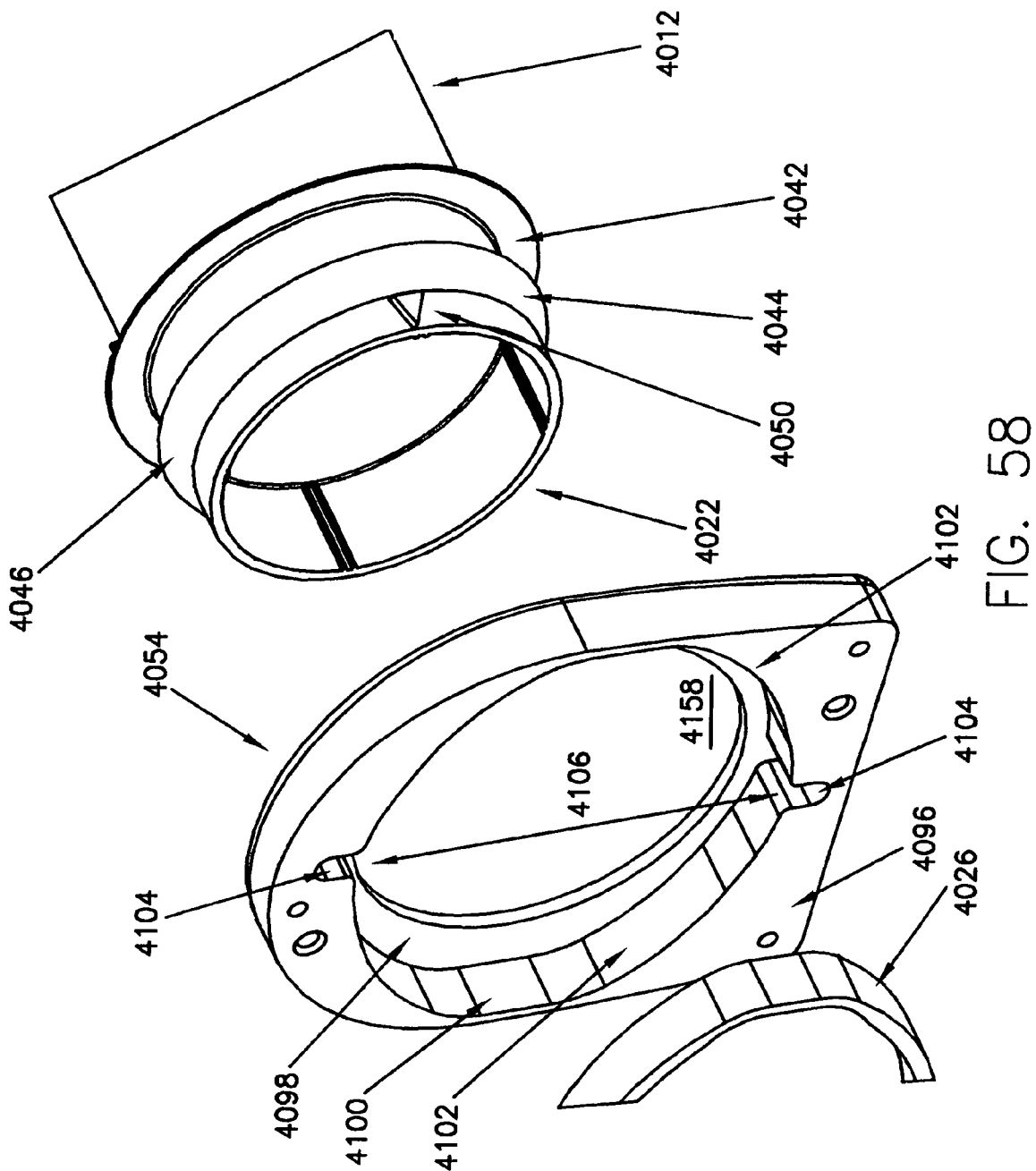
FIG. 58 is an exploded, isometric, rear view perspective of a portion of the syringe interface and syringe system shown in FIGS. 55-57.

As shown in FIGS. 57, 58 and 64, a rear surface 4096 of front plate 4054 includes an indentation or recess 4098 that has essentially the same shape as flex ring 4026. As such, indentation 4098 includes two linear or flattened portions 4100 and two curved portions 4102. (See, e.g., FIGS. 58 and 64.) Two notches 4104 in rear surface 4096 of front plate 4054 are positioned at approximately the center point of curved sections 4102. Notches 4104 accommodate posts 4066 and the associated structures that connect posts 4066 to flex ring 4026. Indentation 4098 is shaped to be larger than flex ring 4026 and a distance 4106 between notches 4104 is greater than a distance 4108 between posts 4066 (see FIGS. 66 and 67) in their relaxed state. Notches 4104 help to prevent flex ring 4026 from rotating within housing 4024 and permit flex ring 4026 to expand upon rotation of rotating ring 4028.

The operation of release/connector mechanism 4010 is illustrated in and described by reference to FIGS. 74-78 and 55-73.

Figure 74:
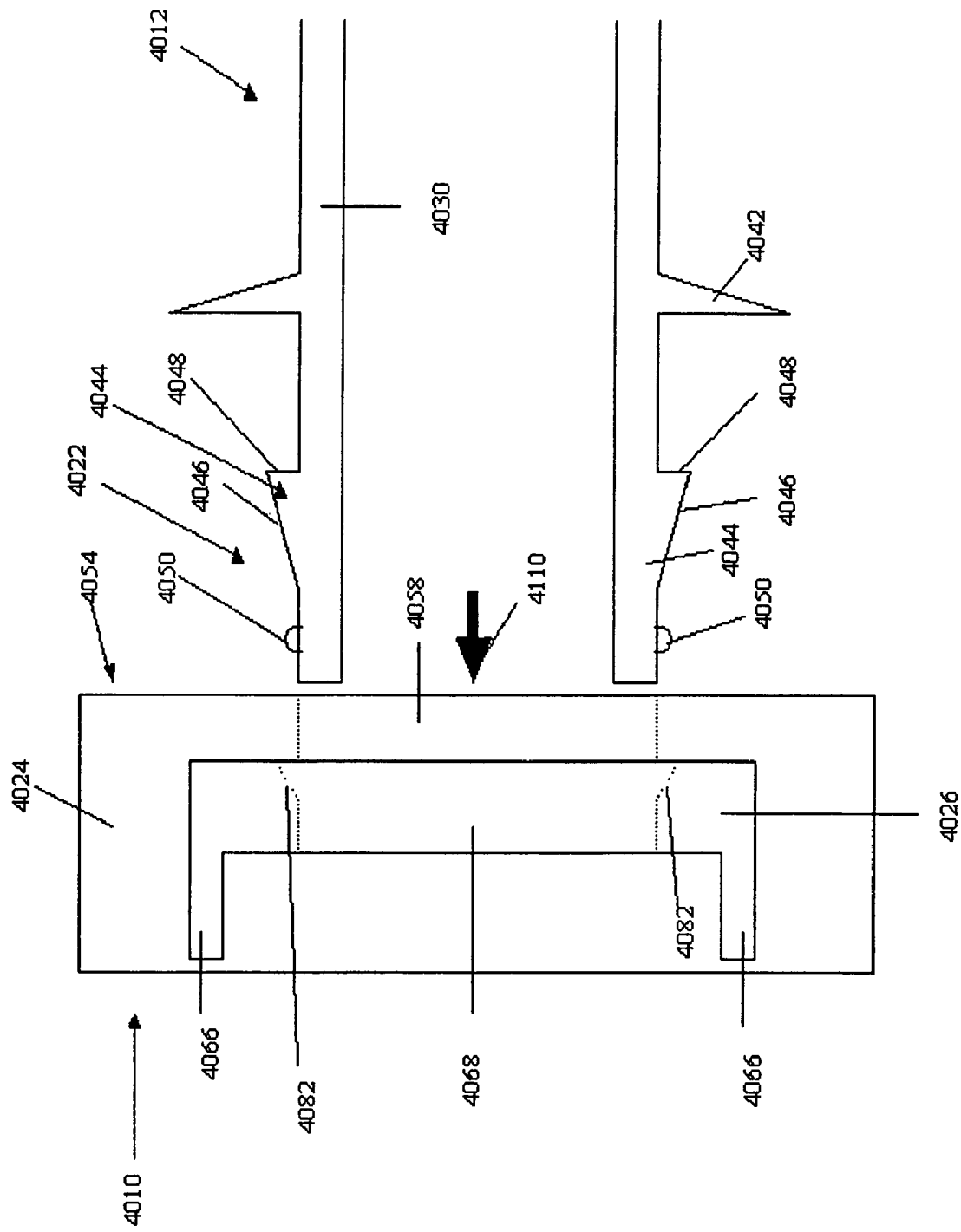
Figure 75:
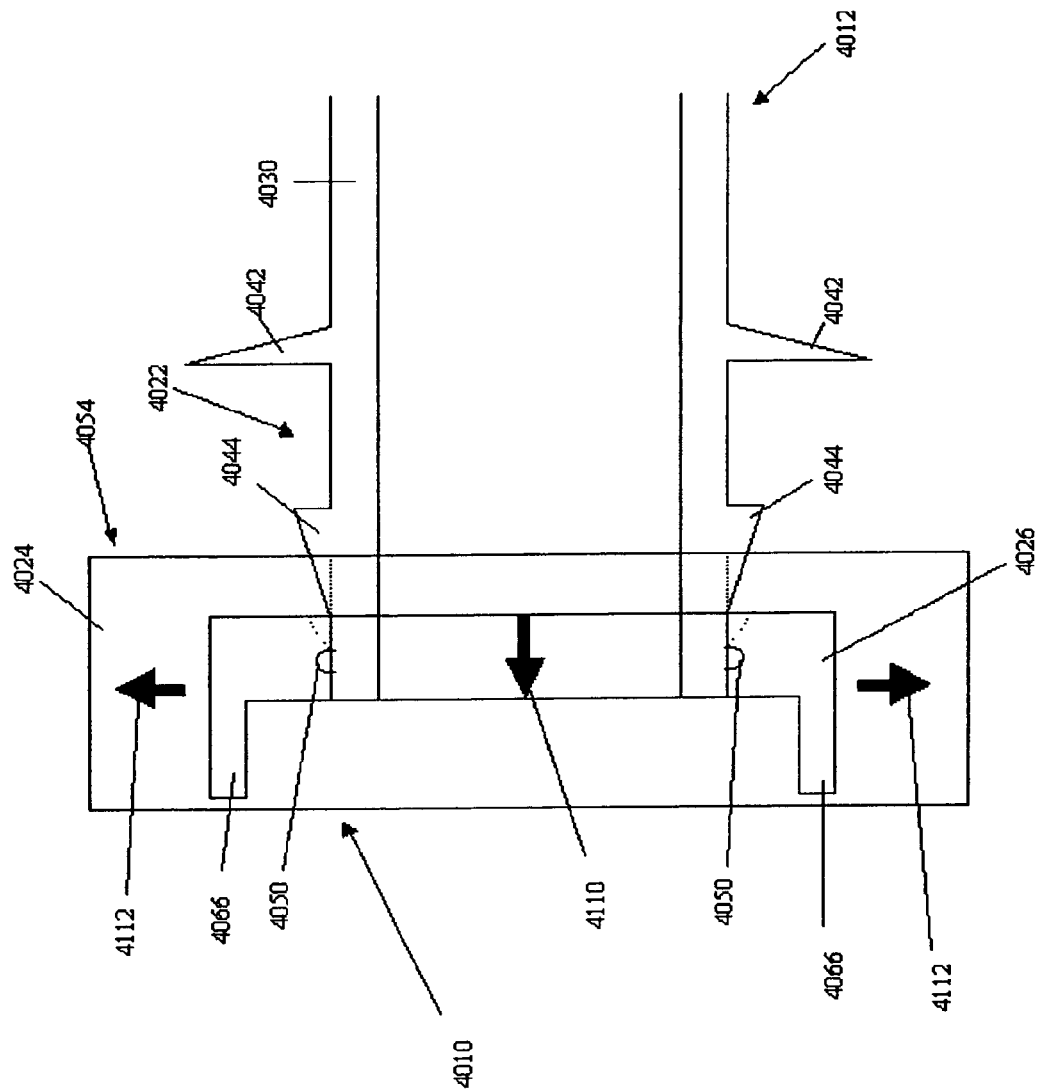
Figure 76:
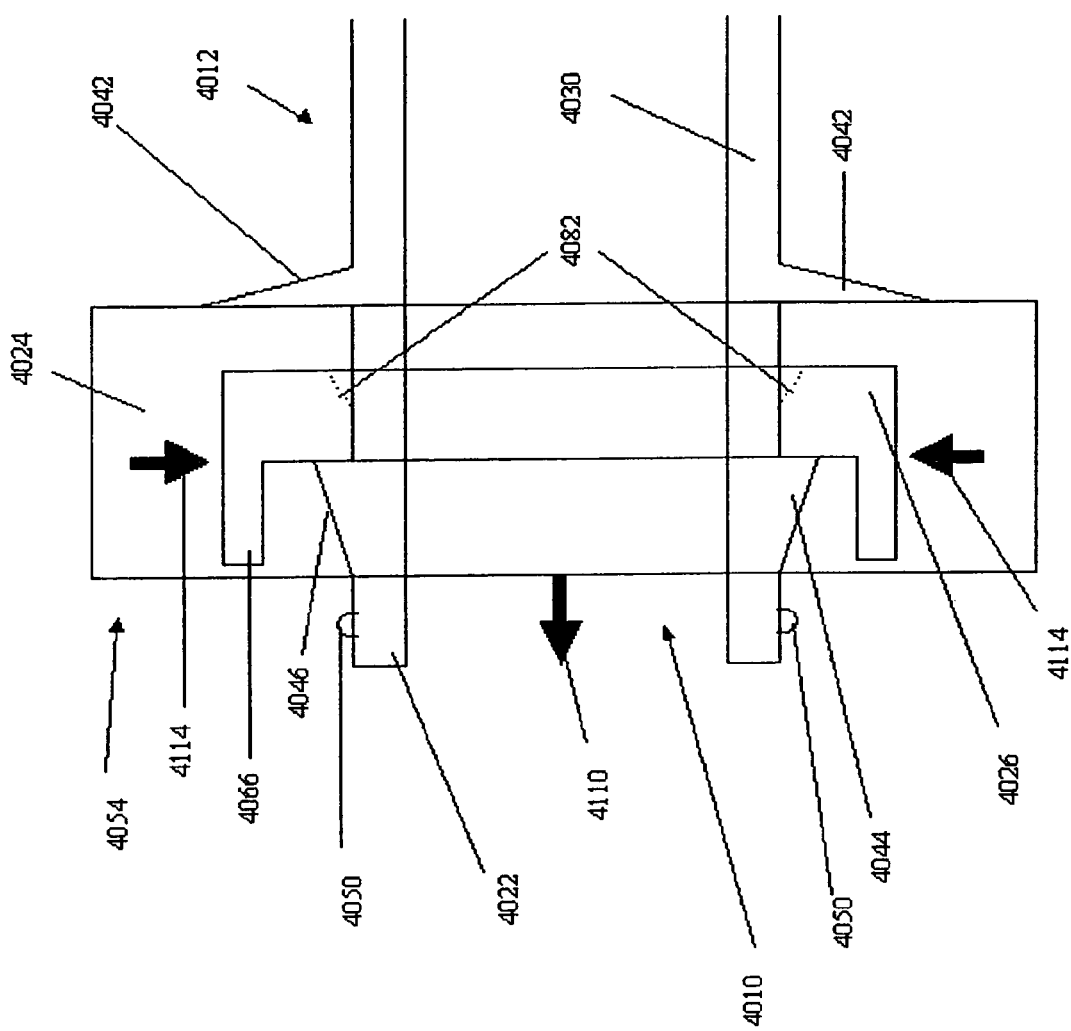

As illustrated in FIGS. 74-76, rear end 4022 of syringe 4012 is inserted into connector housing 4024 through hole or interface 4058 in front plate 4054, in the direction indicated by arrow 4110. Flex ring 4026 sits within indentation 4098 formed in rear surface 4096 of front plate 4054 so that posts 4066 engage notches 4104. Therefore, when inclined surface 4046 of ridge 4044 of syringe 4012 engages chamfers 4082 on flex ring 4026, ridge 4044 pushes open flex ring 4026 in direction 4084 (shown in FIGS. 66 and 67) from its relaxed distance 4108 (see FIG. 77) to its extended (or tensioned) distance 4106 (see FIGS. 58 and 78). FIG. 75 is illustrative of this feature. Flex ring 4026 opens in the direction indicated by arrows 4112.

After ridges 4044 clear the rear edge of flex ring 4026, the elastic nature of flex ring 4026 causes flex ring 4026 to resume its relaxed state in the direction of arrows 4114, as illustrated in FIG. 76. When flex ring 4026 resumes its relaxed state, the shoulder 4048 of ridge 4044 engages the rear edge of flex ring 4026. The syringe 4012 is thereby held in place by flex ring 4026 and cannot be axially removed from release/connector mechanism 4010. When flex ring 4026 resumes its relaxed state, it preferably provides an audible "click" to indicate to the operator that the syringe 4012 has been installed on the injector.

Removal of syringe from release/connector mechanism 4010 preferably requires that syringe 4012 be rotated ¼ turn or an approximate one quarter turn, as described below. This operation is illustrated in and described by reference to FIGS. 77, 78 and 55-73.

Figure 60:
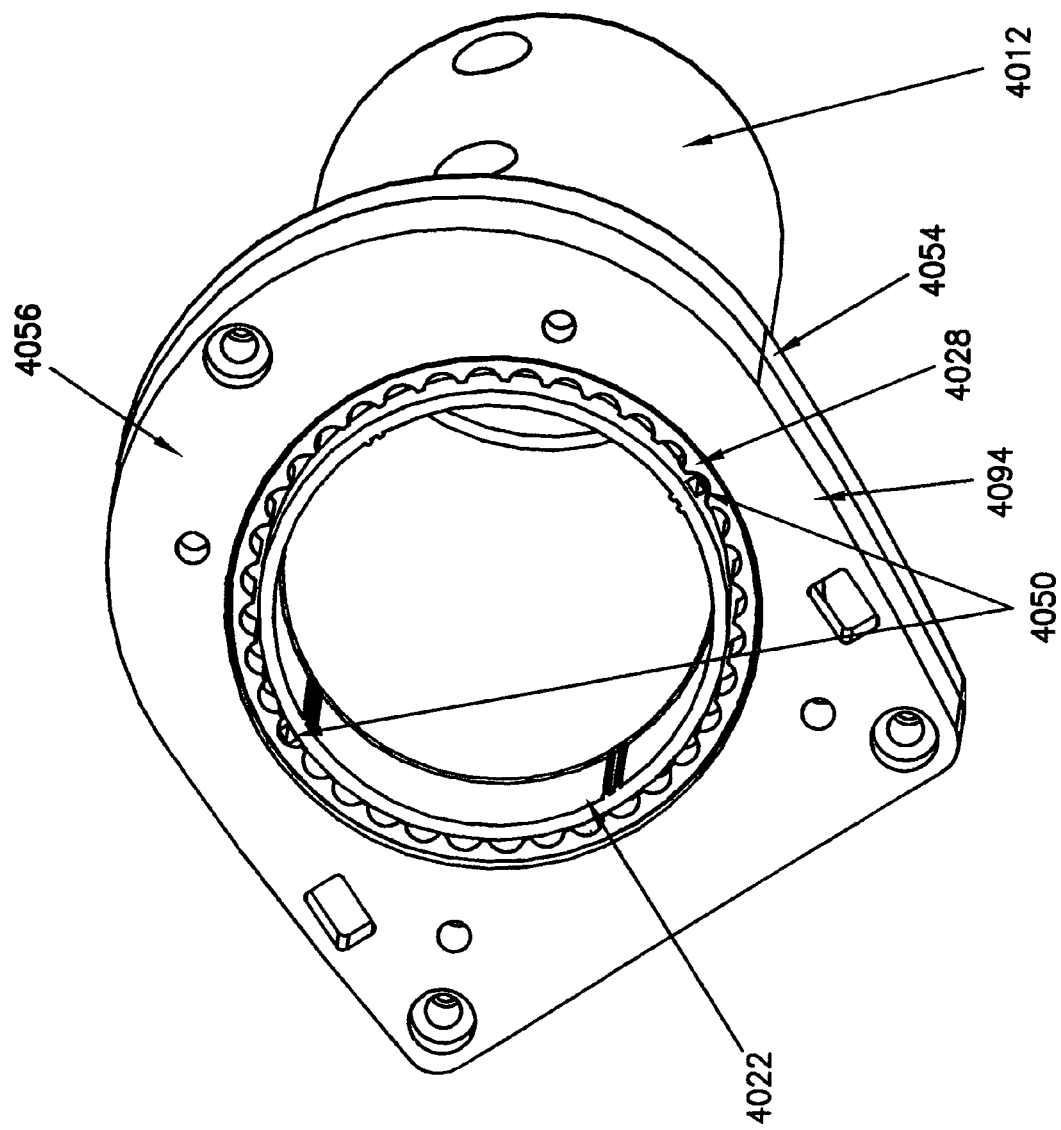
FIG. 60 is an isometric, rear view of the syringe interface and syringe system shown in FIGS. 55-59, detailing the connection of the syringe to the release mechanism.
Figure 77:
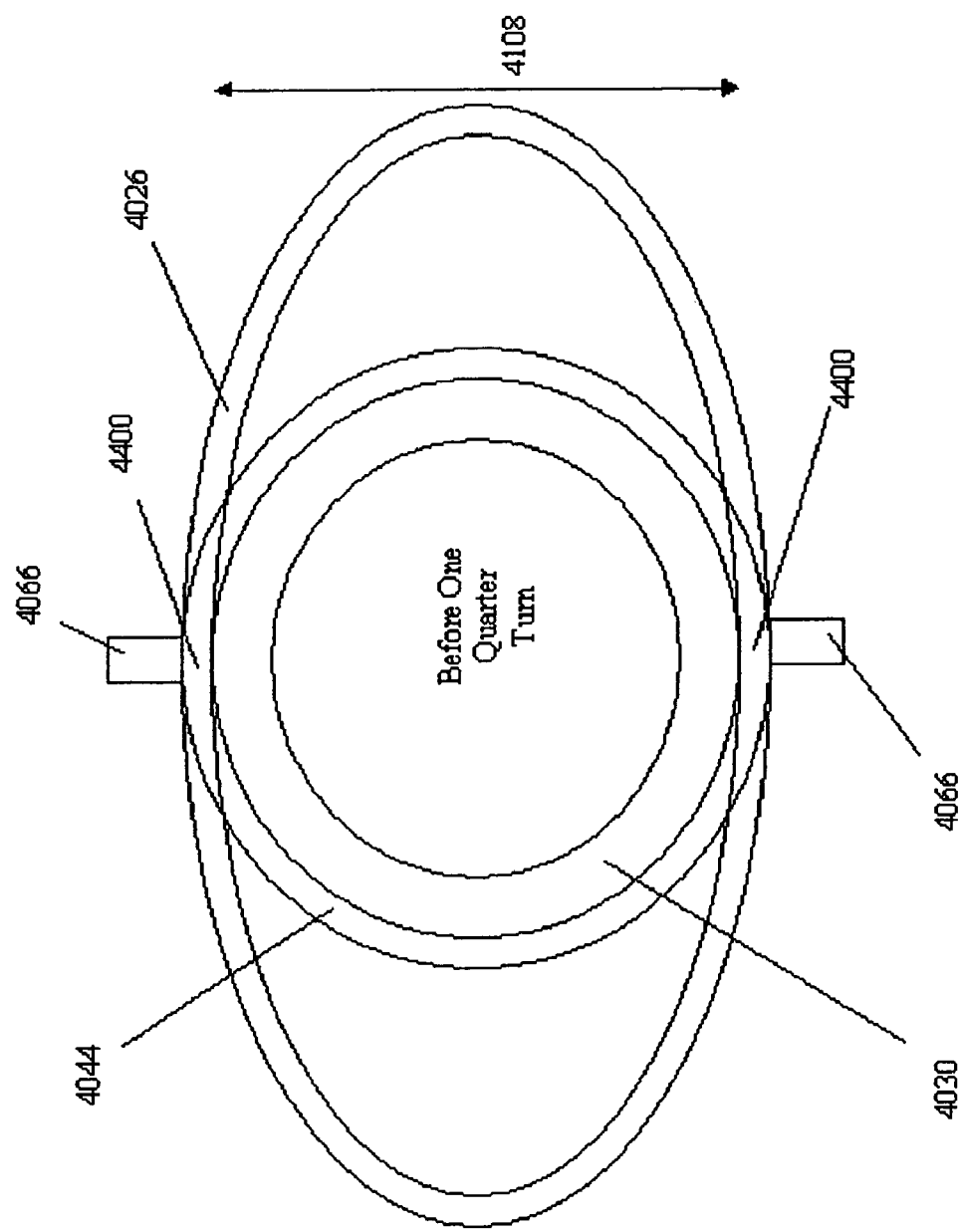

As illustrated in FIGS. 60 and 73, once syringe 4012 has been engaged by flex ring 4026, the two projections 4050 engage two of grooves 4052 in rotating ring 4028. FIG. 77 illustrates a cross-sectional view of the engagement of syringe 4012 and flex ring 4026 (which is shown as an entirely elliptical structure for convenience). (In alternate embodiments, one, three or more projections 4050 may be provided on the syringe 4012.) As best shown in FIGS. 55-57, the projections 4050 are preferably triangular in shape, with a point of the "triangle" being directed first into engagement with the grooves 4052 in rotating ring 4028. This design allows the projections 4050 to readily align with and engage the respective grooves 4052 in the rotating ring 4028 when the syringe 4012 is inserted into the release/connector mechanism 4010, without the operator having to joggle or twist the syringe 4012 to seat the projections 4050.

As syringe 4012 is rotated, in a preferred embodiment, approximately one quarter turn in the counter-clockwise direction, projections 4050, which engage grooves 4052, force rotating ring 4028 also to rotate approximately the same amount in the same direction. While the mechanism 4010 is preferably designed to release syringe 4012 by means of a counter-clockwise rotation, it is specifically contemplated that mechanism 4010 may be adapted to release syringe 4012 by means of a clockwise rotation. (It should be noted that the one-quarter turn to which reference is made herein is not intended to mean exactly one quarter of a turn. The term "one quarter turn" is meant to indicate a turn that is about one quarter turn and preferably in a range from 45 to 90 degrees from the rest position of syringe 4012. Alternately, any suitable range of rotation may be used to facilitate disengagement of the syringe 4012 from mechanism 4010.)

Because posts 4066 (with bearings 4070) of flex ring 4026 engage and ride along cam tracks 4072 on rotating ring 4028, the rotation of ring 4028 will urge flex ring 4026 from its relaxed (i.e., syringe engaged) state to its extended (i.e., syringe disengaged) state. As posts 4066 travel along cam tracks 4072 from the inner-most position 4076 to the outer-most position 4078, flex ring 4026 is stretched from the relaxed distance 4108 to the extended distance 4106 (in the direction of Arrows 4112), at which point the rear edge of flex ring 4026 disengages the shoulder 4048 of syringe 4012. Consequently, the syringe 4012 is disengaged and may be axially removed from flex ring 4026 and mechanism 4010. When the syringe 4012 is removed from the mechanism 4010, the spring force of the flex ring 4026 urges the posts 4066 to travel along the cam tracks 4072 from the outer-most position 4078 to the inner-most position 4076, thereby returning the flex ring 4025 to its relaxed state for receipt of a new syringe. In addition, when the syringe 4012 is disengaged from the flex ring 4026, the operator preferably hears a second audible "click" to indicate that the syringe 4012 has been disengaged from the mechanism 4010 (and, accordingly, the injector).

A third preferred embodiment of the syringe interface/release mechanism is shown in FIGS. 124 and 125. Because the third preferred embodiment is similar in function and structure to the second preferred embodiment illustrated in FIGS. 55-78, for ease of reference the same reference numerals have been used to identify the respective components thereof. The differences between the second and third preferred embodiments are discussed below. The third preferred embodiment shown in FIGS. 124 and 125 includes a pair of return springs 4091 to assist flex ring 4026 and rotating ring 4028 to return to their rest state after syringe 4012 is released from release/connector mechanism 4010. (Optionally, bearings 4093 may be provided for springs 4091. These bearings may be retained in rear plate 4056 by pins (not shown) and formed of Delrin®.) In this embodiment, the return springs 4091 are disposed between the rotating ring 4028 and the rear plate 4056. However, the return springs 4091 may be connected between rotating ring 4028 and the front plate 4054 of housing 4024. The rotating ring 4028 preferably includes a pair of projecting tabs 4095 to which the free ends 4097 of the springs 4091 are connected. As shown, the springs 4091 preferably ride within and are constrained by a pair of complementary shaped recesses 4099 formed in the rear plate 4056. The return springs 4091 are preferably ¾" constant force springs provided by Associated Spring Raymond. The return springs 4091 are especially useful in assisting the flex ring 4026 and the rotating ring 4028 to return to their rest state if the elements of syringe interface/connector mechanism 4010 have become fouled with contrast media during the medical procedure (or over time after repeated use).

As discussed above, FIG. 79 illustrates the efficacy of flange 4042 for preventing contrast media in syringe 4012 from entering a syringe interface and injector of the present invention.

The present invention also includes a construction for a first preferred embodiment of an injector piston and syringe plunger interface assembly 4200 for injector 4014 that engages a plunger within syringe 4012 without regard to the orientation of syringe in release/connector mechanism 4010 or the orientation of the plunger within the syringe 4012. FIGS. 80-109 are illustrative of piston/plunger assembly 4200 and its operation.

Piston/plunger assembly 4200 is positioned movably in an axial relation to injector 4014 and syringe 4012. As shown in FIGS. 85 and 86, piston 4202 includes a rear end 4204 and a front end 4206. Piston 4202 also includes an elongated shaft 4208 extending between rear end 4204 and front end 4206. Rear end 4204 of piston 4202 is connected to a mover or motor drive train within injector 4014. The mover may be any type of mover suitable for moving piston 4202 axially into and out from injector 4014, including a motor and drive train combination.

As shown in FIGS. 80-82, a piston sleeve 4210 surrounds shaft 4208 of piston 4202. Piston sleeve 4210 is freely movable with respect to piston 4202. In other words, piston sleeve 4210 is not connected to piston 4202. Piston sleeve 4210 is essentially a cylindrical tube with a front end 4212 and a rear end 4214. (See FIG. 87 for an enlarged detail of piston sleeve 4210.) A collar 4216 is disposed at front end 4212 of piston sleeve 4210. As shown in FIGS. 88-90, collar 4216 includes a hole 4218 through which piston 4202 is disposed. An annular flange 4219 is provided on a rear side 4220 of collar 4216 for engagement of front end 4212 of piston sleeve 4210. A second annular flange 4222 is provided on a front surface 4224 of collar 4216. Annular flange 4222 engages a plunger cap 4226, which is generally depicted in FIGS. 97-100.

Plunger cap 4226 has a base portion 4230 that extends outwardly from a base thereof. (ee FIGS. 97-100.) The base portion 4230 is connected to a frusto-conical section 4232 that tapers inwardly toward a centerline of plunger cap 4226. An annular groove 4234 is provided in plunger cap 4226 near frusto-conical section 4232. Slots 4236 are disposed within annular groove 4232 for retaining support ring grippers 4238. A top portion 4240 of plunger cap 4226 extends upwardly from annular groove 4234. Top portion 4240 is cone shaped and terminates in a rounded tip 4242. As illustrated in FIG. 98, plunger cap 4226 is essentially a hollow body that defines an interior volume 4244.

Front end 4206 of piston 4202 extends into interior volume 4244 of plunger cap 4226. As shown in FIGS. 107 and 108, front end 4206 of piston 4202 is connected to gripper expander 4246. Gripper expander 4246 is connected to front end 4206 of piston 4202 by any suitable means such as a screw (not shown) disposed through a hole 4248 that extends through the center of gripper expander 4246. (Detailed illustrations of gripper expander 4246 are provided in FIGS. 91-93.)

Gripper expander 4246 has a top surface 4250 and a bottom surface 4252. From top surface 4250, gripper expander 4246 tapers inwardly to form a frusto-conical section 4254. A cylindrical section 4256 extends from frusto-conical section 4254 to bottom surface 4252. When connected to front end 4206 of piston 4202, gripper expander 4246 forms a T-shaped structure with piston 4202, as illustrated in FIGS. 107 and 108.

As illustrated in FIGS. 83, 84, 94-96, 107 and 108, support ring grippers 4238 extend through the slots 4236 in annular groove 4234 of plunger cap 4226. Support ring grippers 4238 are designed to extend outwardly from annular groove 4234 when piston/plunger assembly 4200 is moved in a rearward direction or retracted (into injector 4014). As shown in FIGS. 94-96, support ring grippers 4238 have a body 4258 that is L-shaped in cross-section. On an interior edge 4260, support ring grippers 4238 are provided with a chamfer 4262 that engages with frusto-conical surface 4254 on gripper expander 4246. When gripper expander 4246 moves in the direction of injector 4014, which is indicated by arrows 4264 in FIG. 108, support ring grippers 4238 move outwardly from plunger cap 4226 in the direction of arrows 4266 (also shown in FIG. 108).

A rubber cover 4268 (which is shown in detail in FIGS. 105 and 106) is usually assembled with syringe 4012 and is located therein. Movement of rubber cover 4268 causes the liquid contained in syringe 4012 to be pushed out through the discharge end 4036 and into the patient. Rubber cover 4268 includes a conically shaped top 4270 with a substantially cylindrical 4272 portion extending rearwardly therefrom. Cylindrical portion 4272 may include any number of ridges 4274 and grooves 4276 that may be required for a particular application to assure that the liquid does not pass by the plunger and leak out of the syringe 4012 during, for example, an injection procedure.

The interior of rubber cover 4268 is hollow and, as a result, has a conical inner surface 4278. In addition, at a bottom end 4280, a lip 4282 is provided that defines a circular opening 4284 into the interior of rubber cover 4268. Lip 4282 is designed to be engaged by a rubber cover support ring 4286.

Rubber cover support ring 4286, which is shown in detail in FIGS. 101-104, is constructed of a suitable plastic material. Rubber cover support ring 4286 engages lip 4282 on the interior of rubber cover 4268 and provides additional rigidity to rubber cover 4268. Rubber cover support ring 4286 includes an annular ring 4288 at a bottom portion 4290 thereof. A groove 4292 is provided above annular ring 4288 for engagement of lip 4282 of rubber cover 4268. A frusto-conical section 4294 extends upwardly from groove 4292 and mates within the interior surface 4278 of the rubber cover 4268. A hole 4296 extends through rubber cover support ring 4286. The interior surface of rubber cover support ring 4286 includes a lip 4298 with a chamfered surface 4300. Lip 4298 serves as a location for engagement by support ring grippers 4238.

In an alternate embodiment of rubber cover 4268, rubber cover support ring 4286 may be eliminated altogether. The alternate embodiment of the rubber cover, which is designated 4306, is illustrated in FIGS. 110-113. Since rubber cover 4306 does not include rubber cover support ring 4286, rubber cover 4306 is thicker in cross-section than rubber cover 4268. So that grippers 4238 may engage rubber cover 4306 during at least a retraction operation of injector 4014, rubber cover 4306 includes a lip 4308 on an interior surface.

Rubber cover 4306 has essentially the same shape as rubber cover 4286. Rubber cover 4306 includes a conically shaped top portion 4310 with a rounded tip 4312. At its lower end 4314, rubber cover 4306 includes three ribs 4316 and two grooves 4318 positioned along a cylindrical portion. The interior of rubber cover 4306 defines an interior volume 4320 with tapered sides 4322. Rubber cover 4306 is thicker than rubber cover 4286 so that it has added strength and sealing capabilities (i.e., to the interior of syringe 4012).

The operation of piston/plunger assembly 4200 will now be described in connection with FIGS. 107-109. The operation of piston/plunger assembly 4200 does not differ substantially if rubber cover 4268 (together with rubber cover support ring 4286) or rubber cover 4306 are employed within syringe 4012.

When the operator of injector 4014 desires to advance or push the piston/plunger assembly 4200 forward, he may push one of the buttons 4302 on injector 4014 to actuate forward movement of piston 4202. Movement of piston 4202 in the forward direction pushes rubber cover 4268 in the forward direction. Because forward movement of rubber cover 4268 in the forward direction does not require any connection between piston assembly 4202 and rubber cover 4268, the two are only in a mating engagement with one another. However, if the operator of injector wishes to retract or move rubber cover 4268 in the rearward direction, piston/plunger assembly 4200 must grab onto rubber cover 4268 to pull it toward injector 4014.

To grab onto rubber cover 4268 (and its associated rubber cover support ring 4286, where included), grippers 4238 extend outwardly to grab onto lip 4298 of rubber cover support ring 4286. If the alternative rubber cover 4306 is used, grippers 4238 engage lip 4308. The engagement of lip 4298 (or alternatively lip 4308) by grippers 4238 is described below.

As mentioned above, piston sleeve 4210 is not connected to piston 4202. Instead, it is freely moveably (in the axial direction) with respect to piston 4202. Within injector 4014, there is an o-ring 4304 that matingly engages the exterior surface of piston sleeve 4210. (See FIGS. 107 and 108.) Accordingly, when piston 4202 is withdrawn into injector 4014, piston sleeve 4210 experiences a frictional engagement with o-ring 4304 that tends to hold piston sleeve 4210 in place. In other words, ring 4304 biases piston sleeve 4210 in a forward direction when piston 4202 is retracted in a rearward direction.

Because piston 4202 is connected to gripper expander 4246, as piston 4202 moves into injector 4014, so does gripper expander 4246. However, piston sleeve 4210, collar 4216, and plunger cap 4226, which are the elements connected to one another, are biased in a forward direction by O-ring 4304. Accordingly, when actuated, piston 4202 and gripper expander 4246 move rearward in relation to piston sleeve 4210, collar 4216 and plunger cap 4226. Frusto-conical section 4254 of gripper expander 4246 is then caused to engage chamfered regions 4262 to force grippers 4238 outwardly through slots 4236 in plunger cap 4226, as shown by Arrows 4266 in FIG. 108, and into engagement with lip 4298 (or lip 4308) of support ring 4286. To hold grippers 4238 in place, a rubber sheath (not shown) may be placed over plunger cap 4226. The rubber sheath may also assist in preventing contrast medium from entering plunger cap 4226 through slots 4236.

By this construction, then, rubber cover 4268 connectively engages piston 4202 only when piston 4202 is retracted or moved in a rearward direction into or toward injector 4014. When stationary or when moving forward, rubber cover 4268 does not engage piston 4202 so that syringe 4012 may be easily disengaged from syringe interface 10.

As can be appreciated, the piston/plunger assembly 4200 of the present invention is preferably not orientation specific. That is, engagement between the piston 4202 and the plunger cover 4268 can occur without regard to the orientation of the plunger within the syringe 4012 and/or the orientation of the plunger with respect to the piston 4202. In conjunction with suitable syringe interfaces of the present invention, injector and syringe systems are provided that do not require an operator to orient the syringe in any particular manner with respect to the injector to mount the syringe thereon. The present invention, in at least one aspect, thereby improves and facilitates the mounting and installation of syringes on injectors.

FIG. 114 illustrates an alternate embodiment of the release/connector mechanism 4402 of the present invention. Here, flex ring 4026 does not include bearings 4070 around posts 4066. As mentioned above, this simplifies the construction of connector mechanism 4402. Here, release/connector mechanism 4402 operates in the same manner as connector mechanism 4010 except that posts 4066 engage cam tracks 4072 directly. For convenience, screws 4404 are shown that hold front plate 4054 to rear plate 4056.

FIG. 115 illustrates another embodiment of the syringe interface/connector mechanism 4406 of the present invention. Here, rotating ring 4028 has been eliminated altogether. In this embodiment, grooves 4408 are provided on an inner surface of flex ring 4410 for engagement with projections 4412 on syringe 4414 (see FIG. 117). Posts 4416 extend from upper and lower positions on flex ring 4410 and engage grooves 4418 in back plate 4420 (or, alternatively, in the front plate (not shown)). When syringe 4414, which is illustrated in cross-section in FIG. 117, is rotated (preferably in a counter-clockwise direction), projections 4412 rotate flex ring 4410 so that posts 4416 travel in grooves 4418 to stretch flex ring 4410 and release syringe 4414. For the barrel projections 4412 to engage grooves 4408, the projections 4412 are positioned between ridge 4044 and flange 4042. So that the differences between the two alternative designs may be evaluated, syringe 4414 is illustrated adjacent syringe 4012 (see FIGS. 116 and 117).

Figure 59:
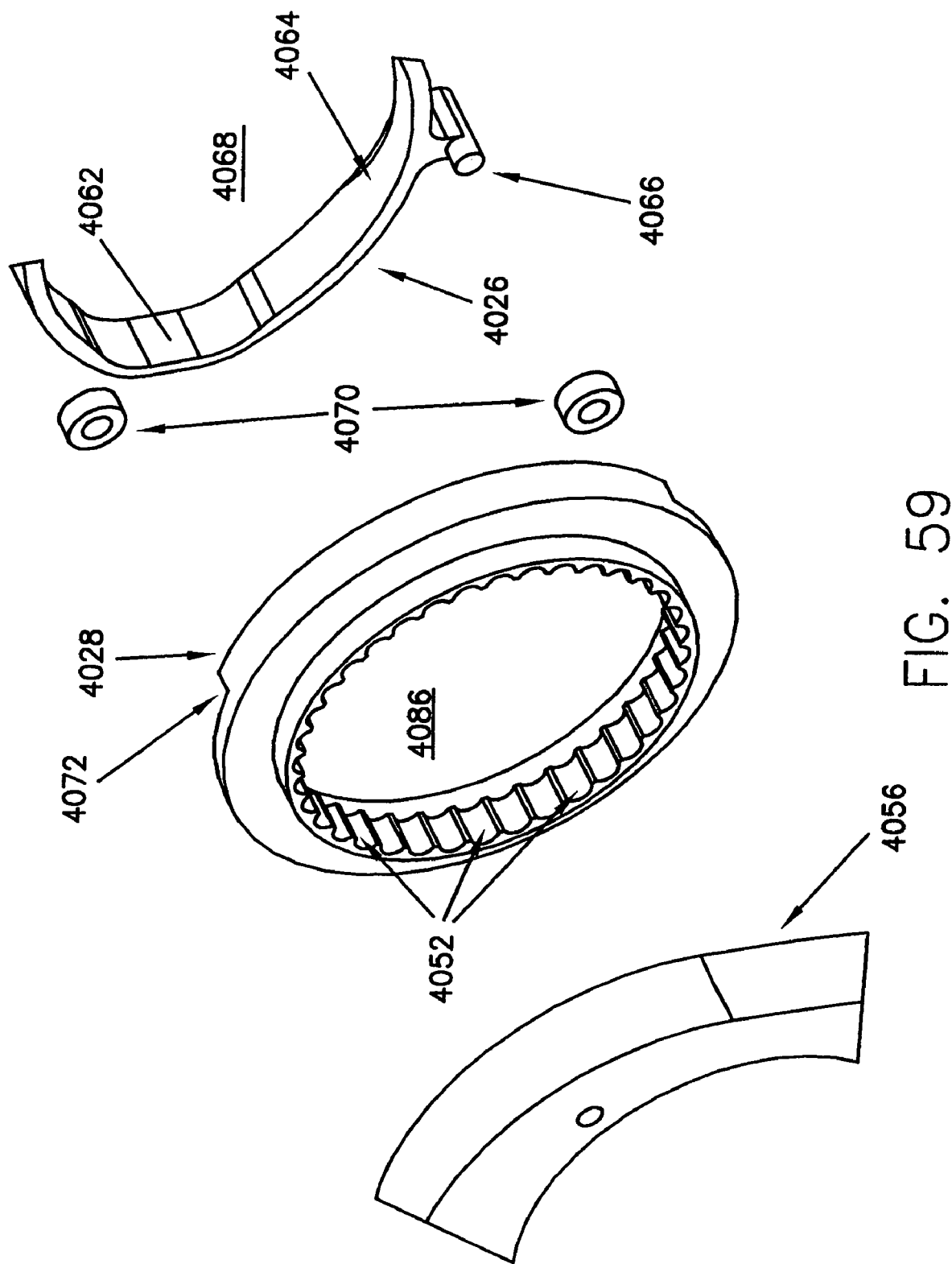
FIG. 59 is an exploded, isometric, rear view perspective of another portion of the syringe interface and syringe system shown in FIGS. 55-57, showing in detail the rear of a portion of a flex ring and a rotating ring of the interface/release mechanism.

FIG. 118 illustrates three alternate embodiments of the different shapes for grooves for rotating ring 4028 or flex ring 4410. It should be noted that the different shapes for grooves 4052 may be used with any alternative embodiment of rotating ring or flex ring described herein. First, in embodiment #1, grooves 4052, which are the same as those depicted in FIG. 59, are illustrated. In embodiment #1, grooves 4052 are semi-cylindrical indentations on the inner surface of rotating ring 4028. Embodiment #2 illustrates grooves 4052' that are triangularly shaped. Embodiment #3 illustrates that grooves 4052'' are U-shaped. Those skilled in the art should readily recognize that grooves 4052, 4052', 4052'' may be of any suitable shape to engage projections 4050 or their equivalent.

Figure 78:
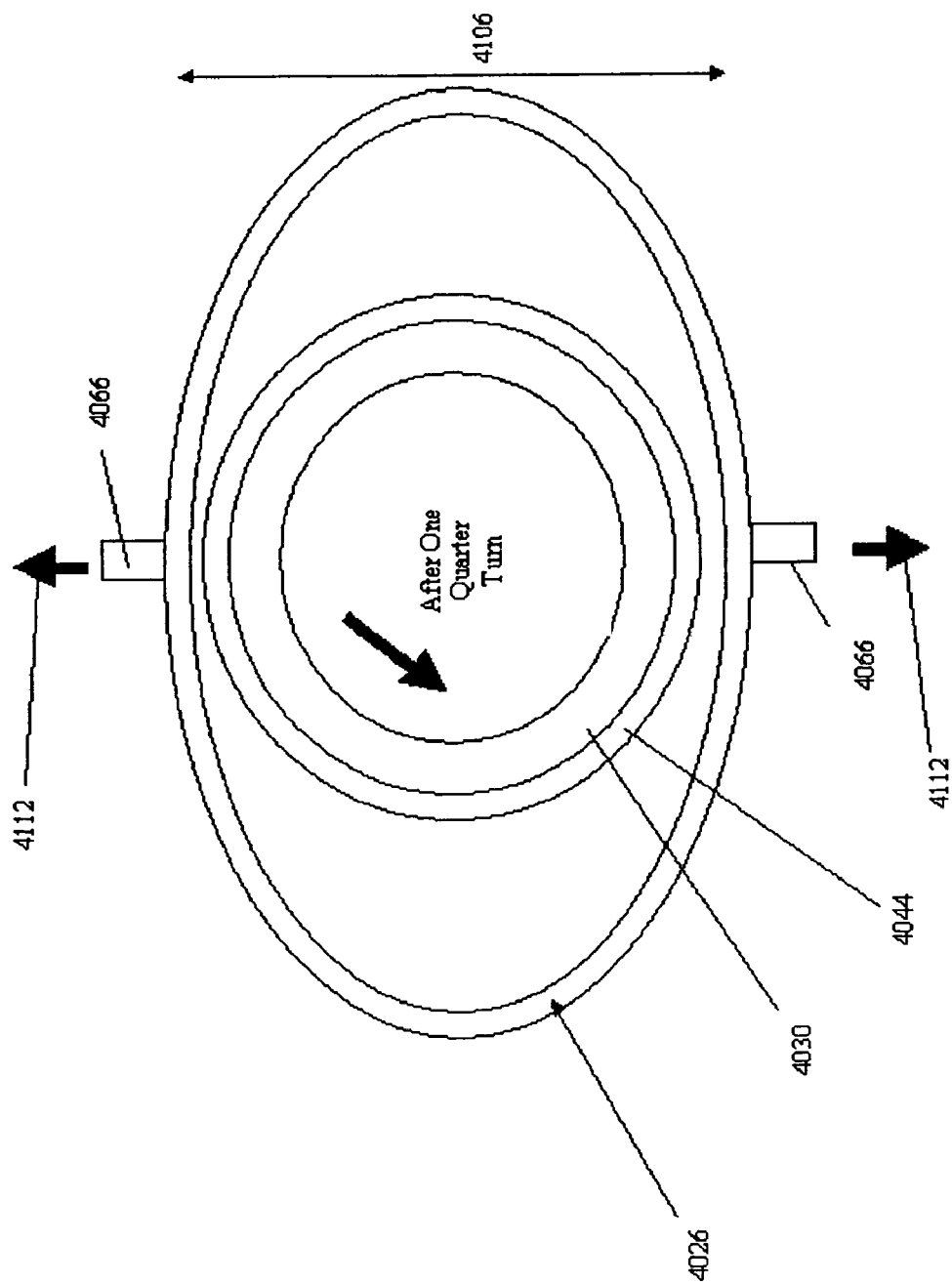
Figure 79:
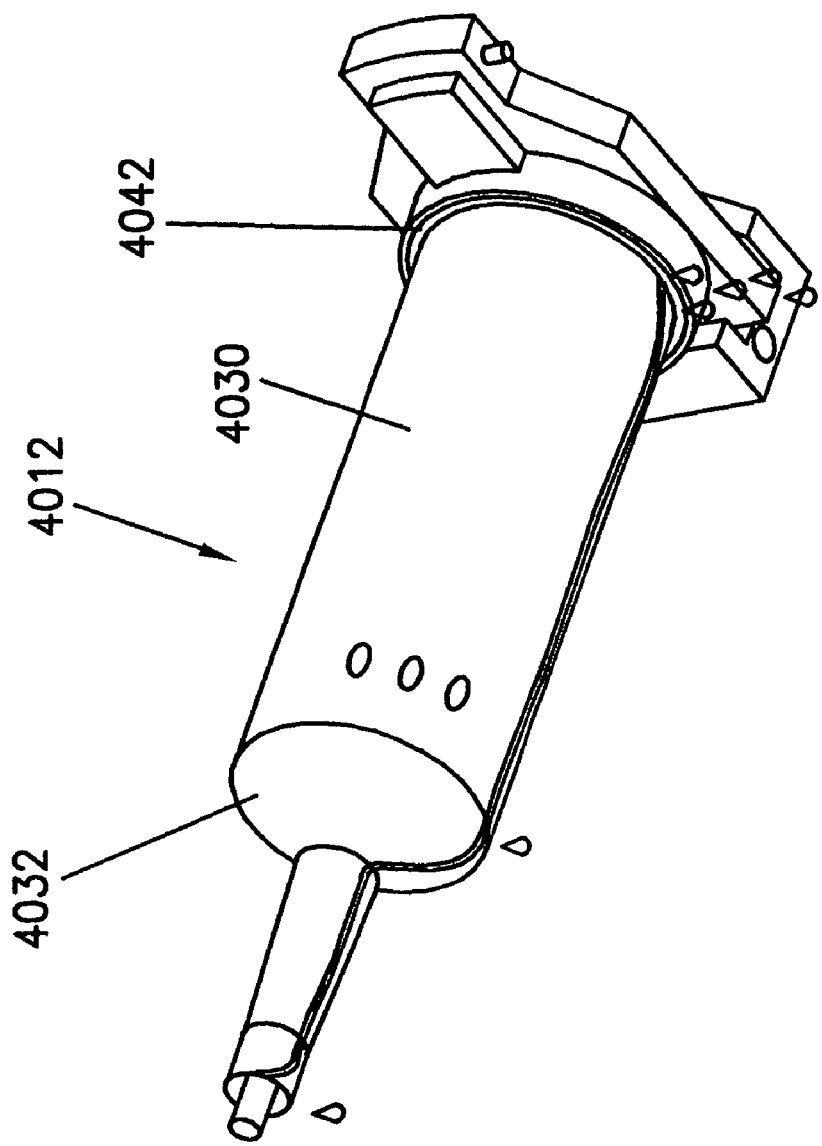

One possible disadvantage of the previously described embodiments of the syringe interface/connector mechanism of the present invention is made apparent by the illustrations in FIGS. 77 and 78. There, it can be observed that flex ring 4026 engages ridge 4044 on syringe 4012 at only two locations 4400 around the periphery of syringe 4012. While this works in most instances to hold syringe 4012 in place, there are some instances where high pressure must be applied to inject contrast medium in syringe 4012 into a patient. Where high pressure (e.g., pressure at or above 1000p.s.i.) is applied, the two regions 4400 may not provide enough contact area with ridge 4044 to hold syringe 4012 securely in release/connector mechanism 4010. In these instances, it is preferred that flex ring 4026 contact most, if not all, of ridge 4044 around the circumference of syringe 4012.

FIG. 119 illustrates an embodiment of the release/connector mechanism 4440 of the present invention that offers a flexible ring 4450 that is circularly shaped to engage a significant portion of ridge 4044 along the periphery of syringe 4012. Flexible ring 4450 is nearly a complete circle with an inner diameter, in a relaxed state, that is just larger than the outer circumference of syringe body 4030. Flexible ring 4450 includes two posts thereon, post 4452 that engages a hole 4456 in a groove 4460 in front plate 4462 and another post 4454 that fits into a hole 4458 in rotating ring 4464. Rotating ring 4464 is nested in an indentation (not shown) in back plate 4466. Screws 4468 may be used to assemble release/connector mechanism 4440.

As with other embodiments, syringe 4012 is inserted through hole 4470 in front plate 4462. When ridge 4044 of syringe 4012 clears flex ring 4450, flex ring 4450 snaps into place around syringe 4012 and provides an audible "click". When in place, projections 4050 on syringe 4012 engage grooves 4472 on the interior surface of rotating ring 4464.

To disengage syringe 4012 from release/connector mechanism 4440, syringe 4012 is rotated approximately one-quarter turn. The rotation of syringe 4012 causes rotating ring 4464 to turn in the direction of arrow 4474. As rotating ring 4464 turns, pressure is applied to post 4454 to cause flex ring 4450 to enter a tensioned state where it has a larger inner diameter. When a sufficient amount of force has been applied to flex ring 4450, it releases syringe 4012 and provides an audible "click" upon doing so.

In the previous embodiments, the flex ring has been shown as a single piece construction. It is possible, however, that flex ring could be constructed from several pieces that are connected in a manner to one another or to the housing for the release/connector mechanism so that the separate elements have a relaxed and a tensioned state (as does the single piece construction).

One possible embodiment of a two-piece "flex ring" is illustrated in FIG. 120. As shown, syringe interface/connector mechanism 4480 includes a front plate 4482 that is similar in design to front plate 4054 (shown in FIGS. 56 and 57). Front plate 4482 includes an indentation 4484 in a rear surface thereof that is sized to accommodate flex ring 4486. Front plate 4482 has a hole 4488 therethrough. It also has notches 4490 that accommodate posts 4492 on flex ring 4486.

Flex ring 4486 is shaped similarly to flex ring 4026. As shown, flex ring 4486 has two separate arcuate pieces 4494, 4496 that are connected together along seams 4498, 4500 on either side. Two springs 4502, 4504 are located on either side of flex ring 4486 to bias flex ring 4486 into a relaxed position around syringe 4012 once inserted therethrough.

A rotating ring 4506 is positioned behind flex ring 4486. Rotating ring 4506 has a hole 4508 therethrough and is provided with a number of grooves 4510 in its inner surface. Rotating ring 4506 is not connected directly to flex ring 4486 (as with other embodiments). Instead, rotating ring 4506 includes two posts 4512, 4514 that extend from a rear surface through rear plate 4516. As with other embodiments, rotating ring 4506 is positioned within an indentation (not shown) on the inner surface of rear plate 4516.

Two semicircular arms 4518, 4520 are positioned behind rear plate 4516. Each arm includes a post 4522, 4524 that engages posts 4492 on flex ring 4486. Each arm also includes a notch 4526, 4528 that engages a post 4512, 4514 on rotating ring, respectively.

The operation of release/connector mechanism 4480 is essentially the same as with previous embodiments. When syringe 4012 is inserted through flex ring 4486, the two segments 4494, 4496 of flex ring 4486 spring apart into a tensioned state until ridge 4044 on syringe 4012 clears the rear edge of the segments 4494, 4496 of flex ring 4486. When ridge 4044 clears flex ring 4486, springs 4502, 4504 return to a relaxed state and draw segments 4494, 4496 into engagement with syringe 4012. When segments 4494, 4496 return to a relaxed state, they preferably provide an audible "click".

To remove syringe 4012 from release/connector mechanism 4480, syringe 4012 is rotated approximately one-quarter turn. As before, syringe 4012 is provided with projections 4050 that engage grooves 4510 on the interior surface of rotating ring 4506. As rotating ring 4506 is turned, arms 4518, 4520 move outwardly from a relaxed position to a tensioned position and apply pressure to posts 4492 to urge segments 4494, 4496 of flex ring 4486 apart. Once the syringe is rotated a sufficient distance, segments 4494, 4496 are sufficiently separated from one another to release syringe 4012, preferably with an audible "click".

FIGS. 121 and 122 illustrate one further example of a release/connector mechanism 4550 according to the teachings of the present invention. Here, instead of providing a flex ring, four segments 4552, 4554, 4556, 4558 are provided around the periphery of the common hole 4560 through connector mechanism 4550. The four segments 4552-4558 may be biased by any suitable mechanism. For example, segments 4552-4558 may be connected to a rotating ring by arms in a similar manner as connector mechanism 4480.

In addition, a front-loading syringe 4612 incorporating syringe encoding is shown in FIG. 126. Syringe 4612 includes a cylindrical body 4630 with a tapering conical portion 4632 at a front end 4634. Conical portion 4632 is integrally connected to a discharge end 4636.

At rear end 4622, syringe 4612 includes two encoding rings 4641, a flange 4642 (which, when syringe 4612 is connected to release mechanism 4010, helps to prevent contrast medium that may leak from, for example, discharge end 4636 from entering release/connector mechanism 4010), an attachment ridge 4644, and preferably two or more, extending release tabs or projections 4650. The rings 4641 preferably extend around the circumference of syringe 4612, but the rings 4641 may be segmented if desired. Also, while two rings 4641 are shown, one, three or more rings 4641 may be provided on syringe 4612 to accommodate varying encoding requirements. The structure and function of the encoding system is described in U.S. application Ser. No. 09/765,498, filed on Jan. 18, 2001, and assigned to the Assignee of the present application, the contents of which are hereby incorporated by reference.

The present invention also provides injectors and injector systems having certain "automated" or "auto" features that facilitate the operation thereof. The auto features of the present invention can be fully automatic, require operator initiation, and/or require some degree of operator, intervention, oversight and/or control. For example, the injectors and injector systems of the present invention may be provided with one or more of the following functions: "auto advance," "auto engage," "auto fill," "auto prime" and "auto retract." Each of these functions, together with their attendant advantages and benefits, is described below in more detail in conjunction with empty, preloaded and/or prefilled syringes. As known in the art, "empty" syringes are syringes that do not contain fluid when mounted on an injector for an injection procedure. Empty syringes typically come in two forms: "plunger-rearward" syringes and "plunger-forward" syringes. Plunger-rearward syringes are syringes having plungers that are initially located at the rearward or proximal ends thereof. Plunger-forward syringes are syringes having plungers that are initially located at the forward or distal ends thereof. "Preloaded" syringes are empty syringes that have been filled with fluid (e.g., by hand or by use of an injector to aspirate fluid into the syringe) prior to an injection procedure, and then stored for subsequent use on an injector for the injection procedure. "Prefilled" syringes are syringes that have been filled with fluid prior to delivery to the customer.

In a preferred embodiment, the injectors and injector systems of the present invention are adapted to automatically identify, for example, the types, sizes, fluid contents (if applicable) and configurations of syringes mounted thereon. Suitable sensors and encoding devices are discussed above and in U.S. Pat. No. 5,383,858 and PCT Publication No. WO 99/65548 (both of which are incorporated herein by reference) to differentiate between varying syringes (e.g., empty, preloaded or prefilled syringes) used on injectors. These sensing schemes, or suitable alternatives as known in the art, could also be used to implement the auto features discussed below.

The "auto engage" feature allows an injector to automatically advance the drive piston thereof to engage a syringe plunger upon installation or attachment of the syringe to the injector. In a preferred embodiment, the auto engage feature occurs without operator intervention. This feature is particularly useful for preloaded and prefilled syringes, which typically have plungers located at some position within the syringe barrel other than at the proximal and distal ends thereof, and plunger-forward syringes. In the case of prefilled syringes, the auto engage feature automatically connects the injector piston and syringe plunger for subsequent priming of the syringe (and associated tubing) and subsequent injection. For plunger-forward syringes, the auto engage feature engages the piston and plunger for subsequent retraction of the plunger for aspiration of fluid, such as contract media, into the syringe.

One embodiment of an auto-engage or auto-dock feature is described in connection with FIG. 127A through 127C, which illustrate a "dual" injector 5500 to which an adapter 5600 and a syringe 5900 are attached. As best shown in FIG. 127B, syringe 5900 includes a flange 5905 which cooperates with front-loading injector 5500 to removably attach syringe 5900 to injector 5500. In that regard, flange 5905 cooperates with a syringe interface 5502, which includes a flex ring 5504 that forms an abutting and releasable connection with syringe flange 5905 in a manner described above. Similarly, as best shown in FIG. 127C, adapter or connector 5600 includes a flange 5605 which cooperates with a syringe interface 5502' of injector 5500 including a flex ring 5504' that forms an abutting and releasable connection with flange 5605.

Syringe 5900 also includes a plunger 5910 that has a generally annular rear base member 5912 and a forward elastomeric cover 5916 attached thereto. A forward surface of piston 5520 is preferably shaped to conform generally to the shape of the inner surface of plunger cover 5916.

A rear section of syringe 5900 can, for example, include indicators such as grooved rings 5920a, 5920b and 5920c (see, for example, FIG. 127B) that cooperate with a light source 5510 and sensors 5512a, 5512b and 5512c of sensors 5512a-e to provide information (via, for example, a binary code) about the configuration of syringe 5900 as described in U.S. patent application Ser. No. 09/796,498, the disclosure of which is incorporated herein by reference. The control system of injector 5500 can thereby be signaled or alerted that syringe 5900 is connected thereto and the operation of injector 5500 can be controlled according to the configuration of syringe 5900.

As used herein, the term "syringe configuration" is used to encompass any or all information about a particular syringe (including syringes used with an intervening adapter), including, but not limited to, information about the mechanical properties of a syringe (for example, material, length and diameter) as well as information about the contents of the syringe (for example, volume and composition). With the advent of new syringes, and especially prefilled syringes, the need to accurately encode and sense (or read) syringe configuration variables is heightened. The syringe configuration information can be used by a powered injector to control the injection procedure as a function of defined syringe configuration/injection parameters. Moreover, a record of data associated with an injection procedure may be kept, for example, to satisfy accurate billing and cost information requirements under managed health care. A record may be maintained of information such as the type of syringe used, the amount of contrast medium used, the type of contrast medium used, the sterilization date, the expiration date, lot codes, the properties of the contrast media, and/or other clinically relevant information. Such information can be recorded digitally for sharing with computerized hospital billing systems, inventory systems, control systems, etc.

Referring, for example, to FIG. 127B, as piston 5520 is advanced toward plunger 5910 a biased (for example, spring-loaded via spring 5574) sensing pin 5570 contacts the rearward or inward surface of plunger cover 5916. Pin 5570 is forced rearward to so that it impinges upon the field of sensor 5578 (for example, an optical sensor). Sensor 5578 can signal the control system of injector 5500 so that the control system stops advancement of piston 5520 after a predetermined amount of time or distance of advancement of piston 5520, so that piston 5520 is brought into engagement with plunger 5910, but advancement of piston 5520 is stopped before movement of syringe plunger 5910. The amount of time between such a signal and the cessation of piston movement can, for example, depend on compliance or tolerance within the piston drive mechanism as well as the type of syringe attached to interface 5502.

Piston 5520 preferably includes retractable pins 5580 that form an abutting connection with one or more ledges, flanges or grooves 5918 formed around the interior circumference of plunger base 5912 when piston 5520 is to be retracted, thereby causing syringe plunger 5910 to retract or move rearward along with piston 5520. In FIGS. 127A and 127B, pins 5580 on piston 5520 are, for example, shown extended to form a connection with plunger 5910 of syringe 5900.

During advancement of piston 5520 to engage plunger 5910 as well as during advancement of piston 5520 to advance plunger 5910 within syringe 5900 (for example, to expel air or fluid contained within syringe 5900), pins 5580 are preferably in a retracted state (as, for example, illustrated for pins 5580' in FIGS. 127A and 127C). If retraction of plunger 5910 is desired, pins 5580 are extended to abut ledge 5918.

In the embodiment of FIGS. 127A through 127C, piston 5520 includes an outer piston section having a rear outer piston sleeve 5530 and forward plunger abutment section 5540 attached thereto. Abutment of a forward facing flange or ledge 5546 of abutment section 5540 with a rear surface of plunger base 5912 causes plunger 5910 to move forward within syringe 5900 with forward movement of piston 5520.

Piston 5520 also includes an inner piston section including a rear inner piston member 5550 and a forward inner member 5560 attached thereto. The inner piston section is movable or slidable in an axial direction relative to the outer piston section to control the state or position of pins 5580. The motion of the inner piston section relative to the outer piston section is preferably limited. For example, such relative motion can be limited using a pin fixed to rear inner piston member 5550. The pin passes through and seats within a slot formed in rear outer piston sleeve. FIG. 127C illustrates, for example, a pin 5552' which is attached to inner piston member 5550' and passes through an elongated slot 5532' of outer piston sleeve 5530' of piston 5520'. Pistons 5520 and 5520' are generally identical in construction and operation and like components are numbered herein similarly with a "'" designation added to the components of piston 5520'.

Pins 5580 are positioned to extend and retract in a radial direction through passages 5542 formed in plunger abutment section 5540. During advancement of piston 5520, friction between outer piston sleeve 5530 and an adjacent wall of injector 5500 causes inner piston member 5550 and forward inner member 5560 to move forward relative to outer piston sleeve 5530 and plunger abutment section 5540 for a distance determined by the cooperation of a pin 5552 (not shown, but identical to pin 5552') and a passage 5532 (not shown, but identical to passage 5532')). Once pin 5552 abuts the forward edge of passage 5532, the outer section and the inner section of piston 5520 will advance together. During the forward movement of forward inner member 5560 relative to plunger abutment section 5540, sloped surfaces 5564 of inner member 5560 contact pins 5580 and cause pins 5580 to be in the retracted state illustrated (see, for example, pins 5580' in FIGS. 127A and 127C).

During retraction of piston 5520, as illustrated, for example, in FIGS. 127A and 127B, the inner section of piston 5520 moves rearward relative to the outer section of piston 5520 for a distance determined by the cooperation of pin 5552 and passage 5532. During the rearward movement of forward inner member 5560 relative to plunger abutment section 5540, sloped surfaces 5568 of inner member 5560 contact pins 5580 and cause pins 5580 to be in the extended state illustrated, for example, in FIGS. 127A and 127B. Plunger 5910 is retracted with further rearward movement of piston 5520 as a result of the abutment of pins 5580 with ledge or flange 5918.

A second syringe generally identical to syringe 5900 can be attached to interface 5510' of injector 5500. Moreover, a number of other types of syringes can be attached to either or both of interfaces 5502 and 5502" through use of adapters as known in the art.

Referring to FIGS. 127A and 127C, for example, a syringe cradle 5610 of adapter 5600 provides for attachment of a syringe 5700 including a syringe plunger 5710 and a cooperating extending plunger pushrod 5720 to injector 5500. A rear portion of adapter section 5600 can, for example, include indicators such as grooved rings 5620a, 5620b and 5620d that cooperate with a light source 5510' and sensors 5512a', 5512b' and 5512d' of sensors 5512a'-e' to provide information (via, for example, a binary code) about the configuration of adapter 5560 and syringe 5700 as described above. The control system of injector 5500 can thereby be signaled or alerted that adapter 5600 is connected thereto and the operation of injector 5500 can be controlled accordingly.

Adapter 5600 further includes a syringe interface or connector 5630 at a forward end thereof to attach syringe 5700 via, for example, cooperation with a rear flange 5730 of syringe 5700. Adapter 5600 preferably further includes a plunger extension carriage 5800 that can form a removable connection with piston 5520' of injector 5500. In that regard, carriage 5800 includes a plunger interface or connector on a rear section thereof that cooperates with piston 5520' to form a releasable connection therewith. As known in the art, many types of interfaces or connectors can be used to connect an injector piston to a plunger or adapter. See, for example, U.S. Pat. Nos. 5,520,653 and 6,336,913, the contents of which are incorporated herein by reference.

Referring, for example, to FIG. 127C, carriage 5800 is, for example, maintained in a rearward position within cradle 5610 by abutment with a biased (for example, spring-loaded) abutment member 5640 (for example, a spring-loaded ball) disposed in passage formed in cradle 5600. As piston 5520' is advanced in a forward direction, a surface 5546' of plunger abutment member 5540' contacts carriage 5800 at a rear surface thereof. Further forward motion of piston 5520' causes carriage 5800 to move forward of (i.e., to overcome the biasing force of) abutment member 5640 so that a biased contact member 5810 of carriage contacts the rearward surface of flange 5724 formed on a rearward end of plunger extension 5720. Preferably the forward surface of contact member 5810 is of a sufficient diameter that it will abut a rearward surface of flange 5724 even if a hole or passage is formed in the rear surface thereof as is the case with many types of syringes. As piston 5520' is advanced, contact member 5810 moves rearward causing biased sensing pin 5570' to move rearward. Eventually, a sensor 5578' senses the rearward movement of pin 5570' relative to sensor 5578' and the control system of injector 5500 can be alerted that carriage 5800 is connected or near connection to plunger extension 5720.

In that regard, carriage 5800 further includes a plunger extension connector to form a releasable connection with plunger extension 5720 of syringe 5700. In the embodiment of FIGS. 127A through 127C, carriage 5800 includes two capture members 5830 that flex radially outward to form a releasable connection with flange 5724 of plunger extension 5720.

In one embodiment, sensor 5578' signals the control system of injector 5500 a known amount of time before flange 5724 is seated in capture member 5830 so that the control system stops advancement of piston 5520' after a secure connection is made between carriage 5800 and plunger extension flange 5724, but before piston 5520' is advanced to a degree to cause injection of fluid from the interior of prefilled, preloaded or empty syringe 5700. Preferably, the axial force required to engage capture members 5830 with flange 5724 is less than the static friction of syringe plunger 5710 within syringe 5700 so that engagement of capture members 5830 with flange 5742 does not cause movement of syringe plunger 5710. The amount of time or distance of piston movement after a signal is received by the injector control system before the advancement of the piston is stopped can be automatically adjusted in accordance with the sensed syringe/adapter configuration.

Piston 5520' includes retractable pins 5580' (which operate in the manner described above for pins 5580). In that regard, pins 5580' form an abutting connection with one or more ledges, flanges or grooves 5840 formed at a known axial position around the interior circumference of syringe carriage 5800 when piston 5520' is to be retracted to draw carriage 5800 rearward. Capture members 5830 maintain a connection with flange 5724 to draw plunger extension 5720 rearward when piston 5520' is retracted.

Figure 130A:
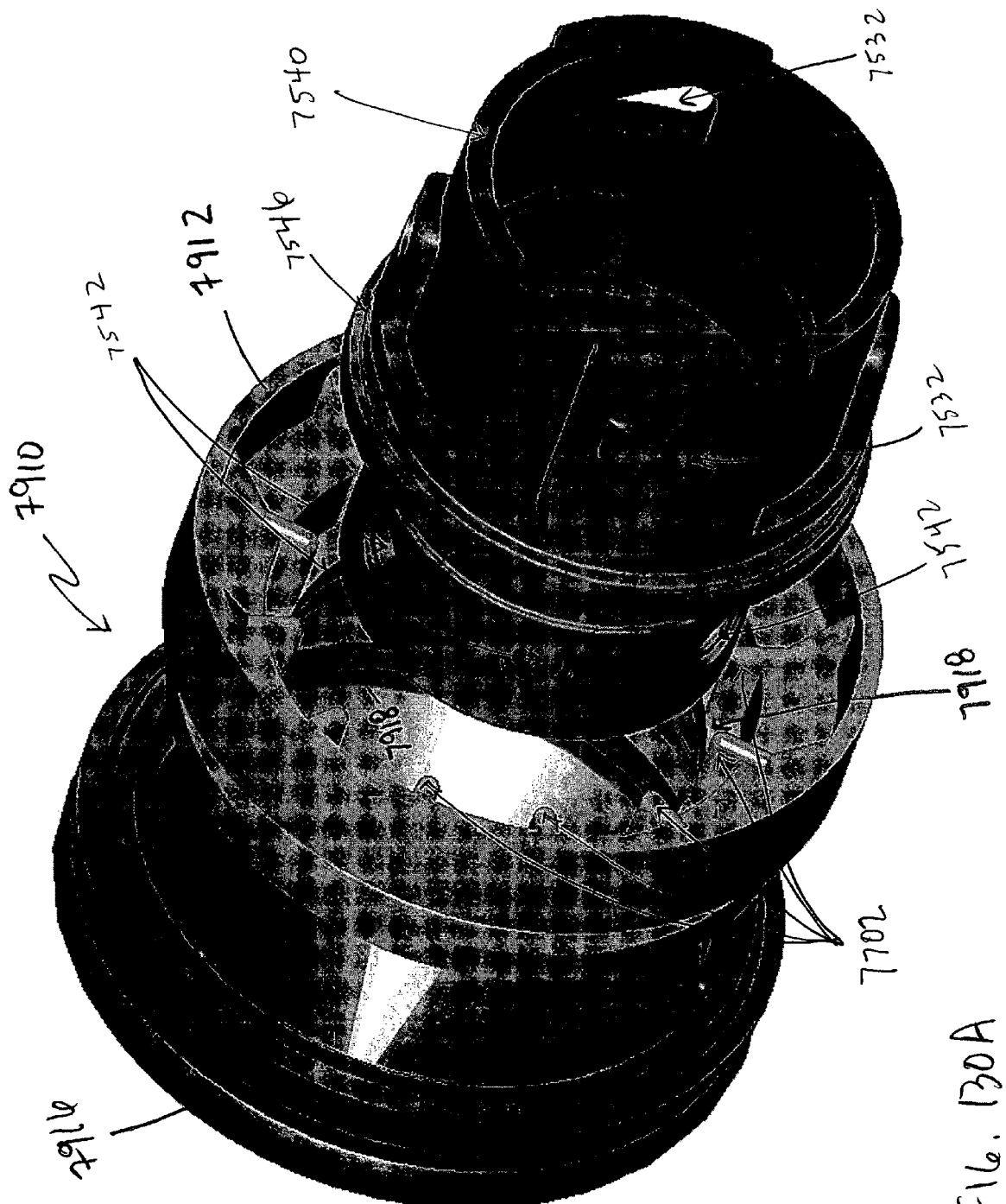

An alternate embodiment similar to that shown in FIGS. 127A-127C is illustrated in FIGS. 130A-130I, wherein like components are numbered therein with a "7000" numeric designation (e.g., plunger 7910 in FIG. 130A and plunger 5910 in FIG. 127A). The embodiment shown in FIGS. 130A-130I operates in a similar manner to that shown in FIGS. 127A-127C, with pertinent differences explained in detail below.

As best shown in FIG. 130A, a syringe 7900 includes a plunger 7910 that has a generally annular rear base member 7912 and a forward elastomeric cover 7916 attached thereto. In an alternate embodiment, the base member 7912 and the cover 7916 may be combined or integrally formed. A forward plunger abutment section 7540 of piston 7520 is preferably shaped to conform generally to the shape of the inner surface of plunger cover 7916.

The base member 7912 preferably includes one or more, and preferably a plurality, of inwardly projecting flanges 7702 spaced around the inner surface thereof and extending rearward from the ledge or retaining shoulder 7918. The flanges 7702 may be evenly or randomly spaced around the plunger 7910. The flanges are adapted to engage one or more outwardly extending flange members 7704 (see FIGS. 130B and 130C) disposed on the abutment section 7540 of the piston 7520, preferably at a position forward of a forward facing flange or ledge 7546 thereof. In a preferred embodiment, the one or more flange members 7704 define a sloped edge 7705 to facilitate engagement with the inwardly projecting flanges 7702 on the plunger 7910. Further, in a preferred embodiment, the piston 7520 includes fewer flange members 7704 than the plunger 7910 includes flanges 7702.

Referring, for example, to FIGS. 130D, 130E, 130H and 130I, as piston 7520 is advanced towards plunger 7910 a biased (for example, by a spring (not shown)) sensing pin 7570 contacts the rearward or inward surface of plunger cover 7916. Pin 7570 is forced rearward to so that it impinges upon the field of sensor 7578 (for example, an optical sensor). Sensor 7578 can signal the control system of injector 5500 to stop advancement of piston 7520 after a predetermined amount of time or distance of advancement of piston 7520, so that piston 7520 is brought into engagement with plunger 7910, but advancement of piston 7520 is stopped before movement of syringe plunger 7910. The amount of time between such a signal and the cessation of piston movement can, for example, depend on compliance or tolerance within the piston drive mechanism as well as the type of syringe attached to interface 5502.

Figure 130B:
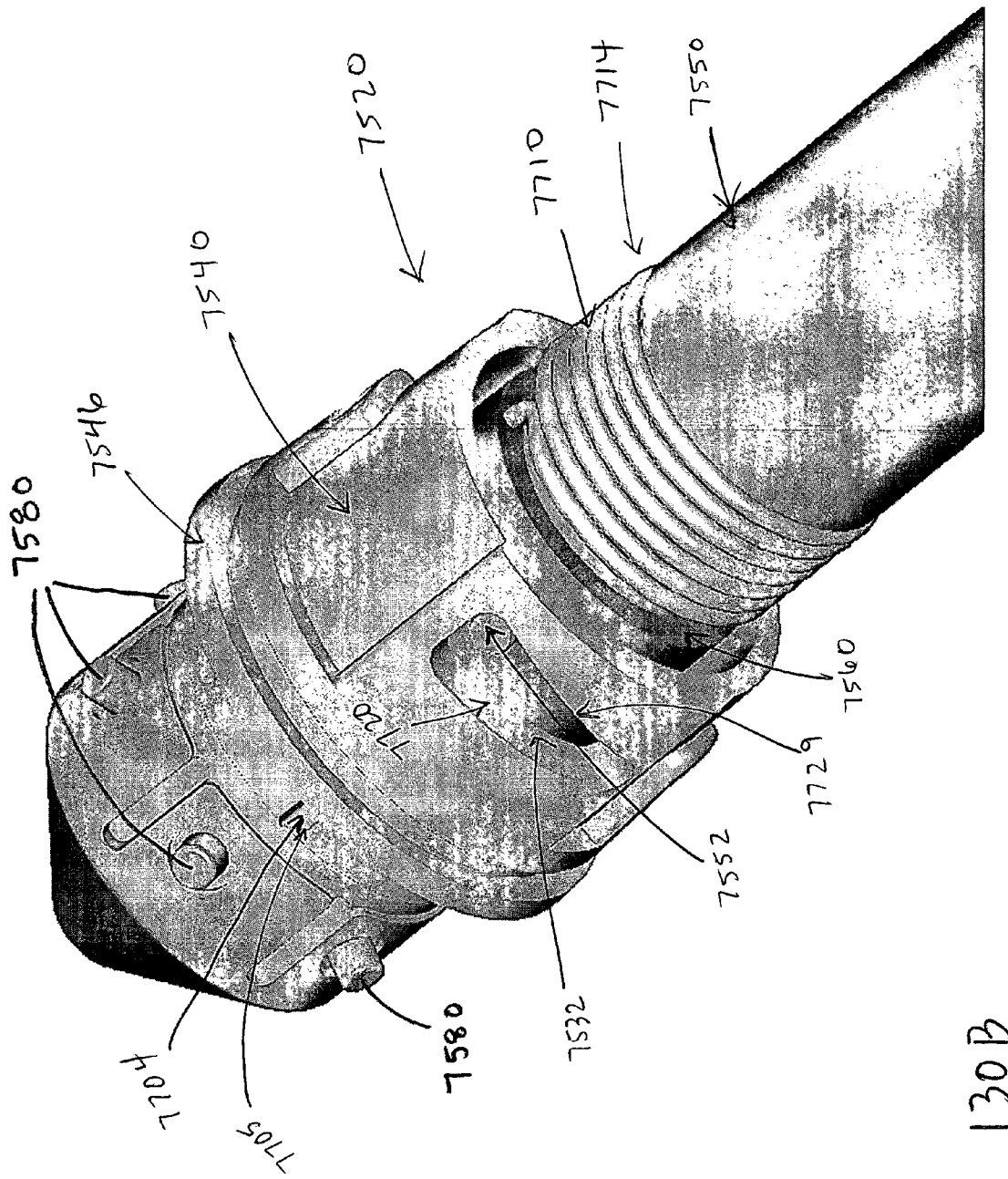
Figure 130D:
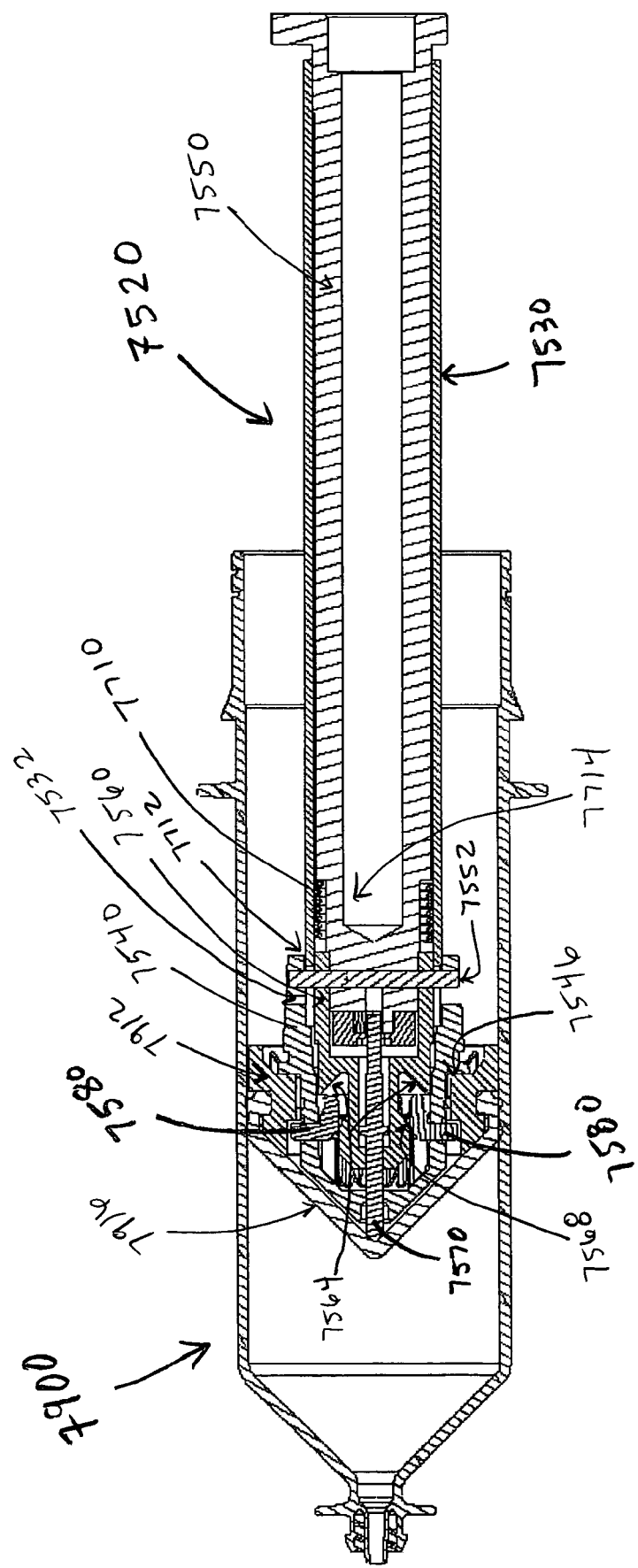
Figure 130E:
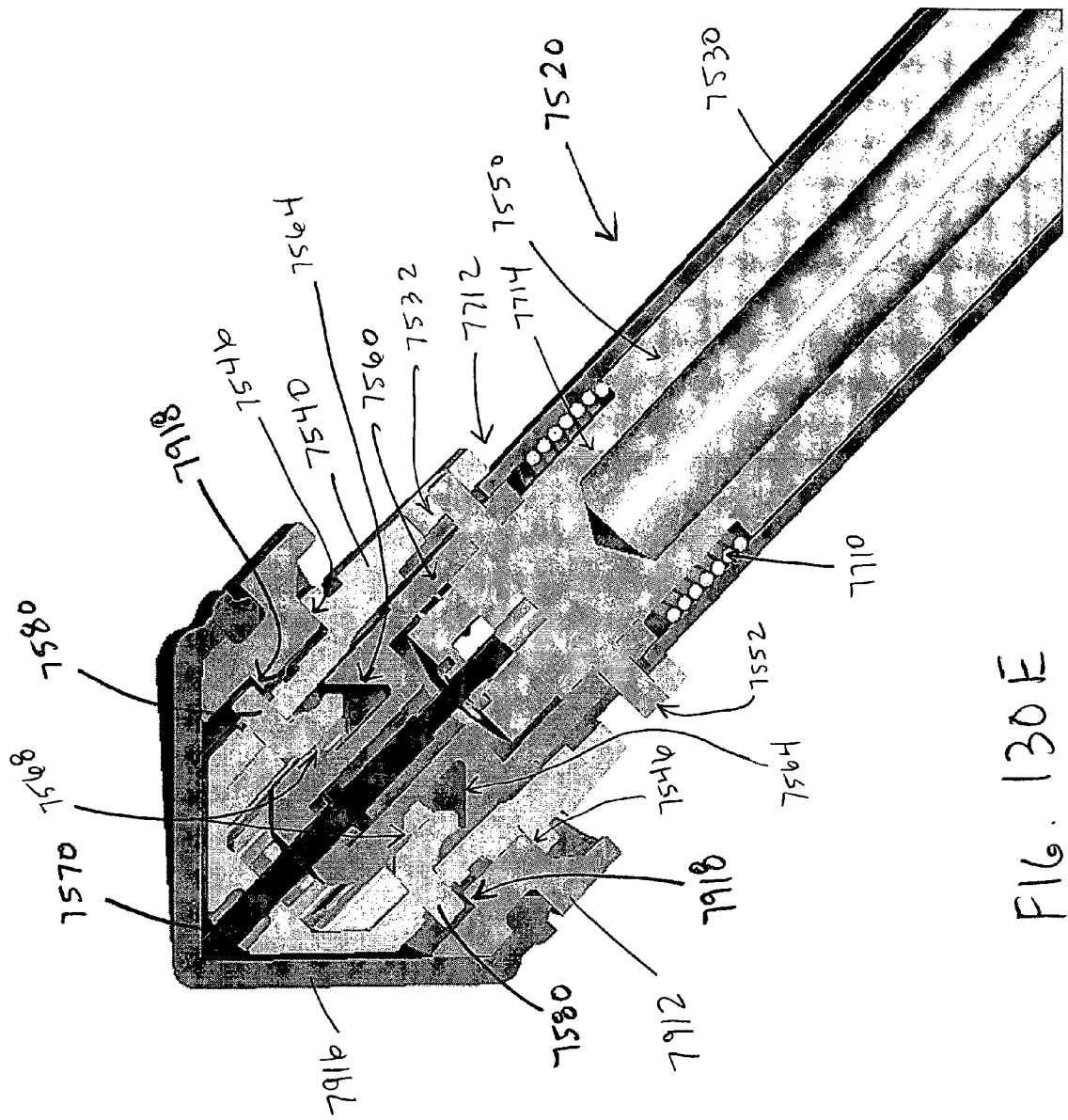
Figure 130G:
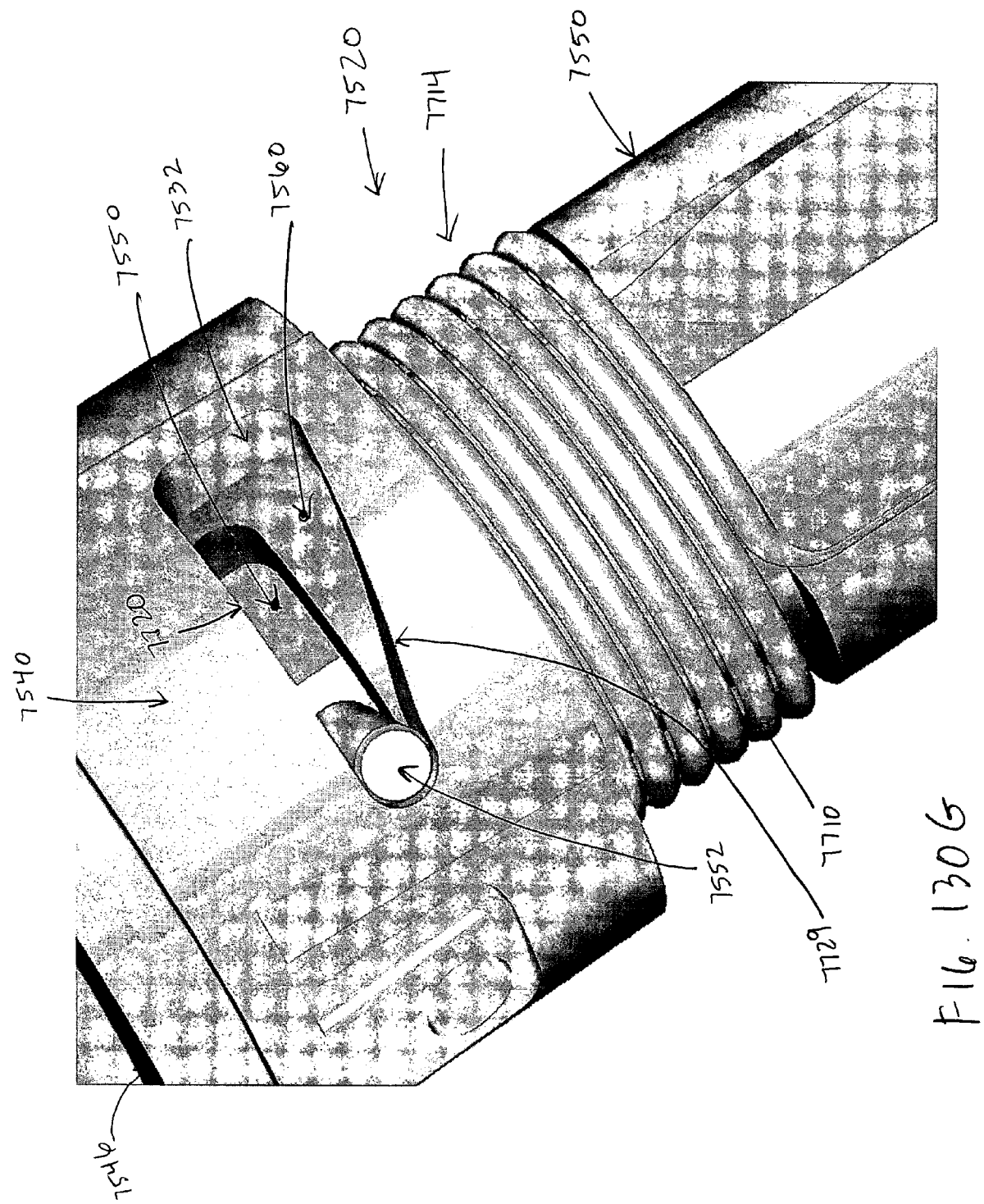

Piston 7520 preferably includes retractable pins 7580 that form an abutting connection with one or more shoulders, ledges, flanges or grooves 7918 formed around the interior circumference of plunger base 7912 when piston 7520 is to be retracted, thereby causing syringe plunger 7910 to retract or move rearward along with piston 7520. In FIGS. 130B, 130D and 130E, pins 7580 on piston 7520 are, for example, shown extended to form a connection with plunger 7910 of syringe 7900.

Figure 130H:
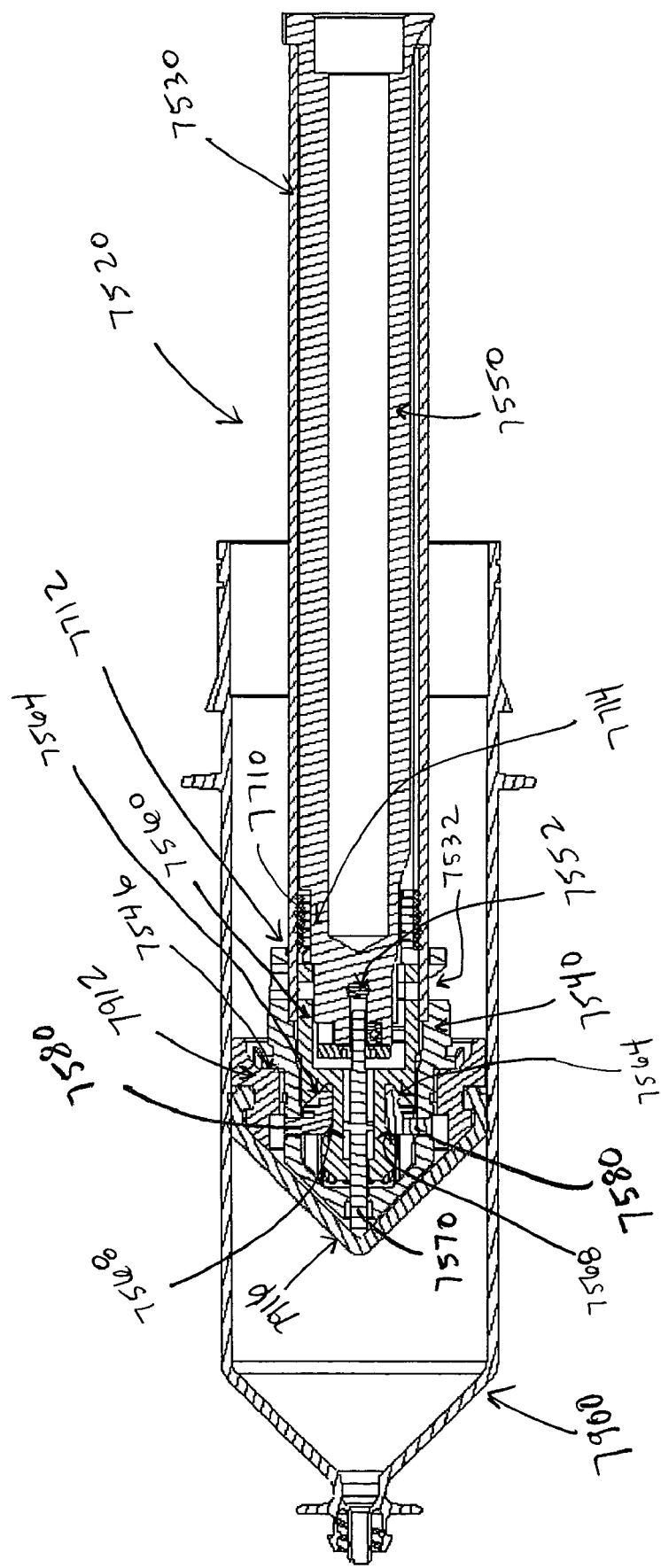
Figure 130I:
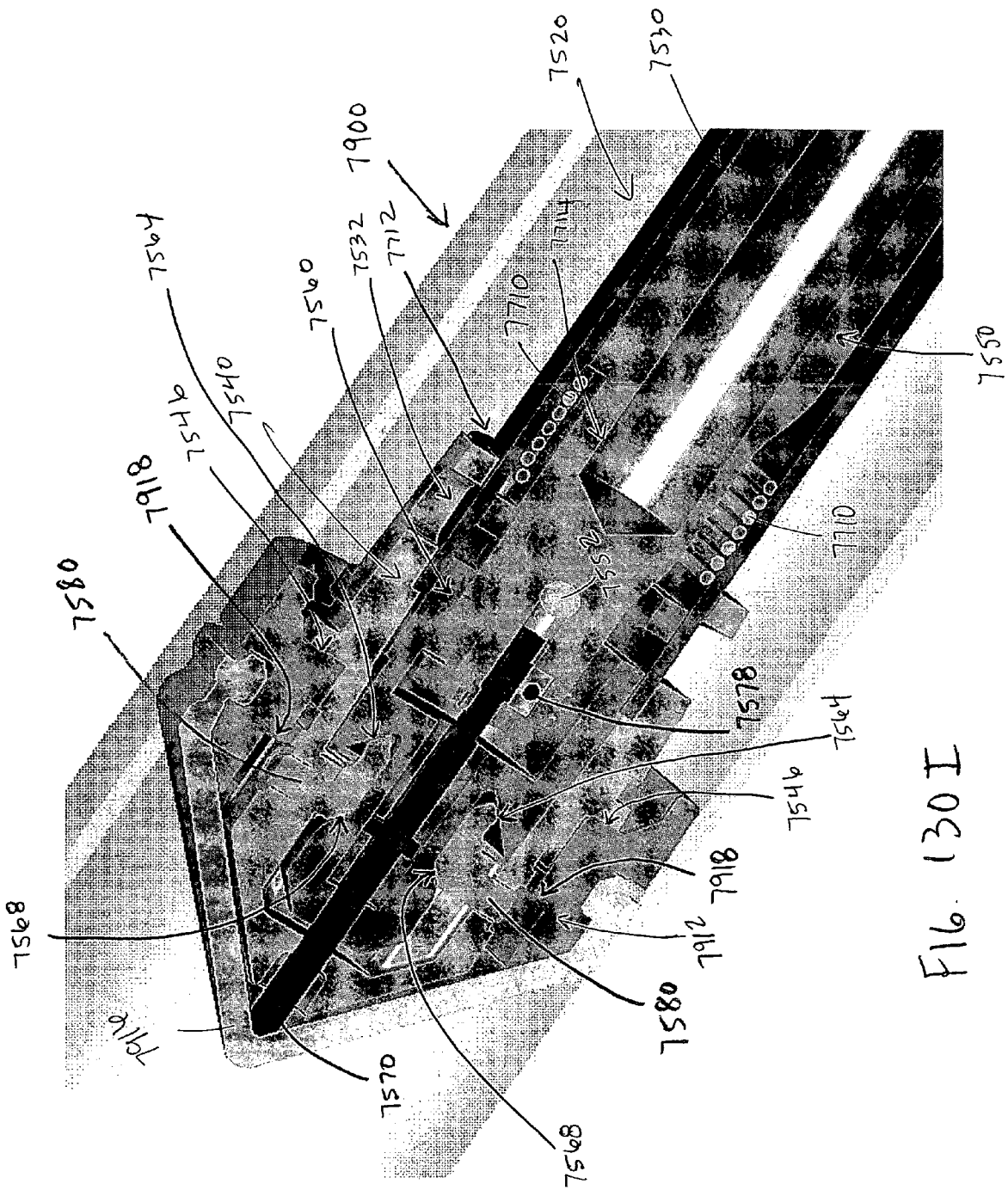

During advancement of piston 7520 to engage plunger 7910, as well as during advancement of piston 7520 to advance plunger 7910 within syringe 7900 (for example, to expel air or fluid contained within syringe 7900), pins 7580 are preferably in a retracted state (as, for example, illustrated for pins 7580 in FIGS. 103F, 130H and 130I). If retraction of plunger 7910 is desired (e.g., to aspirate fluid into the syringe 7900), pins 7580 are extended to abut shoulder or ledge 7918.

As best shown in FIGS. 130B, 130D, 130E, 130G, 130H and 130I, the piston 7520 includes an outer piston section 7712 having a rear outer piston sleeve 7530 and forward plunger abutment section 7540 engaged therewith by a pin 7552. Abutment of a forward facing flange or ledge 7546 of abutment section 7540 with a rear surface of plunger base 7912 causes plunger 7910 to move forward within syringe 7900 with forward movement of piston 7520.

Further, piston 7520 includes an inner piston section 7714 including a rear inner piston member 7550 and a forward inner member 7560 engaged therewith by means of a spring member 7710 and the pin 7552. As shown, for example, in FIG. 130E, the pin 7552 preferably extends through abutment section 7540, the outer sleeve 7530, the forward inner member 7560 and the rear inner member 7550 of the piston 7520. Preferably, as best shown in FIGS. 130B, 130C, 130F, 130G, the pin 7552 moves within or is constrained by an elongated slot, such as the triangular slot 7532, formed in the abutment section 7540. Thus, while the inner piston section 7714 is movable or slidable in an axial direction relative to the outer piston section 7712 to control the state or position of pins 7580, the motion is preferably limited by means of the pin 7552 and the slot 7532.

Pins 7580 are positioned to extend and retract in a radial direction through passages 7542 formed in plunger abutment section 7540. During advancement of piston 7520, friction between outer piston sleeve 7530 and an adjacent wall of injector 5500 causes rear inner piston member 7550 and forward inner member 7560 to move forward relative to outer piston sleeve 7530 and plunger abutment section 7540 for a distance determined by the cooperation of pin 7552 and a forward edge of slot 7532. Once pin 7552 abuts the forward edge of slot or passage 7532, the outer section 7712 and the inner section 7714 of piston 5520 will advance together. During the forward movement of forward inner member 7560 relative to plunger abutment section 7540, sloped surfaces 7564 of inner member 7560 contact pins 7580 and cause pins 7580 to retract into passages 7542 (see, for example, FIG. 130I).

During retraction of piston 7520, as illustrated, for example, in FIGS. 130C-130E, the inner section 7714 of piston 7520 moves rearward relative to the outer section 7712 of piston 7520 for a distance determined by the cooperation of pin 7552 and slot 7532 (see FIGS. 130B and 130C), wherein pin 7552 is positioned, for example, in the most rearward point of slot 7532. During the rearward movement of forward inner member 7560 relative to plunger abutment section 7540, sloped surfaces 7568 of inner member 7560 (see FIGS. 130D and 130E) contact pins 7580 and cause pins 7580 to extend out of passages 7542 and into engagement with the retaining shoulder or ledge 7918 of plunger base 7912. Plunger 7910 is retracted with further rearward movement of piston 7520 as a result of the abutment of pins 7580 with shoulder or ledge 7918.

In some instances, the piston 7520 may retract the plunger 7910 to the rear section of the syringe 7900 before the syringe 7900 is removed form the injector 5500. This plunger retraction could occur automatically or by operator request or intervention. In such cases, the pins 7580 should be retracted out of engagement with the plunger 7910 upon syringe removal even though, as discussed above, piston retraction operates to extend pins 7580 into engagement with plunger 7910, or ready syringe removal from the injector may be prevented or the plunger 7910 may be cocked within or removed from the syringe 7900, thereby potentially causing fluid within the syringe 7900 to spill on the operator, floor, injector, etc.

To facilitate effective syringe removal when the pins 7580 are or may be in an extended state (i.e., to engage plunger 7910), the syringe plunger 7910 includes one or more inwardly projecting flanges or ribs 7702 (see FIG. 130A) adapted to engage one or more outwardly extending flange members or tabs 7704 (see FIGS. 130B and 130C) on the piston 7520. When the syringe 7900 is rotated (e.g., counterclockwise) to remove it from the injector (as described in detail above), the one or more flanges 7702 on the plunger 7910 engage the one or more tabs 7704 on the piston 7520. This engagement causes the abutment section 7540 and the forward inner member 7560 to rotate (against the force of spring member 7710) with respect to outer sleeve 7530 and rear inner piston member 7550. Because pin 7552 engages the abutment section 7540, the outer sleeve 7530, the forward inner member 7560 and the rear inner member 7550 of the piston 7520, during rotation of the abutment section 7540 and the forward inner member 7560 the pin 7552 is caused to ride along the inclined side 7729 of slot 7532 from the position shown in FIGS. 130B and 130C to the position shown in FIGS. 130F and 130G. Thus, as the forward inner member 7560 and the abutment section 7540 are rotated, the forward inner member 7560 and the rear inner member 7550 are also preferably urged forward, causing the sloped surfaces 7564 of the forward inner member 7560 (see FIG. 130I) to engage and retract the pins 7580 out of engagement with the plunger 7910. At this point, the syringe 7900 may be safely removed from the injector.

The embodiment shown in FIGS. 130A-130I may be used with any suitable type or configuration of syringe, as well as with the syringe adapter 5600 and syringe 5700 shown in FIGS. 127A and 127C. Further, any suitable number of pins 7580, flanges 7702 or tabs 7704 may be used depending on the application. The flanges 7702 preferably extend rearward from the shoulder 7918, but they could be placed in any suitable location or orientation on the plunger.

The "auto advance" feature is related to, and may be considered a type or subset of, the auto engage feature as, for example, described above. The auto advance feature allows an injector to automatically advance the plunger of a plunger rearward syringe (i.e., by the drive piston of the injector) to the distal end of the syringe after the syringe is installed on the injector. This feature operates to expel air from an empty, plunger-rearward syringe and to place the syringe plunger in a position to be subsequently retracted to aspirate fluid, such as contrast media, into the syringe for an injection procedure. In a preferred embodiment, the injector senses the mounting or installation of the syringe thereon and automatically advances the piston without operator intervention to drive the plunger to the distal end of the syringe. Of course, this feature would ordinarily be used only with empty syringes (as compared to preloaded or prefilled syringes) to prevent fluid from being expelled therefrom.

As discussed above, in a preferred embodiment, the injectors and injector systems of the present invention may be adapted to automatically differentiate between, for example, empty syringes and preloaded syringes (via, for example, sensors 5512a-d and sensors 5512a'-d'). Because preloaded syringes are empty syringes that have been filled with fluid and stored prior to an injection procedure, and further because operators, depending on the application or need, may or may not preload empty syringes with fluid for storage prior to the injection procedure, the injector may have difficulty differentiating between empty, plunger-rearward syringes and preloaded syringes.

One possible arrangement to address this concern is to assemble the plunger-rearward syringes with their plungers located at positions rearward of the maximum fill volume of the syringes. As can be appreciated, this arrangement will result in preloaded syringes having their plungers located (after loading with fluid) at some position equal to or forward of the maximum fill volume of the syringes. In operation, after a syringe is placed on the injector and identified as an empty syringe, the auto engage feature will drive the piston forward to engage the syringe plunger. If the piston engages the syringe plunger at a position rearward of the maximum fill volume of the syringe, the injector will discern that a plunger-rearward syringe has been installed thereon and the auto advance feature will be enabled to drive the plunger to the distal end of the syringe to expel air therefrom and to place the plunger in position for aspiration of fluid into the syringe. On the other hand, if the piston engages the syringe plunger at a position equal to or forward of the maximum fill volume of the syringe, the injector will discern that a preloaded syringe has been installed thereon. Of course, when the injector determines that a preloaded syringe has been installed thereon, the auto advance feature will not be enabled (i.e., to prevent the piston from advancing the plunger to the distal end of the syringe, thereby expelling the preloaded fluid form the syringe).

The "auto fill" or "auto load" feature allows an injector to automatically retract a syringe plunger (i.e., by means of the injector piston) to draw in or aspirate a programmed amount of fluid, such as contrast media, into the syringe. Preferably, the auto fill feature occurs without operator intervention, thereby allowing the operator to perform other tasks (e.g., programming the scanner or injector, positioning the patient on the scanner table, catherizing the patient) while the syringe is being filled with the required amount of fluid. Of course, this feature typically is not necessary for prefilled or preloaded syringes, which already contain fluid therein.

In a preferred embodiment, the auto fill feature also includes a "trapped air reduction" feature to reduce the amount of air aspirated into the syringe during the fluid aspiration procedure. During an aspiration procedure facilitated by, for example, the auto fill feature, the injector piston retracts the syringe plunger to draw fluid into the syringe. Often, for example, when the aspiration flow rate is sufficiently great, air is aspirated into the syringe along with the fluid. To reduce the amount of air aspirated into the syringe, the trapped air reduction feature reverses the motion of the injector piston (i.e., to slightly advance the injector piston) one or more times during the aspiration procedure. By reducing the amount of air aspirated into the syringe during the fill operation, the quantity and size of air bubbles formed in the syringe, as well as the time required to subsequently expel air from the syringe and connecting tube (i.e., priming the system) are reduced, resulting in a lower probability of an inadvertent air injection.

The "auto prime" feature allows an injector to automatically prime the fluid path (i.e., syringe and connecting tubing) before an injection procedure. Preferably, the volume of fluid contained within a connector tubing used with a syringe is pre-programmed into the injector. For example, a 60' low pressure connecting tubing ("LPCT") provided by Medrad, Inc., the Assignee of the present application, for use with its disposable syringes typically holds approximately 2.78 ml of fluid. Alternately, the operator may manually program the fluid volume contained within the connector tube into the injector.

As will become apparent, the auto prime feature may be functionally dependent, in certain respects, on the auto fill feature described above. When a syringe is filled with fluid (i.e., by means of the auto fill feature), the injector automatically compensates for the connector tube by adding its corresponding fluid volume to the fluid volume desired by the operator to be aspirated into the syringe for an injection operation, which can be set forth as part of an injection protocol input by the operator. For example, if the operator desires to fill the syringe with 150 ml of fluid for an injection procedure, the auto fill feature will compensate for the connector tube fluid volume by automatically adding 2.78 ml of fluid (e.g., for a 60' LPCT), for a total volume of 152.78 ml aspirated into the syringe. After the syringe is filed with fluid, the auto prime feature would then cause the injector piston to advance the syringe plunger to the extent necessary to expel air from the syringe and connector tube system, preferably without prompting by the operator. Once the auto prime function is conducted, fluid should be present at the patient end of the connector tube (i.e., the end that is connected to the catheter).

As can be appreciated, the auto prime feature may save operator time and reduce the amount of wasted fluid. By automatically compensating for the fluid contained within the connector tube, the operator does not have to vigilantly watch the progression of the fluid from the syringe through the connecting tube in order to stop the advancement of the piston before a significant amount of fluid is discharged from the end of the connector tubing. Also, because some operators of conventional injectors advance the piston quickly to lessen the time required to prime the syringe and tubing system, often a significant amount of fluid will be expelled from the end of the connector tubing before the operator stops the piston's advancement. If a sufficient amount of contrast is expelled, the syringe may have to be re-filled (and the syringe and tubing system subsequently re-primed) to insure that it contains a sufficient amount of fluid for the required injection procedure.

While the auto prime feature is preferably intended for use with empty syringes that have been filled with fluid by an aspiration procedure on the injector (i.e., non-prefilled and non-preloaded syringes), the auto prime feature could also be used with prefilled and preloaded syringes.

The "auto retract" feature allows an injector to automatically retract the injector piston after a syringe is removed or disconnected from the injector. At the end of an injection procedure, the injector piston and the syringe plunger is typically located at the distal end of the syringe. Therefore, as described above and in U.S. Pat. Nos. 5,383,858 and 5,300,031 (both of which are incorporated herein by reference), after the syringe is disconnected from the injector, the injector piston often extends from the front of the injector (or within a pressure jacket attached to the front of the injector). Especially in the case of plunger-rearward syringes, preloaded syringes and prefilled syringes, the piston usually must be retracted in order to mount a new syringe onto the injector for the next injection procedure. To save operator time in retracting the piston, the auto retract feature automatically retracts the piston after the injector senses that the syringe has been removed therefrom (e.g., after an injection procedure) to place the injector piston in position to accept a new syringe. If plunger-forward syringes are being used on the injector, the auto retract feature may be deactivated to prevent unnecessary and/or redundant piston movements. The auto retract feature could be manually deactivated by the operator or automatically by the injector. For example, when a plunger-forward syringe is installed on and identified by the injector, the injector could automatically initiate a default setting to deactivate the auto retract feature for subsequent syringes until an operator override is activated or until the system detects the attachment of a prefilled, preloaded or plunger-rearward syringe. When the injector detects a prefilled or preloaded syringe, the system can compensate for any residual air remaining in the syringe by adjusting the amount of priming to be conducted. For example, if the prefilled syringe typically contains approximately 1.2 ml of air or "dead space" and is connected to a 60' LPCT (accommodating approximately 2.78 ml of fluid), the injector system would prime approximately 3.97 ml from the syringe and connecting tube system.

As will be appreciated, depending on operator need, the auto features described above could be used independently or in conjunction with one another to facilitate injector use. For example, the auto features described above could be used with a plunger rearward syringe in the following manner. After an operator installs the plunger rearward syringe on an injector, the auto advance feature advances the syringe plunger to the distal end of the syringe (i.e., to expel air from the syringe and to place the plunger into position to aspirate fluid thereinto). The auto fill feature subsequently aspirates a predetermined amount of fluid into the syringe, based on the desired operator amount for the injection procedure and, preferably, compensating for the fluid volume of the connector tubing. The auto prime feature then automatically advances the injector piston and syringe plunger to remove air from the syringe and connecting tube system. Subsequently, after the injection procedure is completed and the syringe is removed from the injector, the auto retract feature retracts the injector piston to place the injector in position for the next injection procedure with a plunger rearward syringe, a preloaded syringe or a prefilled syringe.

As another example, the auto features could be used with a prefilled syringe or a preloaded syringe in the following manner. After an operator places the prefilled syringe or preloaded syringe on the injector, the auto engage feature advances the injector piston into the syringe to mate or engage with the syringe plunger. The auto prime feature then advances the piston and plunger to expel air from and thereby prime the syringe and connector tubing system. Subsequently, after the injection procedure is completed and the syringe is removed from the injector, the auto retract feature retracts the injector piston to place the injector in position for the next injection procedure with a plunger rearward syringe, a preloaded syringe or a prefilled syringe.

As yet another example, the auto features could be used with a plunger forward syringe in the following manner. After an operator places the plunger forward syringe on the injector, the auto engage feature advances the injector piston into the syringe to mate or engage with the syringe plunger. The auto fill feature subsequently aspirates a predetermined amount of fluid into the syringe, based on the desired operator amount for the injection procedure and, preferably, compensating for the fluid volume of the connector tubing. The auto prime feature then automatically advances the injector piston and syringe plunger to remove air from the syringe and connecting tube system. Subsequently, after the injection procedure is completed and the syringe is removed from the injector, the auto retract feature retracts the injector piston (if, for example, the default setting to deactivate the auto retract feature for plunger forward syringes has been overridden by the operator) to place the injector in position for the next injection procedure with a plunger rearward syringe, a preloaded syringe or a prefilled syringe. If new plunger forward syringes are to be used with the injector (and the default setting to deactivate the auto retract feature for plunger forward syringes has not been overridden by the operator), then the auto retract feature will not operate and the piston is left in its extended position for the next syringe.

The injectors and injector systems of the present invention may also include additional features complementary to one or more of the auto features described above to further enhance the usefulness of the auto features and to free operators to perform additional functions. For example, the injectors and injector systems of the present invention may be provided with an attachment device for holding fluid sources, such as bottles or bags, during the auto fill function. By holding the fluid source during the auto fill function, the need for the operator to hold the fluid source during filling of the syringe is eliminated, thereby freeing the operator for other activities preparatory to the injection procedure. Of course, the fluid source attachment device would provide benefit to the operator apart from the auto fill function. For example, if the auto fill feature were not available on a particular injector, the fluid source attachment device would still function to hold the fluid source during operator-enabled filling operations.

In addition, the injectors, syringes and injectors systems of the present invention may be provided with an attachment device for holding the patient end of the connector tubing during the priming function (e.g., auto prime or operator-enabled priming). By holding the patient end of the connector tubing, preferably in the vertical direction to prevent fluid from dripping out of the patient end, the connector tubing attachment device frees the operator for other activities preparatory to the injection procedure. Of course, various other injector operations (injection protocol programming, check for air, etc.) are or may be conducted between the various auto functions.

A number of the above identified auto features (for example, auto loading and auto priming) and other injector features of the present invention are discussed in connection with a representative example of injector 5500 and graphical user interfaces for control thereof in, for example, a computerized tomography (CT) environment. In a CT environment, a control unit (control room unit) for control of injector 5500 is placed in a control room (see, for example, FIG. 128A), which is shielded from radiation used to produce the CT scan. Injector 5500 is positioned within a scan room with the CT scanner and a scan room control unit (scan room unit) in communication with injector 5500 and in communication with the control room unit. The scan room unit can duplicate some or all of the control features found on the control room unit as known in the art. Moreover, the scan room unit can include injector control features in addition to those found on the control room unit as known in the art. Other control units such as a handheld control unit can be provided as known in the art.

In a typical procedure, the operator of the CT procedure first programs the protocol for the injection procedure using the control room unit. Several screen captures of an embodiment of a graphical user interface (GUI) 6000 for the control room unit are illustrated in FIG. 128A through 128D (which can, for example, be operated in the manner of a touch screen). See also, U.S. Pat. No. 6,339,718, the contents of which are incorporated herein by reference. In this embodiment, the control system of injector 5500 includes three modes of injection selectable by the operator as illustrated, for example, in the interface screen or display of FIG. 128B. The screen of FIG. 128B can, for example, be displayed upon activation of a modify switch or button 6005 on the interface screen or display of FIG. 128A. These modes of operation include a mode for sequential injection from syringes 5900A and 5900B, a mode for simultaneous injection from syringes 5900A and 5900B into a single injection site and a mode for simultaneous injection from syringes 5900A and 5900B into different injection sites.

In the case of a sequential injection, a fluid can be injected from only one of syringe 5900A or 5900B at a time. For example, syringe 5900A can contain contrast medium, while syringe 5900B can contain a flushing fluid such as saline, which can be sequentially injected into a patient using a variety of protocols as known in the art. An example of a fluid path for sequential injection is illustrated in FIG. 129A. In FIG. 129A, tubing from each of syringes 5900A and 5900B come together via a T-connector 6400 for fluid connection to the injection site on the patient.

A plurality of phases of sequential injection can be entered using control room interface 6000. FIG. 128C, for example, illustrates a six-phase, sequential injection protocol in which 2 ml of saline from syringe 5900B is first injected at a flow rate of 4.0 ml/sec in a first phase. The second phase is a hold phase in which injector 5500 holds the injection until the user reactivates the injection, using, for example, the scanning room display start switch, hand control switch or other control. In the third phase, 60 ml of fluid is injected from syringe 5900A at a flow rate of 4.0 ml/sec. In the fourth phase, 60 ml of fluid is once again injected from syringe 5900A at a flow rate of 4.0 ml/sec. In the fifth phase, the injection is paused for 10 sec. In the sixth and final phase, 10 ml of saline is injected from syringe 5900B at a flow rate of 2.0 ml/sec.

During simultaneous injection into a single site (using for example the fluid path of FIG. 129A), syringe 5900A can, for example, be loaded or filled with contrast medium, while syringe 5900B can, for example, be loaded with a diluent or flushing fluid such as saline. In this mode, contrast medium or other fluid in syringe 5900A can, for example, be diluted or mixed with fluid in syringe 5900B to a desired concentration by simultaneous injection from syringe 5900A and, 5900B as programmed by the operator. For example, FIG. 128D illustrates a setup for simultaneous injection of 50 ml of a mixture of 80% fluid from syringe 5900A and 20% fluid from syringe 5900B with a flow rate of 5 ml/sec. Piston 5520 and piston 5520' of injector 5500 will thus be advanced in a controlled manner such that 40 ml of fluid from syringe 5900A and 10 ml of fluid from syringe 5900B will be simultaneously injected into a single injection site over a period of 10 seconds.

In the case of a simultaneous injection to different injection sites (see FIG. 129B), syringe 5900A and syringe 5900B can, for example both be filled with the same injection fluid (for example, contrast medium). Injection of the contrast medium at two different sites, as opposed to a single site, can, for example, enable delivery of a desired amount of contrast medium to a region of interest at a lower flow rate and a lower pressure at each site than possible with injection into a single site. For example, half the contrast medium desired for delivery to a patient's P's heart can be injected into a vein on each of the patient's P's arms (see FIG. 129B), rather than injection of the entire amount into a single injection site on one of the patient's P's arm. The lower flow rates and pressures enabled by simultaneous injection into multiple sites can, for example, reduce the risk of vascular damage and extravasation.

After setting the desired protocols at the control room unit in any of the above injection modes, the operator typically enters the scan room for final preparations of injector 5500 and/or final preparations of the patient. In the embodiment of FIGS. 129A and 129B, the scan room unit is part of or in incorporated in injector head 5500 with a control/display GUI or interface 6100 positioned on an upper side of injector 5500. Incorporating the scan room unit into injector head 5500 can, for example, reduce the use of space within the scan room as compared to a separate control unit.

Control room interface 6000 preferably includes a lock protocol function 6010, which can, for example, be a button, micro-switch or touch screen area activated by the operator to "lock" the protocol. Subsequent editing of the injection protocol preferably deactivates protocol function lock 6010. Alternatively, activation of protocol lock 6010 can prevent editing of the set protocol until protocol lock 6010 is deactivated. Activation and deactivation of protocol lock 6010 preferably changes the state (for example, activates and deactivates, respectively) an indicator (for example, a light) 6110 on interface 6100. When activated, indicator 6110 ensures the operator that another has not altered the set protocols while the operator is in the scan room. In that regard, editing of the set protocol is associated with deactivation of protocol lock 6010, and deactivation of protocol lock 6010 results in a change of state (for example, deactivation) of indicator 6110. The protocol lock can, for example, lock out further protocol editing and be password encoded for extra assurance that undesired protocol changes are not entered.

After connection of empty syringes 5900A and 5900B to injector 5500, the configurations of syringes 5900A and 5900B are preferably sensed as described above. After auto docking or auto engaging as well as auto advancing preferably proceeds as described above, the injector system is ready for filling of empty syringes 5900A and 5900B. In the embodiment of FIGS. 129A and 129B, syringes 5900A and 5900B are in fluid connection with sources or reservoirs of injection fluid, 6200 and 6300, respectively. For example, source 6200 can be a reservoir of contrast medium, while source 6300 can be a reservoir of a flushing or diluting fluid such as saline. A valve system, which can, for example, include check valves 6210 and 6310, can be provided to control fluid flow as known in the art and to prevent cross contamination between patients when, for example, sources 6200 and/or 6300 are used with multiple patients.

Auto loading and/or auto priming can begin automatically upon setting of protocols as described above. Alternatively, auto loading can be manually initiated, at least in part, by the operator via activation of an auto load switch 6120 as well as fill switches or buttons 6122 and 6124 for each of syringes 5900A and 5900B, respectively, on scan room unit interface 6100. A display area 6130 of interface 6100 can, for example, include a numeric display as well as a graphical display of the amount of fluid in each of syringes 5900A and 5900B. Different colors can be used to denote the different syringes and the different fluids therein.

In the example of simultaneous injection of 50 ml of a mixture of 80% contrast medium from syringe 5900A and 20% saline from syringe 5900B into a single injection site, the steps of auto loading, auto priming and injection are described in connection with FIGS. 128D through 128J. In FIGS. 128D and 128E, display area 6130 as well as a display area 6030 of control unit interface 6000 indicate that auto loading has not yet been initiated. Each of syringes 5900A and 5900B are indicated to be empty (0 ml volume). FIG. 128F illustrates display area 6130 after activation of the auto load switch. The numeric portion of the display indicates that 14 ml of saline will be loaded into syringe 5900B, while 41 ml of contrast medium will be loaded into syringe 5900. For the tubing set used in the example of FIGS. 128D through 128J, 4 ml of saline and 1 ml of contrast are required to prime the tubing. Upon confirmation/acceptance of the fill volumes, the operator activates each of fill switches or buttons 6122 and 6124 to begin loading of contrast and saline into syringes 5900A and 5900B, respectively. Upon completion of loading, display area 6130 appears as illustrated in FIG. 128G. Upon activation of an auto prime switch or button 6140, 1 ml of contrast is injected from syringe 5900A and 4 ml of saline are injected from syringe 5900B to prime the fluid path and tubing set. The tubing can now be connected to a patient catheter. Display 6130 now appears as illustrated in FIG. 128H, wherein 40 ml of contrast are indicated to be present within syringe 5900A and 10 ml of saline are indicated to be present in syringe 5900B.

Syringes 5900A and 5900B are now in a state to commence injection. Preferably, injector 5500 requires the operator to perform a check for air in the fluid path as known in the art. In that regard, the injector system can prevent injection until an air check confirmation button or switch 6150 on scan room unit interface 6100 is activated. After arming injector 5500 by, for example, activating an arm switch or button on interface 6000 or a similar arm switch or button 6150 on interface 6100, the injection can be initiated. As know in the art, arming the injector can initiate a number of self or internal tests and state checks to ensure that injector 5500 is ready for injection.

FIG. 128I illustrates the state of display area 6130 halfway through the injection procedure, while FIG. 128J illustrates the state of display area 6130 upon completion of the injection procedure. The graphical representation and numeric data of display area 6130 can also be reflected in similar display area 6030 of interface 6000. As seen in the representative example of FIGS. 128D through 128J, the injector system of the present invention provides for a wide range of injected contrast and other fluid concentrations adjusted during injection through appropriate loading of syringes 5900A and 5900B with respective fluids, and appropriate control of the simultaneous injection thereof into a single site. Moreover, the concentration of contrast and other fluids can be readily varied, adjusted or changed during an injection procedure if desired for a particular procedure.

The foregoing description and accompanying drawings set forth the preferred embodiments of the invention at the present time. Various modifications, additions and alternative designs will, of course, become apparent to those skilled in the art in light of the foregoing teachings without departing from the scope of the disclosed invention. For example, the respective mating connection and release mechanisms on the injectors and the syringes described above may be interchanged. The scope of the invention is indicated by the following claims rather than by the foregoing description. All changes and variations that come within the meaning and range of equivalency of the claims are to be embraced within their scope.

What is claimed is:

1. A syringe comprising:
a body; and
a plunger movably disposed within the body, the plunger comprising:
a cylindrical wall extending in a longitudinal direction and having a circumferentially continuous inner surface and an outer surface, the inner surface defining a retaining shoulder formed in a radial direction and extending along the circumference of the cylindrical wall; and
a plurality of inwardly projecting flanges extending rearwardly from the retaining shoulder and fixedly disposed on the circumferentially continuous inner surface of the cylindrical wall, wherein the plurality of inwardly projecting flanges extending a length in a longitudinal direction and are fixedly connected along the length to the cylindrical wall,
wherein the inwardly projecting flanges are continuously supported in the longitudinal direction by the circumferentially continuous inner surface of the cylindrical wall,
wherein the outer surface is defined by a wall that is planar in axial and annular directions.

2. The syringe of claim 1 wherein the plurality of flanges are evenly spaced along the cylindrical wall.

3. The fluid injection system of claim 1 wherein the plurality of inwardly projecting flanges project radially and terminate a distance radially inward from the circumferentially continuous inner surface.

4. The fluid injection system of claim 1 wherein the inwardly projecting flanges terminate at an axial position and are rigidly supported in the radial direction by the inner surface at the axial position.

5. The fluid injection system of claim 1 wherein the inwardly projecting flanges extend radially at least to an inner most radial position of the retaining shoulder.

6. The syringe of claim 1 wherein the plurality of inwardly projecting flanges extend inwardly a length to decrease a diameter formed by the circumferentially continuous inner surface.

7. A fluid injection system comprising:
an injector comprising:
  a housing; and
  a drive member at least partially disposed within the housing, the drive member comprising:
    at least one retaining member; and one or more outwardly extending flange members; and
a syringe comprising:
  a body; and
  a plunger movably disposed within the body, the plunger comprising:
    a cylindrical wall extending in a radial direction and having a circumferentially continuous inner surface and an outer surface, the inner surface defining a retaining shoulder formed in a radially inward direction and extending along the circumference of the cylindrical wall; and
    a plurality of inwardly projecting flanges extending rearwardly from the retaining shoulder and fixedly disposed on the circumferentially continuous inner surface of the cylindrical wall, wherein the plurality of inwardly projecting flanges extending a length in a longitudinal direction and are fixedly connected along the length to the cylindrical wall,
    wherein each of the inwardly projecting flanges are continuously supported in the longitudinal direction by the circumferentially continuous inner surface of the cylindrical wall;
wherein the at least one retaining member on the drive member of the injector is adapted to engage the retaining shoulder on the cylindrical plunger wall to enable the drive member to retract the plunger within the body of the syringe; and
wherein the plurality of inwardly projecting flanges on the cylindrical plunger wall are adapted to engage the one or more outwardly extending flange members on the drive member when the syringe body is rotated about its longitudinal axis, the one or more outwardly extending flange members operable to cause the at least one retaining member on the drive member to disengage the retaining shoulder on the cylindrical wall of the plunger upon rotation of the syringe body.

8. The fluid injection system of claim 7 wherein the plurality of inwardly projecting flanges are radially spaced along the circumferentially continuous inner surface of the cylindrical wall.

9. The fluid injection system of claim 7 wherein the plurality of flanges are evenly spaced along the inner surface of the cylindrical wall.

10. A syringe comprising:
a body; and
a plunger movably disposed within the body, the plunger comprising:
  a cylindrical wall having a continuous inner surface and an outer surface, the inner surface defining a retaining shoulder formed and extending along the circumference of the cylindrical wall; and
  a plurality of inwardly projecting flanges extending radially from the continuous inner surface and rearwardly from the retaining shoulder, wherein the plurality of inwardly projecting flanges includes a proximal end and a distal end,
  wherein the distal end connects to the retaining shoulder and the proximal end connects to the cylindrical wall,
  wherein the outer surface is defined by a wall that is planar in axial and annular directions.

11. The syringe of claim 10 wherein the inwardly projecting flanges are continuously supported in the longitudinal direction by the inner surface of the cylindrical wall.

12. The syringe of claim 10 wherein the plurality of inwardly projecting flanges extend inwardly a length to decrease a diameter formed by the circumferentially continuous inner surface.

* * * * *

UNITED STATES PATENT AND TRADEMARK OFFICE
CERTIFICATE OF CORRECTION

| | | |
|---|---|---|
| PATENT NO. | : 7,666,169 B2 | Page 1 of 1 |
| APPLICATION NO. | : 10/722370 | |
| DATED | : February 23, 2010 | |
| INVENTOR(S) | : Cowan et al. | |

It is certified that error appears in the above-identified patent and that said Letters Patent is hereby corrected as shown below:

TITLE PAGE

Item (54), in Title, in Column 1, Line 1, and in Column 1, Line 1 in the Specification, delete "PLUNGERS" and insert -- PLUNGER --, therefor.

IN THE SPECIFICATION

In Column 5, Line 29, delete "injectors" and insert -- injectors. --, therefor.

In Column 39, Line 44, delete "(ee" and insert -- (See --, therefor.

Signed and Sealed this
Eleventh Day of September, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,666,169 B2 | |
| APPLICATION NO. | : 10/722370 | |
| DATED | : February 23, 2010 | |
| INVENTOR(S) | : Cowan et al. | |

It is certified that error appears in the above-identified patent and that said Letters Patent is hereby corrected as shown below:

TITLE PAGE

Item (54), in Title, in Column 1, Line 1, and in Column 1, Line 1 in the Specification, delete "PLUNGERS" and insert -- PLUNGER --, therefor.

IN THE SPECIFICATION

In Column 5, Line 29, delete "injectors" and insert -- injectors. --, therefor.

In Column 39, Line 44, delete "(ee" and insert -- (See --, therefor.

IN THE CLAIMS

In Claim 1, Column 58, Line 48, delete "cylindrical wall," and insert -- cylindrical wall, and --, therefor.

In Claim 3, Column 58, Line 53, delete "The fluid injection system of claim 1 wherein" and insert -- The syringe of claim 1, wherein --, therefor.

In Claim 4, Column 58, Line 57, delete "The fluid injection system of claim 1 wherein" and insert -- The syringe of claim 1, wherein --, therefor.

In Claim 5, Column 58, Line 51, delete "The fluid injection system of claim 1 wherein" and insert -- The syringe of claim 1, wherein --, therefor.

In Claim 7, Column 59, Line 25, delete "wherein each of the inwardly projecting flanges are" and insert -- wherein each of the inwardly projecting flanges is --, therefor.

This certificate supersedes the Certificate of Correction issued September 11, 2012.

Signed and Sealed this
Thirtieth Day of October, 2012

David J. Kappos
*Director of the United States Patent and Trademark Office*

CERTIFICATE OF CORRECTION (continued)
U.S. Pat. No. 7,666,169 B2

IN THE CLAIMS

In Claim 9, Column 60, Lines 10-11, delete "the plurality of flanges are evenly spaced" and insert -- the plurality of inwardly projecting flanges are evenly spaced --, therefor.

In Claim 10, Column 60, Lines 23-24, delete "wherein the plurality of inwardly projecting flanges includes" and insert -- wherein each of the plurality of inwardly projecting flanges includes --, therefor.

In Claim 10, Column 60, Line 27, delete "cylindrical wall" and insert -- cylindrical wall, and --, therefor.

In claim 11, Column 60, Lines 31-32, delete "are continuously supported in the longitudinal direction" and insert -- are continuously supported in a longitudinal direction --, therefor.